US011793400B2

(12) United States Patent
Patel

(10) Patent No.: US 11,793,400 B2
(45) Date of Patent: Oct. 24, 2023

(54) OCCLUSION-CROSSING DEVICES

(71) Applicant: AVINGER, INC., Redwood City, CA (US)

(72) Inventor: Himanshu N. Patel, San José, CA (US)

(73) Assignee: Avinger, Inc., Redwood City, CA (US)

( * ) Notice: Subject to any disclaimer, the term of this patent is extended or adjusted under 35 U.S.C. 154(b) by 0 days.

(21) Appl. No.: 17/763,810

(22) PCT Filed: Oct. 6, 2020

(86) PCT No.: PCT/US2020/054395
§ 371 (c)(1),
(2) Date: Mar. 25, 2022

(87) PCT Pub. No.: WO2021/076356
PCT Pub. Date: Apr. 22, 2021

(65) Prior Publication Data
US 2022/0346638 A1    Nov. 3, 2022

Related U.S. Application Data

(60) Provisional application No. 62/923,347, filed on Oct. 18, 2019.

(51) Int. Cl.
*A61B 17/3207* (2006.01)
*A61B 1/05* (2006.01)
(Continued)

(52) U.S. Cl.
CPC ............ *A61B 1/05* (2013.01); *A61B 1/00172* (2013.01); *A61B 1/3137* (2013.01);
(Continued)

(58) Field of Classification Search
CPC .... A61B 17/320758; A61B 17/320783; A61B 2017/00331; A61B 2017/22094;
(Continued)

(56) References Cited

U.S. PATENT DOCUMENTS 3,367,727 A    2/1968  Ward et al.
3,908,637 A    9/1975  Doroshow
(Continued)

FOREIGN PATENT DOCUMENTS

CN    1875242 A    12/2006
CN    1947652 A     4/2007
(Continued)

OTHER PUBLICATIONS

Aziz et al.; Chronic total occlusions—a stiff challege requiring a major breakthrough: is there light at the end of the tunnel?; Heart; vol. 91; suppl. III; pp. 42-48; Jun. 2005.
(Continued)

*Primary Examiner* — Tuan V Nguyen
(74) *Attorney, Agent, or Firm* — Shay Glenn LLP

(57) ABSTRACT

A catheter system includes a catheter that includes an outer shaft and a rotatable inner shaft having a drill tip. The catheter can be configured to bend laterally when the inner shaft is rotating within the other shaft for maneuvering within a blood vessel, for example, as the drill tip crosses an occlusion. Catheter bending can be activated by translating the inner shaft relative to the outer shaft in a distal direction, proximal direction, or both. The outer shaft may include a locking feature to rotatably lock the inner shaft with the outer shaft and allowing bidirectional lateral bending of the catheter. The inner shaft can include one or more imaging sensors for collecting images outside of the catheter. The inner shaft may be removable from the outer shaft, for example after an occlusion is crossed, to allow insertion of a guidewire or other device within the outer shaft.

25 Claims, 69 Drawing Sheets

(51) Int. Cl.
*A61B 1/313* (2006.01)
*A61B 1/00* (2006.01)
*A61B 5/00* (2006.01)
A61B 90/00 (2016.01)
A61B 17/00 (2006.01)
A61B 17/22 (2006.01)
A61B 17/32 (2006.01)

(52) U.S. Cl.
CPC .... *A61B 5/0066* (2013.01); *A61B 17/320758* (2013.01); *A61B 2017/00331* (2013.01); *A61B 2017/00473* (2013.01); *A61B 2017/22094* (2013.01); *A61B 2017/320004* (2013.01); *A61B 2090/3735* (2016.02)

(58) Field of Classification Search
CPC ...... A61B 2017/320004; A61B 5/0066; A61B 2090/3735
See application file for complete search history.

(56) References Cited

U.S. PATENT DOCUMENTS

| | | |
|---|---|---|
| 4,178,935 A | 12/1979 | Gekhaman et al. |
| 4,487,206 A | 12/1984 | Aagard |
| 4,527,553 A | 7/1985 | Upsher |
| 4,552,554 A | 11/1985 | Gould et al. |
| 4,578,061 A | 3/1986 | Lemelson |
| 4,611,600 A | 9/1986 | Cohen |
| 4,621,353 A | 11/1986 | Hazel et al. |
| 4,639,091 A | 1/1987 | Huignard et al. |
| 4,651,753 A | 3/1987 | Lifton |
| 4,654,024 A | 3/1987 | Crittenden et al. |
| 4,681,106 A | 7/1987 | Kensey et al. |
| 4,686,982 A | 8/1987 | Nash |
| 4,691,708 A | 9/1987 | Kane |
| 4,729,763 A | 3/1988 | Henrie |
| 4,771,774 A | 9/1988 | Simpson et al. |
| 4,781,186 A | 11/1988 | Simpson et al. |
| 4,841,977 A | 6/1989 | Griffith et al. |
| 4,857,046 A | 8/1989 | Stevens et al. |
| 4,920,961 A | 5/1990 | Grossi et al. |
| 4,926,858 A | 5/1990 | Gifford, III et al. |
| 5,000,185 A | 3/1991 | Yock |
| 5,018,529 A | 5/1991 | Tenerz et al. |
| 5,041,082 A | 8/1991 | Shiber |
| 5,047,040 A | 9/1991 | Simpson et al. |
| 5,085,662 A | 2/1992 | Willard |
| 5,099,850 A | 3/1992 | Matsui et al. |
| 5,178,153 A | 1/1993 | Einzig |
| 5,182,291 A | 1/1993 | Gubin et al. |
| 5,190,050 A | 3/1993 | Nitzsche |
| 5,192,291 A | 3/1993 | Pannek, Jr. |
| 5,312,415 A | 5/1994 | Palermo |
| 5,312,425 A | 5/1994 | Evans et al. |
| 5,321,501 A | 6/1994 | Swanson et al. |
| 5,333,142 A | 7/1994 | Scheps |
| 5,358,472 A | 10/1994 | Vance et al. |
| 5,366,464 A | 11/1994 | Belknap |
| 5,372,601 A | 12/1994 | Lary |
| 5,383,460 A | 1/1995 | Jang et al. |
| 5,383,467 A | 1/1995 | Auer et al. |
| 5,425,273 A | 6/1995 | Chevalier |
| 5,425,371 A | 6/1995 | Mischenko |
| 5,429,136 A | 7/1995 | Milo et al. |
| 5,431,673 A | 7/1995 | Summers et al. |
| 5,437,284 A | 8/1995 | Trimble |
| 5,459,570 A | 10/1995 | Swanson et al. |
| 5,460,168 A | 10/1995 | Masubuchi et al. |
| 5,465,147 A | 11/1995 | Swanson |
| 5,507,725 A | 4/1996 | Savage et al. |
| 5,507,760 A | 4/1996 | Wynne et al. |
| 5,507,795 A | 4/1996 | Chiang et al. |
| 5,517,998 A | 5/1996 | Madison |
| 5,556,405 A | 9/1996 | Lary |
| 5,607,394 A | 3/1997 | Andersen et al. |
| 5,620,426 A | 4/1997 | Braithwaite |
| 5,632,754 A | 5/1997 | Farley et al. |
| 5,632,755 A | 5/1997 | Nordgren et al. |
| 5,674,232 A | 10/1997 | Halliburton |
| 5,681,336 A | 10/1997 | Clement et al. |
| 5,690,634 A | 11/1997 | Muller et al. |
| 5,722,403 A | 3/1998 | McGee et al. |
| 5,728,148 A | 3/1998 | Bostrom et al. |
| 5,749,846 A | 5/1998 | Edwards et al. |
| 5,795,295 A | 8/1998 | Hellmuth et al. |
| 5,807,339 A | 9/1998 | Bostrom et al. |
| 5,830,145 A | 11/1998 | Tenhoff |
| 5,836,957 A | 11/1998 | Schulz et al. |
| 5,843,050 A | 12/1998 | Jones et al. |
| 5,843,103 A | 12/1998 | Wulfman |
| 5,851,212 A | 12/1998 | Zirps et al. |
| 5,868,778 A | 2/1999 | Gershony et al. |
| 5,872,879 A | 2/1999 | Hamm |
| 5,904,651 A | 5/1999 | Swanson et al. |
| 5,907,425 A | 5/1999 | Dickensheets et al. |
| 5,935,075 A | 8/1999 | Casscells et al. |
| 5,938,602 A | 8/1999 | Lloyd |
| 5,938,671 A | 8/1999 | Katoh et al. |
| 5,951,482 A | 9/1999 | Winston et al. |
| 5,951,581 A | 9/1999 | Saadat et al. |
| 5,951,583 A | 9/1999 | Jensen et al. |
| 5,956,355 A | 9/1999 | Swanson et al. |
| 5,957,952 A | 9/1999 | Gershony et al. |
| 5,987,995 A | 11/1999 | Sawatari et al. |
| 5,997,558 A | 12/1999 | Nash |
| 6,001,112 A | 12/1999 | Taylor |
| 6,007,530 A | 12/1999 | Dornhofer et al. |
| 6,010,449 A | 1/2000 | Selmon et al. |
| 6,013,072 A | 1/2000 | Winston et al. |
| 6,017,359 A | 1/2000 | Gershony et al. |
| 6,027,514 A | 2/2000 | Stine et al. |
| 6,032,673 A | 3/2000 | Savage et al. |
| 6,048,349 A | 4/2000 | Winston et al. |
| 6,080,170 A | 6/2000 | Nash et al. |
| 6,106,515 A | 8/2000 | Winston et al. |
| 6,110,164 A | 8/2000 | Vidlund |
| 6,120,515 A | 9/2000 | Rogers et al. |
| 6,120,516 A | 9/2000 | Selmon et al. |
| 6,134,002 A | 10/2000 | Stimson et al. |
| 6,134,003 A | 10/2000 | Tearney et al. |
| 6,152,938 A | 11/2000 | Curry |
| 6,152,951 A | 11/2000 | Hashimoto et al. |
| 6,160,826 A | 12/2000 | Swanson et al. |
| 6,175,669 B1 | 1/2001 | Colston et al. |
| 6,176,871 B1 | 1/2001 | Pathak et al. |
| 6,183,432 B1 | 2/2001 | Milo |
| 6,193,676 B1 | 2/2001 | Winston et al. |
| 6,206,898 B1 | 3/2001 | Honeycutt et al. |
| 6,228,076 B1 | 5/2001 | Winston et al. |
| 6,241,744 B1 | 6/2001 | Imran et al. |
| 6,283,957 B1 | 9/2001 | Hashimoto et al. |
| 6,285,903 B1 | 9/2001 | Rosenthal et al. |
| 6,290,668 B1 | 9/2001 | Gregory et al. |
| 6,294,775 B1 | 9/2001 | Seibel et al. |
| 6,299,622 B1 | 10/2001 | Snow et al. |
| 6,307,985 B1 | 10/2001 | Murakami et al. |
| 6,375,615 B1 | 4/2002 | Flaherty et al. |
| 6,402,719 B1 | 6/2002 | Ponzi et al. |
| 6,416,527 B1 | 7/2002 | Berg et al. |
| 6,445,939 B1 | 9/2002 | Swanson et al. |
| 6,445,944 B1 | 9/2002 | Ostrovsky |
| 6,447,525 B2 | 9/2002 | Follmer et al. |
| 6,451,036 B1 | 9/2002 | Heitzmann et al. |
| 6,454,717 B1 | 9/2002 | Pantages et al. |
| 6,454,779 B1 | 9/2002 | Taylor |
| 6,482,216 B1 | 11/2002 | Hiblar et al. |
| 6,482,217 B1 | 11/2002 | Pintor et al. |
| 6,485,413 B1 | 11/2002 | Boppart et al. |
| 6,497,649 B2 | 12/2002 | Parker et al. |
| 6,501,551 B1 | 12/2002 | Tearney et al. |
| 6,503,261 B1 | 1/2003 | Bruneau et al. |
| 6,511,458 B2 | 1/2003 | Milo et al. |
| 6,517,528 B1 | 2/2003 | Pantages et al. |

(56) References Cited

U.S. PATENT DOCUMENTS

| | | |
|---|---|---|
| 6,542,665 B2 | 4/2003 | Reed et al. |
| 6,544,230 B1 | 4/2003 | Flaherty et al. |
| 6,546,272 B1 | 4/2003 | MacKinnon et al. |
| 6,551,302 B1 | 4/2003 | Rosinko et al. |
| 6,563,105 B2 | 5/2003 | Seibel et al. |
| 6,564,087 B1 | 5/2003 | Pitris et al. |
| 6,565,588 B1 | 5/2003 | Clement et al. |
| 6,572,563 B2 | 6/2003 | Ouchi et al. |
| 6,572,643 B1 | 6/2003 | Gharibadeh |
| 6,575,995 B1 | 6/2003 | Huter et al. |
| 6,579,298 B1 | 6/2003 | Bruneau et al. |
| 6,599,296 B1 | 7/2003 | Gillick et al. |
| 6,615,071 B1 | 9/2003 | Casscells, III et al. |
| 6,629,953 B1 | 10/2003 | Boyd |
| 6,638,233 B2 | 10/2003 | Corvi et al. |
| 6,645,217 B1 | 11/2003 | MacKinnon et al. |
| 6,657,727 B1 | 12/2003 | Izatt et al. |
| 6,666,874 B2 | 12/2003 | Heitzmann et al. |
| 6,687,010 B1 | 2/2004 | Horii |
| 6,728,571 B1 | 4/2004 | Barbato |
| D489,973 S | 5/2004 | Root et al. |
| 6,730,063 B2 | 5/2004 | Delaney et al. |
| 6,758,854 B1 | 7/2004 | Butler et al. |
| 6,760,112 B2 | 7/2004 | Reed et al. |
| 6,800,085 B2 | 10/2004 | Selmon et al. |
| 6,818,001 B2 | 11/2004 | Wulfman et al. |
| 6,824,550 B1 | 11/2004 | Noriega et al. |
| 6,830,577 B2 | 12/2004 | Nash et al. |
| 6,845,190 B1 | 1/2005 | Smithwick et al. |
| 6,852,109 B2 | 2/2005 | Winston et al. |
| 6,853,457 B2 | 2/2005 | Bjarklev et al. |
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Tearney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,682,319 B2 | 3/2010 | Martin et al. |
| 7,706,863 B2 | 4/2010 | Imanishi et al. |
| 7,728,985 B2 | 6/2010 | Feidchtein et al. |
| 7,729,745 B2 | 6/2010 | Maschke |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,002,763 B2 | 8/2011 | Berthiaume et al. |
| 8,059,274 B2 | 11/2011 | Splinter |
| 8,062,316 B2 | 11/2011 | Patel et al. |
| 8,068,921 B2 | 11/2011 | Prakash et al. |
| 8,313,493 B2 | 11/2012 | Fisher |
| 8,361,097 B2 | 1/2013 | Patel et al. |
| 8,548,571 B2 | 10/2013 | He et al. |
| 8,548,603 B2 | 10/2013 | Swoyer et al. |
| 8,632,557 B2 | 1/2014 | Thatcher et al. |
| 8,644,913 B2 | 2/2014 | Simpson et al. |
| 8,647,335 B2 | 2/2014 | Markus |
| 8,696,695 B2 | 4/2014 | Patel et al. |
| 8,911,459 B2 | 12/2014 | Simpson et al. |
| 9,119,662 B2 | 9/2015 | Moberg |
| 9,125,562 B2 | 9/2015 | Spencer et al. |
| 9,333,007 B2 | 5/2016 | Escudero et al. |
| 9,345,398 B2 | 5/2016 | Tachibana et al. |
| 9,345,406 B2 | 5/2016 | Spencer et al. |
| 9,345,510 B2 | 5/2016 | Patel et al. |
| 9,345,511 B2 | 5/2016 | Smith et al. |
| 9,351,757 B2 | 5/2016 | Kusleika |
| 9,498,247 B2 | 11/2016 | Patel et al. |
| 9,498,600 B2 | 11/2016 | Rosenthal et al. |
| 9,557,156 B2 | 1/2017 | Kankaria |
| 9,572,492 B2 | 2/2017 | Simpson et al. |
| 9,579,157 B2 | 2/2017 | Moberg |
| 9,592,075 B2 | 3/2017 | Simpson et al. |
| 9,642,646 B2 | 5/2017 | Patel et al. |
| 9,788,790 B2 | 10/2017 | Black et al. |
| 9,854,979 B2 | 1/2018 | Smith et al. |
| 9,918,734 B2 | 3/2018 | Patel et al. |
| 9,949,754 B2 | 4/2018 | Newhauser et al. |
| 10,052,125 B2 | 8/2018 | Rosenthal et al. |
| 10,130,386 B2 | 11/2018 | Simpson et al. |
| 10,213,224 B2 | 2/2019 | Guggenheimer et al. |
| 10,244,934 B2 | 4/2019 | Tachibana et al. |
| 10,314,667 B2 | 6/2019 | Garvey et al. |
| 10,335,173 B2 | 7/2019 | Carver et al. |
| 10,342,491 B2 | 7/2019 | Black et al. |
| 10,349,974 B2 | 7/2019 | Patel et al. |
| 10,357,277 B2 | 7/2019 | Patel et al. |
| 10,363,062 B2 | 7/2019 | Spencer et al. |
| 10,406,316 B2 | 9/2019 | Garvey et al. |
| 10,470,795 B2 | 11/2019 | Patel et al. |
| 10,548,478 B2 | 2/2020 | Simpson et al. |
| 10,568,520 B2 | 2/2020 | Patel et al. |
| 10,568,655 B2 | 2/2020 | Simpson et al. |
| 10,722,121 B2 | 7/2020 | Smith et al. |
| 10,729,326 B2 | 8/2020 | Spencer et al. |
| 10,860,484 B2 | 10/2020 | Simpson et al. |
| 10,869,685 B2 | 12/2020 | Patel et al. |
| 10,932,670 B2 | 3/2021 | Smith et al. |
| 10,952,615 B2 | 3/2021 | Kankaria |
| 10,952,763 B2 | 3/2021 | Newhauser et al. |
| 11,033,190 B2 | 6/2021 | Patel et al. |
| 11,096,717 B2 | 8/2021 | Gupta et al. |
| 11,134,849 B2 | 10/2021 | Simpson et al. |
| 11,135,019 B2 | 10/2021 | Spencer et al. |
| 11,147,583 B2 | 10/2021 | Patel et al. |
| 11,206,975 B2 | 12/2021 | Tachibana et al. |
| 11,224,459 B2 | 1/2022 | Patel et al. |
| 11,278,248 B2 | 3/2022 | Christensen |
| 11,284,839 B2 | 3/2022 | Black et al. |
| 11,284,916 B2 | 3/2022 | Patel et al. |
| 11,344,327 B2 | 5/2022 | Fernandez et al. |
| 2001/0005788 A1 | 6/2001 | McGuckin, Jr. |

(56) References Cited

U.S. PATENT DOCUMENTS

| | | |
|---|---|---|
| 2001/0020126 A1 | 9/2001 | Swanson et al. |
| 2002/0019644 A1 | 2/2002 | Hastings et al. |
| 2002/0072706 A1 | 6/2002 | Hiblar et al. |
| 2002/0082585 A1 | 6/2002 | Carroll et al. |
| 2002/0082626 A1 | 6/2002 | Donohoe et al. |
| 2002/0097400 A1 | 7/2002 | Jung et al. |
| 2002/0111548 A1 | 8/2002 | Swanson et al. |
| 2002/0115931 A1 | 8/2002 | Strauss et al. |
| 2002/0147459 A1 | 10/2002 | Bashiri et al. |
| 2002/0158547 A1 | 10/2002 | Wood |
| 2003/0002038 A1 | 1/2003 | Mawatari |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |
| 2003/0097044 A1 | 5/2003 | Rovegno |
| 2003/0120150 A1 | 6/2003 | Govari |
| 2003/0120295 A1 | 6/2003 | Simpson et al. |
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2003/0139751 A1 | 7/2003 | Evans et al. |
| 2003/0181855 A1 | 9/2003 | Simpson et al. |
| 2004/0002650 A1 | 1/2004 | Mandrusov et al. |
| 2004/0039371 A1 | 2/2004 | Tockman et al. |
| 2004/0057667 A1 | 3/2004 | Yamada et al. |
| 2004/0059257 A1 | 3/2004 | Gaber |
| 2004/0082850 A1 | 4/2004 | Bonner et al. |
| 2004/0092915 A1 | 5/2004 | Levatter |
| 2004/0093001 A1 | 5/2004 | Hamada |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0193140 A1 | 9/2004 | Griffin et al. |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0027199 A1 | 2/2005 | Clarke |
| 2005/0043614 A1 | 2/2005 | Huizenga et al. |
| 2005/0054947 A1 | 3/2005 | Goldenberg |
| 2005/0075660 A1 | 4/2005 | Chu et al. |
| 2005/0085708 A1 | 4/2005 | Fauver et al. |
| 2005/0085721 A1 | 4/2005 | Fauver et al. |
| 2005/0105097 A1 | 5/2005 | Fang-Yen et al. |
| 2005/0141843 A1 | 6/2005 | Warden et al. |
| 2005/0154407 A1 | 7/2005 | Simpson |
| 2005/0159712 A1 | 7/2005 | Andersen |
| 2005/0159731 A1 | 7/2005 | Lee |
| 2005/0171478 A1 | 8/2005 | Selmon et al. |
| 2005/0177068 A1 | 8/2005 | Simpson |
| 2005/0182295 A1 | 8/2005 | Soper et al. |
| 2005/0187571 A1 | 8/2005 | Maschke |
| 2005/0192496 A1 | 9/2005 | Maschke |
| 2005/0197623 A1 | 9/2005 | Leeflang et al. |
| 2005/0201662 A1 | 9/2005 | Petersen et al. |
| 2005/0203553 A1 | 9/2005 | Maschke |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0011820 A1 | 1/2006 | Chow-Shing et al. |
| 2006/0032508 A1 | 2/2006 | Simpson |
| 2006/0046235 A1 | 3/2006 | Alexander |
| 2006/0049587 A1 | 3/2006 | Cornwell |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235262 A1 | 10/2006 | Arnal et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2006/0264743 A1 | 11/2006 | Kleen et al. |
| 2006/0264907 A1 | 11/2006 | Eskridge et al. |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038125 A1 | 2/2007 | Kleen et al. |
| 2007/0038173 A1 | 2/2007 | Simpson |
| 2007/0050019 A1 | 3/2007 | Hyde |
| 2007/0078469 A1 | 4/2007 | Soito et al. |
| 2007/0078500 A1 | 4/2007 | Ryan et al. |
| 2007/0081166 A1 | 4/2007 | Brown et al. |
| 2007/0088230 A1 | 4/2007 | Terashi et al. |
| 2007/0106155 A1 | 5/2007 | Goodnow et al. |
| 2007/0135712 A1 | 6/2007 | Maschke |
| 2007/0167710 A1 | 7/2007 | Unal et al. |
| 2007/0196926 A1 | 8/2007 | Soito et al. |
| 2007/0213618 A1 | 9/2007 | Li et al. |
| 2007/0219484 A1 | 9/2007 | Straub |
| 2007/0250080 A1 | 10/2007 | Jones et al. |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0015618 A1 | 1/2008 | Sonnenschein et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0095421 A1 | 4/2008 | Sun et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0132929 A1 | 6/2008 | O'Sullivan et al. |
| 2008/0139897 A1 | 6/2008 | Ainsworth et al. |
| 2008/0146942 A1 | 6/2008 | Dala-Krishna |
| 2008/0147000 A1 | 6/2008 | Seibel et al. |
| 2008/0154293 A1 | 6/2008 | Taylor et al. |
| 2008/0154296 A1 | 6/2008 | Taylor et al. |
| 2008/0177138 A1 | 7/2008 | Courtney et al. |
| 2008/0186501 A1 | 8/2008 | Xie |
| 2008/0207996 A1 | 8/2008 | Tsai |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024084 A1 | 1/2009 | Khosla et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0028507 A1 | 1/2009 | Jones et al. |
| 2009/0043191 A1 | 2/2009 | Castella et al. |

(56) References Cited

U.S. PATENT DOCUMENTS

| | | |
|---|---|---|
| 2009/0073444 A1 | 3/2009 | Wang |
| 2009/0076447 A1 | 3/2009 | Casas et al. |
| 2009/0093764 A1 | 4/2009 | Pfeffer et al. |
| 2009/0099641 A1 | 4/2009 | Wu et al. |
| 2009/0125019 A1 | 5/2009 | Douglass et al. |
| 2009/0135280 A1 | 5/2009 | Johnston et al. |
| 2009/0137893 A1 | 5/2009 | Seibel et al. |
| 2009/0152664 A1 | 6/2009 | Tian et al. |
| 2009/0185135 A1 | 7/2009 | Volk |
| 2009/0196477 A1 | 8/2009 | Cense et al. |
| 2009/0196554 A1 | 8/2009 | Irisawa |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppart et al. |
| 2009/0234220 A1 | 9/2009 | Maschke |
| 2009/0235396 A1 | 9/2009 | Wang et al. |
| 2009/0244485 A1 | 10/2009 | Walsh et al. |
| 2009/0244547 A1 | 10/2009 | Ozawa |
| 2009/0264826 A1 | 10/2009 | Thompson |
| 2009/0268159 A1 | 10/2009 | Xu et al. |
| 2009/0284749 A1 | 11/2009 | Johnson et al. |
| 2009/0292199 A1 | 11/2009 | Bielewicz et al. |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0004544 A1 | 1/2010 | Toida |
| 2010/0021926 A1 | 1/2010 | Noordin |
| 2010/0049225 A1 | 2/2010 | To et al. |
| 2010/0080016 A1 | 4/2010 | Fukui et al. |
| 2010/0082000 A1 | 4/2010 | Honeck et al. |
| 2010/0125253 A1 | 5/2010 | Olson |
| 2010/0130996 A1 | 5/2010 | Doud et al. |
| 2010/0198081 A1 | 8/2010 | Hanlin et al. |
| 2010/0217245 A1 | 8/2010 | Prescott |
| 2010/0241147 A1 | 9/2010 | Maschke |
| 2010/0253949 A1 | 10/2010 | Adler et al. |
| 2010/0292539 A1 | 11/2010 | Lankenau et al. |
| 2010/0292721 A1 | 11/2010 | Moberg |
| 2010/0312263 A1 | 12/2010 | Moberg et al. |
| 2010/0317973 A1 | 12/2010 | Nita |
| 2010/0324472 A1 | 12/2010 | Wulfman |
| 2011/0023617 A1 | 2/2011 | Yu et al. |
| 2011/0028977 A1 | 2/2011 | Rauscher et al. |
| 2011/0040238 A1 | 2/2011 | Wulfman et al. |
| 2011/0058250 A1 | 3/2011 | Liu et al. |
| 2011/0060186 A1 | 3/2011 | Tilson et al. |
| 2011/0071401 A1 | 3/2011 | Hastings et al. |
| 2011/0092955 A1 | 4/2011 | Purdy et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0144673 A1 | 6/2011 | Zhang et al. |
| 2011/0201924 A1 | 8/2011 | Tearney et al. |
| 2011/0208222 A1 | 8/2011 | Ljahnicky et al. |
| 2011/0257478 A1 | 10/2011 | Kleiner et al. |
| 2011/0264125 A1 | 10/2011 | Wilson et al. |
| 2011/0270187 A1 | 11/2011 | Nelson |
| 2011/0295148 A1 | 12/2011 | Destoumieux et al. |
| 2011/0301625 A1 | 12/2011 | Mauch et al. |
| 2011/0319905 A1 | 12/2011 | Palme et al. |
| 2012/0002928 A1 | 1/2012 | Irisawa |
| 2012/0004506 A1 | 1/2012 | Tearney et al. |
| 2012/0123352 A1 | 5/2012 | Fruland et al. |
| 2012/0136350 A1 | 5/2012 | Goshgarian et al. |
| 2012/0238869 A1 | 9/2012 | Schmitt et al. |
| 2012/0259337 A1 | 10/2012 | del Rio et al. |
| 2012/0277730 A1 | 11/2012 | Salahieh et al. |
| 2012/0289971 A1 | 11/2012 | Segermark et al. |
| 2013/0023865 A1 | 1/2013 | Steinke et al. |
| 2013/0035692 A1 | 2/2013 | Sorensen et al. |
| 2013/0072787 A1 | 3/2013 | Wallace et al. |
| 2013/0184549 A1 | 7/2013 | Avital et al. |
| 2013/0211221 A1 | 8/2013 | Sunnarborg et al. |
| 2013/0223798 A1 | 8/2013 | Jenner et al. |
| 2013/0223801 A1 | 8/2013 | Bhagavatula et al. |
| 2013/0255069 A1 | 10/2013 | Higashi et al. |
| 2013/0266259 A1 | 10/2013 | Bhagavatula et al. |
| 2013/0287282 A1 | 10/2013 | Yokota et al. |
| 2013/0317519 A1 | 11/2013 | Romo et al. |
| 2013/0325003 A1 | 12/2013 | Kapur et al. |
| 2013/0331819 A1 | 12/2013 | Rosenman et al. |
| 2014/0005534 A1 | 1/2014 | He et al. |
| 2014/0046250 A1 | 2/2014 | Jain et al. |
| 2014/0128893 A1 | 5/2014 | Guggenheimer et al. |
| 2014/0187949 A1 | 7/2014 | Zhao et al. |
| 2014/0222042 A1 | 8/2014 | Kessler et al. |
| 2014/0222047 A1 | 8/2014 | Vreeman |
| 2014/0275996 A1 | 9/2014 | Stigall |
| 2014/0291985 A1 | 10/2014 | Cabrera et al. |
| 2014/0343410 A1 | 11/2014 | Graf et al. |
| 2014/0371718 A1 | 12/2014 | Alvarez et al. |
| 2015/0025310 A1 | 1/2015 | Everingham et al. |
| 2015/0036146 A1 | 2/2015 | Staloff |
| 2015/0141816 A1 | 5/2015 | Gupta et al. |
| 2015/0146211 A1 | 5/2015 | Bhagavatula et al. |
| 2015/0320975 A1 | 11/2015 | Simpson et al. |
| 2016/0144155 A1 | 5/2016 | Simpson et al. |
| 2016/0228146 A1 | 8/2016 | Escudero et al. |
| 2016/0310700 A1 | 10/2016 | Drake et al. |
| 2016/0354109 A1 | 12/2016 | Guggenheimer et al. |
| 2016/0354110 A1 | 12/2016 | Guggenheimer et al. |
| 2017/0172666 A1 | 6/2017 | Govari et al. |
| 2018/0042520 A1 | 2/2018 | Patel et al. |
| 2018/0084985 A1 | 3/2018 | Saw et al. |
| 2018/0146978 A1* | 5/2018 | Patel ................. A61B 1/00165 |
| 2018/0200488 A1 | 7/2018 | Drake et al. |
| 2018/0207417 A1 | 7/2018 | Zung et al. |
| 2018/0364024 A1 | 12/2018 | Baca et al. |
| 2019/0029714 A1 | 1/2019 | Patel et al. |
| 2019/0110809 A1 | 4/2019 | Rosenthal et al. |
| 2019/0313941 A1 | 10/2019 | Radjabi |
| 2020/0060718 A1 | 2/2020 | Patel et al. |
| 2021/0059713 A1 | 3/2021 | Patel et al. |
| 2021/0076949 A1 | 3/2021 | Smith et al. |
| 2021/0177262 A1 | 6/2021 | Spencer et al. |
| 2021/1077262 | 6/2021 | Spencer et al. |
| 2021/0267621 A1 | 9/2021 | Simpson et al. |
| 2021/0330345 A1 | 10/2021 | Newhauser et al. |
| 2021/0345903 A1 | 11/2021 | Patel et al. |
| 2022/0007941 A1 | 1/2022 | Kankaria |
| 2022/0031168 A1 | 2/2022 | Patel et al. |
| 2022/0039658 A1 | 2/2022 | Smith et al. |
| 2022/0039828 A1 | 2/2022 | Patel et al. |
| 2022/0071656 A1 | 3/2022 | Patel et al. |
| 2022/0079617 A1 | 3/2022 | Gupta et al. |
| 2022/0095926 A1 | 3/2022 | Simpson et al. |
| 2022/0125525 A1 | 4/2022 | Spencer et al. |
| 2022/0168011 A1 | 6/2022 | Patel et al. |
| 2022/0273336 A1 | 9/2022 | Fernandez et al. |
| 2022/0273337 A1 | 9/2022 | Patel et al. |

FOREIGN PATENT DOCUMENTS

| | | |
|---|---|---|
| CN | 101601581 A | 12/2009 |
| CN | 103027727 A | 4/2013 |
| CN | 104968285 A | 10/2015 |
| DE | 202006018883.5 U | 2/2007 |
| EP | 0347098 A2 | 12/1989 |
| EP | 0808638 A1 | 11/1997 |
| EP | 0845692 B1 | 11/2005 |
| EP | 1859732 A1 | 11/2007 |
| EP | 2090245 A1 | 8/2009 |
| EP | 2353526 B1 | 9/2013 |
| EP | 2942028 A1 | 11/2015 |
| JP | S62-275425 A | 11/1987 |
| JP | 03502060 A | 2/1990 |
| JP | 05103763 A | 4/1993 |
| JP | 06027343 A | 2/1994 |
| JP | H07184888 A | 7/1995 |
| JP | 07308393 A | 11/1995 |
| JP | 2002214127 A | 7/2002 |
| JP | 2004509695 A | 4/2004 |

(56) References Cited

FOREIGN PATENT DOCUMENTS

| | | |
|---|---|---|
| JP | 2004516073 A | 6/2004 |
| JP | 2005114473 A | 4/2005 |
| JP | 2005230550 A | 9/2005 |
| JP | 2005249704 A | 9/2005 |
| JP | 2005533533 A | 11/2005 |
| JP | 2008175698 A | 7/2006 |
| JP | 2006288775 A | 10/2006 |
| JP | 2006313158 A | 11/2006 |
| JP | 2006526790 A | 11/2006 |
| JP | 2006326157 A | 12/2006 |
| JP | 200783053 A | 4/2007 |
| JP | 200783057 A | 4/2007 |
| JP | 2007225349 A | 9/2007 |
| JP | 2007533361 A | 11/2007 |
| JP | 2008023627 | 2/2008 |
| JP | 2008128708 A | 6/2008 |
| JP | 2008145376 A | 6/2008 |
| JP | 2008183208 A | 8/2008 |
| JP | 2008253492 A | 10/2008 |
| JP | 200914751 A | 1/2009 |
| JP | 2009509690 A | 3/2009 |
| JP | 200978150 A | 4/2009 |
| JP | 2009066252 A | 4/2009 |
| JP | 2009201969 A | 9/2009 |
| JP | 2010042182 A | 2/2010 |
| JP | 2010518900 A | 6/2010 |
| JP | 2011521747 A | 7/2011 |
| JP | 2012143558 A | 8/2012 |
| JP | 2012229976 A | 11/2012 |
| JP | 2012533353 A | 12/2012 |
| JP | 2013512736 A | 4/2013 |
| JP | 2013/524930 A | 6/2013 |
| JP | 2015533584 A | 11/2015 |
| JP | 2016508758 A | 3/2016 |
| KR | 2007/0047221 A | 5/2007 |
| RU | 2185859 C2 | 7/2002 |
| RU | 2218191 C2 | 12/2003 |
| WO | WO91/17698 A1 | 11/1991 |
| WO | WO99/23958 A1 | 5/1999 |
| WO | WO00/54659 A1 | 9/2000 |
| WO | WO01/15609 A1 | 3/2001 |
| WO | WO01/76680 A1 | 10/2001 |
| WO | WO2006/133030 A2 | 12/2006 |
| WO | WO2008/005888 A2 | 1/2008 |
| WO | WO2008/029506 A1 | 3/2008 |
| WO | WO2008/042987 A2 | 4/2008 |
| WO | WO2008/051951 A1 | 5/2008 |
| WO | WO2008/065600 A2 | 6/2008 |
| WO | WO2008/086613 A1 | 7/2008 |
| WO | WO2008/087613 A2 | 7/2008 |
| WO | WO2009/005779 A1 | 1/2009 |
| WO | WO2009/006335 A1 | 1/2009 |
| WO | WO2009/009799 A1 | 1/2009 |
| WO | WO2009/009802 A1 | 1/2009 |
| WO | WO2009/023635 A1 | 2/2009 |
| WO | WO2009/024344 A1 | 2/2009 |
| WO | WO2009/094341 A2 | 7/2009 |
| WO | WO2009/140617 A2 | 11/2009 |
| WO | WO2009/148317 A1 | 12/2009 |
| WO | WO2010/039464 A1 | 4/2010 |
| WO | WO2010/056771 A1 | 5/2010 |
| WO | WO2011/044387 A2 | 4/2011 |
| WO | WO2011/062087 A1 | 5/2011 |
| WO | WO2012/057940 A1 | 5/2012 |
| WO | WO2012/061935 A1 | 5/2012 |
| WO | WO2012/123737 A1 | 9/2012 |
| WO | WO2012/166332 A1 | 12/2012 |
| WO | WO2013/033490 A1 | 3/2013 |
| WO | WO2013/056262 A1 | 4/2013 |
| WO | WO2014/077870 A1 | 5/2014 |
| WO | WO2014/093148 A2 | 6/2014 |
| WO | WO2015/074018 A1 | 5/2015 |
| WO | WO2015/101747 A1 | 7/2015 |
| WO | WO2015/120146 A1 | 8/2015 |
| WO | WO2015/165736 A1 | 11/2015 |
| WO | WO2016/007652 A1 | 1/2016 |
| WO | WO2017/007853 A1 | 1/2017 |
| WO | WO2017132247 A1 | 8/2017 |
| WO | WO2017/161166 A1 | 9/2017 |
| WO | WO2018/094041 A1 | 5/2018 |
| WO | WO2019/204797 A1 | 10/2019 |

OTHER PUBLICATIONS

Bayer Material Science: ; Snap-Fit Joints for Plastics; 26 pages; retrieved from the Internet: ( https://web.archive.org/web/20121119232733if_/http://fab.cba.mit.edu:80/classes/S62.12/people/vemelle.noel/Plastic_Snap_fit_design.pdf) on Sep. 26, 2018.

Choma et al.; Sensitivity advantage of swept source and fourier domain optical coherence tomography; Optics Express; 11(18); pp. 2183-2189; Sep. 8, 2003.

De Boer et al.; Improved signai-to-noise ratio in spectral-domain compared with time-domain optical coherence tomography; Optics Letters: 28(21); pp. 2067-2069; Nov. 2003.

Emkey et al.; Analysis and evaluation of graded-index fiber-lenses; Journal of Lightwave Technology; vol. LT-5; No. 9; pp. 1156-1164; Sep. 1987.

Gonzalo et al.; Optical coherence tomography patterns of stent restenosis; Am. Heart J.; 158(2); pp. 284-293; Aug. 2009.

Han et al.; In situ Frog Retina Imaging Using Common-Path OCT with a Gold-Coated Bare Fiber Probe; CFM6; San Jose, California; CLEO, May 4, 2008; 2 pages.

Leitgeb et al.; Performance of fourier domain vs time domain optical coherence tomography; Optics Express; 11(8); pp. 889-894; Apr. 21, 2003.

Linares et al.; Arbitrary single-mode coupling by tapered and nontapered grin fiber lenses; Applied Optics; vol. 29; No. 28; pp. 4003-4007; Oct. 1, 1990.

Merriam Webster; Proximal (Definition); 10 pages; retrieved from the internet (https://www.merriam-webster.com/dictionary/proximal) on Jun. 9, 2021.

Muller et al.; Time-gated infrared fourier-domain optical coherence tomography; CFM5; San Jose, California; CLEO May 4, 2008; 2 pages.

Rollins et al.; Optimal interferometer designs for optical coherence tomography; Optics Letters; 24(21); pp. 1484-1486; Nov. 1999.

Schmitt et al.; A new rotational thrombectomy catheter: System design and first clinical experiences; Cardiovascular and Interventional Radiology; Springer-Verlag; 22(6); pp. 504-509; Nov. 1, 1999.

Sharma et al.; Common-path optical coherence tomography with side-viewing bare fiber probe for endoscopic optical coherence tomography; Rev. Sci. Instrum.; vol. 78; 113102: 5 pages; Nov. 6, 2007.

Sharma et al.; Optical coherence tomography based on an all-fiber autocorrelator using probe-end reflection as reference; CWJ13; San Francisco, California; CLEO May 16, 2004; 4 pages.

Shinkle et al.; Evaluation of stent placement and outcomes with optical coherence tomography; Interv. Cardiol.; 2(4); pp. 535-543; (manuscript version, 12 pages); Aug. 2010.

Stamper et al.; Plaque characterization with optical coherence tomography. Journal of the American College of Cardiology. 47(8); pp. 69-79; Apr. 18, 2006.

Suparno et al.; Light scattering with single-mode fiber collimators; Applied Optics; vol. 33; No. 30; pp. 7200-7205; Oct. 20, 1994.

Tanaka et al.; Challenges on the frontier of intracoronary imaging: atherosclerotic plaque macrophage measurement by optical coherence tomography; Journal of Biomedical Optics; 15(1); pp. (011104-1)-(011104-8); Jan.-Feb. 2010.

Wang et al.; Common-path endoscopic Fourier domain OCT with a reference Michelson interferometer; Proceedings of the SPIE; vol. 7566; pp. 75660L-75660L-7; Jan. 2010.

Wikipedia; Hinge; 4 pages; retrieved from the internet (https://en.wikipedia.org/w/index.php?title=Hinge&oldid=479569345) on Jun. 9, 2021.

Tachibana et al.; U.S. Appl. No. 17/645,722 entitled "Atherectomy catheter drive assemblies," filed Dec. 22, 2021.

(56) References Cited

OTHER PUBLICATIONS

Black et al.; U.S. Appl. No. 17/652,073 entitled "Optical coherence tomography for biological imaging," filed Feb. 22, 2022.
Patel et al.; U.S. Appl. No. 17/762,815 entitled "Atherectomy catheter with shapeable distal tip," filed Mar. 23, 2022.
Patel et al.; U.S. Appl. # 17/816,673 entitled "Atherectomy catheter with serrated cutter," filed Aug. 1, 2022.

* cited by examiner

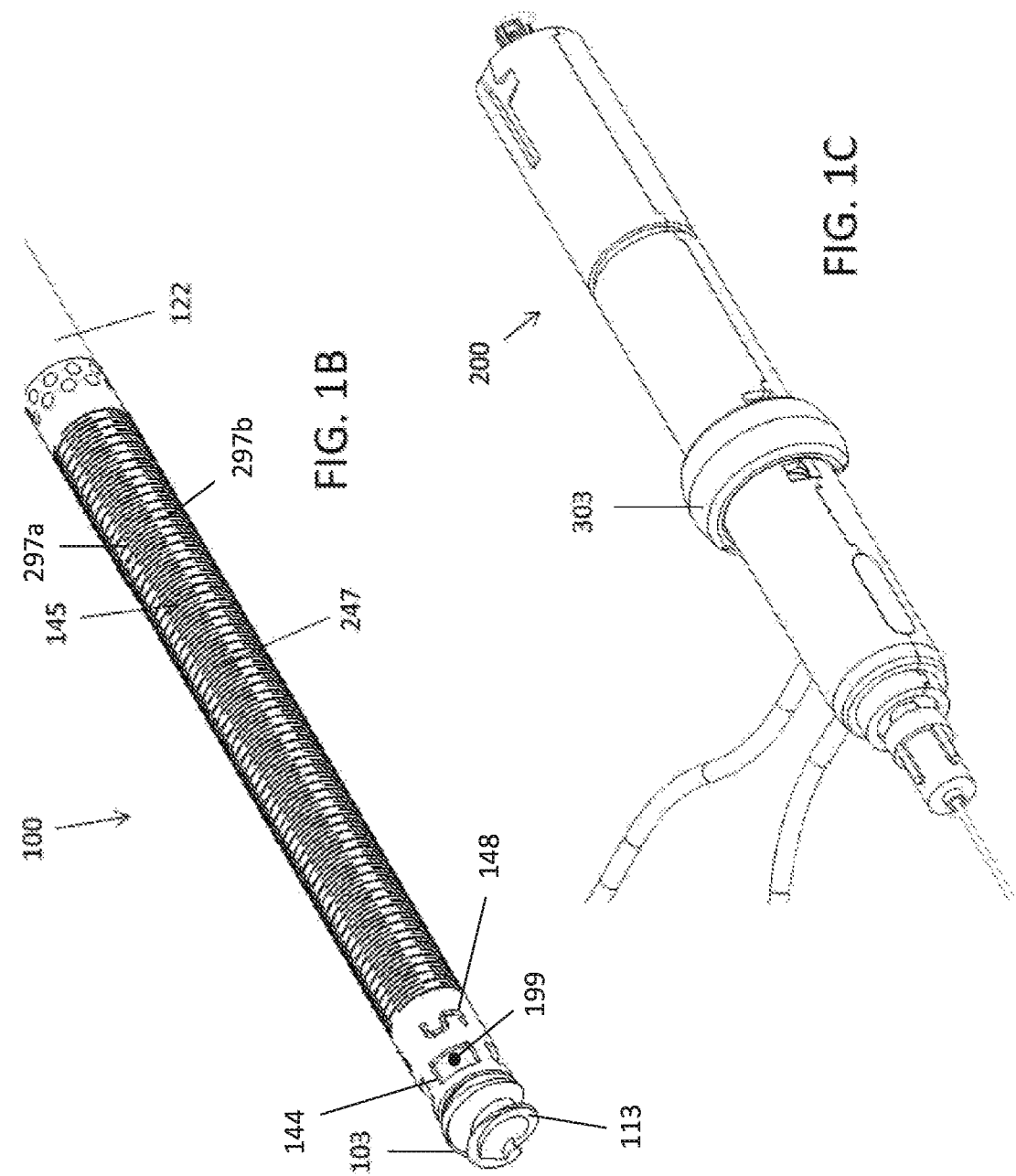

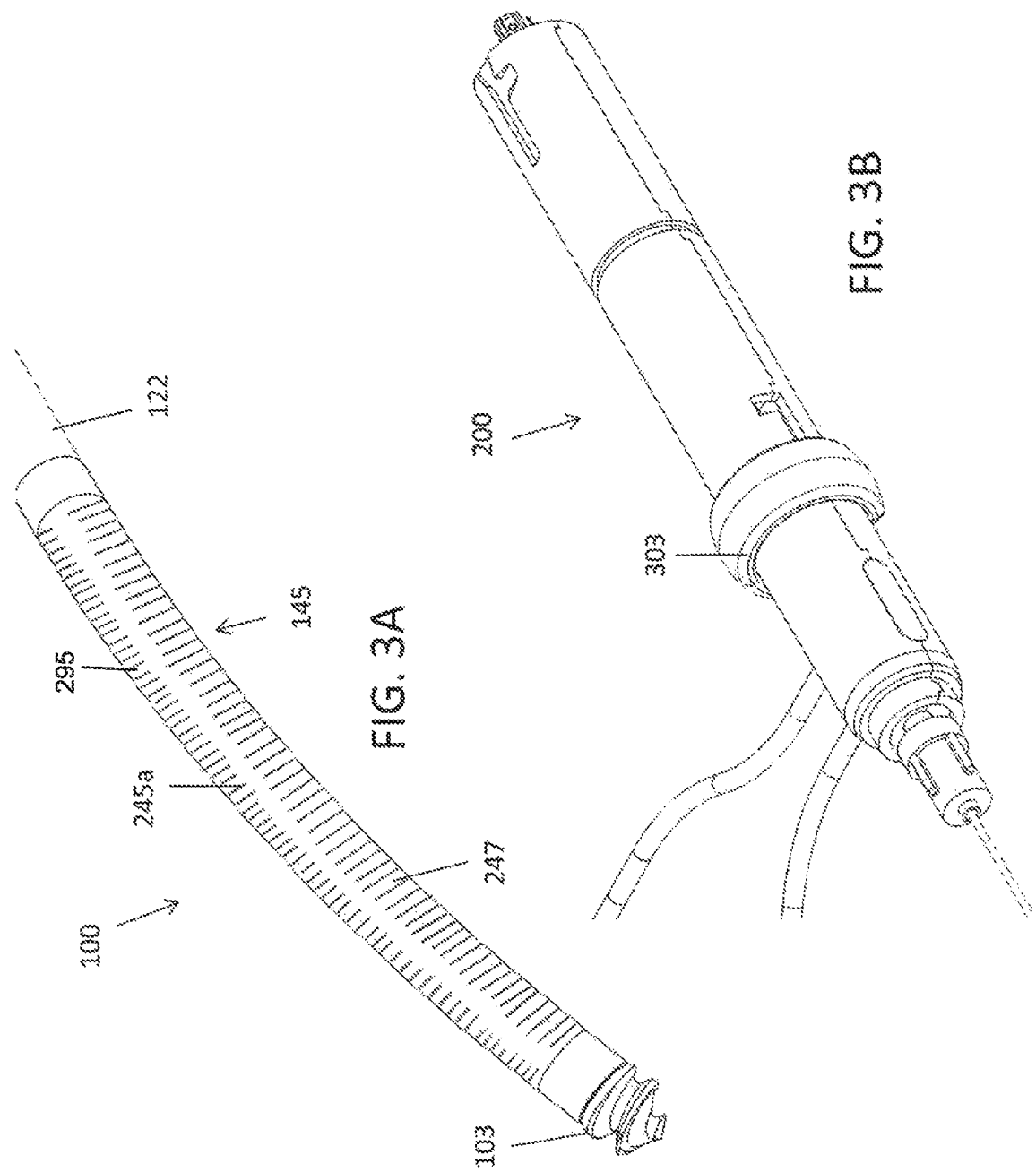

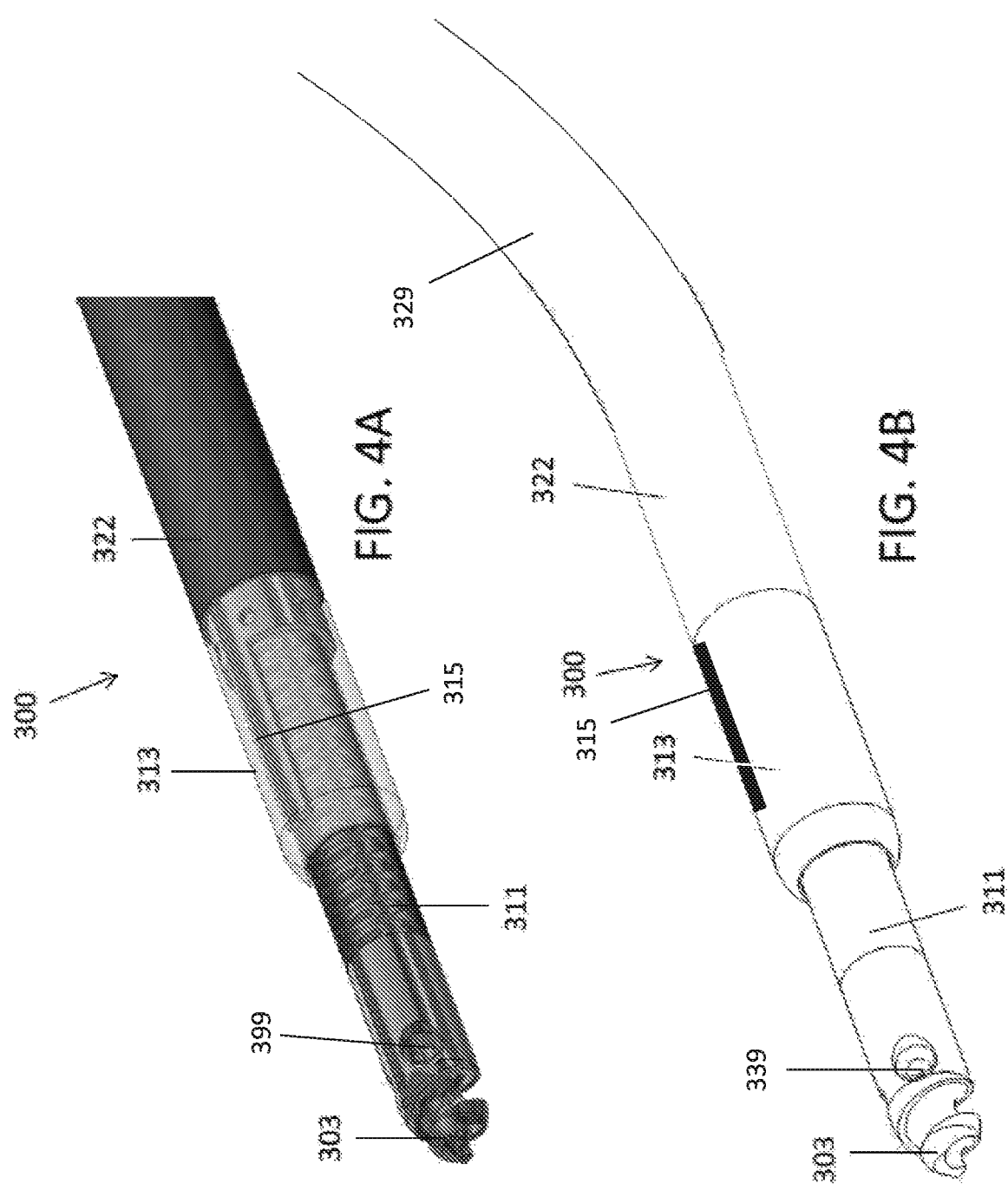

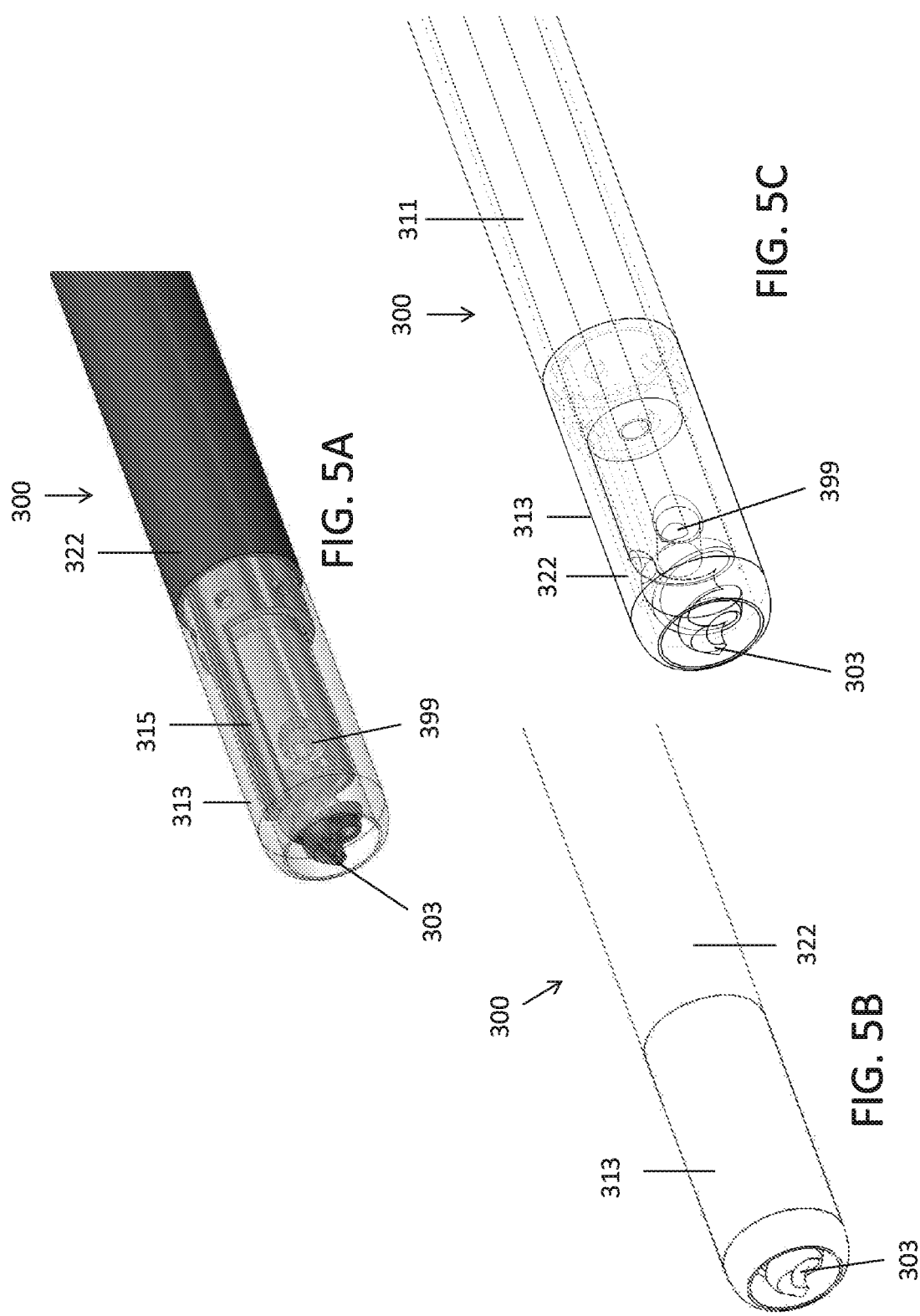

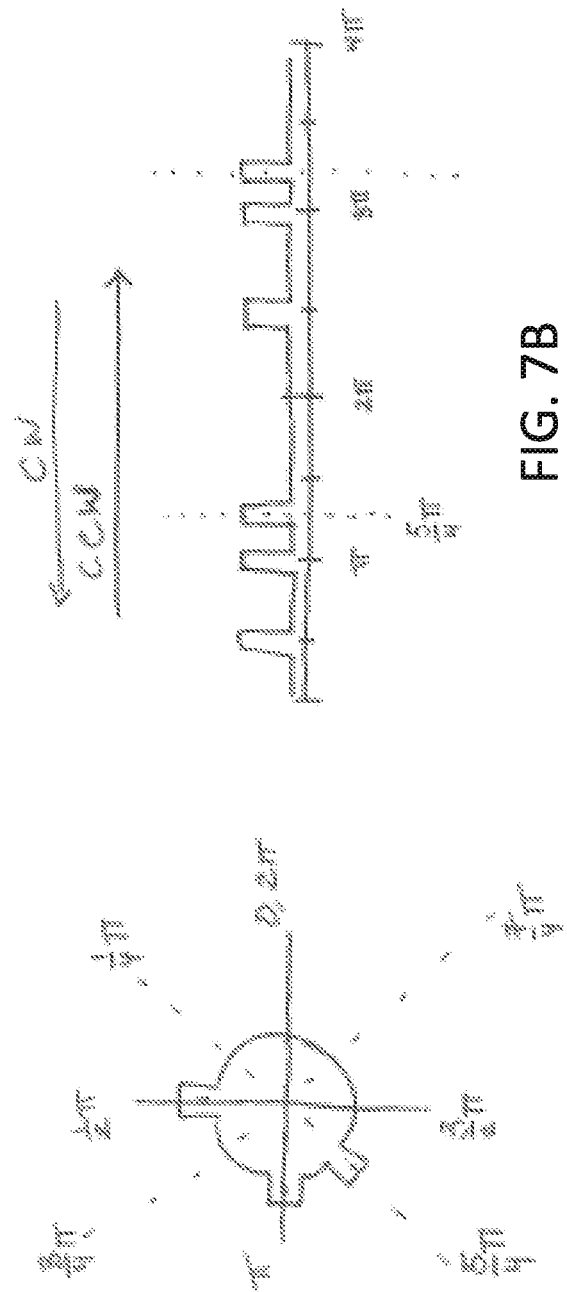

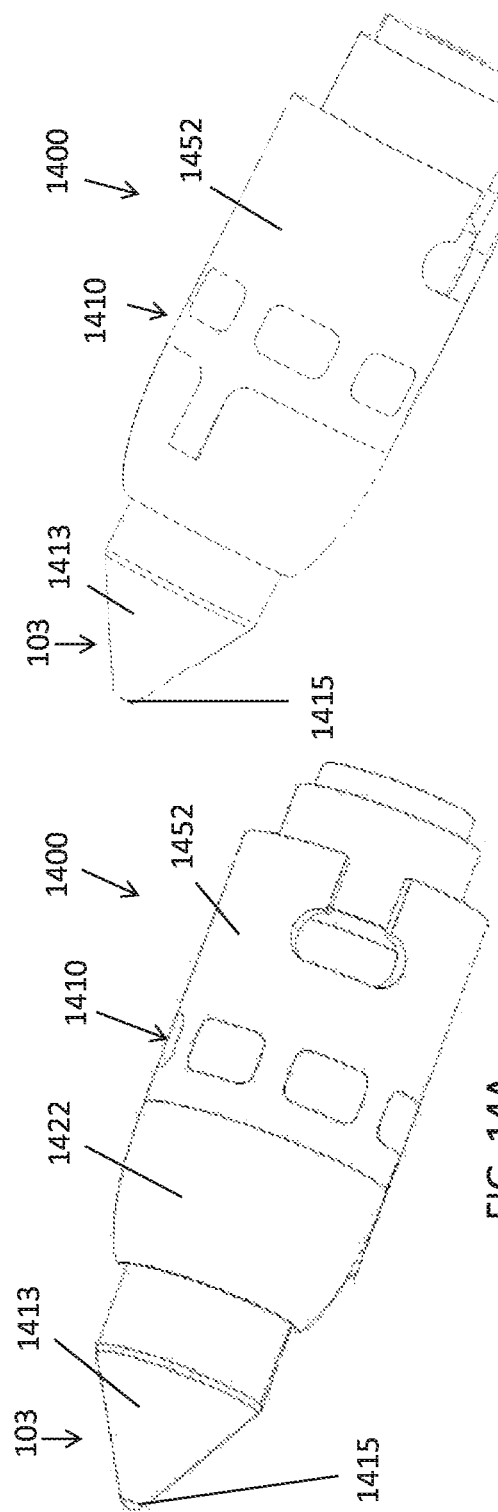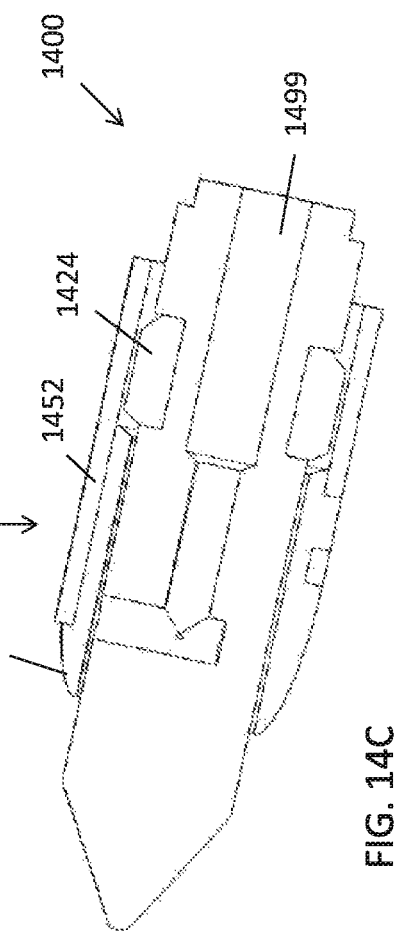
FIG. 14A
FIG. 14B
FIG. 14C

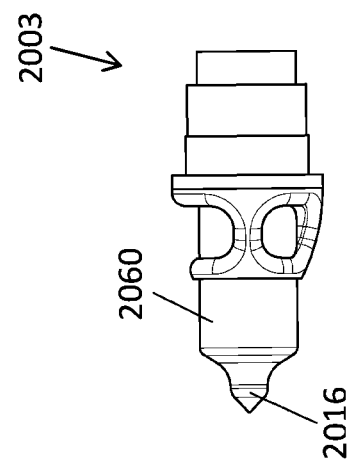
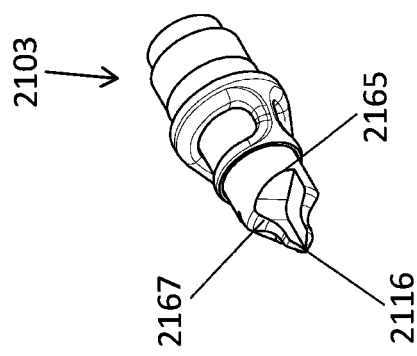
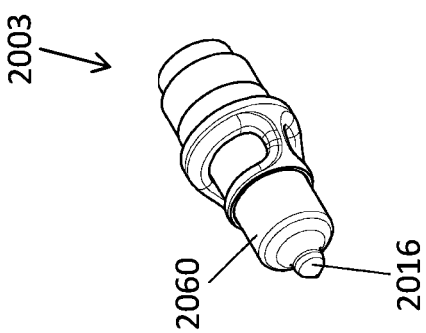
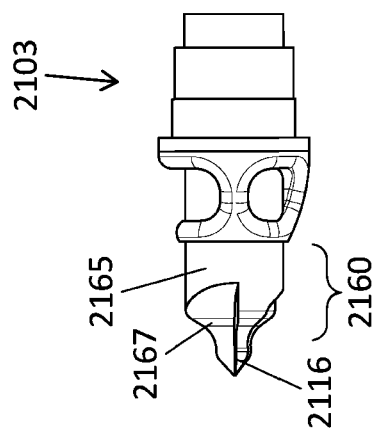

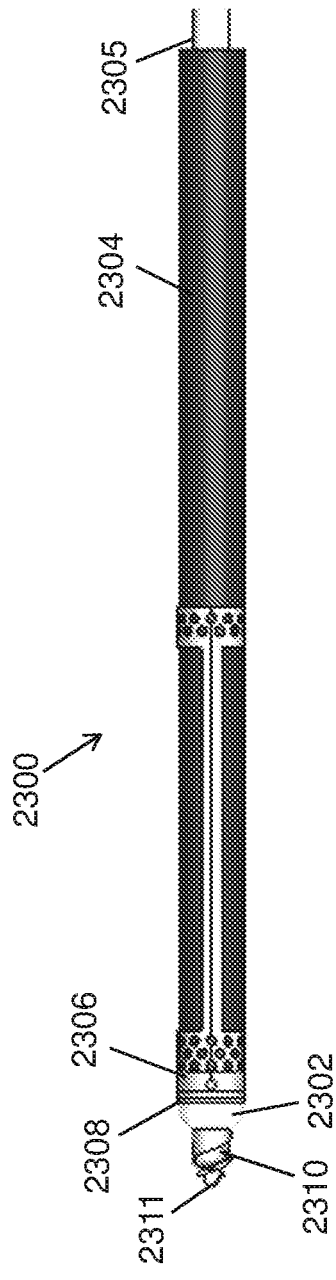
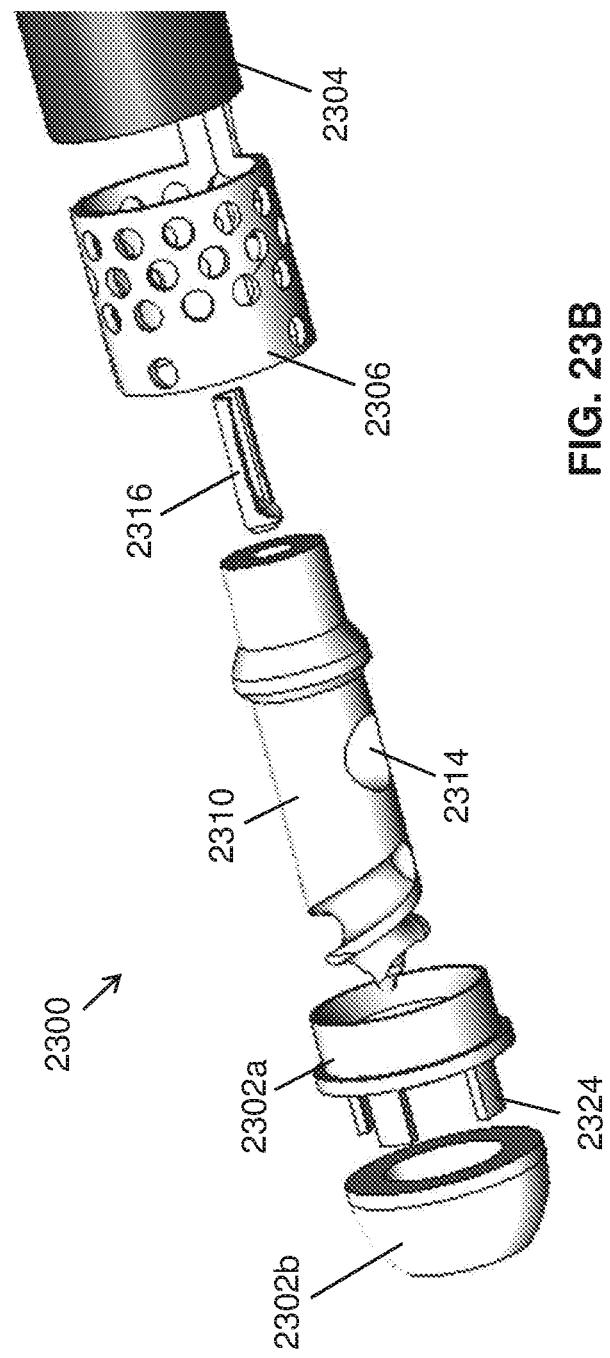
FIG. 23A
FIG. 23B

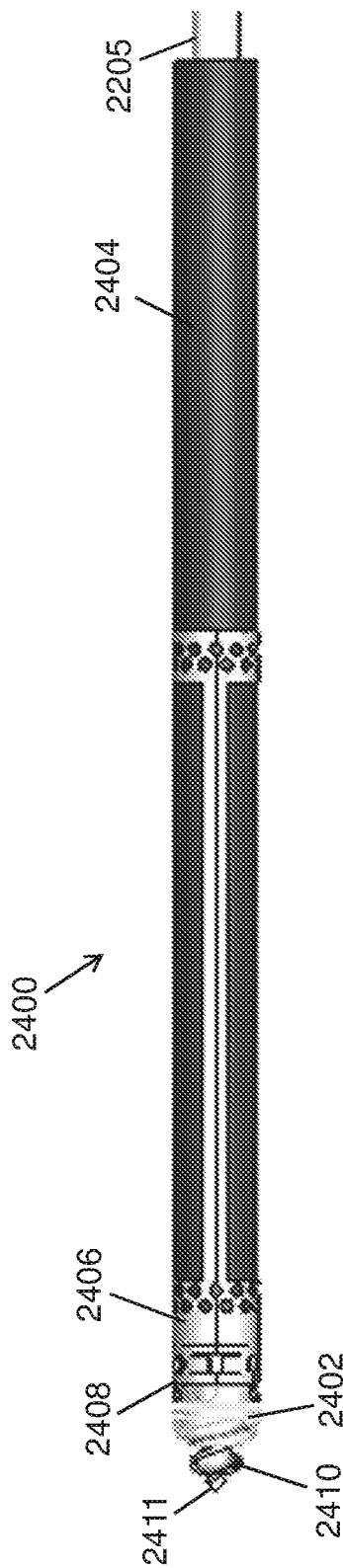
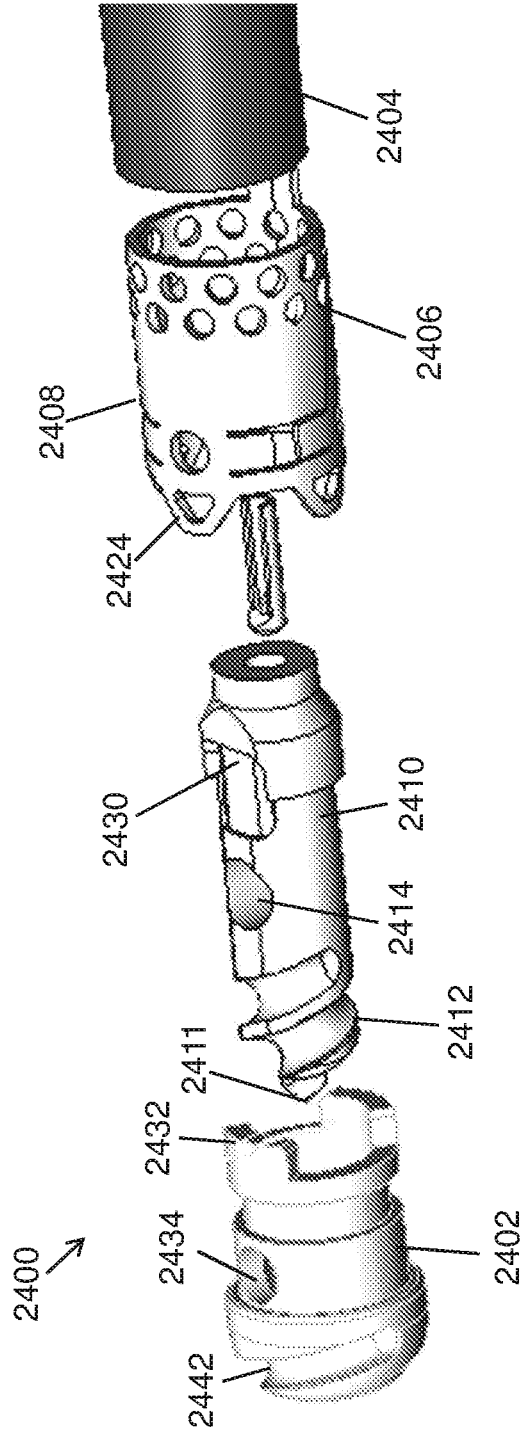
FIG. 24A
FIG. 24B

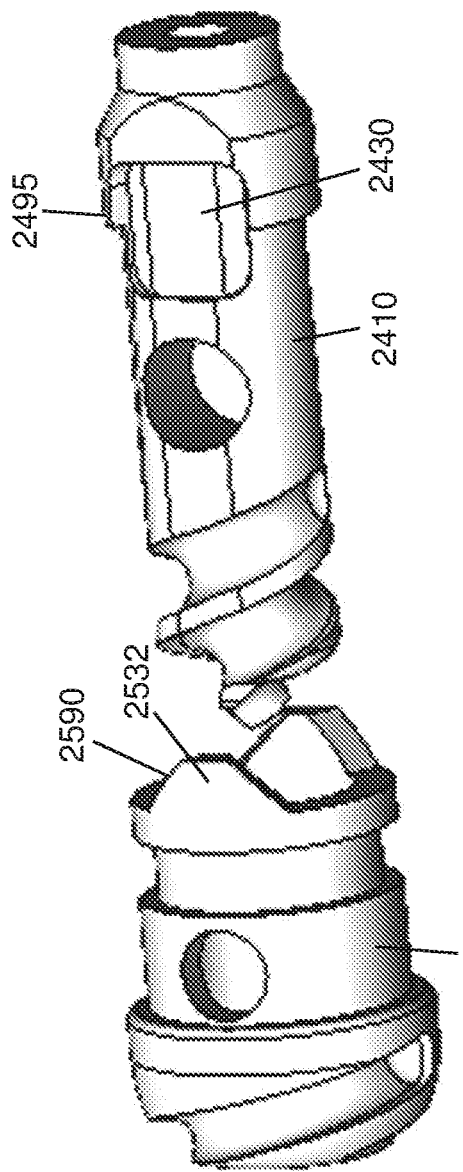
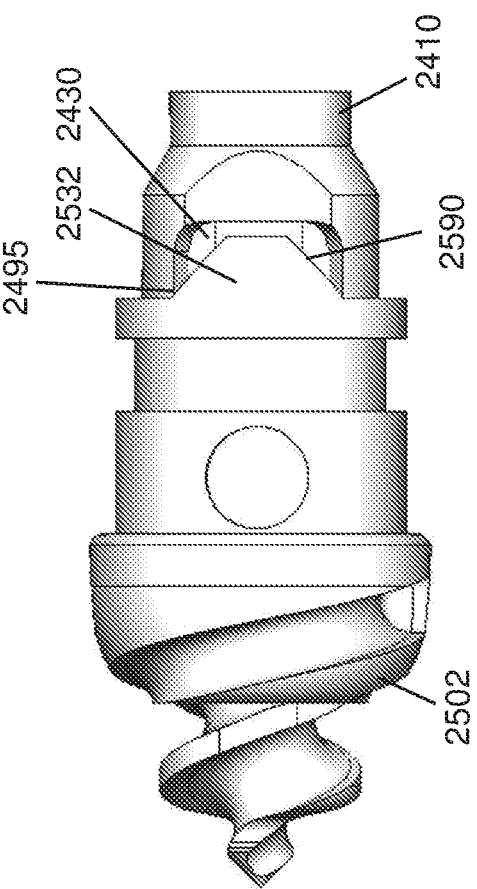
FIG. 25A
FIG. 25B

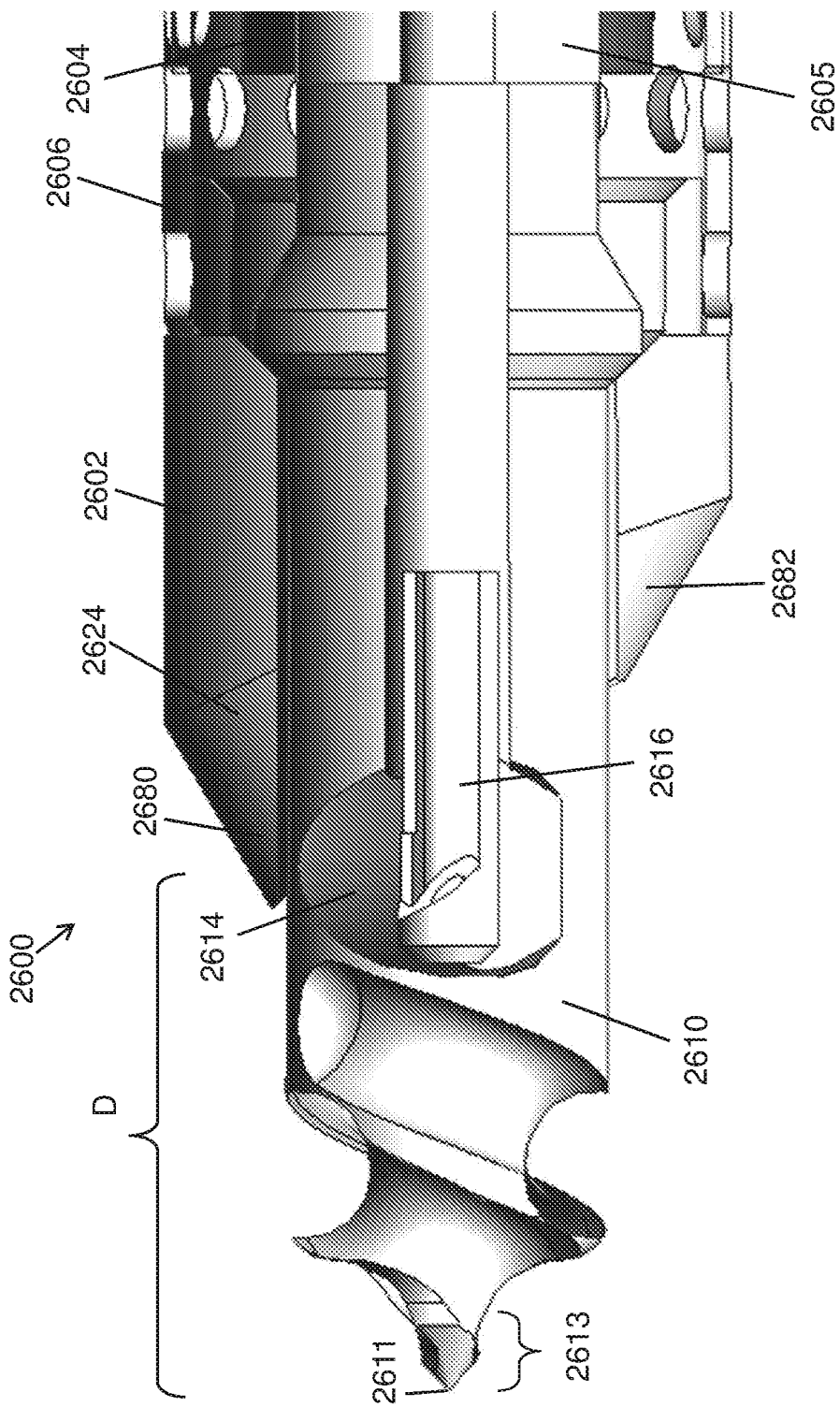

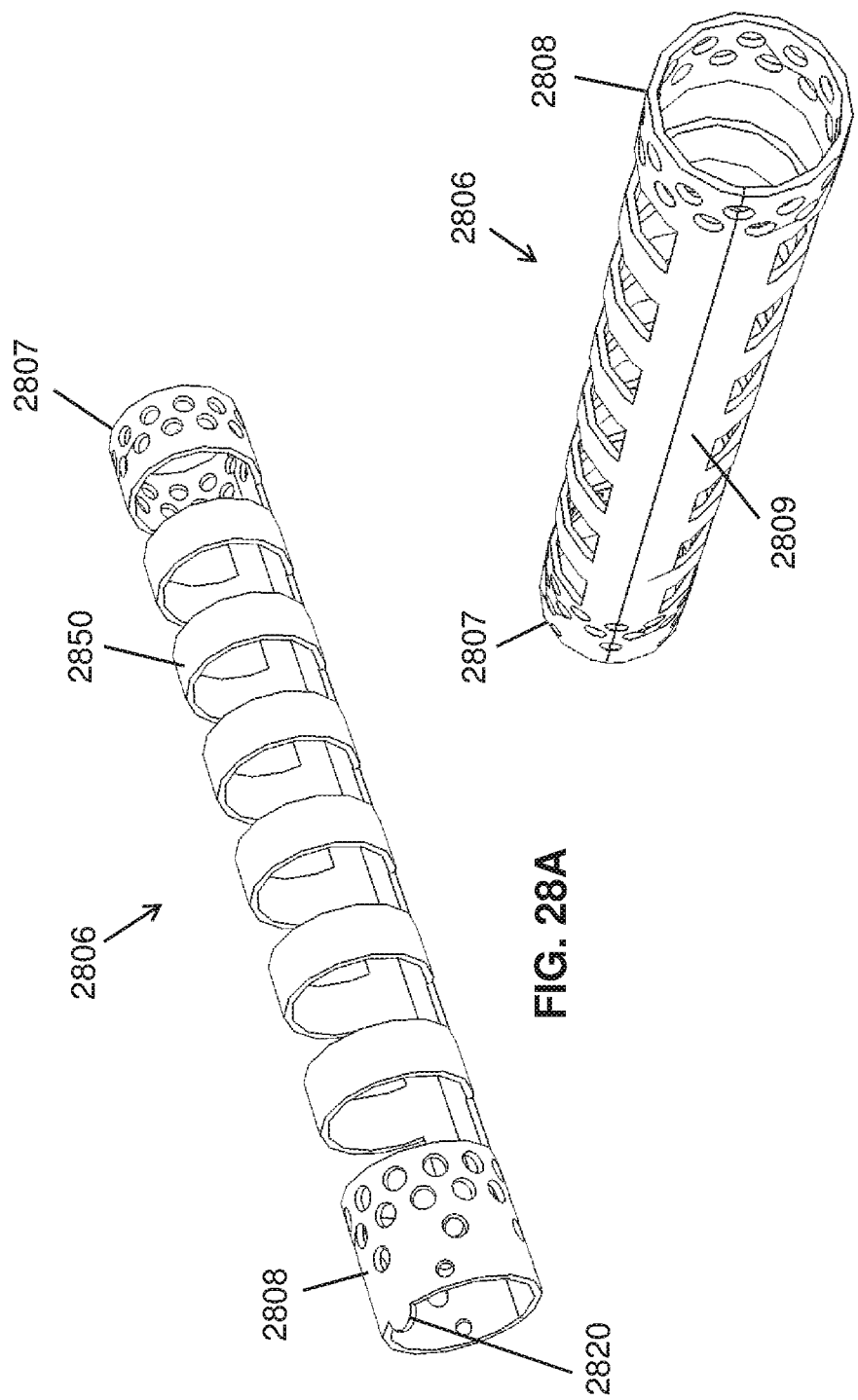

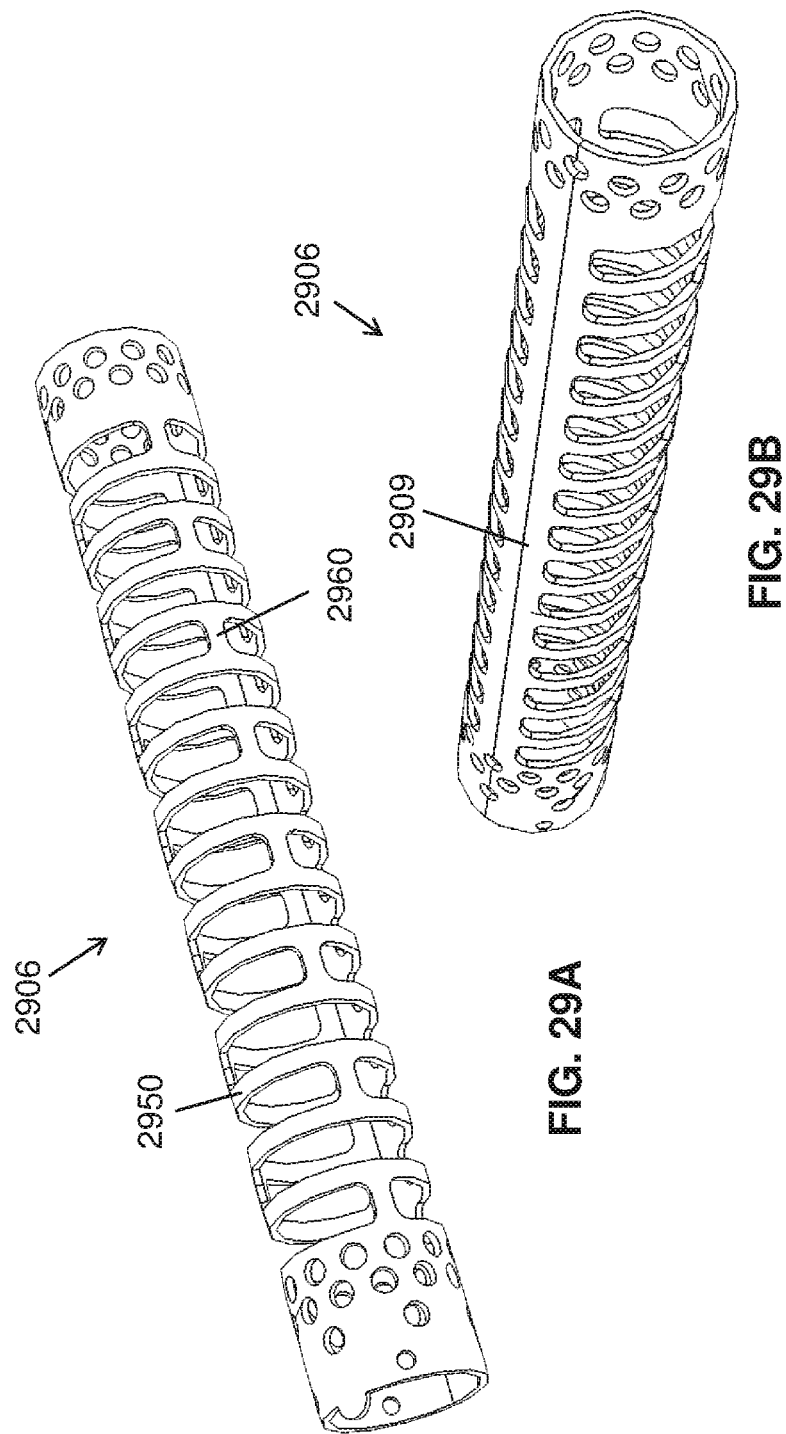

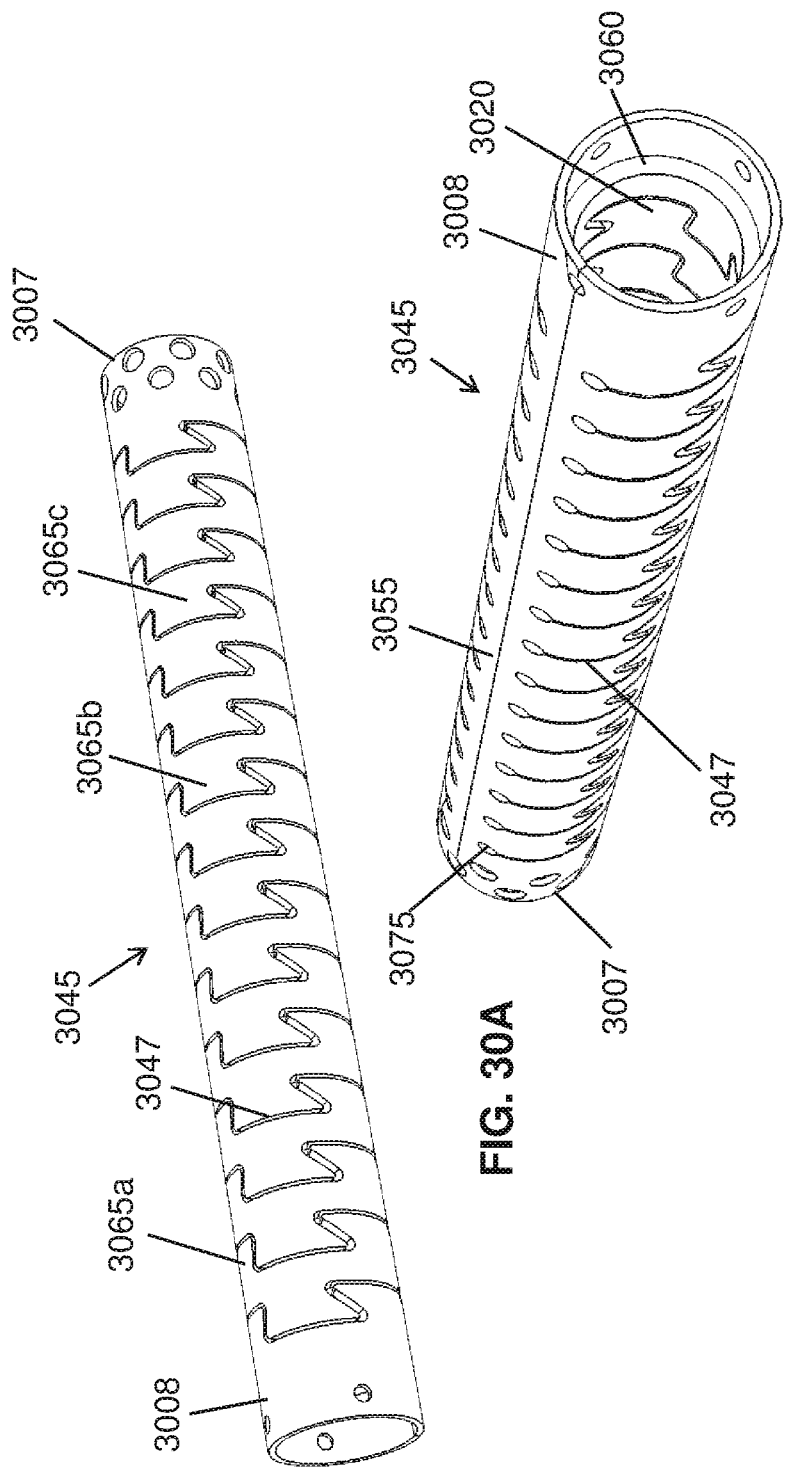

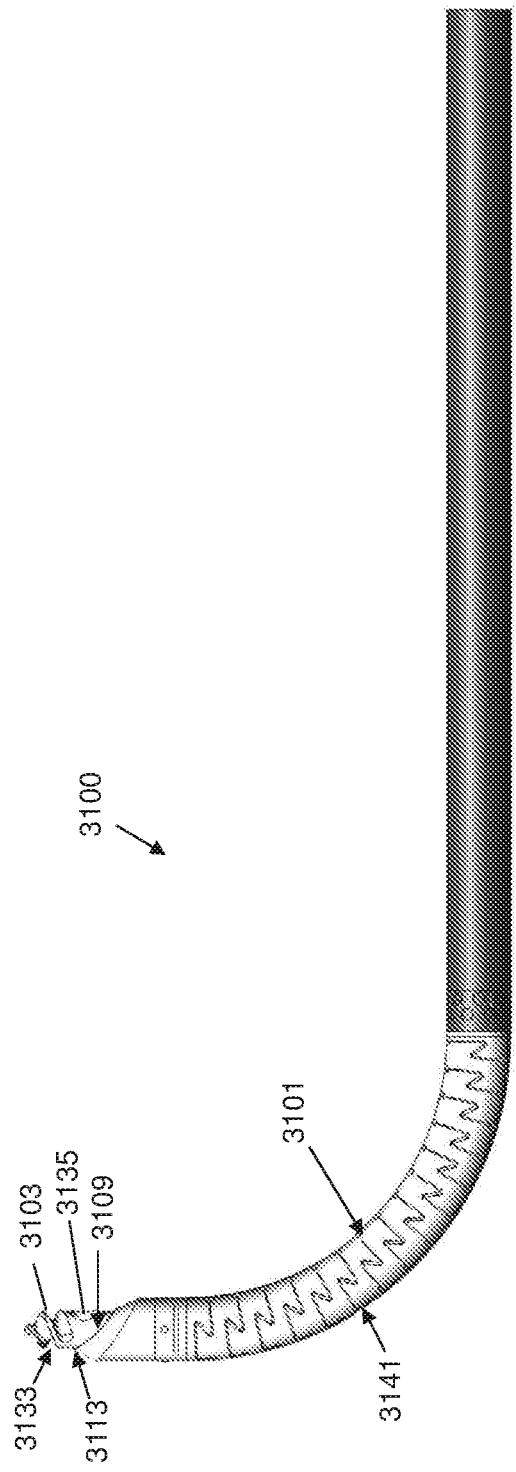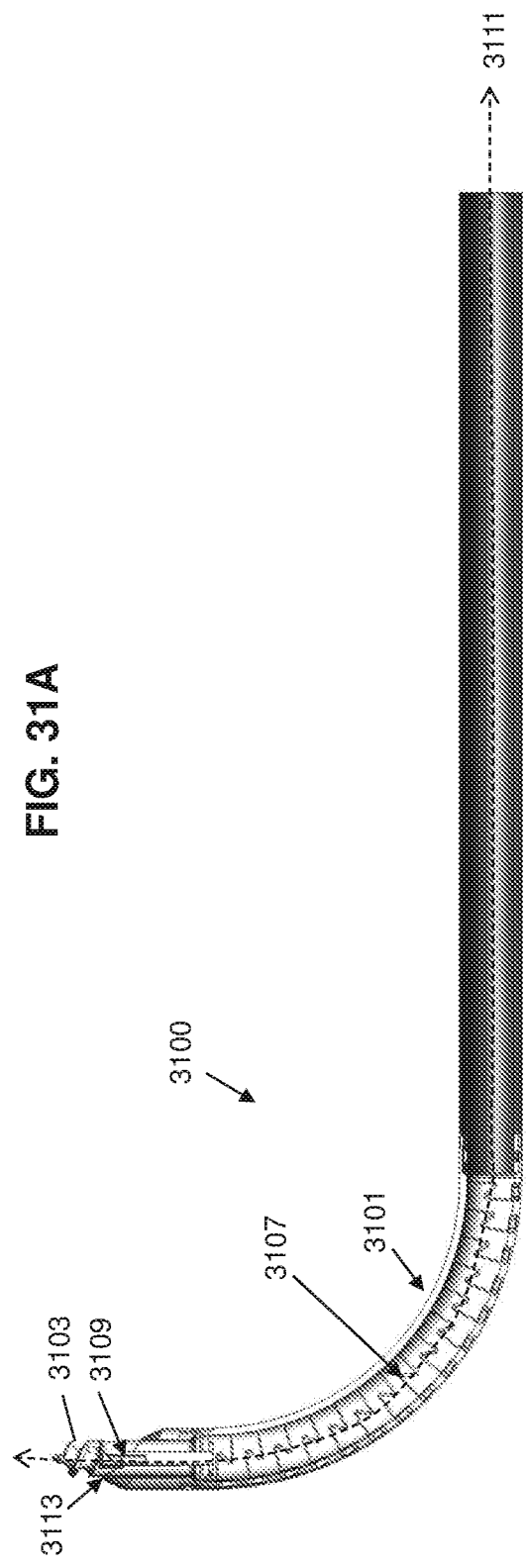

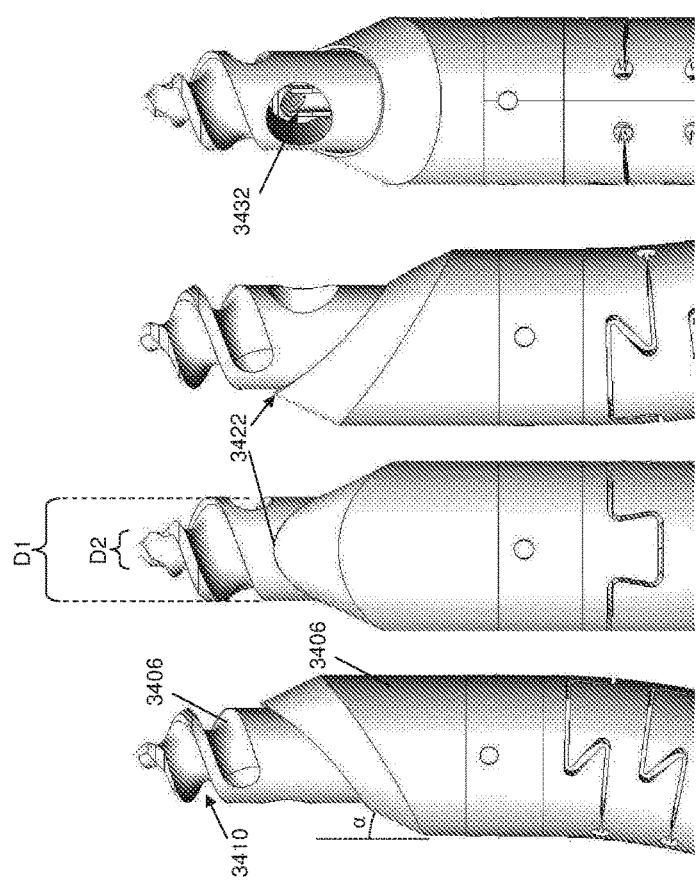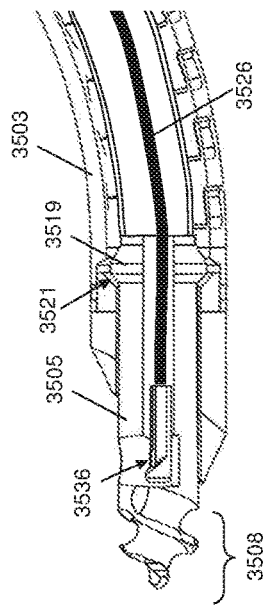

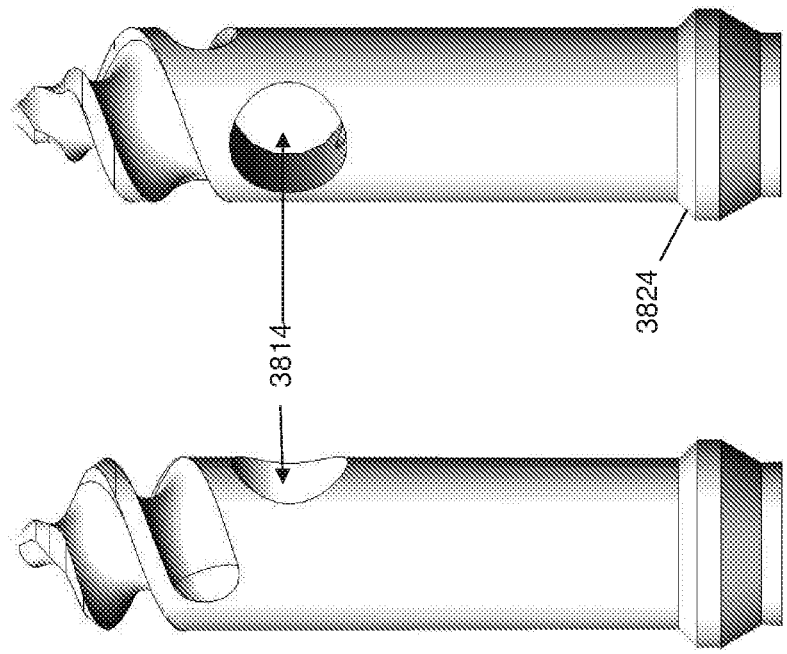
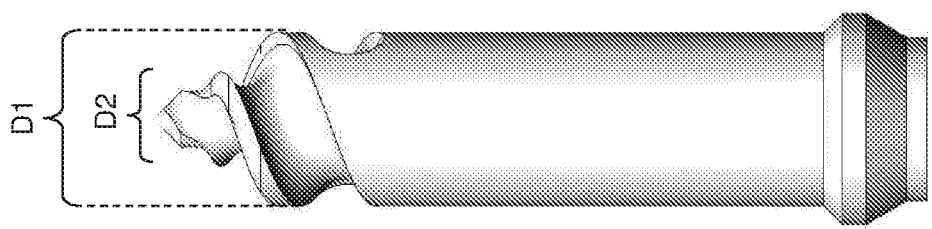
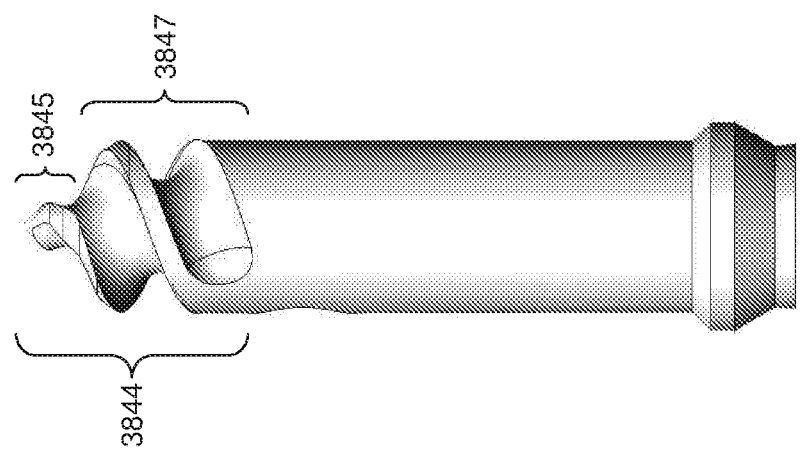
FIG. 38A  FIG. 38B  FIG. 38C  FIG. 38D

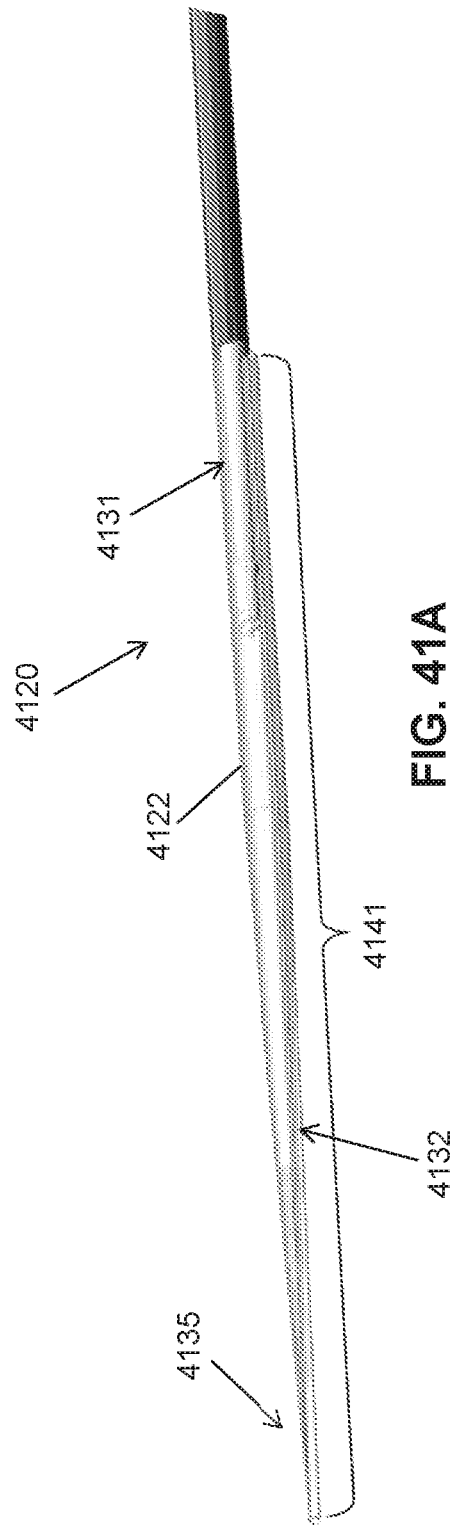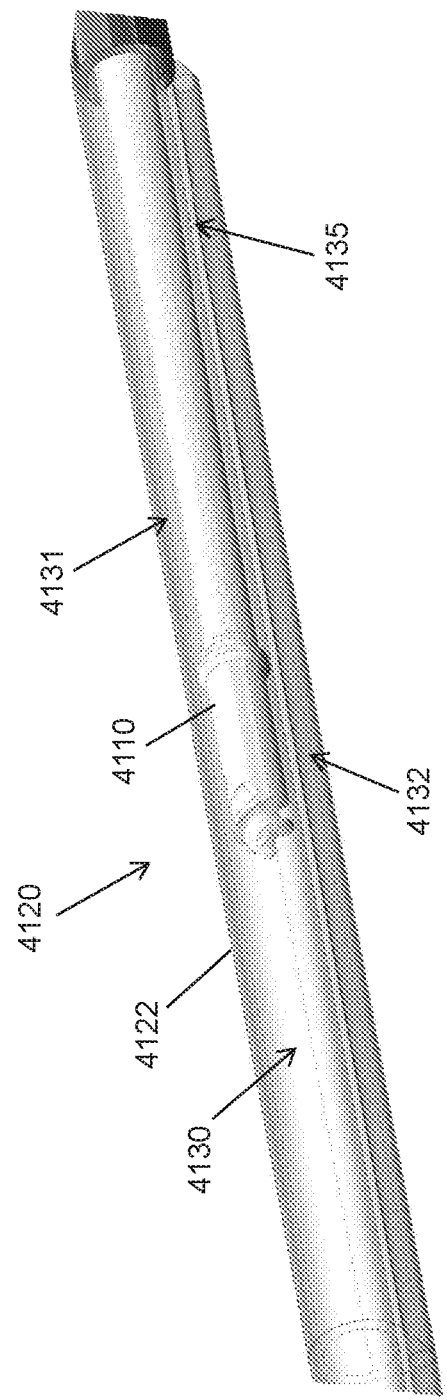
FIG. 41A
FIG. 41B

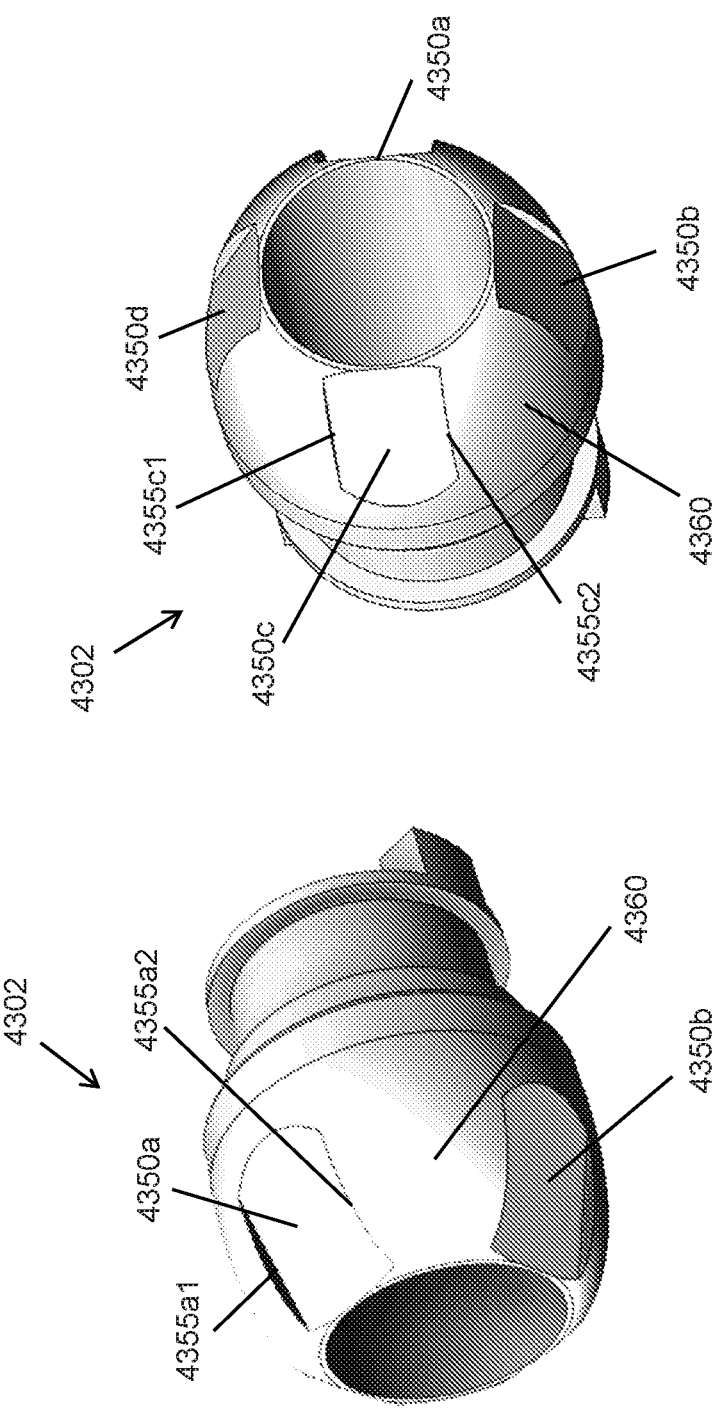

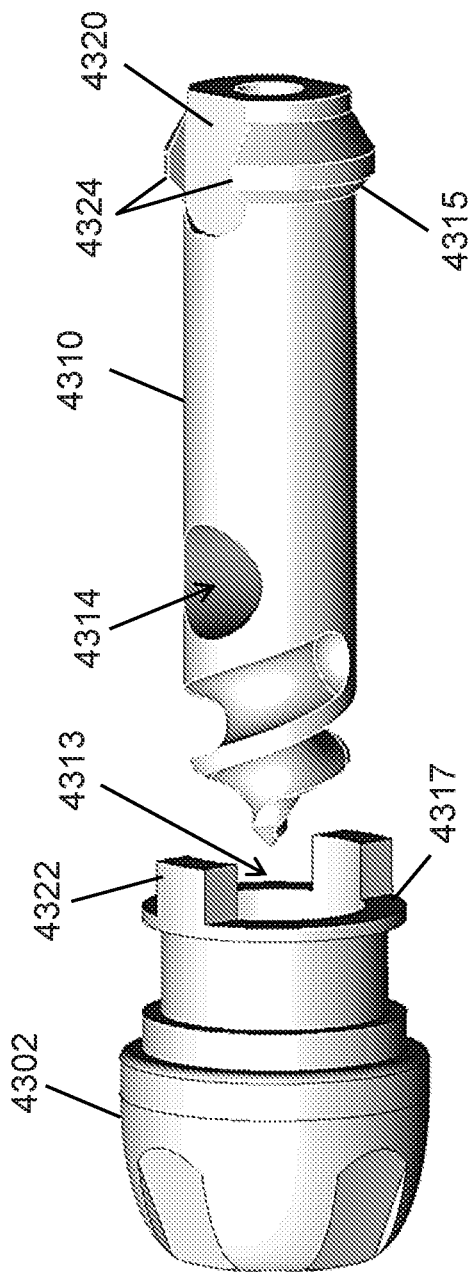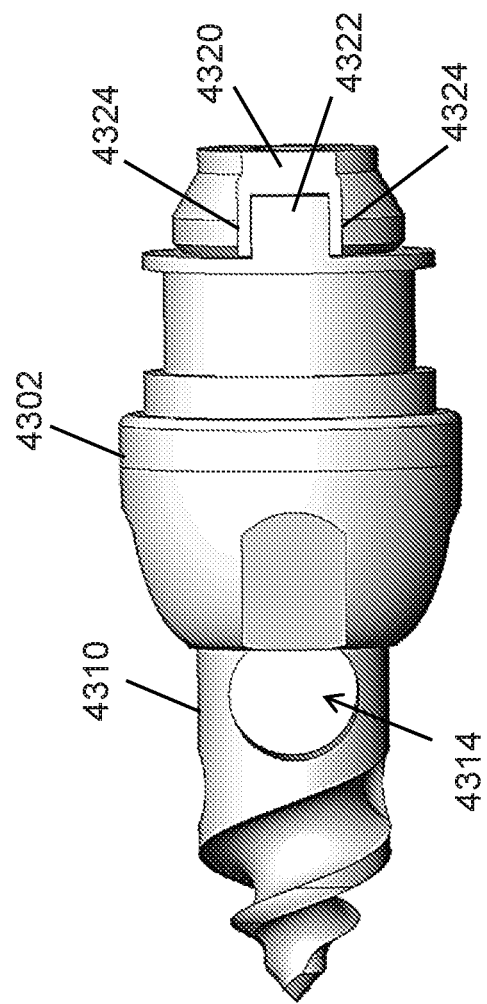
FIG. 43E
FIG. 43F

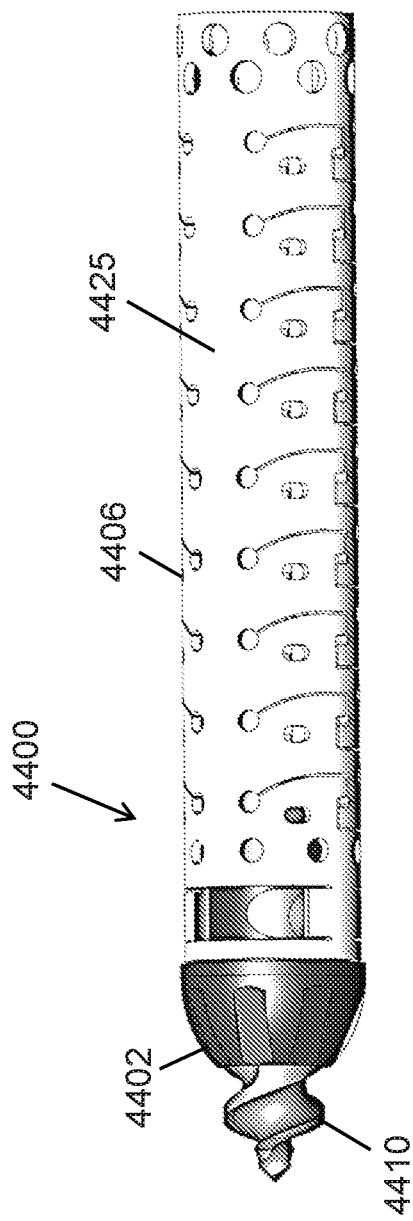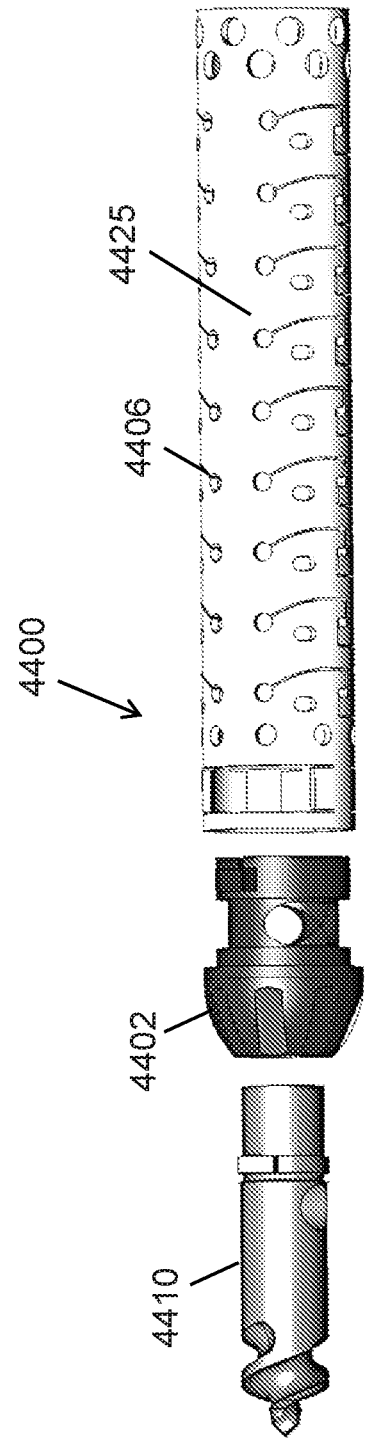
FIG. 44A
FIG. 44B

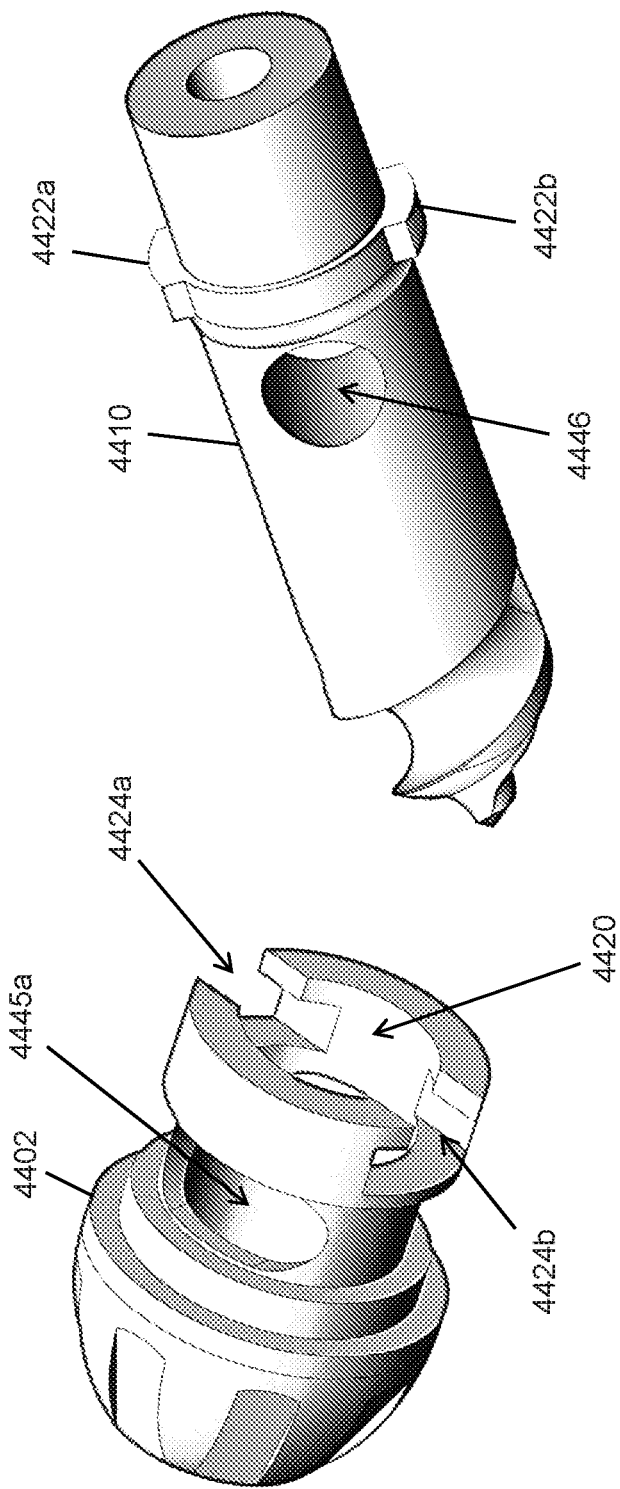

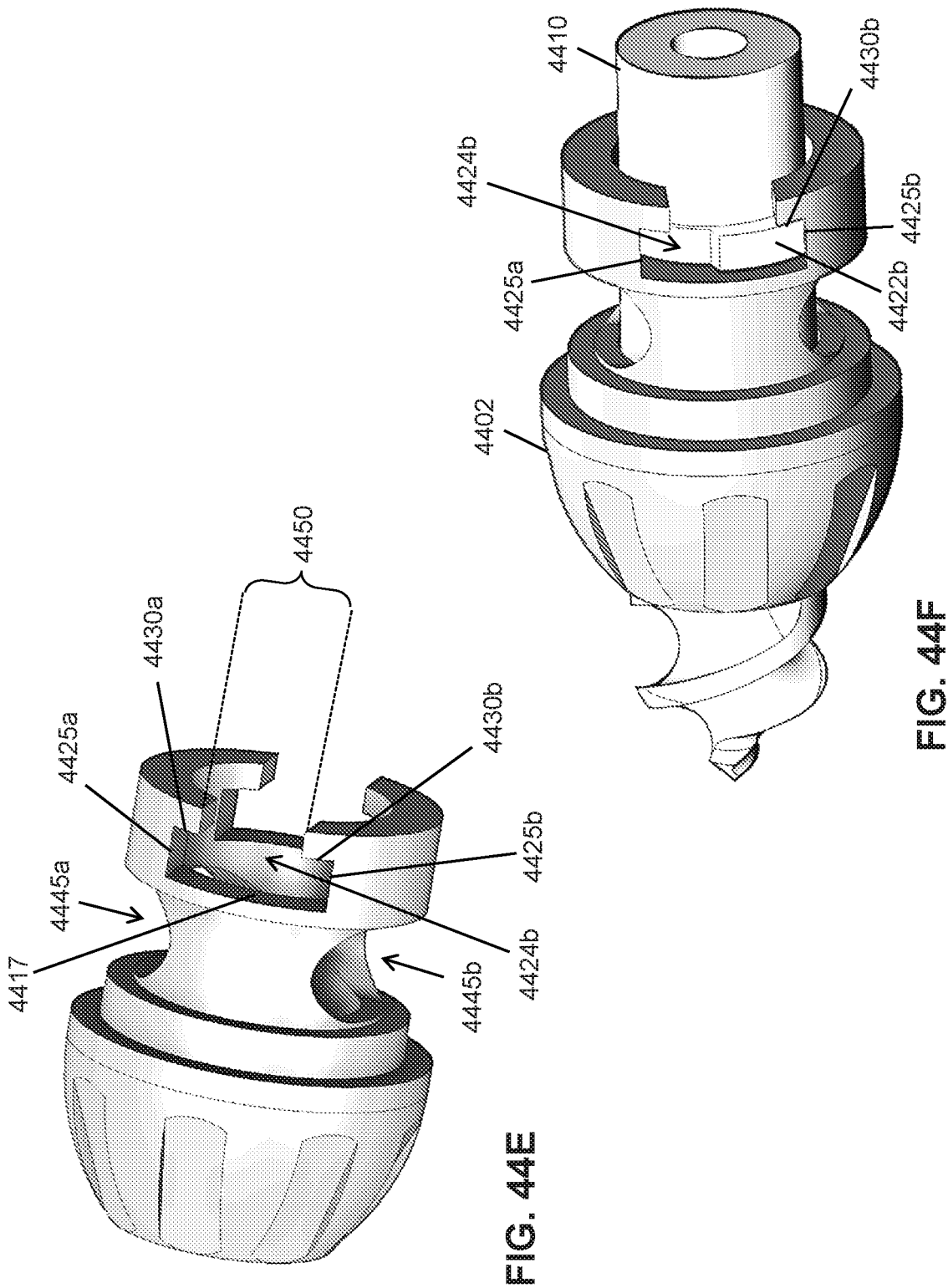

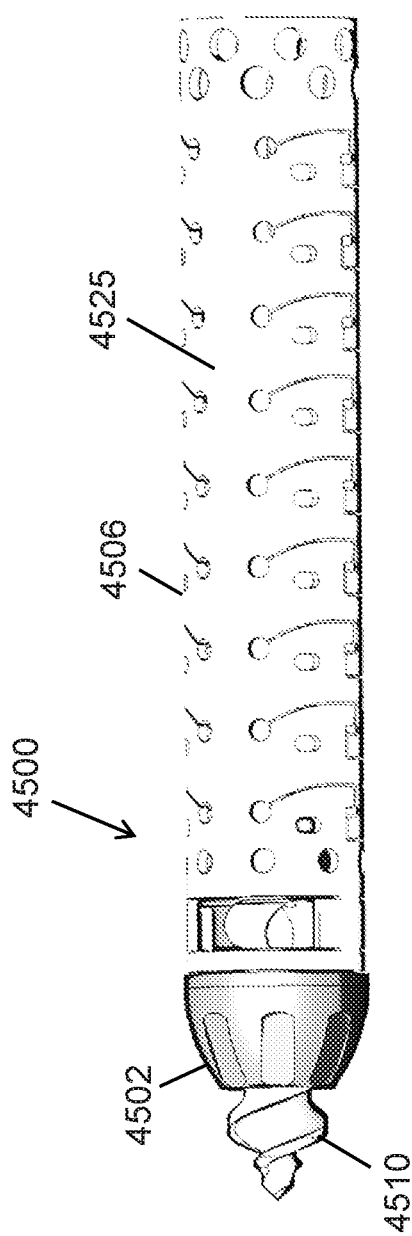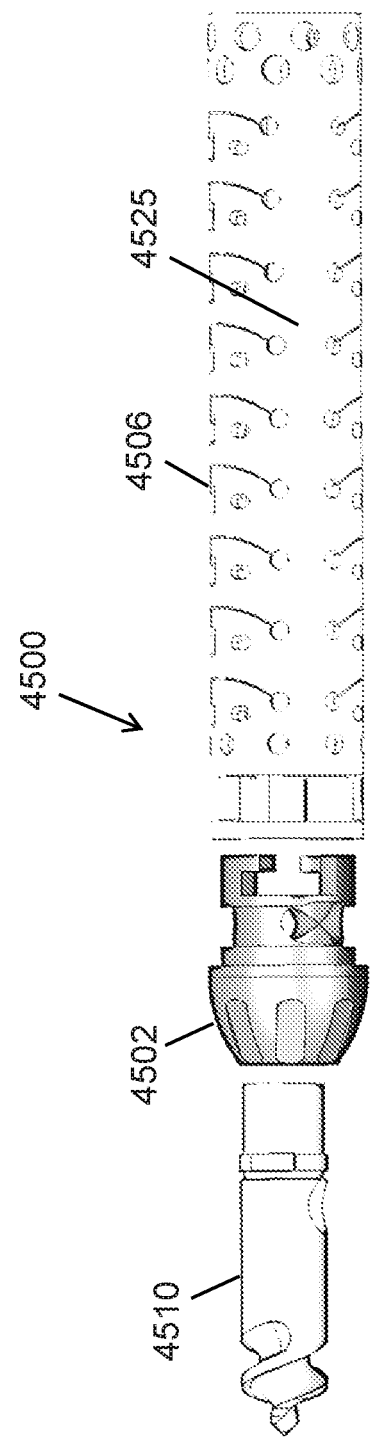
FIG. 45A
FIG. 45B

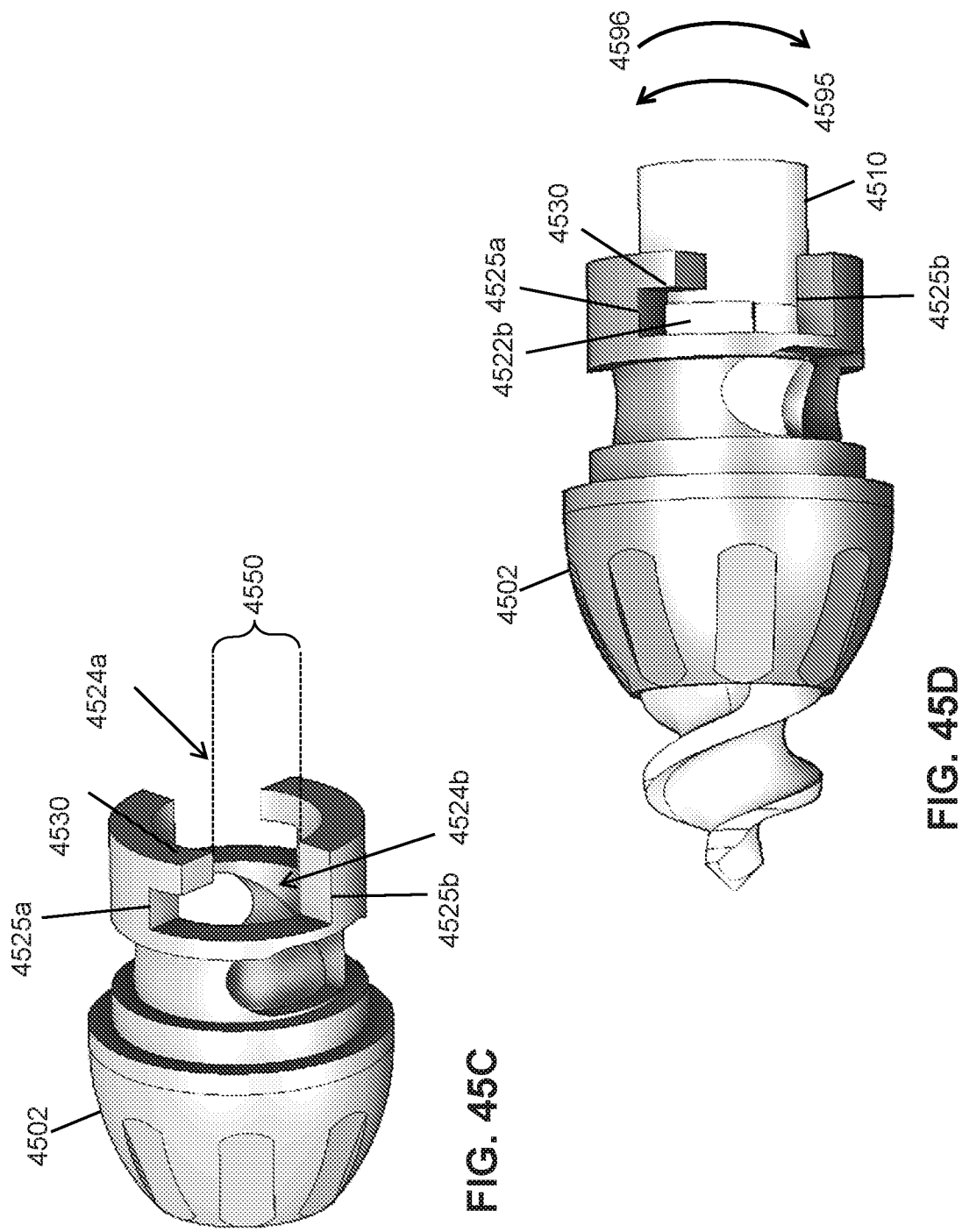

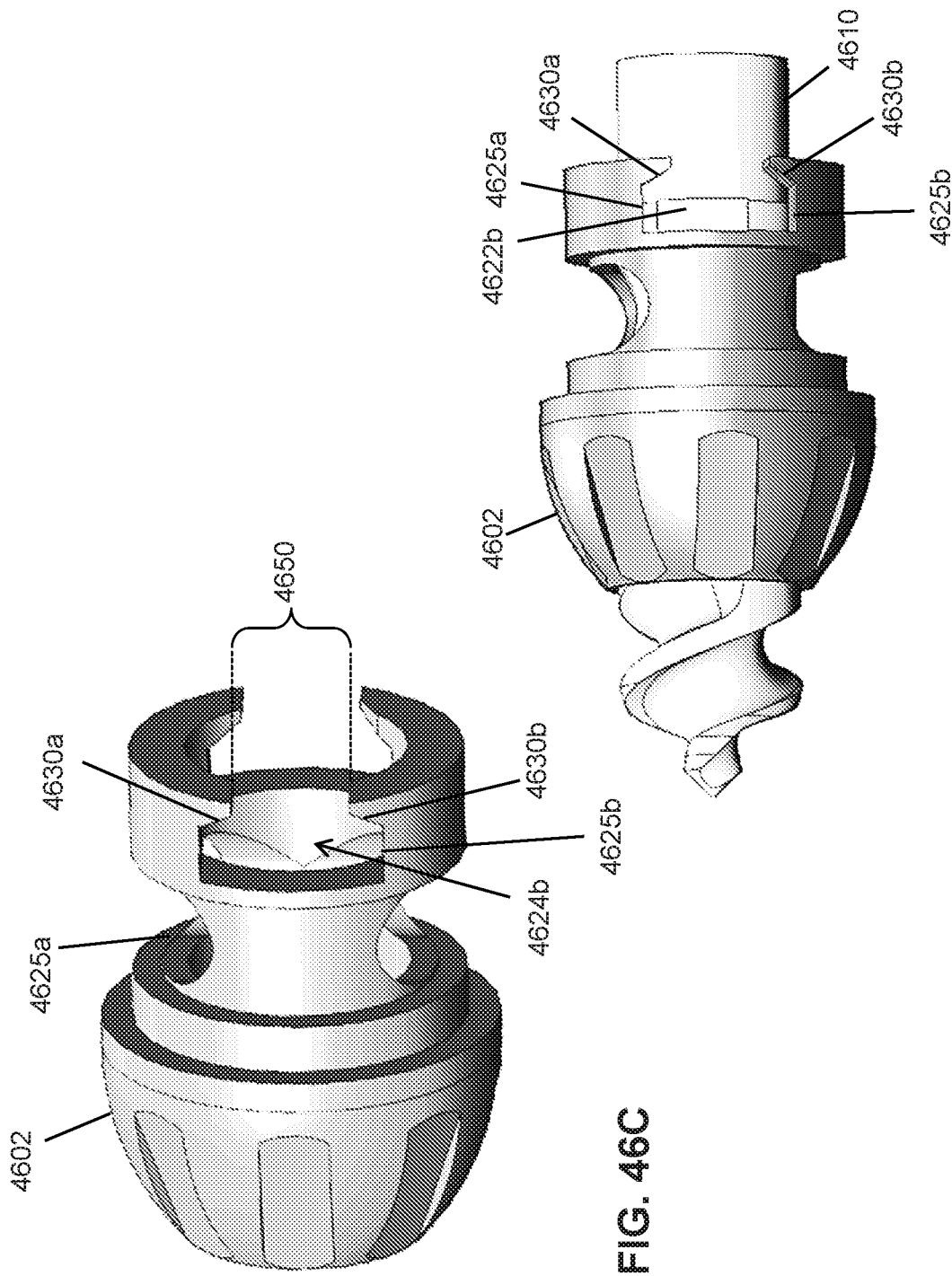

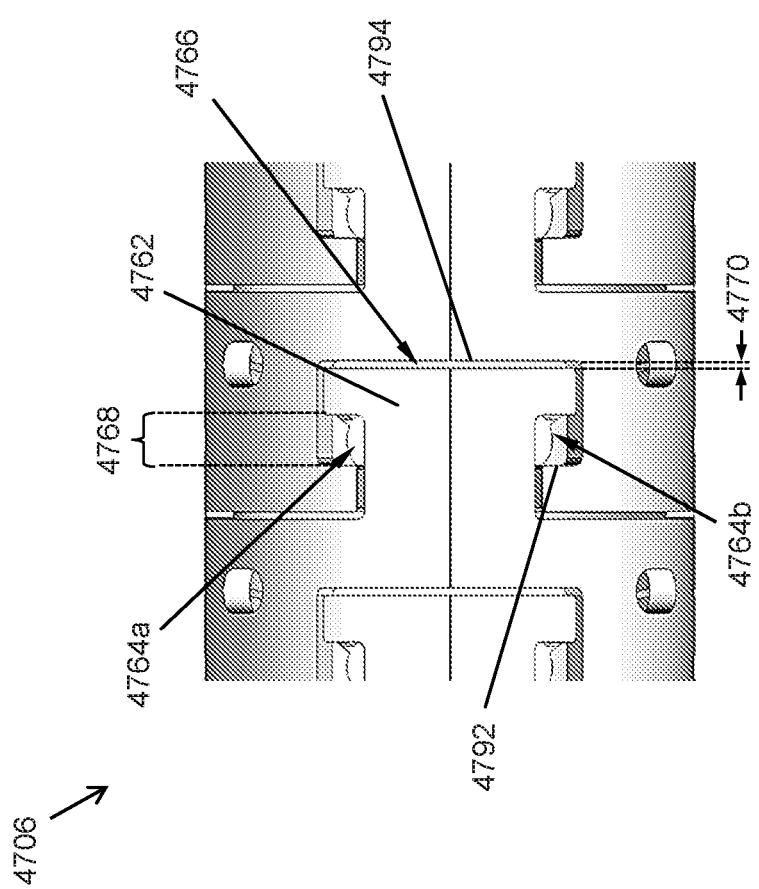

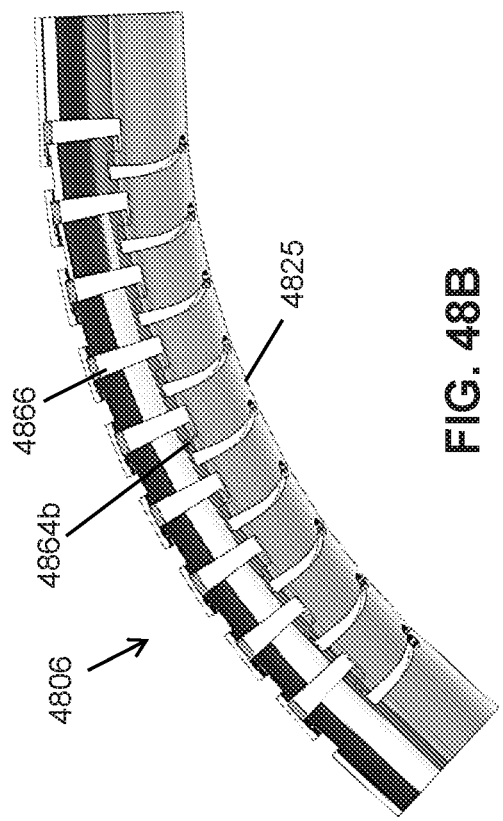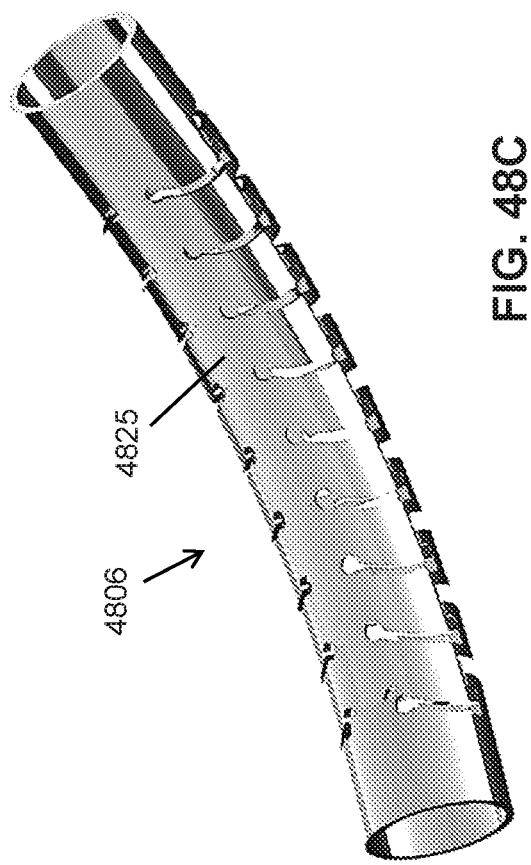

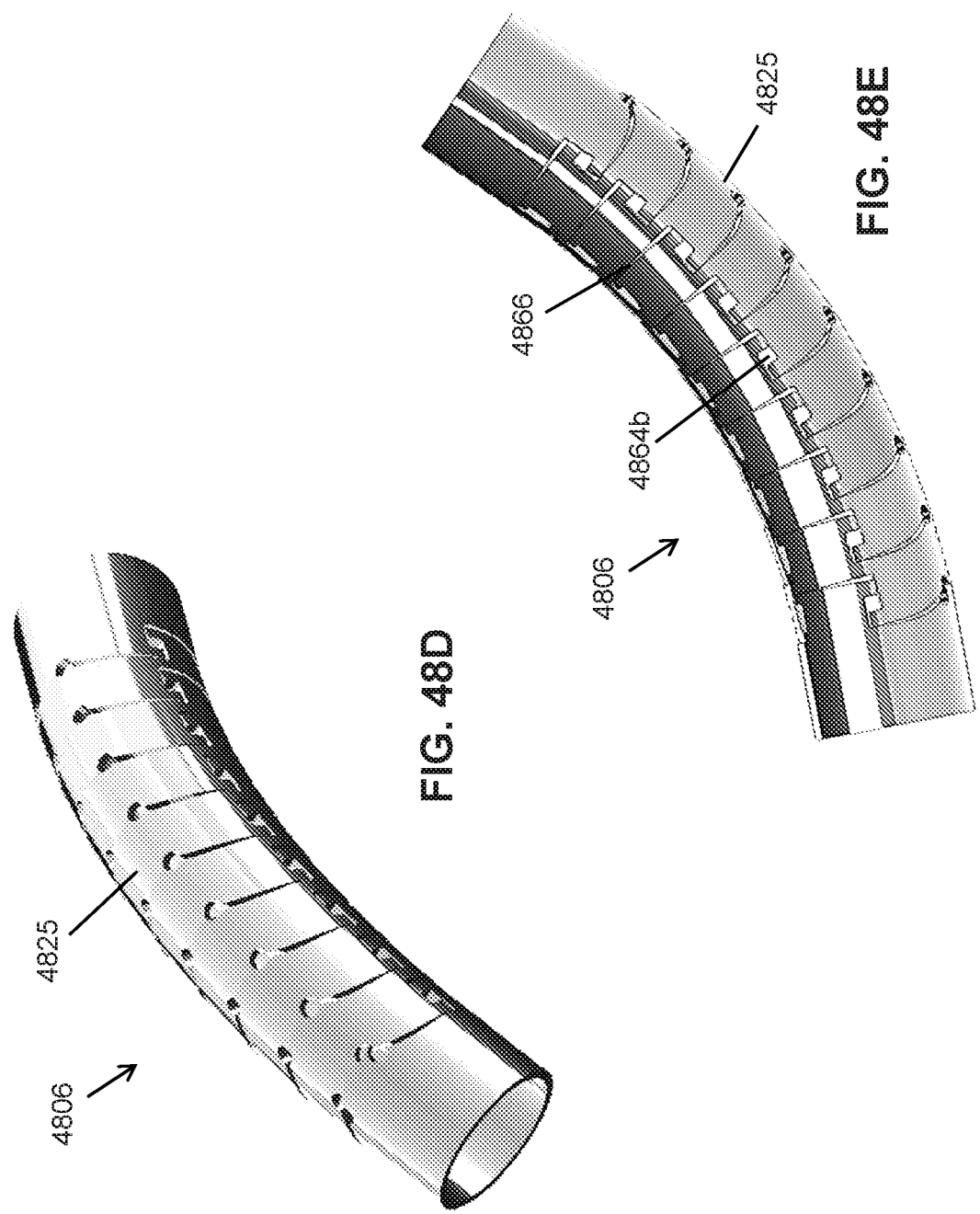

OCCLUSION-CROSSING DEVICES

CROSS REFERENCE TO RELATED APPLICATIONS

This application is the U.S. National Stage Entry of International Patent Application No. PCT/US2020/054395, filed Oct. 6, 2020, titled "OCCLUSION-CROSSING DEVICES," which claims priority to U.S. Provisional Patent Application No. 62/923,347, filed Oct. 18, 2019, titled "OCCLUSION-CROSSING DEVICE," each of which is incorporated herein by reference in its entirety.

This application may be related to International Patent Application No. PCT/US2019/028415, filed Apr. 19, 2019, titled "OCCLUSION-CROSSING DEVICES," which claims priority to U.S. Provisional Patent Application No. 62/768,769, filed Nov. 16, 2018, titled "OCCLUSION CROSSING DEVICES" and to U.S. Provisional Patent Application No. 62/660,185, filed Apr. 19, 2018, titled "OCCLUSION CROSSING DEVICES," each of which is incorporated herein by reference in its entirety.

This application may also be related to U.S. application Ser. No. 15/954,407, filed Apr. 16, 2018, titled "OCCLUSION-CROSSING DEVICES," which is a continuation of U.S. application Ser. No. 14/433,786, titled "OCCLUSION-CROSSING DEVICES", filed Apr. 6, 2015, which is a 371 U.S. national stage application of PCT/US2013/064346, titled "OCCLUSION-CROSSING DEVICES," filed Oct. 10, 2013, which claims priority to U.S. Provisional Patent Application No. 61/712,149, titled "OCCLUSION-CROSSING DEVICES," filed Oct. 10, 2012 and to U.S. Provisional Patent Application No. 61/799,505, titled "OCCLUSION-CROSSING DEVICES," filed Mar. 15, 2013. U.S. application Ser. No. 14/433,786, titled "OCCLUSION-CROSSING DEVICES", filed Apr. 6, 2015 is also a continuation-in-part of U.S. patent application Ser. No. 13/433,049, filed Mar. 28, 2012, titled "OCCLUSION-CROSSING DEVICES, IMAGING, AND ATHERECTOMY DEVICES," now U.S. Pat. No. 8,644,913, which claims priority to U.S. Provisional Patent Application No. 61/468,396, filed Mar. 28, 2011 and titled "OCCLUSION-CROSSING DEVICES, IMAGING, AND ATHERECTOMY DEVICES" and U.S. Provisional Patent Application No. 61/548,179, filed Oct. 17, 2011 and titled "OCCLUSION-CROSSING DEVICES, IMAGING, AND ATHERECTOMY DEVICES," each of which are incorporated by reference in their entirety This application may also be related to U.S. patent application Ser. No. 15/324,325, field Jan. 6, 2017, titled "HIGH SPEED CHRONIC TOTAL OCCLUSION CROSSING DEVICES", which is a 371 U.S. national stage application of International Patent Application No. PCT/US2015/039585, filed on Jul. 8, 2015, titled "HIGH SPEED CHRONIC TOTAL OCCLUSION CROSSING DEVICES", which claims priority to U.S. Provisional Application No. 62/022,101, filed Jul. 8, 2014, titled "HIGH SPEED CHRONIC TOTAL OCCLUSION CROSSING DEVICES" and U.S. Provisional Application No. 62/073,850, filed Oct. 31, 2014, titled "HIGH SPEED CHRONIC TOTAL OCCLUSION CROSSING DEVICES"; each of these patent applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are catheters and specifically, catheters that may include a rotating distal tip having both a directional cutting element and an OCT imaging sensor.

BACKGROUND

Peripheral artery disease (PAD) and coronary artery disease (CAD) affect millions of people in the United States alone. PAD and CAD are silent, dangerous diseases that can have catastrophic consequences when left untreated. CAD is the leading cause of death for in the United States while PAD is the leading cause of amputation in patients over 50 and is responsible for approximately 160,000 amputations in the United States each year.

Coronary artery disease (CAD) and Peripheral artery disease (PAD) are both caused by the progressive narrowing of the blood vessels most often caused by atherosclerosis, the collection of plaque or a fatty substance along the inner lining of the artery wall. Over time, this substance hardens and thickens, which may interfere with blood circulation to the arms, legs, stomach and kidneys. This narrowing forms an occlusion, completely or partially restricting flow through the artery. Blood circulation to the brain and heart may be reduced, increasing the risk for stroke and heart disease.

Interventional treatments for CAD and PAD may include endarterectomy and/or atherectomy. Endarterectomy is surgical removal of plaque from the blocked artery to restore or improve blood flow. Endovascular therapies such as atherectomy are typically minimally invasive techniques that open or widen arteries that have become narrowed or blocked. Other treatments may include angioplasty to open the artery. For example, a balloon angioplasty typically involves insertion of a catheter into a leg or arm artery and positioning the catheter such that the balloon resides within the blockage. The balloon, connected to the catheter, is expanded to open the artery. Surgeons may then place a wire mesh tube, called a stent, at the area of blockage to keep the artery open.

Such minimally invasive techniques (e.g., atherectomy, angioplasty, etc.) typically involve the placement of a guidewire through the occlusion. Using the guidewire, one or more interventional devices may be positioned to remove or displace the occlusion. Unfortunately, placement of the guidewire, while critical for effective treatment, may be difficult. In particular, when placing a guidewire across an occlusion, it may be difficult to pass the guidewire through the occlusion while avoiding damage to the artery. For example, it is often difficult to prevent the guidewire from directing out of the lumen into the adventitia and surrounding tissues, potentially damaging the vessel and preventing effective treatment of the occlusion.

As a result, occlusion-crossing devices, intended to assist in the passing through the occlusion, have been developed. Many of the devices, however, are ill equipped to be used with imaging, thereby making placement of the guidewire cumbersome and difficult. Moreover, many of the occlusion-crossing devices are too large to be used in small-diameter peripheral arteries or in coronary arteries. Furthermore, it has proven difficult to pass a device through an occlusion, as the tip of the device, and particularly the tip of a rotating device, may be deflected away from the occlusion, and in some cases enter the wall of the vessel lumen, such as the adventitia. In general, it may be desirable to avoid penetrating the lumen of the vessel.

Accordingly, occlusion crossing catheter devices designed to address some of these concerns are described herein.

SUMMARY OF THE DISCLOSURE

The present invention relates to occlusion crossing apparatus (e.g., devices, systems, etc.) having an outer shaft and an inner shaft that may be moved within the outer shaft, and may be rotated relative to the outer shaft to rotate a distal tip region that includes an OCT imaging sensor. These apparatuses may be configured as a catheter including both an inner shaft and an outer shaft; the inner shaft may be removable from the outer shaft to leave the inner lumen of the outer shaft open so that other elements, such as a guide wire or guide catheter, may be inserted through the outer shaft.

Thus, in general these apparatuses may include an outer shaft with a central passage or lumen that opens distally, extending along the length of the shaft body, into which the inner shaft may be passed so that a tip region of the inner shaft may extend from the distal end of the outer shaft. The inner shaft and outer shaft may be configured to limit the distal movement of the inner shaft relative to the outer shaft to prevent the outer shaft from extending beyond a predetermined distance from the distal end opening of the outer shaft. In general, the apparatuses described herein may be configured as: (1) guidewire support/placement apparatuses (e.g., catheters); (2) support/placement imaging apparatuses (e.g., catheters); (3) occlusion crossing apparatuses (e.g., catheters); or (4) occlusion crossing imaging apparatuses (e.g., catheters). Any of these apparatuses may include one or more of the elements described herein, and any of these apparatus variations may be used to treat a disorder, particularly peripheral artery disease. A system may include the outer shaft and the inner shaft. In some variations the apparatus may also include one or more additional elements, such as a driver (e.g., for rotating the inner shaft and/or bending the outer or inner shaft, and/or advancing the inner and/or outer shaft. For convenience, in the description below, these apparatuses may be referred to as occlusion crossing apparatuses or as occlusion crossing catheters.

In general, an apparatus as described herein may include a flexible elongate outer shaft, a proximal handle (or handle region), and a flexible elongate outer shaft having a distal rotating tip. The distal rotating tip may have a corkscrew-like rotating tip with a distal central extension configured to guide the tip into an occlusion (e.g., preventing deflection of the tip). The apparatus may also or alternatively include a laterally-offset distal-most tip (pointed or rounded) on the outer shaft, e.g., on one side of the outer shaft, e.g., at one region of distal opening of the outer shaft.

Any of the apparatuses described herein may include one or more tissue dissecting cutting edges on the rotating distal tip; these edges may be formed of a threaded (e.g., fluted) distal end region. In some variations, a forward edge of the catheter includes one or more helical edges, which may be referred to as wedges. The helical edges may be arranged at the distal end of the device. The edge may have a small diameter, particularly as compared with the ultimate diameter of the device. In one embodiment, the rotatable distal tip includes helical flutes that terminate in distal cutting surfaces. The distal cutting surfaces can come together at sharp points configured to slice through tissue. The rotatable distal tip can further include a distal protruding end having a smaller diameter than the more proximal region that is cylindrical and may help center the tip around the occlusion. Other tip designs are possible. For example, the tip can include grinding edges and/or paddles.

Any of the apparatus variations described herein may include a central lumen e.g., through the outer shaft, through which a guidewire may be passed for placement across an occlusion using the device after removing the inner shaft (e.g., by withdrawing proximally). The central lumen typically extends along the length of the outer shaft from the proximal end or a region distal to the proximal end, to the distal end of the catheter. Thus, the apparatus may include a distal opening, as mentioned. This opening may be angled, and/or may be inwardly beveled, which may help both in visualizing (providing a fiduciary on the circumference of the outer shaft) and for centering the outer shaft and thus the entire apparatus within the vessel to prevent it from poking into the lumen walls. The central lumen of the outer shaft may be referred to as a guidewire lumen. In some variations, the apparatus is configured to pass through a lesion or occlusion (or an occluded region or regions of a vessel) to position the apparatus beyond the occlusion before a guidewire is passed through the outer shaft. The lumen may be any biological vessel lumen, such as an artery, vein, or duct, for example a peripheral artery, vein, or bile duct.

The apparatuses described herein can be configured to apply optical coherence tomography (OCT) to image the tissue. Thus, the apparatuses described herein can include an imaging sensor, such as an OCT imaging sensor. An OCT imaging sensor may include the distal end of an optical fiber and a mirror for directing light in/out of the optical fiber. The optical fiber may be affixed to the distal tip structure. The imaging sensor may be oriented to image the vessel ahead of the apparatus, perpendicular to the apparatus, and/or behind the apparatus tip. The mirror or reflector may be used to direct the light path entering and exiting the end of the optical fiber to fix the imaging direction for the apparatus. For example, the optical fiber and mirror may be fixed to the rotating distal tip region and may be embedded in a transparent or translucent medium (including transparent cement or other fixative).

For example, described herein are occlusion crossing apparatuses, such as occlusion crossing systems. Any of these systems may include any of: an outer shaft defining a lumen and a distal opening that is angled relative to a central axis of the outer shaft to form a distal-most tip, and a first engagement region within the lumen; and an inner shaft extending within the lumen and configured to rotate with respect to the outer shaft, the inner shaft including a distal end having a fluted tip that is configured to extend through the distal opening, a side-facing optical imaging window (e.g., for any imaging technique, such as coherence tomography, OCT) on a lateral side of the inner shaft at a distal end region of the inner shaft, and a second engagement region on an outer surface of the inner shaft configured to engage with the first engagement region to limit a distal movement of the inner shaft within the outer shaft; wherein the distal-most tip of the distal opening is configured to occlude the OCT imaging window at a defined rotational position as the inner shaft is rotated relative to the outer shaft while the first engagement region is engaged with the second engagement region, to provide a registration mark for OCT imaging.

In some variations an occlusion crossing system may include: an outer shaft defining a lumen and a distal opening that is angled relative to a central axis of the outer shaft to form a distal-most tip, a first engagement region within the lumen, and a backbone region at a distal end portion of the outer shaft that is configured to bias lateral bending of the distal end portion in a plane that includes the midline of the central axis and also includes the distal-most tip; and an inner shaft extending within the lumen and configured to rotate with respect to the outer shaft, the inner shaft including a distal end having a fluted tip that is configured to extend through the distal opening, a side-facing optical coherence tomography (OCT) imaging window on a lateral side of the inner shaft at a distal end region of the inner shaft, and a second engagement region on an outer surface of the inner shaft configured to engage with the first engagement region to limit a distal movement of the inner shaft within the outer shaft; wherein the distal-most tip of the distal opening is configured to occlude the OCT imaging window at a defined rotational position as the inner shaft is rotated relative to the outer shaft while the first engagement region is engaged with the second engagement region to provide a registration mark for OCT imaging indicating the direction of bending.

Any of the apparatuses described herein may be bendable, e.g., may include a bending or biasing region that is part of the outer and/or inner shafts. For example, any of these apparatuses may include an outer shaft that has a backbone region at a distal end portion of the outer shaft that is configured to bias lateral bending of the distal end portion. In some variations the direction of biasing may be fixed relative to the distal-most tip of the outer shaft. For example, the device may be configured to bend in a plane that includes the midline of the central axis and the distal-most tip.

As mentioned, the distal opening may be circumferentially beveled. For example, the distal opening may be beveled at an angle to the outer side of the outer shaft towards the inner lumen (e.g., at an angle of between about 5 degrees and 80 degrees, between about 10 degrees and 70 degrees, between about 12 degrees and 60 degrees, between about 15 degrees and 50 degrees, etc.).

In any of these variations, the inner shaft may be configured to be removed proximally from the outer shaft, which may leave an open lumen through the outer shaft. The inner shaft outer diameter is typically smaller than the outer shaft inner diameter, at least over proximal portion of the outer shaft (excluding the engagement regions on the inner and outer shaft).

In general, the inner shaft may be configured so that distal motion out of the outer shaft distal opening is limited. The distal motion may be limited by engaging a first engagement region on the inner wall of the outer shaft with a second engagement region on the outer surface of the inner member. For example, the second engagement region may be a ring (e.g., an annular ring around the having a rounded profile. In any of these apparatuses the distal end region of the outer member may have a narrower inner diameter as compared to the more proximal end of the device. The inner and/or outer member may have a lip or rim (an annulus, annular lip, ledge, ramp, etc.) that is wider than the outer diameter of the distal end region of the inner shaft (e.g., the region of the inner shaft distal to it) and is also wider in diameter as compared to the inner diameter of this distal end region of the outer member, so that the first engagement region on the outer shaft (the region where the inner diameter narrows) engages with the second engagement region on the inner shaft (the region where the outer diameter gets larger). The first and second engagement regions are configured so that the inner shaft may against (e.g., may rotate along) the outer shaft with little friction. For example, one or both surfaces of the engagement regions may be configured to reduce friction and/or may lubricated or may include a lubricant. In some variations the engagement regions (one or both) may include a coating of diamond-like carbon (DLC) that forms a shell layer that is both hard and lubricious.

In addition pushing the inner shaft distally so that the second engagement surface drives distally against the outer shaft's first engagement surface may bend the distal end of the apparatus in the predetermined direction established by the backbone region described in greater detail below.

Any of the apparatuses described herein may include visualization integrated into the apparatus. For example, any of these apparatuses may include an imaging window (which may include an imaging sensor or an optical fiber connected to an imaging sensor) on a side of the distal end region of the inner shaft. In some variations the side-facing imaging window is a side-facing optical coherence tomography (OCT) imaging window. For example, any of these apparatuses may include an inner shaft comprises a fiber optic coupled to the OCT imaging window and extending proximally through the inner shaft.

As mentioned above, any of these apparatuses may include a proximal attachment configured to couple the inner member with a rotational driver and an imaging sub-system. The proximal attachment may be a handle or mount. The proximal attachment may include a driver for driving rotational movement of the inner shaft; the proximal attachment may alternatively or additionally couple to the imaging window (e.g., to a fiber optic) for processing the imaging.

The imaging, for example OCT imaging using the apparatus may be configured to image the vessel laterally and/or in some variations distally (or laterally and distally) of the distal end region of the inner shaft. Because the imaging window may be rotated with the tip (e.g., drill or fluted tip) of the inner shaft, the imaging may provide a panoramic view of the walls of the lumen. In any of these variations, the distal-most tip of the outer shaft may protrude into the field of view of the rotating imaging window when the inner shaft is pushed distally (to the stop position where the first and second engagement regions are engaged or just about to engage). This protrusion may occlude a fraction of the field of view of the rotating inner shaft (e.g., between about 0.5 degrees and 20 degrees, between about 1 degrees and 15 degrees, less than 15 degrees, less than 12 degrees, less than 10 degrees, etc.). This obstruction of the outer shaft relative to the inner shaft may therefore provide reference (e.g., fiducial) marking on the imaging to show the relative positions of the outer shaft. This reference frame may be even more important when the apparatus is configured to bend (e.g., by driving the inner member distally) in a predefined direction relative to the fiducial (e.g., towards the fiducial making or away from the fiducial marking), which may help with steering the apparatus.

Thus, the imaging window (e.g., the OCT imaging window) may be a side-facing imaging window that is at or near the distal end of the inner shaft. For example, the side-facing imaging window may be adjacent to the fluted tip. In some variations the side-facing (e.g., OCT) imaging window overlaps with the fluted tip.

As mentioned, the distal end region of the apparatus (e.g., the distal end region of the outer shaft) may be configured to bend in a predetermined direction when the second engagement region of the inner member is driven distally against the first engagement region of the outer member.

Any of the apparatuses described herein may be configured to prevent the device from deflecting off of an occlusion (and potentially entering the luminal wall), and in particular may be configured to allow distal end of the inner and/or outer shafts to remain centered relative to the target (e.g., occlusion) being passed. At least two of the features described briefly above may be included (either together or separately). For example, a distal-most facing tip on the outer shaft may help prevent the outer shaft or outer and inner shaft from deflecting. In any of these variations, the distal opening (either angled or perpendicular to the long axis of the outer member) may be circumferentially beveled inward from an outer surface of the outer shaft, as mentioned above. This circumferential bevel extending from the outer surface of the outer shaft may also help prevent deflection of the outer member and/or prevent the outer member from entering into the adventitia of the vessel lumen. The bevel may be particularly effective when the outer shaft has a distal-most tip as described above.

Alternatively or additionally, any of these apparatuses may include a protrusion on the threaded distal end of the inner shaft that extends beyond the threaded and/or fluted distal end. This protrusion may extend distally sufficiently (e.g., between about 0.1 mm and about 7 mm, between 0.2 mm and about 5 mm, between about 0.5 mm and about 3 mm, greater than 0.1 mm, greater than about 0.2 mm, greater than about 0.3 mm, greater than about 0.4 mm, greater than about 0.5 mm, greater than about 0.6 mm, greater than about 0.7 mm, greater than about 0.8 mm, greater than about 0.9 mm, etc.). The protrusion may have a diameter (over the majority of the protruding length) that is less than about 75% (e.g., less than about 60%, less than about 50%, less than about 40%, less than about 30%, less than about 25%, less than about 20%, less than about 15%, etc.) of the diameter of the threaded and/or fluted region proximal to the protrusion.

For example, described herein are occlusion crossing systems that include: an outer shaft defining a lumen and a distal opening and a first engagement region within the lumen; and an inner shaft extending within the lumen and configured to rotate with respect to the outer shaft, the inner shaft including: a distal end having a first fluted tip region that is configured to extend through the distal opening, wherein the first fluted tip region has a first diameter, a second tip region extending from the first fluted tip region, wherein the second tip region has a diameter that is less than 60% the diameter of the first diameter. Any of these systems may also include a side-facing optical coherence tomography (OCT) imaging window on a lateral side of the inner shaft at a distal end region of the inner shaft, and a second engagement region on an outer surface of the inner shaft configured to limit a distal movement of the inner shaft within the outer shaft.

An occlusion crossing system may include: an outer shaft defining a lumen and a distal opening that is angled relative to a central axis of the outer shaft to form a distal-most tip, and a first engagement region within the lumen; and an inner shaft extending within the lumen and configured to rotate with respect to the outer shaft, the inner shaft including: a distal end having a first fluted tip region that is configured to extend through the distal opening, wherein the first fluted tip region has a first diameter, a second tip region extending from the first fluted tip region, wherein the second tip region has a diameter that is less than 60% the diameter of the first diameter, a side-facing optical coherence tomography (OCT) imaging window on a lateral side of the inner shaft at a distal end region of the inner shaft, and a second engagement region on an outer surface of the inner shaft configured to limit a distal movement of the inner shaft within the outer shaft; wherein the distal-most tip of the distal opening is configured to occlude the OCT imaging window at a defined rotational position as the inner shaft is rotated relative to the outer shaft while the first engagement region is engaged with the second engagement region to provide a registration mark for OCT imaging.

The first diameter may be approximately the same as a diameter of the inner shaft in the region proximal to the fluted tip region. The second tip region may be fluted and/or threaded, and may be flued or threaded with a different pitch, direction or width (flute width) than the first tip region. The second tip region may extend to a point.

Any of these apparatuses may be configured to bend, as mentioned above; for example the outer shaft may comprise a backbone region at a distal end portion of the outer shaft that is configured to bias lateral bending of the distal end portion. The distal end region of the outer shaft may be configured to bend in a predetermined direction when the second engagement region of the inner member is driven distally against the first engagement region of the outer member.

The distal opening may be circumferentially beveled, as mentioned above. The inner shaft may be configured to be removed proximally from the outer shaft.

In any of the variations of the apparatuses including OCT imaging as described herein, the inner shaft may comprise a fiber optic coupled to the OCT imaging window and extending proximally through the inner shaft. As mentioned, any of these apparatuses may include a proximal attachment configured to couple the inner member with a rotational driver and an imaging sub-system, for example, coupling the fiber optic to an OCT processing sub-system for OCT imaging. The side-facing OCT imaging window may be adjacent to the fluted tip and/or may overlap with the fluted tip.

An occlusion crossing device may include: an outer shaft defining a lumen and a distal opening that is angled relative to a central axis of the outer shaft to form a distal-most tip, wherein the distal opening is circumferentially beveled inward from an outer surface of the outer shaft, further wherein a distal portion of the outer shaft includes a backbone that extends longitudinally along at least a portion of the outer shaft, wherein the backbone is configured to bias lateral bending of the distal portion; an inner shaft extending within the lumen and configured to rotate with respect to the outer shaft, the inner shaft including a distal end having a drill tip that is configured to extend through the distal opening.

Any of these apparatuses may include an imaging element coupled to the inner shaft and configured to rotate with the inner shaft. The imaging element may comprise an optical coherence tomography (OCT) imaging window, or a direct-imaging element such as an imaging sensor (e.g. CCD, etc.). The imaging element may comprise an optical fiber that extends within the inner shaft and substantially along a central axis of the inner shaft.

As mentioned above, the distal-most tip may be configured to pass in front of the imaging element as the imaging element rotates, forming a registration marker. The device of claim 27, further comprising a handle attached to the inner shaft and the outer shaft and configured rotate the inner shaft.

The handle (e.g., the proximal attachment, which may be configured as a handle) may be configured to rotate the inner shaft and therefore the drill tip (e.g., the fluted or threaded distal end at speeds of greater than 500 rpm.

The backbone may be part of a selective bending support of the outer shaft, the selective bending support at least partially surrounding a flexible tube of the outer shaft.

In general, the outer shaft and/or the inner shaft may include a braided material. Specifically, the flexible tube may include a braided material. The braided material may be made of a metal material that is surrounded by a polymeric laminate.

The outer shaft may include circumferential cuts that extend at least partially through a thickness of the outer shaft, wherein the backbone is between the circumferential cuts. The outer shaft may include multiple backbones. The inner shaft may be removably coupled with the outer shaft.

For example, an occlusion crossing device may include: an outer shaft comprising: a flexible tube, and a selective bending support that at least partially a surrounds a distal end of the flexible tube, the selective bending support including a backbone that extends longitudinally along a portion of the flexible tube, wherein the backbone is configured to bias lateral bending of the distal end of the outer shaft in a direction; and an inner shaft extending within the outer shaft and configured to rotate with respect to the outer shaft, the inner shaft having a drill tip that extends through an opening at a distal end of outer shaft. The selective bending support may include a plurality of ribs connected to the backbone and encompassing the flexible tube. For example, the selective bending support may include three or more ribs. The flexible tube may include a braided metal material, such as a braided metal material encased in a laminate material to make the flexible tube substantially impervious to fluid.

Any of these devices may include an optical fiber extending within the inner shaft and coupled to the inner shaft. The optical fiber may include an image sensor configured to sense image data from outside of the occlusion crossing device.

In any of these apparatuses, the drill tip may include a window to provide the image sensor imaging access outside of the occlusion crossing device. The inner shaft may be removably coupled to the outer shaft via a connector. In some variations, the inner shaft moves longitudinally with respect to the outer shaft when a force is applied to the inner shaft in a longitudinal direction to cause the distal end of the device to bend in the direction toward the backbone.

In any of the apparatuses described herein, at least a portion of the selective bending support may radially overlap with at least a portion of the drill tip.

Also described herein are method of using any of these apparatuses. For example, described herein are methods of crossing an occlusion in a vessel. In some variations, the method may include: inserting a catheter within the vessel, the catheter including an outer shaft and an inner shaft, the outer shaft having a distal opening that is angled relative to a central axis of the outer shaft to form a distal-most tip, wherein the distal opening is circumferentially beveled inward from an outer surface of the outer shaft, the inner shaft having a drill tip at distal end of the catheter; causing a distal portion of the catheter to bend in a lateral direction with respect to a central axis of the catheter, wherein the lateral direction is defined by a backbone that extends longitudinally along at least a portion of the outer shaft; rotating the inner shaft with respect to the outer shaft; moving the catheter distally to cross the occlusion within the vessel; and removing the inner shaft from the outer shaft while the outer shaft remains within the vessel.

Any of these methods may include inserting a guidewire within the outer shaft after removing the inner shaft; these methods may further include using the guidewire to perform an atherectomy procedure.

Any of these atherectomy procedures may include the use of one or more of a balloon, stent, tube and medicament.

In general, the apparatuses described herein are configured so that the inner shaft may be rotated to rotate the fluted tip; this tip may be rotate either clockwise or counterclockwise, and depending on the direction and configuration of the flutes or threads of the tip region may either cut into the tissue (the occlusion) or may push against the tissue (without necessarily cutting). This may be helpful for positioning the apparatus and/or preventing it from penetrating the vessel wall. For example, any of the methods described herein may include rotating the inner shaft in a first direction to cut through the occlusion when advancing and rotating the inner shaft in a second direction to advance without cutting.

For example, a method of crossing an occlusion in a vessel may include: advancing an outer shaft into the vessel distally so that a distal-most tip of the outer shaft, which is formed by an opening of the outer shaft that is angled relative to a central axis of the outer shaft, is driven distally within a lumen of the vessel, wherein the distal opening is circumferentially beveled inward from an outer surface of the outer shaft; advancing an inner shaft distally into the outer shaft until a fluted distal end of the inner shaft extends out of the opening beyond the distal-most tip to a stop position in which the inner shaft is limited from extending distally further from the outer shaft; rotating the inner shaft with respect to the outer shaft in a first direction to cut tissue of the occlusion; and advancing the outer shaft and inner shaft together distally to cross the occlusion.

For example, a method of crossing an occlusion in a vessel may include: advancing an outer shaft into the vessel distally so that a distal-most tip of the outer shaft, which is formed by an opening of the outer shaft that is angled relative to a central axis of the outer shaft, is driven distally within a lumen of the vessel, wherein the distal opening is circumferentially beveled inward from an outer surface of the outer shaft; advancing an inner shaft distally into the outer shaft until a fluted distal end of the inner shaft extends out of the opening beyond the distal-most tip to a stop position in which the inner shaft is limited from extending distally further from the outer shaft, wherein the fluted distal end of the inner shaft includes a first fluted tip region having a first diameter and a second fluted tip region extending distally from the first fluted tip region has a second diameter that is less than 60% of the first diameter; rotating the inner shaft with respect to the outer shaft in a first direction to cut tissue of the occlusion; rotating the inner shaft with respect to the outer shaft in a second direction to less engage the walls of the vessel without cutting; and advancing the outer shaft and inner shaft together distally to cross the occlusion while rotating the inner shaft in the first direction. In general, rotating the inner shaft with respect to the outer shaft to cut tissue of the occlusion may include advancing the second fluted tip region into the occlusion before the rest of the inner shaft is advanced into the occlusion to prevent deflection of the inner shaft as it is advanced.

A method of crossing an occlusion in a vessel may include: advancing an outer shaft into the vessel distally so that a distal-most tip of the outer shaft, which is formed by an opening of the outer shaft that is angled relative to a central axis of the outer shaft, is driven distally within a lumen of the vessel, wherein the distal opening is circumferentially beveled inward from an outer surface of the outer shaft; advancing an inner shaft distally into the outer shaft until a fluted distal end of the inner shaft extends out of the opening beyond the distal-most tip to a stop position in which the inner shaft is limited from extending distally further from the outer shaft; imaging the lumen of the vessel though an imaging window on a lateral side of the inner shaft while rotating the inner shaft with respect to the outer shaft in a first direction so that the distal-most tip of the distal opening occludes the imaging window at a defined rotational position as the inner shaft is rotated relative to the outer shaft to provide a registration mark for the imaging; and advancing the outer shaft and inner shaft together distally to cross the occlusion while rotating the inner shaft in the first direction.

According to some embodiments, an imaging device includes: an inner shaft operatively coupled to a rotational driver for rotating the inner shaft, the inner shaft including a distal end having a drill tip configured to pass through an occlusion within a blood vessel, the inner shaft further including an optical coherence tomography (OCT) imaging element at distal end region of the inner shaft that is configured to collect images outside of the catheter; and an outer shaft removably coupled to the inner shaft, the outer shaft including: a first lumen that accommodates the inner shaft so that the inner shaft can rotate and translate longitudinally within the outer shaft, the outer shaft including a window or a transparent material so that the OCT element can collect images through the outer shaft as the inner shaft rotates and translates within the first lumen, wherein a distal end of the first lumen is closed to prevent the drill tip from translating through a distal end of the outer shaft, and a second lumen parallel to the first lumen and that extends longitudinally along at least a portion of the outer shaft, the second lumen configured to accommodate a guidewire.

In some variations, the distal end of the outer shaft is tapered. The inner shaft may be configured to be removed proximally from the outer shaft. The second lumen may run along substantially a full length of the outer shaft. The rotational driver may be configured to rotate the inner shaft at speeds of greater than 500 rpm. The imaging element may include an imaging fiber that extends within the inner shaft. A distal end region of the inner shaft inner shaft may include an imaging window. The outer shaft may be rotatably coupled to the inner shaft at a connector at a proximal region of the inner and outer shafts. The connector may be part of a handle of the device. The rotational driver may be at a handle of the device. A distal portion of the outer shaft may include a backbone that extends longitudinally along at least a portion of the outer shaft, wherein the backbone is configured to bias lateral bending of the distal portion along a plane. The second lumen may be radially aligned with the backbone with respect to a longitudinal axis of the device. A distal portion of the outer shaft may include a fluid flushing port configured to expel a fluid.

According to some embodiments, a catheter system includes: an inner shaft operatively coupled to a rotational driver for rotating the inner shaft, the inner shaft including a distal end having a drill tip configured to pass through an occlusion within a blood vessel, the inner shaft further including an optical coherence tomography (OCT) imaging element at distal end region of the inner shaft that is configured to collect images outside of the catheter, wherein the inner shaft is configured to interchangeably couple with a first outer shaft and a second outer shaft, wherein: the first outer shaft includes a first lumen configured to accommodate the inner shaft, the first outer shaft including a window or a transparent material so that the OCT element can collect images through the first outer shaft as the inner shaft rotates and translates within the first lumen, wherein a distal end of the first lumen is closed to prevent the drill tip from translating through a distal end of the first outer shaft; and the second outer shaft includes a central lumen and a distal opening that allows the drill tip to pass therethrough, wherein a bendable distal portion of the second outer shaft includes a backbone configured to cause the bendable distal portion of the outer shaft and the inner shaft positioned therein to bend laterally when the inner shaft is pull proximally with respect to the second outer shaft.

In some variations, the first outer shaft includes a second lumen configured to accommodate a guidewire. The system may further include a handle having a connector configured to rotatably lock the inner shaft to the second outer shaft, wherein the connector allows the inner shaft to rotate with respect to the first or second outer shaft when the inner shaft is rotatably locked to the first or second outer shaft. The connector may be configured to provide longitudinal movement between the inner shaft and the second outer shaft such that the inner shaft can translate longitudinally a small distance to activate the bendable distal portion. The connector may include one or more of a luer lock, a valve connector, a joint fitting and a gasket joint. The handle may include the rotational driver. A distal portion of the outer shaft may include a fluid flushing port configured to expel a fluid.

According to some embodiments, an occlusion crossing device includes: an inner shaft operatively coupled to a rotational driver for rotating the inner shaft, the inner shaft including a distal end having a drill tip configured to pass through an occlusion within a blood vessel, the inner shaft further including an optical coherence tomography (OCT) imaging element at distal end region of the inner shaft that is configured to collect images outside of the device; an outer shaft removably coupled to the inner shaft, the outer shaft including a lumen that accommodates the inner shaft so that the inner shaft can rotate and translate longitudinally within the outer shaft; and an expandable sack coupled to a distal portion of the outer shaft, the expandable sack including a cap portion and an opening arranged to allow blood flowing distally from a proximal location along the outer shaft to pass through the opening into the cap portion and expand the cap portion.

In some variations, the expandable sack is configured to contact inner surfaces of the blood vessel when expanded so as to limit blood flow distally past the expandable sack within the blood vessel. The expandable sack may be configured to collapse radially toward the outer shaft when the inner shaft is pulled proximally. The expandable sack may include one or more tethers that extend from an edge of the cap portion and that couples the cap portion to a proximal portion of the expandable sack. The edge may at least partially define the opening of the expandable sack. The expandable sack may at least partially on a bendable portion at the distal portion of the outer shaft. The expandable sack may include a flexible polymer material configured to collapse against an outer surface of the outer shaft when the expandable sack is in a collapsed state. The expandable sack may include a collapsible cage structure having a plurality of wires of rigid material, wherein the cap portion is covered with a sheath that allows the cap portion to expand radially outward by the force of blood flowing into the cap portion. A distal end of the outer shaft may include one or more ports configured to expel a fluid at a distal portion of the device. The one or more ports may be connected to one or more channels for carrying the fluid to the one or more ports. A tip region at a distal end of the outer shaft may be tapered. At least a portion of the tip region may be configured to pass in front of the imaging element as the imaging element rotates such that the tip region serves as a registration marker. A distal portion of the outer shaft may include a backbone that extends longitudinally along at least a portion of the outer shaft, wherein the backbone is configured to bias lateral bending of the distal portion. The device may further include a handle attached to the inner shaft and the outer shaft, wherein the rotational driver is part of the handle. The rotational driver may be configured to rotate the drill tip at speeds of greater than 500 rpm. The outer shaft may include circumferential cuts that extend at least partially through a thickness of the outer shaft. The outer shaft may include a first engagement region on an inner surface of the outer shaft that is configured to extend through a distal opening of the outer shaft, wherein the inner shaft includes a second engagement region on an outer surface of the inner shaft that is configured to engage with the first engagement region to limit a distal movement of the inner shaft within the outer shaft. A distal end region of the inner shaft may include a side-facing imaging window on a lateral side of the inner shaft. A distal-most tip of the outer shaft may be configured to occlude an imaging window of the inner shaft at a defined rotational position as the inner shaft is rotated relative to the outer shaft to provide a registration mark for OCT imaging. A distal portion of the outer shaft may include a fluid flushing port configured to expel a fluid.

According to some embodiments, an occlusion crossing device includes: an inner shaft operatively coupled to a rotational driver for rotating the inner shaft, the inner shaft including a distal end with a drill tip body configured to pass through an occlusion within a blood vessel, the inner shaft further including an optical coherence tomography (OCT) imaging element at a distal end region of the inner shaft that is configured to collect images outside of the device; an outer shaft removably coupled to the inner shaft so that the inner shaft can rotate and translate longitudinally within the outer shaft in a distal direction and a proximal direction; and a collar rotatably coupled to a distal end of the outer shaft and having a central opening to accommodate the drill tip body therein, wherein the drill tip body and the collar include a locking feature configured to lock the collar to the drill tip body so that the collar and drill tip body are rotatable together, wherein when the collar is locked with the drill tip body: distal movement of the inner shaft relative to the outer shaft causes the occlusion crossing device to bend, and proximal movement of the inner shaft relative to the outer shaft causes the occlusion crossing device to straighten.

In some variations, the locking feature may be configured to unlock the collar from the drill tip body by stopping rotation of the drill tip body and translating the drill tip body proximally relative to the collar. Unlocking the collar from the drill tip body may further include rotating the drill tip body relative to the collar by less than a full rotation before translating the drill tip body proximally relative to the collar. The locking feature may allow the drill tip body and the inner shaft to be removed from the outer shaft. The drill tip body may include a stop that prevents the drill tip body from extending completely through the central opening of the collar when the drill tip body is translated in the distal direction. The stop of the drill tip body may be configured to press against a proximal edge of the collar to prevent the drill tip body from extending completely through the central opening of the collar. The locking feature may include one or more keyways of the collar that is configured to retain one or more keys of the drill tip body to lock the collar and the drill tip body. The collar may be configured to remain at a position longitudinally with respect to the outer shaft when rotating with respect to the outer shaft. An outer surface of the collar may include one or more abrasive surface features configured to cut tissue. The one or more abrasive surface features may include one or more protrusions, one or more indentations or an adhered abrasive material. The outer shaft may include a backbone that extends longitudinally along at least a portion of the outer shaft, wherein the backbone may be configured to bias lateral bending of a distal portion of the occlusion crossing device along a plane. The occlusion crossing device may further include a handle having a connector configured to rotatably lock the inner shaft to the outer shaft, wherein the connector may allow the inner shaft to rotate with respect to the outer shaft when the inner shaft is rotatably locked to the outer shaft. The connector may be configured to provide longitudinal movement between the inner shaft and the outer shaft such that the inner shaft can translate longitudinally a small distance to activate lateral bending of the backbone. The connector may include one or more of a luer lock, a valve connector, a joint fitting, and a gasket joint. The outer shaft may include a backbone that is configured to bend the occlusion crossing device upon application of a pushing force on the inner shaft, wherein the occlusion crossing device is configured to bend toward the backbone in response to the pushing force such that a side of the outer shaft opposite the backbone expands. The occlusion crossing device may be configured to straighten or bend away from the backbone upon application of a pulling force on the inner shaft. An optical window of the collar may be configured to align with an optical window of the drill tip body when the collar and the drill tip body are locked. The optical window of the collar may be longitudinally aligned with one or more optical windows of the outer shaft. The inner shaft may be operatively coupled to a rotational driver configured to rotate the inner shaft relative to the outer shaft.

According to some embodiments, a method of operating an occlusion crossing device is described, where the occlusion crossing device includes an inner shaft having a distal end with a drill tip body attached thereto, and an outer shaft having a distal end with a collar rotatably coupled thereto, the method includes: engaging a locking feature of the collar and the drill tip body by distally translating the inner shaft and the drill tip body within the outer shaft and rotating the inner shaft and the drill tip body with respect to the collar; spinning the inner shaft while the collar and the drill tip body are locked together so that the collar spins with the drill tip body and the inner shaft; laterally bending the occlusion crossing device in a first direction by applying a pushing force on the inner shaft while the collar and the drill tip body are locked together; and straightening the occlusion crossing device by applying a pulling force on the inner shaft while the collar and the drill tip body are locked together.

In some variations, the method may further include removing the inner shaft from the outer shaft by: stopping spinning of the inner shaft, the drill tip body, and the collar; disengaging the locking feature of the collar and the drill tip body by rotating inner shaft and the drill tip body less than one full rotation; and proximally translating the inner shaft with respect to the outer shaft until the inner shaft is removed from a lumen of the outer shaft. The method may further include removing the inner shaft from the outer shaft by: stopping spinning of the inner shaft, the drill tip body, and the collar; and proximally translating the inner shaft with respect to the outer shaft to disengage the locking feature of the collar and the drill tip body and remove the inner shaft from the outer shaft. The locking feature may include a key protruding from an outer surface of the drill tip body and a keyway at a proximal end of the collar, wherein the engaging the locking feature includes capturing the key within the keyway. Capturing the key within the keyway may include rotating the drill tip body to align the key with a gap of the keyway and distally translating the drill tip body with respect to the outer shaft so that the key enters the keyway. The method may further include removing the inner shaft from the outer shaft by rotating the drill tip body to align the key with the gap of the keyway and proximally translating the drill tip body with respect to the outer shaft so that the key exits the keyway. The method may further include inserting a guidewire or a guide catheter within the outer shaft after removing the inner shaft from the outer shaft. Rotating the inner shaft and the drill tip body with respect to the collar may include rotating the inner shaft and the drill tip body less than one full rotation with respect to the collar. The inner shaft, the drill tip body, and the collar may be spun in a clockwise direction or a counterclockwise direction. The pushing force may be applied while the inner shaft, the drill tip body. Applying the pushing force may cause the occlusion crossing device to bend toward a backbone of the outer shaft, wherein the backbone may extend longitudinally along at least a portion of the outer shaft. The method may further include laterally bending the occlusion crossing device in a second direction opposite the first direction by applying a further pulling force on the inner shaft while the collar and the drill tip body are locked together. The method may further include collecting images outside of the occlusion crossing device using an optical coherence tomography (OCT) imaging element coupled to the inner shaft. The occlusion crossing device may include a handle having a connector configured to rotatably lock the inner shaft to the outer shaft, wherein the connector allows the inner shaft to rotate with respect to the outer shaft when the inner shaft is rotatably locked to the outer shaft. The drill tip body may include a stop that prevents the drill tip body from extending completely through a central opening of the collar when the drill tip body is distally translated within the collar.

According to some embodiments, an occlusion crossing device includes: an outer shaft; a rotatable inner shaft comprising a distal cutting tip and an optical coherence tomography (OCT) imaging element; and a collar rotatably attached to the outer shaft and configured to removably couple the inner shaft within the outer shaft, wherein the collar comprises a locking mechanism, the locking mechanism configured such that: when the locking mechanism is engaged, the collar is rotatable with the inner shaft relative to outer shaft, translation of the inner shaft relative to the outer shaft in a first axial direction causes the occlusion crossing device to bend, and translation of the inner shaft relative to the outer shaft in a second axial direction causes the occlusion crossing device to straighten; and when locking mechanism is disengaged, the rotatable inner shaft is removable from within the outer shaft.

In some variations, the first direction may be a distal direction and the second direction may be a proximal direction. The occlusion crossing device may be configured to bend and straighten while the inner shaft is rotated. The locking mechanism, when engaged, may enable translation movement of the inner shaft with respect to the collar by less than 1 mm. The locking mechanism may be configured to disengage by translating the inner shaft proximally relative to the collar while the inner shaft is not rotating. The locking mechanism may be further configured to disengage by rotating the inner shaft relative to the collar by less than a full rotation before translating the inner shaft proximally relative to the collar. The distal cutting tip may include a spiral drill tip body. The occlusion crossing device of claim 35, wherein the inner shaft includes a stop configured to engage with a proximal edge of the collar to limit distal translation of the inner shaft. The locking mechanism may include one or more keyways of the collar that are configured to retain one or more keys of the drill tip body to lock the collar and the drill tip body. The one or more keyways may lock the collar and the drill tip body such that the inner shaft can be translated relative to the outer shaft in a second axial direction to bend the occlusion crossing device. Translating the inner shaft relative to the outer shaft in the first axial direction may cause the occlusion crossing device to bend in a first lateral direction, and wherein translating the inner shaft relative to the outer shaft in the second axial direction may cause the occlusion crossing device to bend in a second lateral direction opposite the first lateral direction. The one or more keyways may include an angled undercut edge configured to urge the one or more keys out of the one or more keyways to unlock the collar and the drill tip body. The one or more keyways may include an undercut edge configured to retain the one or more keys within the one or more keyways when the drill tip body is rotated relative to the collar in a first rotational direction, and wherein the one or more keyways includes a gap configured to allow the one or more keys to escape the one or more keyways when the drill tip body is rotated relative to the collar in a second rotational direction and translated in a second axial direction relative to the outer shaft. An outer surface of the collar may include one or more abrasive surface features configured to cut tissue. The one or more abrasive surface features may include one or more protrusions, one or more indentations or an adhered abrasive material. The outer shaft may include a backbone that extends longitudinally along at least a portion of the outer shaft, wherein the backbone is configured to bias lateral bending of a distal portion of the occlusion crossing device along a plane. The occlusion crossing device may further include a handle having a connector configured to rotatably lock the inner shaft to the outer shaft, wherein the connector allows the inner shaft to rotate with respect to the outer shaft when the inner shaft is rotatably locked to the outer shaft. The connector may be configured to provide longitudinal movement between the inner shaft and the outer shaft such that the inner shaft can translate to activate lateral bending of the occlusion crossing device. The connector may include one or more of a luer lock, a valve connector, a joint fitting, and a gasket joint. The outer shaft may include a backbone that is configured to bend the occlusion crossing device upon application of a pushing force on the inner shaft, wherein the occlusion crossing device may be configured to bend toward the backbone in response to the pushing force such that a side of the outer shaft opposite the backbone expands. The occlusion crossing device may be configured to straighten or bend away from the backbone upon application of a pulling force on the inner shaft. The cutting tip may include an optical window therein configured to align with the OCT imaging element to enable imaging therethrough. The collar may further include an optical window configured to align with the optical window of the cutting tip when the locking mechanism is engaged. The optical window of the collar may be longitudinally aligned with one or more optical windows of the outer shaft. The inner shaft may be configured to operatively couple to a rotational driver to rotate the inner shaft relative to the outer shaft.

According to some embodiments, a method of operating an occlusion crossing device is described, where the occlusion crossing device including an inner shaft having cutting tip attached thereto and an outer shaft having a collar rotatably coupled thereto, the method including: placing the inner shaft within the outer shaft; engaging a locking feature of the collar to removably couple the outer shaft to the inner shaft; spinning the inner shaft while the locking feature is engaged so that the collar spins with the inner shaft; laterally bending the occlusion crossing device by translating the inner shaft relative to the outer shaft in a first axial direction while the locking feature is engaged; and straightening the occlusion crossing device by translating the inner shaft relative to the outer shaft in a second axial direction while the locking feature is engaged.

In some variations, the method may further include laterally bending the occlusion crossing device by further translating the inner shaft relative to the outer shaft in the second axial direction while the locking feature is engaged. One or more keyways of the collar may capture one or more keys of a drill tip body coupled to the inner shaft therein when the locking feature is engaged such that the inner shaft can be translated relative to the outer shaft in the second axial direction to bend the occlusion crossing device. Translating the inner shaft relative to the outer shaft in the first axial direction may cause the occlusion crossing device to bend a first lateral direction, and translating the inner shaft relative to the outer shaft in the second axial direction may cause the occlusion crossing device to bend a second lateral direction opposite the first lateral direction. The method may further include removing the inner shaft from the outer shaft by: stopping spinning of the inner shaft; disengaging the locking feature by rotating inner shaft less than one full rotation; and translating the inner shaft relative to the outer shaft in the second axial direction until the inner shaft is removed from a lumen of the outer shaft. The method may further include removing the inner shaft from the outer shaft by: stopping spinning of the inner shaft; and translating the inner shaft relative to the outer shaft in the second axial direction to disengage the locking feature and remove the inner shaft from the outer shaft. The locking feature may be engaged when the inner shaft is spinning in a first rotational direction, the method further including: rotating the inner shaft in a second rotational direction; and translating the inner shaft relative to the outer shaft in the second axial direction to remove the inner shaft from a lumen of the outer shaft. One or more keyways may capture one or more keys therein when the locking feature is engaged. The method may further include disengaging the locking feature by releasing the one or more keys from the one or more keyways. The one or more keyways may include an angled undercut edge configured to urge the one or more keys out of the one or more keyways to disengage the locking feature. The one or more keyways may include an undercut edge configured to retain the one or more keys within the one or more keyways when the inner shaft is rotated relative to the outer shaft in a first rotational direction, and wherein the one or more keyways may include a gap configured to allow the one or more keys to escape the one or more keyways when the inner shaft is rotated relative to the outer shaft in a second rotational direction and translated in a second axial direction relative to the outer shaft. The method may further include capturing images outside of the occlusion crossing device using an optical coherence tomography (OCT) imaging element coupled to the inner shaft. One or more of the outer shaft, the collar, and the inner shaft may include a window to allow capturing of the images outside of the occlusion crossing device.

According to some embodiments, an occlusion crossing device includes: an outer shaft; a rotatable inner shaft comprising a distal cutting tip; and a collar rotatably attached to the outer shaft and configured to removably couple the inner shaft within the outer shaft, wherein the collar includes a locking feature configured such that: when the locking feature is engaged: the collar is rotatable with the inner shaft relative to outer shaft, translation of the inner shaft relative to the outer shaft in a first axial direction causes the occlusion crossing device to bend in a first lateral direction, and translation of the inner shaft relative to the outer shaft in a second axial direction causes the occlusion crossing device to bend in a second lateral direction opposite the first lateral direction or to straighten; and when locking feature is disengaged, the inner shaft is removable from within the outer shaft.

In some variations, the occlusion crossing device may further include an optical coherence tomography (OCT) imaging element coupled to the inner shaft. One or more of the outer shaft, the collar, and the inner shaft may include a window to allow capturing of the images outside of the occlusion crossing device. The outer shaft may include a backbone that is configured to bend the occlusion crossing device upon translation of the inner shaft when the locking feature is engaged. The occlusion crossing device may be configured to bend toward the backbone upon translation of the inner shaft in the first axial direction and bend away from the backbone upon translation of the inner shaft in the second axial direction. The outer shaft may include stop elements that limit bending in the first lateral direction and the second lateral direction. The first axial direction may be in a distal direction and the second axial direction is in a proximal direction. The collar may include an undercut edge configure to engage with the inner shaft to limit translation of the inner shaft in the second axial direction when the locking feature is engaged. The locking feature may be configured to disengage by rotating the inner shaft relative to the outer shaft by less than a full rotation and translating the inner shaft relative to the outer shaft in the second axial direction. The locking feature may be configured to disengage by stopping rotation of the inner shaft and translating the inner shaft relative to the outer shaft in the second axial direction. The locking feature may be configured to be engaged when the inner shaft is rotated in a first rotational direction, wherein the locking feature is configured to disengage by rotating the inner shaft relative in a second rotational direction and translating the inner shaft relative to the outer shaft in the second axial direction. The occlusion crossing device may further include a handle having a connector configured to rotatably lock the inner shaft to the outer shaft, wherein the connector allows the inner shaft to rotate with respect to the outer shaft when the inner shaft is rotatably locked to the outer shaft. The connector may be configured to provide longitudinal movement between the inner shaft and the outer shaft such that the inner shaft can translate to activate lateral bending of the occlusion crossing device. The connector may include one or more of a luer lock, a valve connector, a joint fitting, and a gasket joint. The inner shaft may include a stop configured to engage with the collar to limit translation of the inner shaft in the first axial direction.

These and other aspects and advantages are described herein.

BRIEF DESCRIPTION OF THE DRAWINGS

FIGS. 1A-3B show an occlusion crossing device having a selective bending feature.

FIGS. 4A-5C show an occlusion crossing device having separable inner and outer shafts.

FIGS. 7A-7B show an exemplary method for detecting the position of the driveshaft of a catheter.

FIGS. 14A-14C show the distal portion of another embodiment of an occlusion crossing device.

FIGS. 20A-20B show another exemplary tip for use with an occlusion crossing device.

FIGS. 21A-21B show another exemplary tip for use with an occlusion crossing device.

FIG. 22A shows a side view, FIG. 22B shows a perspective exploded view, and FIG. 22C shows a longitudinal section view of the occlusion-crossing device.

FIGS. 23A-23C show another exemplary occlusion crossing device having a selective bending support. FIG. 23A shows a side view, FIG. 23B shows a perspective exploded view, and FIG. 23C shows a longitudinal section view of the occlusion-crossing device.

FIGS. 24A-24C show another exemplary occlusion crossing device having a selective bending support. FIG. 24A shows a side view, FIG. 24B shows a perspective exploded view, and FIG. 24C shows a longitudinal section view of the occlusion crossing device.

FIGS. 25A and 25B show different views of an exemplary collar that may replace the collar of the occlusion crossing device shown in FIGS. 24A-24C.

FIGS. 26A-26C show another exemplary occlusion crossing device having an angled outer shaft tip. FIG. 26A shows a side view, FIG. 26B shows a perspective exploded view, and FIG. 26C shows a longitudinal section view of the occlusion crossing device.

FIGS. 28A and 28B show perspective views of an exemplary selective bending support for an occlusion crossing device.

FIGS. 29A and 29B show perspective views of another exemplary selective bending support for an occlusion crossing device.

FIGS. 30A and 30B show perspective views of an exemplary selective bending feature for an occlusion crossing device.

FIGS. 31A and 31B show examples of occlusion crossing apparatuses; FIG. 31A show a side perspective view of an occlusion crossing apparatus in a bent configuration; FIG. 31B shows a central cross-section through the device of FIG. 31A.

FIG. 33A is slightly deflected, while each of FIGS. 33B and 33C are progressively more deflected.

FIGS. 34A-34D illustrate show left side, back, right side, and front views, respectively, of the distal end of one example of an apparatus (occlusion crossing apparatus) in which the inner shaft is distally extended to engage the outer shaft.

FIG. 35 is a sectional view through one example of an occlusion crossing apparatus (system) showing the inner shaft with a fluted distal end and an outer shaft, where the inner and outer shafts are engaged.

FIGS. 38A-38D show right side, back, left side, and front views, respectively, of one example of a distal end region of an inner shaft.

FIGS. 41A and 41B show an example of a catheter device with an outer shaft adapted for collecting images within a blood vessel. FIG. 41B shows a close up of a portion of FIG. 41A.

FIGS. 43A-43I show another variation of a catheter device having a locking feature for the collar to rotate with the drill tip body and the inner drive shaft: FIG. 43A shows a side view of the catheter device in an assembled state; FIG. 43B shows an exploded side view of the catheter device; FIG. 43C shows a perspective view of the collar illustrating surface features on the collar; FIG. 43D shows another perspective view of the collar; FIG. 43E shows a close-up view of the collar rotatably coupled to the outer shaft; FIG. 43F shows a close-up view of a distal portion of the outer shaft; FIG. 43G shows a close-up view of the collar and a drill tip body of the catheter device; FIG. 43H shows a close-up view of the drill tip body coupled to the collar; and FIG. 43I shows a close-up view of the collar and a distal portion of the outer shaft illustrating features for rotatably coupling the collar and the outer shaft.

FIGS. 44A-44I show a further variation of a catheter device having a locking feature for the collar to rotate with the drill tip body and the inner drive shaft: FIG. 43A shows a side view of the catheter device in an assembled state; FIG. 43B shows an exploded side view of the catheter device; FIG. 44C shows a perspective view of the collar; FIG. 44D shows a perspective view of the drill tip body; FIG. 44E shows another perspective view of the collar illustrating a keyway feature for rotationally coupling the collar to the drill tip body; FIG. 44F shows the collar coupled to the drill tip body; FIG. 44G shows the collar and a distal portion of the outer shaft illustrating features for rotatably coupling the collar and the outer shaft; FIG. 44H shows the collar rotatably coupled to the outer shaft; and FIG. 44I shows a distal portion of the outer shaft.

FIGS. 45A-45D show yet another variation of a catheter device having a locking feature for the collar to rotate with the drill tip body and the inner drive shaft: FIG. 45A shows a side view of the catheter device in an assembled state; FIG. 45B shows an exploded side view of the catheter device; FIG. 45C shows a perspective view of the collar; and FIG. 45D shows a perspective view of the collar engaged with the drill tip body.

FIGS. 46A-46D show a further variation of a catheter device having a locking feature for the collar to rotate with the drill tip body and the inner drive shaft: FIG. 46A shows a side view of the catheter device in an assembled state; FIG. 46B shows an exploded side view of the catheter device; FIG. 46C shows a perspective view of the collar; and FIG. 46D shows a perspective view of the collar engaged with the drill tip body.

FIGS. 47A-47C show a scaffold configured for unidirectional bending: FIG. 47A shows a side of the scaffold having a backbone; FIG. 47B shows a side of the scaffold opposite the backbone; and FIG. 47C shows a close-up view of bending features of the scaffold.

FIGS. 48A-48E show a scaffold configured for bidirectional bending: FIG. 48A shows a close-up view of bending features of the scaffold; FIG. 48B shows a side of the scaffold opposite the backbone as the scaffold is bending toward the backbone; FIG. 48C shows a side of the scaffold having the backbone as the scaffold is bending toward the backbone; FIG. 48D shows a side of the scaffold having the backbone as the scaffold is bending away form the backbone; and FIG. 48E shows a side of the scaffold opposite the backbone as the scaffold is bending away form the backbone.

DETAILED DESCRIPTION

Figure 1A:
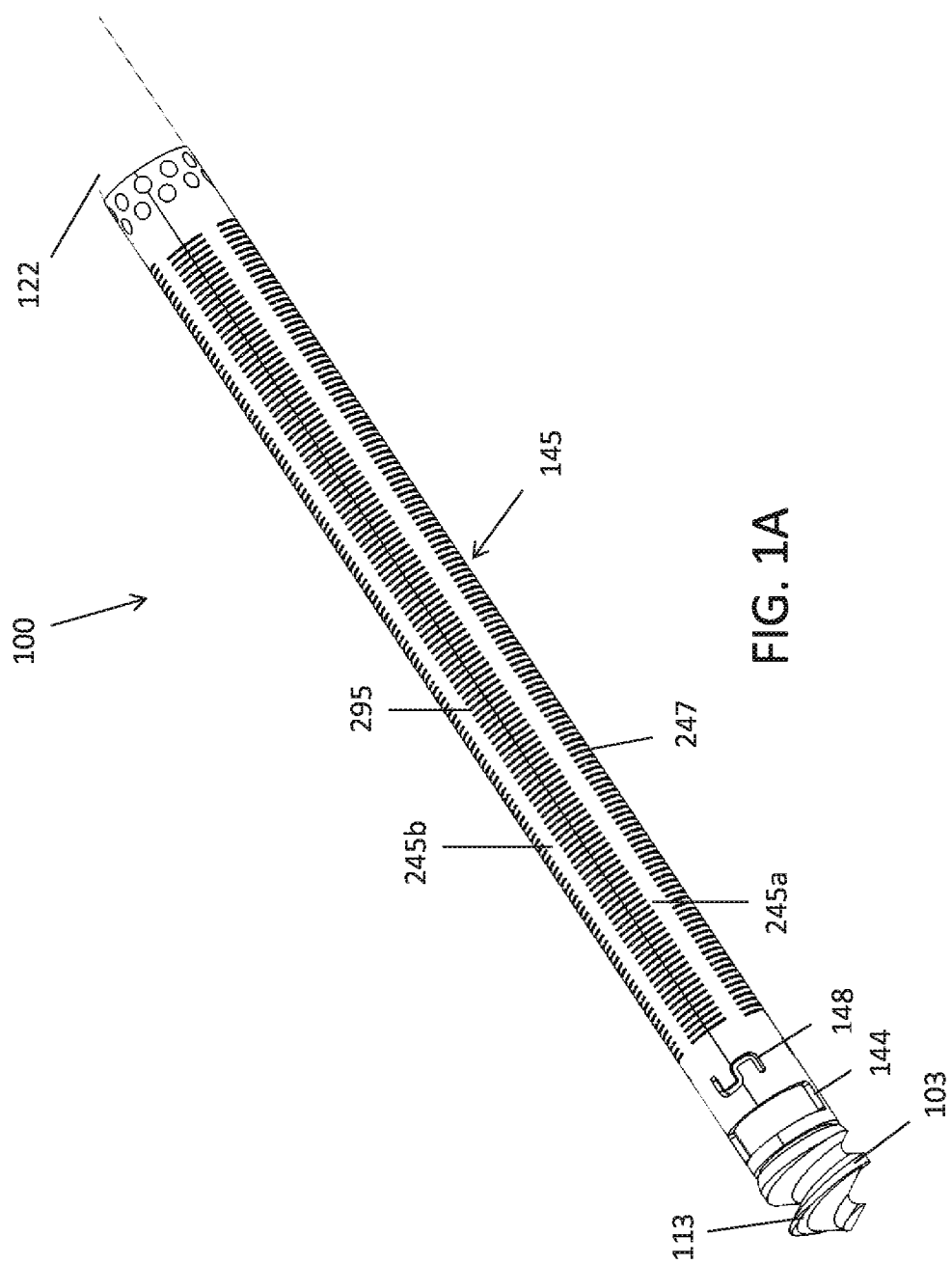
Figure 1D:
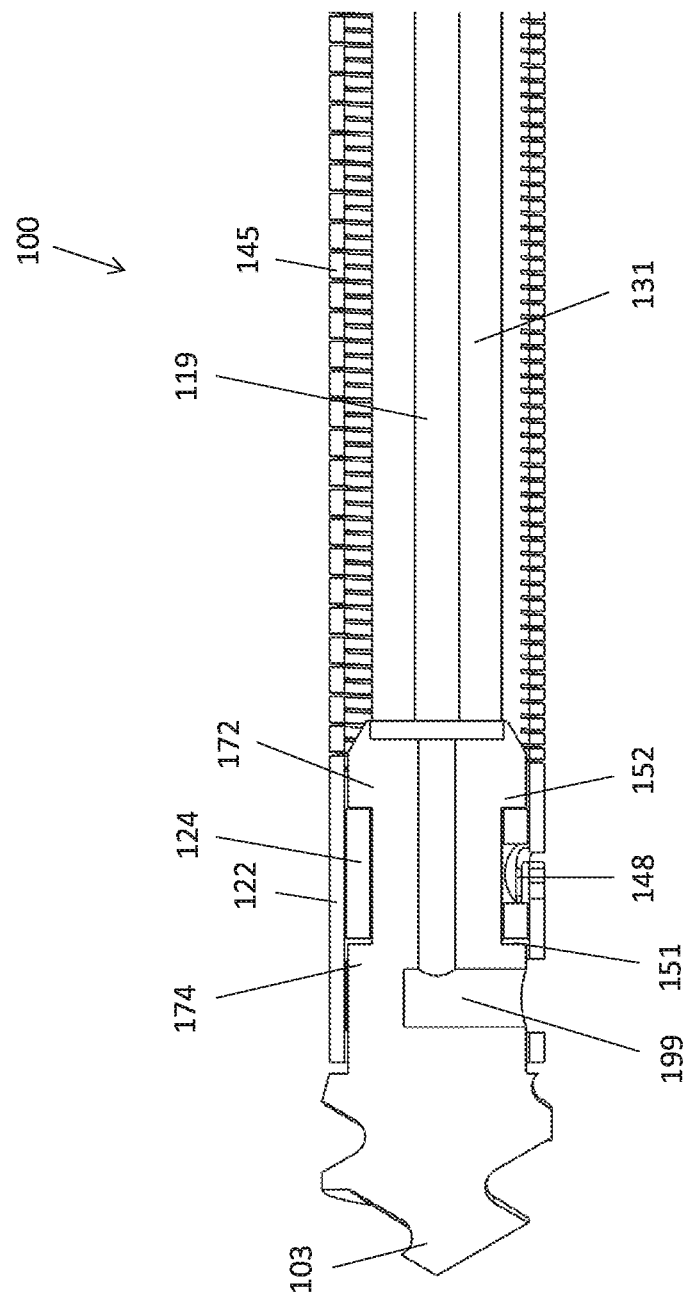

Described herein are occlusion-crossing apparatuses (e.g., systems and devices) having a low profile so as to be usable in small-diameter arteries and coronary arteries, e.g., through a 5 French catheter or smaller. In general, the devices described herein can have on-board imaging, such as optical coherence tomography (OCT) imaging. The optical fiber for OCT imaging can extend substantially along the central axis of the device, thereby decreasing the profile of the device and allowing for rotation at high speeds. The devices can also include a rotatable pointed tip, allowing for forward drilling. In some embodiments, the device can include an articulating distal end to enable steering of the device.

For convenience, these apparatuses may generally be referred to as catheters or occlusion crossing catheters. It is to be understood that these catheters may include both an outer shaft and a concentrically arranged (and removable) inner shaft.

Referring to FIGS. 1A-3B, in one embodiment, an exemplary catheter 100 includes an outer shaft 122 and an inner shaft 131 (also referred to as an inner driveshaft) connected to a distal drill tip 103 (also referred to herein as a tip body). The inner shaft 131 can be configured to rotate with respect to the outer shaft 122 to rotate the drill tip 103. The elongate outer shaft 122 can be hollow and can have an inner diameter of approximately 1 mm and an outer diameter of approximately 1.5 mm. In some embodiments, at least a portion of the outer shaft 122 is flexible. For example, a portion of the outer shaft 122 may include a flexible tube. In some embodiments, at least a portion of the outer shaft 122 can have a coiled construction, whereby the coils are wound by laying one coil over another. For example, the outer shaft 122 can include at least two coil layers. Further, the coil layers can be counter-wound, such that one coil layer, such as the inner coil layer, has a left hand lay and another layer, such as the outer coil layer, has a right hand lay. The coil can provide torque in the direction that tightens the outer layer, cinching down on the inner layer. A third counter wound coil can be added to generate torque in both directions. In another embodiment, at least a portion of the outer shaft 122 is made of a braided material (e.g., wire or mesh). In yet another embodiment, at least a portion of the outer shaft 122 can be a laser-cut tube. In some embodiments, the flexible portion is made of multiple materials. For example, the flexible portion may include a metal support structure that is at least partially surrounded by a polymeric material. The support structure (e.g., coiled, braided and/or laser cut material) may be at least partially laminated with (e.g., fused with) the polymeric material. For example, the support structure (e.g., coiled, braided and/or laser cut material) may be embedded within (e.g., substantially covered with) the laminate material. In some embodiments, the laminate material (e.g., substantially) completely covers all surfaces of the support structure, making the flexible portion of the outer shaft (e.g., substantially) impervious to fluids. In some embodiments, the outer shaft 122 includes a polymeric liner inside the braided portion of the outer shaft to reduce friction with the rotating inner shaft 131. The outer shaft 122 can further include one or more imaging windows 144 at a distal end thereof, which is described further in detail herein A bushing 124 (see FIG. 1D) can be attached to the outer shaft 122, such as through a tab and slot mechanism 148. The bushing 124 can act as a bearing surface relative to the inner shaft or drill tip 103. Further, the bushing 124 can include edges or lips 151, 152 on either side configured to interact with the inner driveshaft 131 or the drill tip 103, as discussed further below.

The drill tip 103 can be configured, for example, to separate, dissect, or shred tissue. In some embodiments, the drill tip 103 can include sharp spiraling flutes 113 that come to a point in the center of the device. Further, the flutes 113 can be angled such that they have sharper edges when rotated in one direction than in another direction. As a result, the drill tip 103 with flutes 113 can have an active and passive modes depending upon the direction of rotation of the drill tip 103. In passive mode, the drill tip 103 with flutes 113 can be less aggressive, providing blunt dissection of tissue. In active mode, the drill tip 103 with flutes 113 can be more aggressive, providing cutting and auguring to make its way through harder material.

The inner driveshaft 131 (see FIG. 1D) can be connected to the distal drill tip 103 and can extend down the center of the outer shaft 122. The inner driveshaft 131 can be configured to rotate in either a single direction or in both the clockwise and counterclockwise directions so as to rotate the drill tip 103 relative to the shaft 122 (about the bushing 124) in either a single direction or in the clockwise or counterclockwise direction. Annular rings 174, 172 can be positioned around a distal portion of the inner driveshaft 131 and/or the drill tip 103. The rings 174, 172 can be positioned against the edges 151, 152 of the bushing 124. The annular bushing 124 can allow relative rotation of the inner driveshaft 131 relative to the bushing 124 while preventing axial movement (and allowing for articulation in some embodiments, as described further below). In some embodiments, the inner shaft 131 is configured to rotate in only a single direction. In some embodiments, the inner shaft 131 is configured to rotate in both directions. In some cases, the catheter device includes a control button (or other type of switch) to control the direction of rotation of the inner shaft. In some embodiments, the control button is on the handle.

The occlusion crossing devices described herein can include at least one bendable portion to allow the occlusion crossing device to maneuver within a vessel before, during and/or after crossing an occlusion. For example, a distal end of the occlusion crossing device can be configured to bend laterally in a controlled manner to direct the drill tip at a desired location within the vessel. In some cases, this bending is achieved through an articulation feature that includes a backbone. The backbone may be a relatively inflexible portion along a length of the device, which biases deflection of the device in one or more lateral directions. In some cases, the backbone may be continuous rib spanning across at least part of the length of the device. In some cases, the backbone is part of the outer shaft. The device may include one backbone or multiple backbones. In some designs, two or more backbones may provide more lateral stability compared one backbone.

In the example of FIGS. 1A-3B, catheter 100 can include a selective bending feature 145 at a distal portion of the outer shaft 122 selective bending feature. The selective bending feature 145 can be configured to control lateral bending of the distal portion of the outer shaft. The selective bending feature 145 can be coupled to a flexible portion of the outer shaft (e.g., braided or coiled portion), which can include a support structure (e.g., coiled, braided and/or laser cut material) as described herein. As shown in FIGS. 1A and 1B, the selective bending feature 145 can include one or more backbones 245a,b and a series of circumferential cuts 247. The circumferential cuts can extend circumferentially partially around the outer shaft between the one or more backbones. In some embodiments, the circumferential cuts can be formed by laser cutting. In some cases, the circumferential cuts extend though the thickness of the outer shaft. In some cases, the circumferential cuts extend partially though the thickness of the outer shaft. When a force is applied to the inner shaft 131 longitudinally and distally, the one or more backbones 245a,b can cause the outer shaft to preferentially bend laterally toward the backbones 245a,b. The one or more backbones can be positioned on only one side of the catheter (e.g., span less than 180 degrees, less than 150 degrees, or less than 90 degrees). In some embodiments, and as shown in FIG. 1A, a series of small circumferential cuts 295 can extend between the two backbones 245a,b in order to provide added flexibility during bending. The circumferential cuts 247, 295 can be configured as incomplete rings or spirals about the outer shaft 122. Referring to FIG. 1B, in some embodiments, the circumferential rings 247 can include one or more breaks 297a,b therein designed to provide additional tensile strength and compression resistance for the selective bending feature 145.

The selective bending feature 145 can be attached to the inner shaft 131 such that movement of the driveshaft 131 can activate the selective bending feature. Further, in some embodiments, a handle 200 (see FIGS. 1C, 2B and 3B) can be used to activate movement of the inner driveshaft 131. In some embodiments, the handle 200 includes one or more activators (e.g., buttons, levers, switches) for controlling the speed and/or direction of the inner driveshaft 131. In some cases, the handle 200 includes one or more activators (e.g., buttons, levers, switches) for controlling distal and proximal movement of the inner driveshaft 131 relative to the outer shaft 122.

Figure 2A:
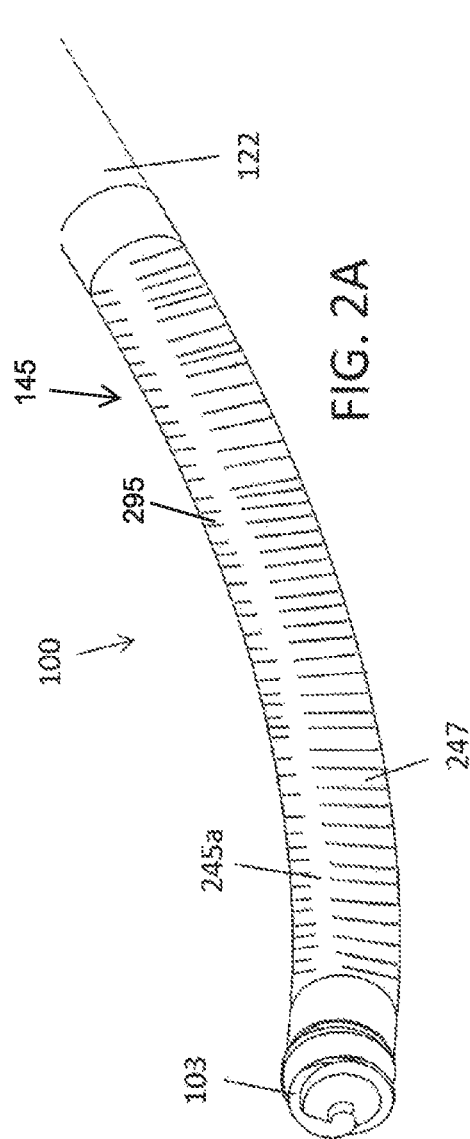
Figure 2B:
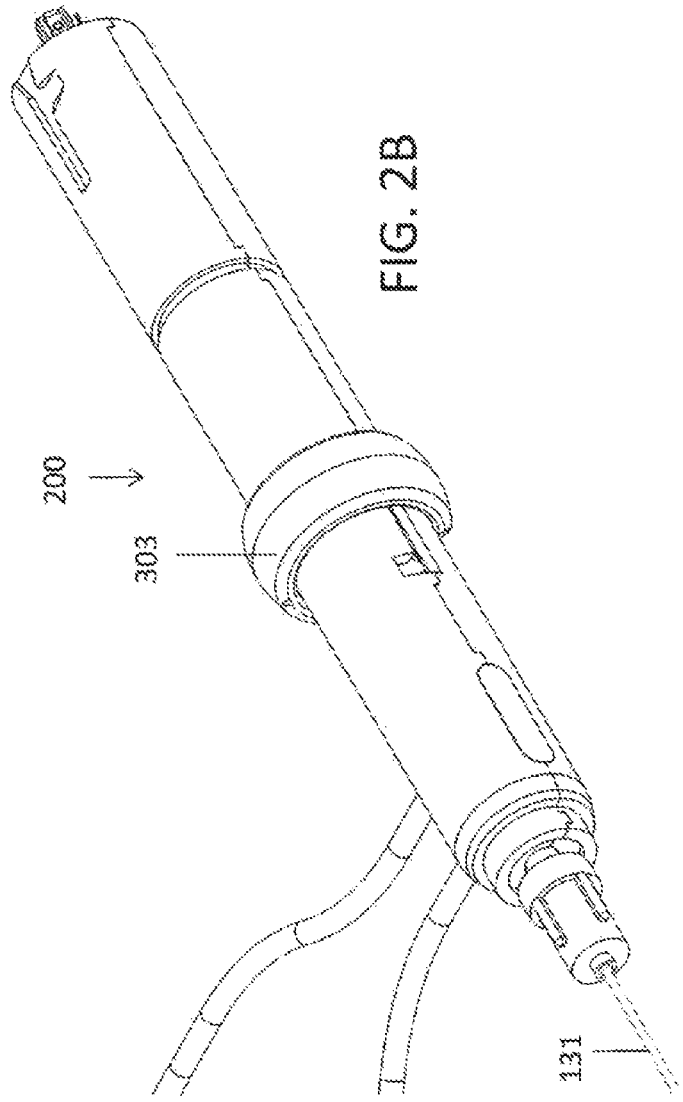

Referring to FIGS. 2A-2B, as the driveshaft 131 is pushed distally, the annular ring 172 can push distally on the proximal lip 152 of the bushing 124 (see FIG. 1D), causing the circumferential cuts 247 to spread apart or open while the backbones 245a,b maintain their length (and the circumferential cuts 295 move closer together). As a result, the selective bending feature 145 can bend towards the backbones 245a,b. As shown in FIG. 2B, this bending mechanism can be activated on the handle 200, such as by moving a ring 303 (also referred to as a slider) distally and/or pushing or moving a button or lever.

Likewise, referring to FIGS. 3A-3B, as the driveshaft 131 is pulled proximally, the annular ring 174 can hit the distal lip 151 of the bushing 124. As further distal force is applied by the driveshaft 131, the circumferential cuts 247 can begin to move closer together and/or the material between the cuts 247 can overlap while the backbones 245a,b maintain their length (and the cuts 295 move further apart). As a result, the selective bending feature 145 can bend towards the circumferential cuts 247 and away from the backbones 245a,b. As shown in FIG. 3B, this bending mechanism can be activated on the handle 200, such as by moving the ring 303 proximally and/or pushing or moving a button or lever.

The bending movement of the selective bending feature 145 can advantageously allow the device 100 to be steered when used in the vessel, such as for re-entry if the drill tip extends out of the occlusion or lumen. In some embodiments, the catheter 100 can be configured to bend in only one direction by either pushing or pulling on the driveshaft 131 and return to the straight configuration shown in FIG. 1A by movement of the driveshaft 131 in the opposite direction.

The catheter 100 can further include an imaging element 199 attached to the driveshaft 131 and configured to rotate therewith. The imaging element 199 may include one or more sensors for collecting image data (e.g., light). The imaging element 199 can be the distal end of an OCT fiber 119 extending down the center of the driveshaft 131. The imaging element 199 can provide imaging (through windows 144) as the catheter 100 is used in the vessel, thereby assisting in occlusion crossing.

Figure 15:
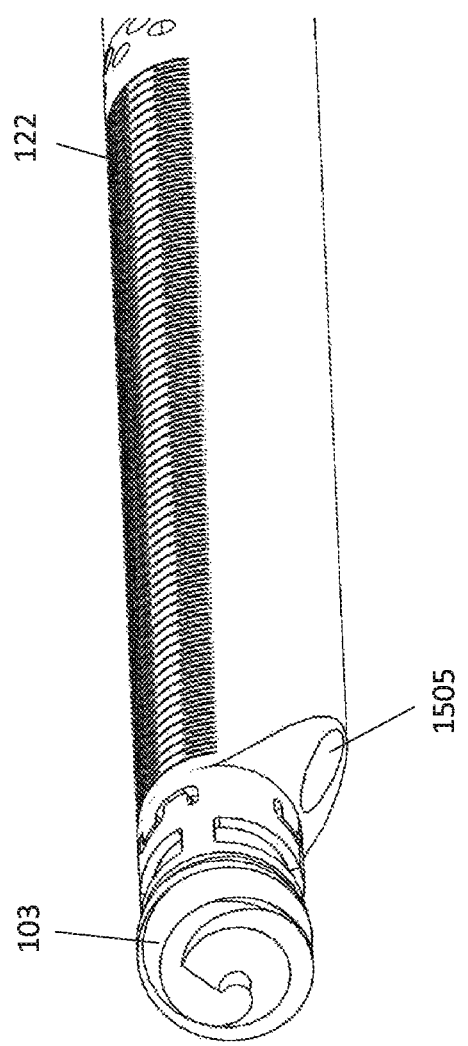
FIG. 15 shows the occlusion crossing device FIGS. 1A-3B with a monorail guidewire lumen.

Referring to FIG. 15, in some embodiments, a monorail guidewire lumen 1505 can extend along the outer shaft 122.

The guidewire lumen 1505 can run, for example, between the two backbones 245a,b so as to not add additional stiffness to the flexible area with the circumferential cuts 247. In some embodiments, the outer shaft includes more than one guidewire lumen. Thus, the outer shaft can define at least two lumens: a main lumen for the inner shaft and one or more guidewire lumens for a guidewire. These configurations can allow the inner shaft to remain in the main lumen of the outer shaft 122 while the guidewire (with any intervention devices (e.g., a balloon, stent, tube, medicament and/or other angioplasty device uses the guidewire lumen. In some cases, the inner shaft is still removable from the outer shaft so that the main lumen may also be used for a guidewire.

In some embodiments, the catheter 100 can be used with a sheath. The sheath can be hollow and include a hemostasis valve attached at the proximal end with a flush port on the side to facilitate flushing through the sheath. The sheath can also facilitate guidewire placement to the target site, particularly for embodiments of the catheter 100 that do not include a monorail guidewire lumen. That is, the catheter 100 can be used to cross the occlusion, the sheath can be placed thereover, the device removed, and then the guidewire can be introduced.

In some embodiments, the catheter devices described herein can be used for procedures other than occlusion crossing. For example, the catheter devices can be used for other atherectomy procedures, such as for placement of a balloon, stent, tube and/or medicament. In some cases, the catheter devices can be used as an imaging device. For example, the drill tip can be replaced with a blunter tip (i.e., not designed for occlusion crossing). In some cases, the inner shaft is replaced with a guidewire or other intervention device.

Alterative drill tip designs for catheter 100 are possible. In some embodiments, as described further below with respect to FIGS. 14A and 14B, the distal drill tip 103 can have a smooth angled surface that is non-fluted.

FIGS. 30A and 30B show an alternative selective bending feature 3045 according to some embodiments. The selective bending feature 3045 can include a proximal end 3007, a distal end 3008 and a lumen 3020 for accommodating an inner shaft (e.g. 113). The selective bending feature 3045 is similar to the selective bending feature 145 in that selective bending feature 3045 can be biased to bend toward the backbone 3055. That is, when a compressive load is placed on the selective bending feature 3045, the selective bending feature 3045 bends towards straight backbone 3055. Compared to selective bending feature 145, the selective bending feature 3045 can include one backbone 3055. The selective bending feature 3045 can further include cuts 3047 (e.g., laser cuts) having a jigsaw pattern that define tongue elements 3065a,b,c opposite the backbone 3055. In some embodiments, the jigsaw pattern includes holes 3075 where the cuts 3047 terminate at the backbone 3055. The tongue elements 3065a,b,c can have a tapered structure configured to dictate the amount of deflection of the selective bending feature 3045 in both directions. For example, the tongue elements 3065a,b,c can force the selective bending feature 3045 to lock with respect to each other, thereby keeping the selective bending feature 3045 aligned and resistant to twisting when under torsion when deflected. This can also prevent the selective bending feature 3045 from over-bending. As shown in FIGS. 30A and 30B, the inner diameter of the selective bending feature 3045 can include an annular ledge 3060 configured to mate with an end of the flexible portion of the outer shaft. The selective bending feature 3045 can be coupled to the flexible portion of the outer shaft using any technique, such as welding, adhesive, fastener(s), or a combination thereof.

Figure 16:
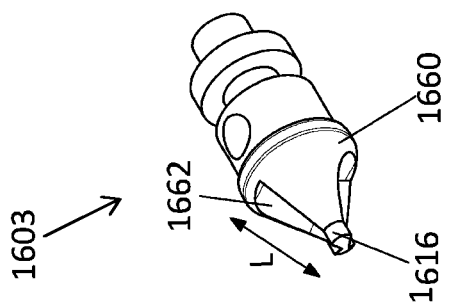
FIG. 16 shows an exemplary tip for use with an occlusion crossing device.
Figure 19B:
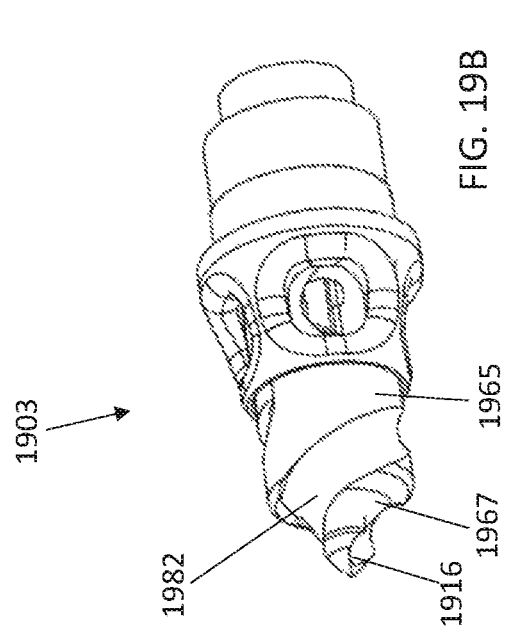
FIGS. 19A-19D show another exemplary tip for use with an occlusion crossing device.
Figure 19D:
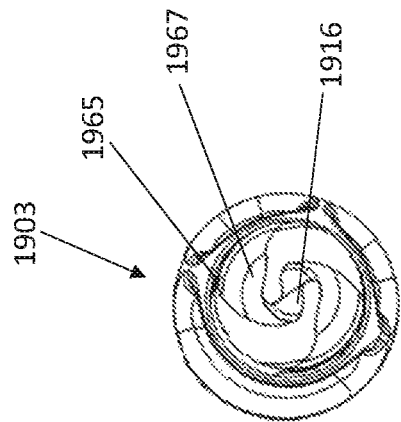
Figure 19A:
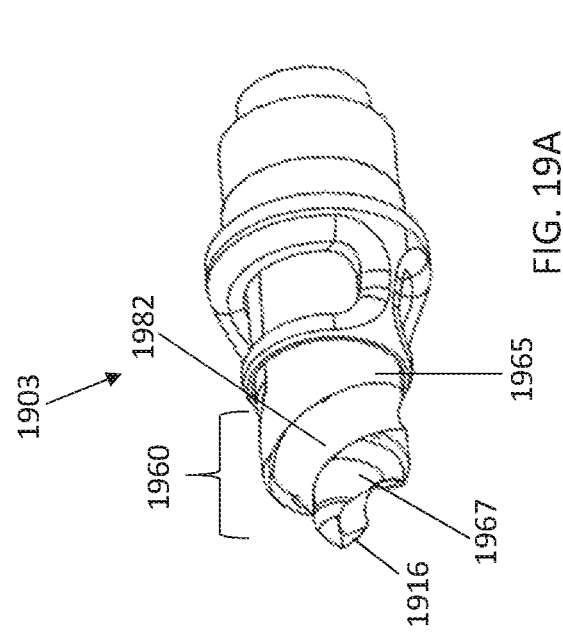
Figure 19C:
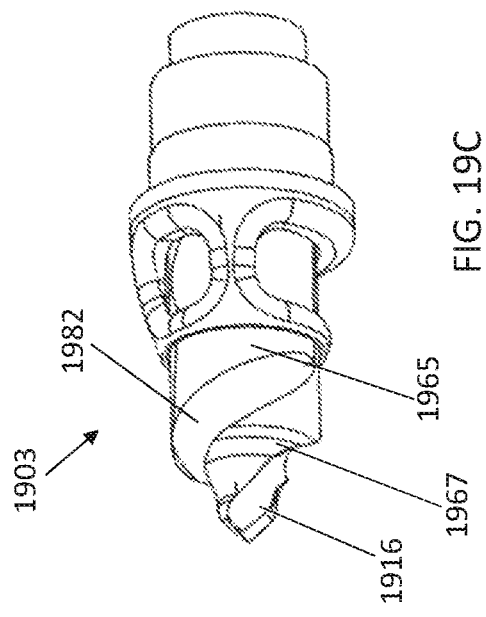

Further, referring to FIG. 16, in some embodiments, a distal drill tip 1603 (e.g., for use in place of drill tip 103) can include a cone-shaped body 1660 with a sharp central extension 1616 extending distally from the drill tip 1603. The central extension 1616 can be positioned in the center of the drill tip 1603 (e.g., along the central longitudinal axis of the tip 1603) and can function to create a pilot hole in the occlusion to guide the rest of the tip 1603 therethrough. The central extension 1616 can have diameter that is substantially smaller than the diameter of the rest of the drill tip 1603. For example, the diameter of the central extension 1616 can be 10-30%, such as 15%-25% of the diameter of the rest of the drill tip 1603. Similarly, the central extension 1616 can have a length that is approximately 10-30%, such a 15-35% of the total length L of the cone-shaped drill tip 1603. The central extension 1616 can be substantially cylindrical with a pointed drill tip thereon. The angle of the pointed tip can extend at between 15 and 75 degrees, such as between 20 and 60 degrees, such as between 30 and 45 degrees relative to the central longitudinal axis of the drill tip 1603. In some embodiments, having a minimum angle of 30 degrees at the pointed drill tip ensures that the drill tip 1616 does not cut into the sidewall of a lumen when traversing through a sharp curve (e.g., at the aortic bifurcation). In contrast, in some embodiments, having a maximum angle of 45 degrees ensures that the extension 1616 is able to drill into an occlusion (e.g., without deflecting off of the occlusion as can occur with a blunt tip). As shown in FIG. 16, the drill tip 1603 can further include two or more axially extending flutes 1662 along the cone-shaped body 1660 to create additional cutting edges as the drill tip 1603 is rotated through the occlusion. The flutes can continue into the extension 1616 to create side flutes therein.

Figure 17:
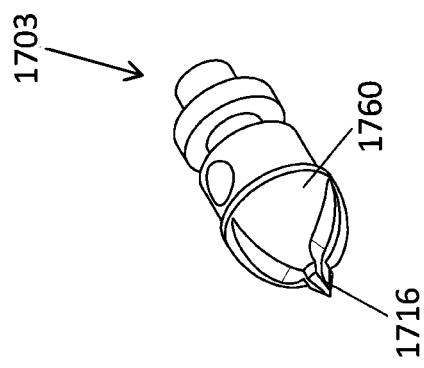
FIG. 17 shows another exemplary tip for use with an occlusion crossing device.

FIG. 17 shows another exemplary distal drill tip 1703 that is similar to distal drill tip 1603 except that the body 1760 is substantially bullet-shaped (or rounded, semi-circular). Further, the central extension 1716 can have a continuous taper from the distal tip to the body 1760 rather than having a cylindrical portion.

Figure 18:
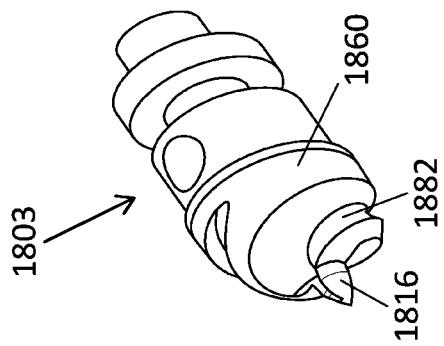
FIG. 18 shows another exemplary tip for use with an occlusion crossing device.

FIG. 18 shows another exemplary distal drill tip 1803 that is similar to distal tip 1703 except that the body 1860 includes one or more spiral flutes 1882 extending along the body 1760 and the extension 1816.

The drill tips 103, 1603, 1703, 1803 can have a diameter, for example, of between 4 French and 8 French (between 1⅓ mm and 2⅔ mm).

Referring to FIGS. 4A-5C, in another embodiment, an exemplary catheter 300 includes an inner shaft 311, an outer shaft 322, and a distal drill tip 303 connected to the inner shaft 311. Further, the outer shaft 322 can be separable from the inner shaft 311. For example, the inner shaft 311 can include one or more connectors that allow the outer shaft 322 to be removably coupled to the inner shaft 311. In some embodiments, the connector(s) is a luer connector, though other connectors such as valve connectors, joint fittings, and/or gasket joints may be used. The connector(s) may be located anywhere along the catheter. In some embodiments, the connector(s) is near the proximal end that allows attachment and detachment from a connector on a proximal end of the outer shaft 322, as described below with respect to handle 900.

In some embodiments, a distal portion 313 of the outer shaft 322 can be clear or transparent, such as made of a clear or transparent plastic, in order to allow imaging therethrough. In some embodiments, the outer shaft 322 can further include a preformed bend 329 therein to help orient or steer the device. A marker 315, such as a metal marker, can extend within the distal portion 313 to indicate the relative orientation of the catheter 300 when in use. For example, as shown in FIG. 4B, the innermost portion of the bend 329 can align with the marker 315.

Further, in some embodiments, the inner shaft 311 can move longitudinally within the hollow outer shaft 322 by sliding a ring on a handle (such as handle 200) connected to the catheter 300 to allow the inner shaft 311 to be exposed (as shown in FIGS. 4A-4B) or fully covered (as shown in FIGS. 5A-5C). In use, the inner shaft 311 can thus be extended out of the outer shaft to help drill through the occlusion and pulled in when dissection is not required (or when only blunt dissection is required). In some embodiments, the inner shaft 311 can be configured to be fixed at various points relative to the outer shaft 322 so as to vary the amount of exposed drill tip 103. Further, the shaft 311 can be fully removed from the outer shaft 322 to allow for placement of a guidewire therethrough.

Further, the device 300 can include an imaging element 399 similar to as described above with respect to device 100. The catheter 300 can be configured to image with the imaging element 399 both when the inner shaft 311 is extended distally out of the outer shaft 322 and when the inner shaft 311 is positioned within the outer shaft 322 (through the transparent distal portion 313).

The device 300 can include a drill tip 103 that is similar to any of the drill tips described above with respect to claim 100. The drill tips used for the device 300, however, can have a smaller diameter so as to fit through the outer shaft 322. For example, the diameter of the drill tips can be less than or equal to 7 French (less than or equal to 2⅓ mm) in diameter, such as between 1 mm and 2⅓ mm in diameter.

An exemplary drill tip 1903 for use with device 300 is shown in FIGS. 19A-19D. The drill tip 1903 is similar to drill tip 1803 except that the body 1960 is not continuously tapered, but rather includes a proximal cylindrical portion 1965 and a central tapered section 1967. The flutes 1982 extend through the cylindrical portion 1965, the central tapered section 1967, and the central extension 1916.

Another drill tip 2003 is shown in FIGS. 20A-20B. The drill tip 2003 is similar to drill tip 1903 except that it does not include any flutes. Rather, the drill tip 2003 includes a cylindrical body 2060 from which the central extension 2016 extends.

Another drill tip 2103 is shown in FIGS. 21A-21B. The drill tip 2103 is similar to drill tip 1603 except that the body 2160 is not continuously tapered, but rather includes a proximal cylindrical portion 2165 and a central tapered fluted section 2067. Further, the extension 2116 is continuously tapered.

The device 300 can further or alternatively include any of the features, materials, and/or dimensions described above with respect to device 100.

Referring to FIGS. 8A-10, in another embodiment, an exemplary catheter 800 can include both a separable inner shaft 811 and outer shaft 822 and a selective bending feature 845 on the distal end of the outer shaft 822.

Figure 8A:
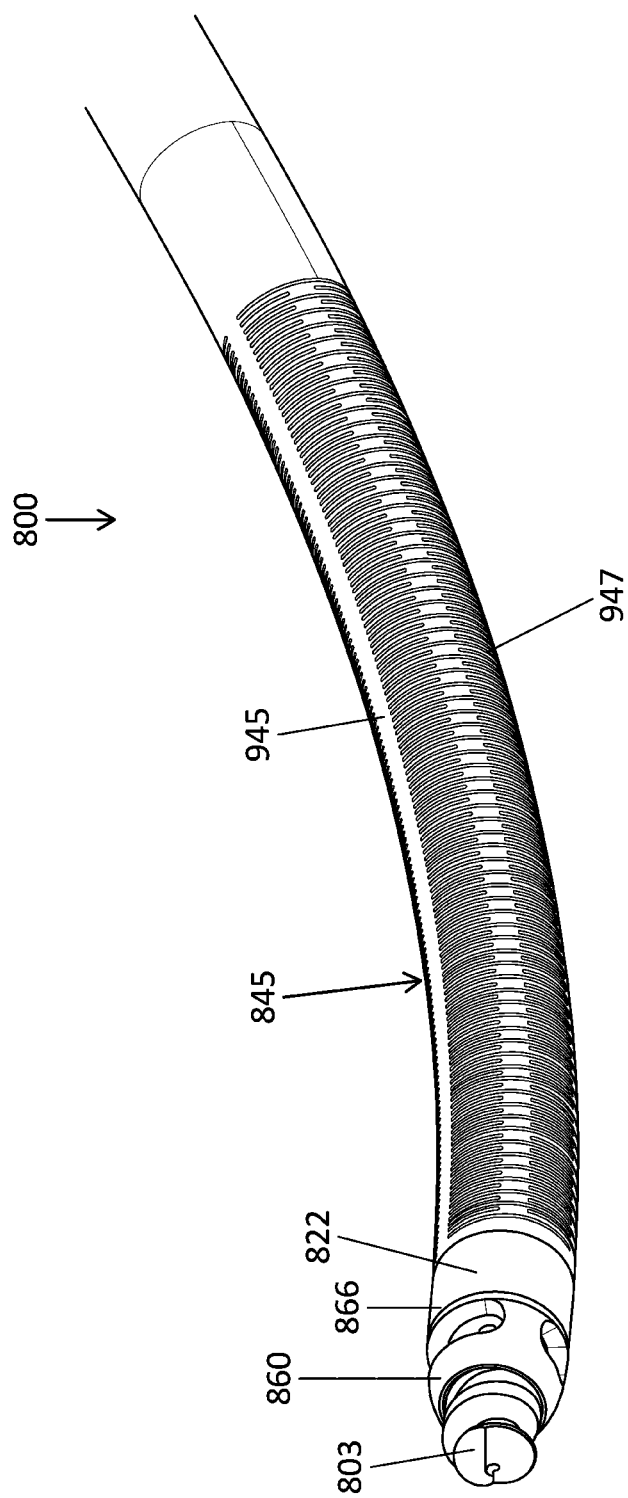
FIGS. 8A-8B show articulation of an occlusion crossing device having a selective bending feature and separable inner and outer shafts.
Figure 8B:
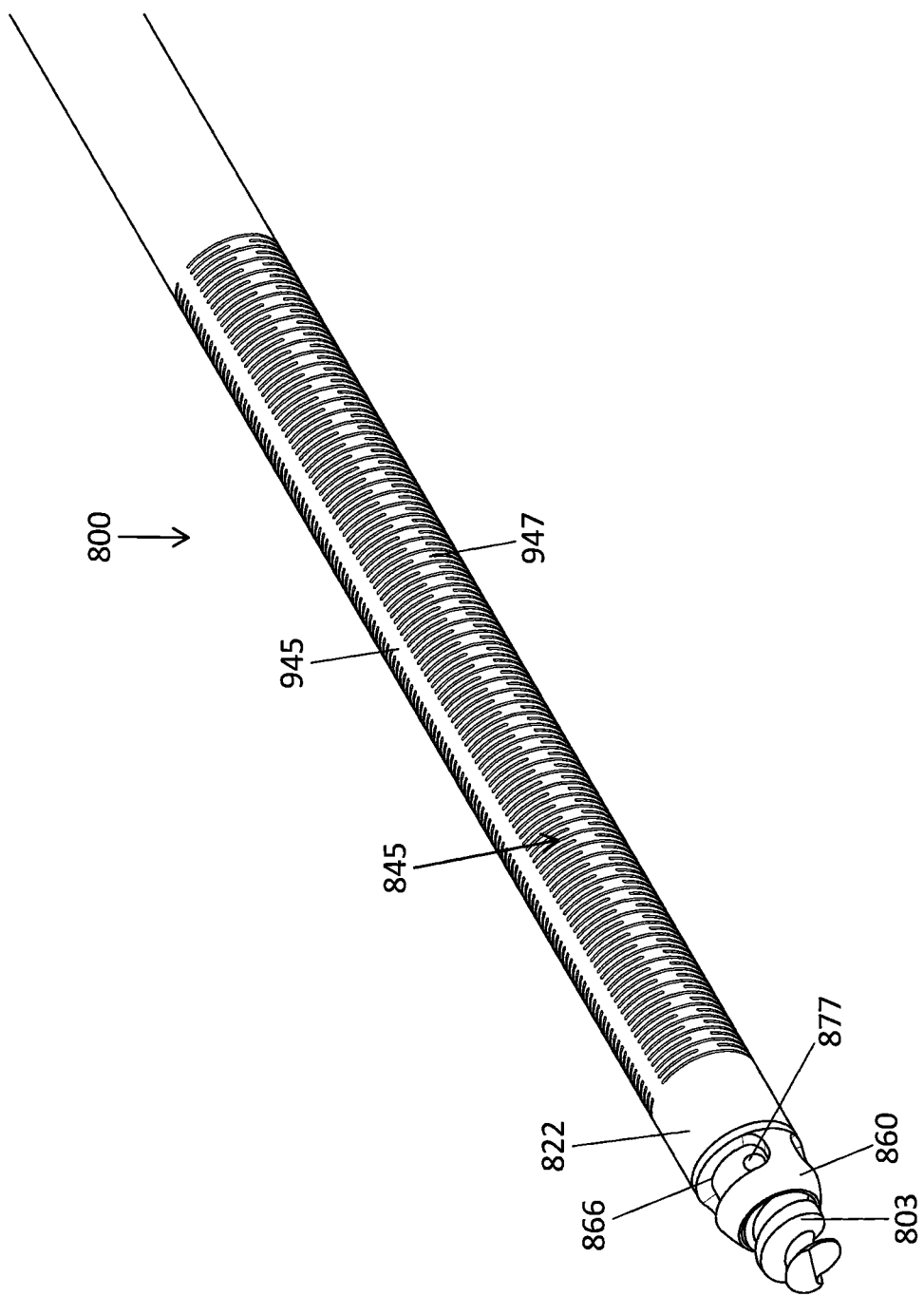
Figure 9A:
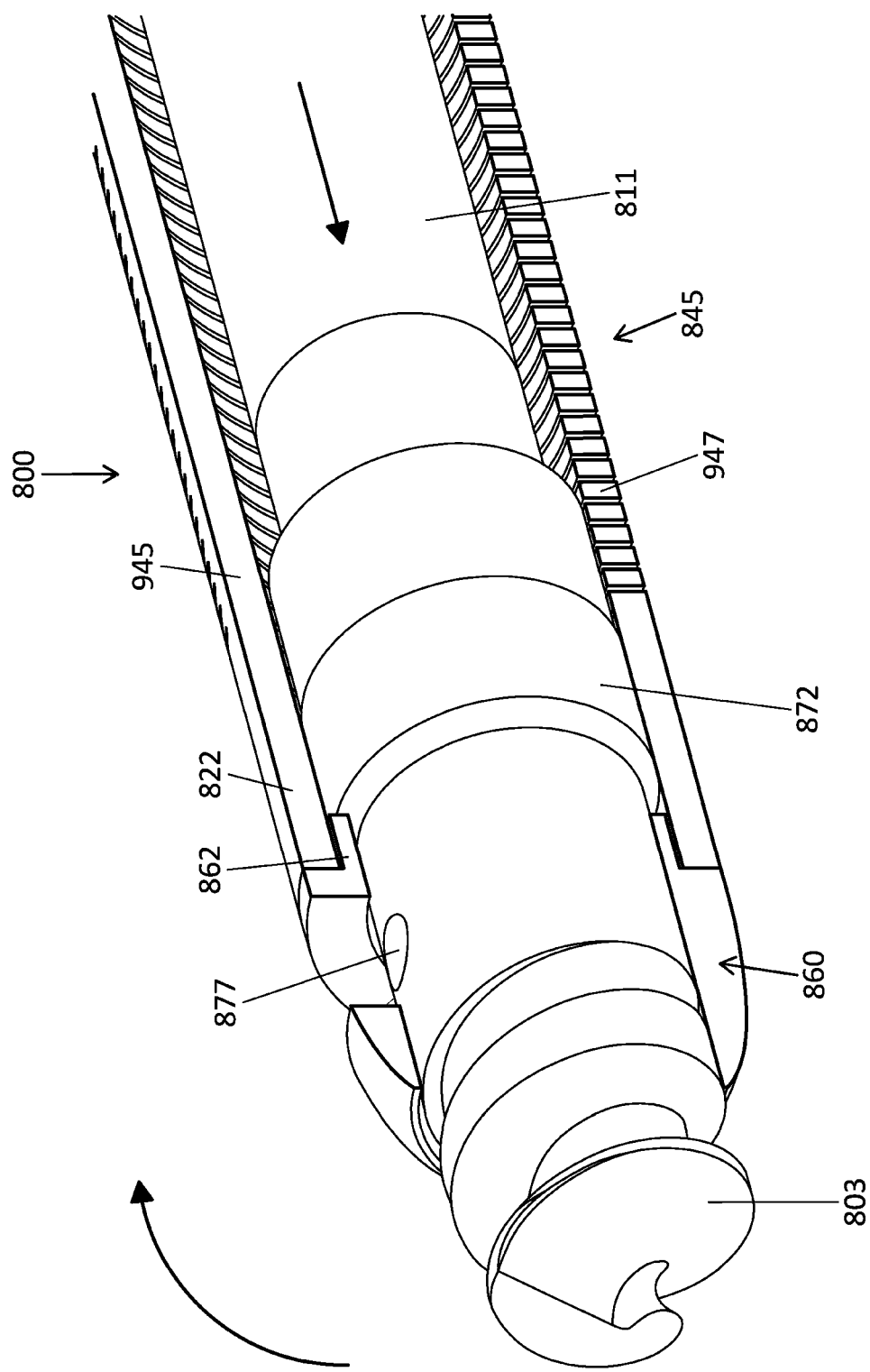
FIGS. 9A and 9B show the inner shaft of the occlusion crossing device of FIGS. 8A-8B positioned inside of the outer shaft for cutting and imaging.
Figure 9B:
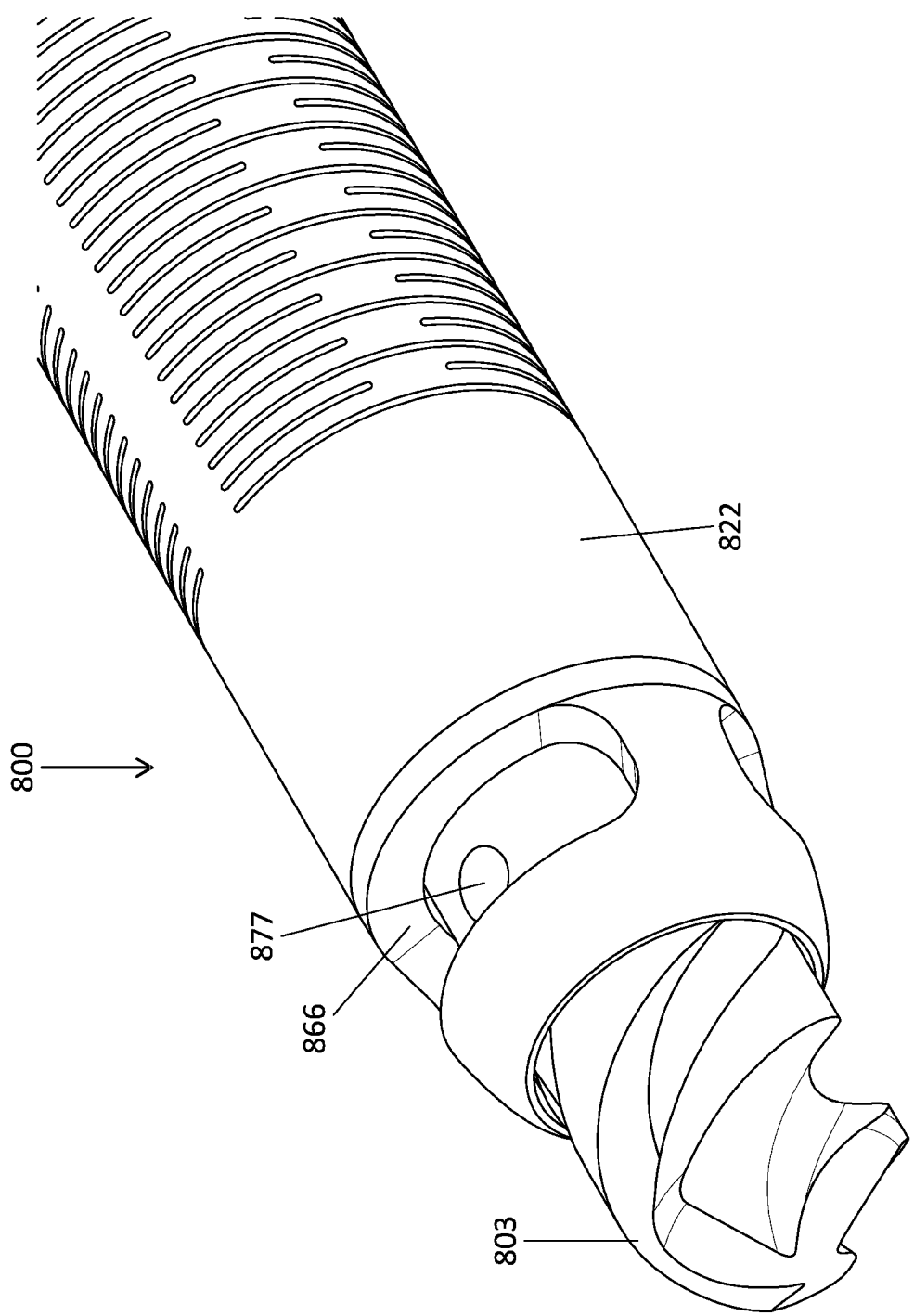

Referring to FIGS. 8A-8B, the selective bending feature 845 can include a backbone 945 and a series of circumferential cuts 947. Further, as shown in FIG. 9A, the outer shaft 822 can include a collar 860, which may be attached to the selective bending feature 845 of the outer shaft 822. The collar 860 can provide a shape to the distal end of the outer shaft 822 to facilitate maneuvering of the catheter in the vessel. For example, the collar 860 may have a tapered and/or curved outer surface. The collar may be considered an extension of the outer shaft 822. For example, the collar may be considered a distal end of the outer shaft, where the distal end (e.g., collar) can include an aperture for the drill tip 803 to extend through. The collar may be part of (e.g., integrally formed with) the outer shaft or may be a separate piece. In some embodiments, the collar is fixedly coupled to the outer shaft (e.g., by weld, fastener(s) and/or adhesive). In some embodiments, the collar is removably coupled to the outer shaft. In some embodiments, the collar engages with the outer shaft. In some cases, a portion of the collar radially overlaps (e.g., fits within) another portion of the outer shaft. For example, an inner ledge 862 of the collar 860 may fit within a distal portion of the selective bending feature of the outer shaft 822.

As described herein, the outer shaft can cooperate with the inner shaft to provide the biased bending of the distal end of the catheter. In the example of FIGS. 8A-10, the inner shaft 811 can be configured to move longitudinally with respect the outer shaft 822. The outer shaft 822 can include an inner ledge 862 configured to extend radially inwards relative to the outer shaft 822. Likewise, the inner shaft 811 can include an annular member 872, such as a plastic bearing, that has a greater diameter than the rest of the inner shaft 811. Thus, when the inner shaft 811 is pushed distally, the annular member 872 of the inner shaft 811 can push against the inner ledge 862 of the outer shaft 822 (e.g., of the collar 860). As a result, the outer shaft 822 can bend at the cuts 947 towards the backbone 945 (as shown by the arrows in FIG. 9A). For example, the force applied to the inner shaft 862 can cause the cuts 947 to expand such that the outer shaft 811 preferentially bends toward the backbone 945. This is because the backbone 945 can be relatively rigid compared to the side of the outer shaft 811 with cuts 947. If the outer shaft includes multiple backbones (e.g., FIGS. 1A-3B), the outer shaft can preferentially bend toward the side of the outer shaft having the backbones.

Figure 10:
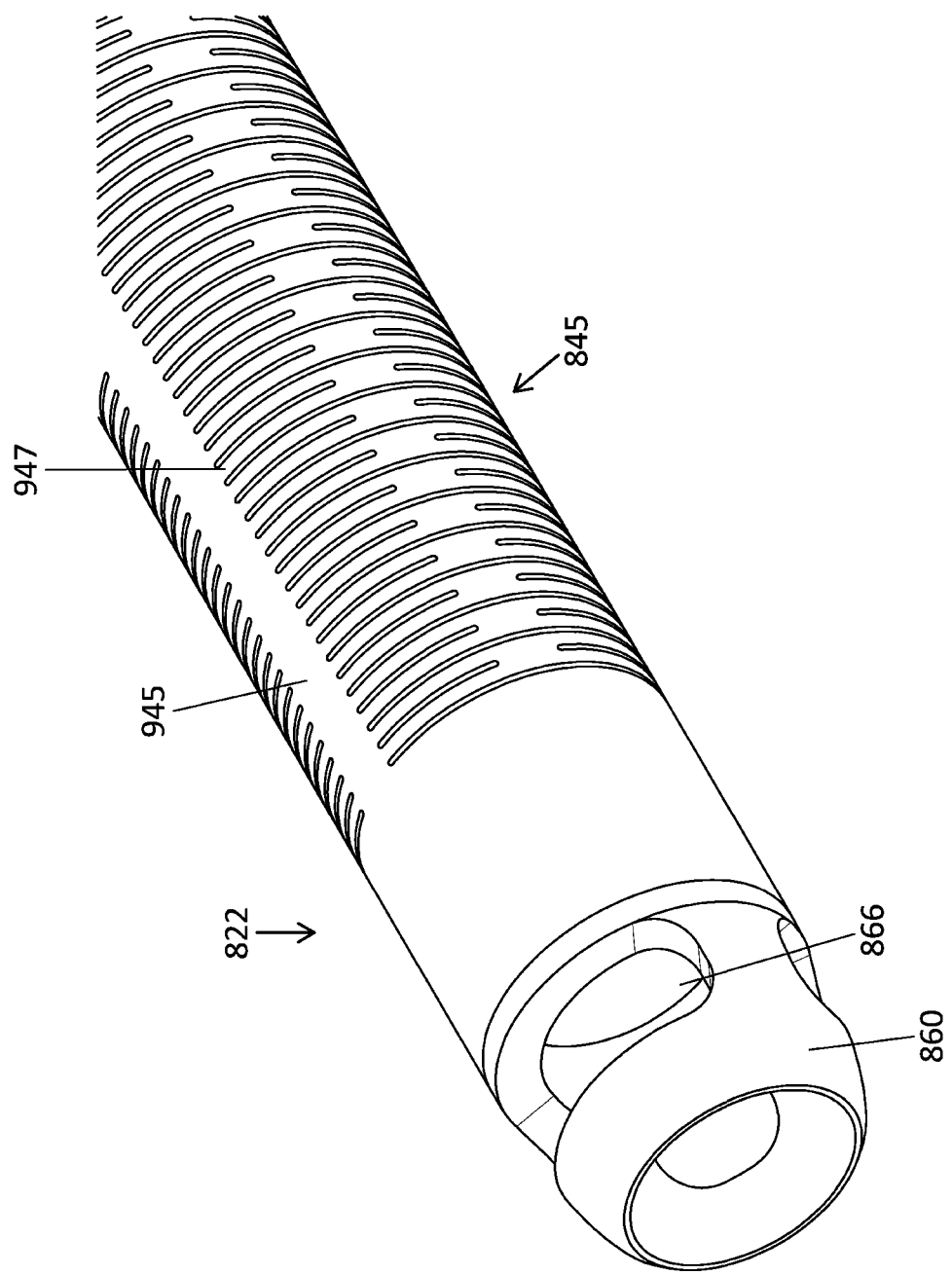
FIG. 10 shows the outer shaft of the occlusion crossing device of FIGS. 8A-8B with the inner shaft removed.

As shown in FIG. 10, the inner shaft 811 can be fully removable from the outer shaft 822 and collar 860 by pulling the inner shaft 811 proximally. By doing so, the outer shaft 822 can be used as a sheath, e.g., for guidewire placement. For example, after the inner shaft 811 with drill tip 803 is used to cross (e.g., drill through) the occlusion, the inner shaft 811 (with drill tip 803) can be removed from the outer shaft 811 by pulling proximally. The guidewire may then be placed within (e.g., pushed through) the lumen of the outer shaft 811 where the inner shaft 811 once was. In this way, the guidewire may be placed through the occlusion. If the guidewire has any intervention devices (e.g., a balloon, stent, tube, medicament and/or other angioplasty device), the intervention device can be used to treat the occluded area of the vessel. In some cases, a first guidewire is used to perform a first intervention and a second guidewire is used to perform a second intervention. In a specific example, the first guidewire may include a balloon to widen the vessel; and the first guidewire may then be removed and replaced with a second guidewire to insert a stent.

Further, the inner shaft 811 can include an imaging element 877 element similar to as described above with respect to devices 100 and 300 that is rotatable with the inner shaft 811. The imaging element 877 can image through imaging windows 866 in the collar 860. Further, the inner ledge 862 can also function to properly align the imaging element 877 with the imaging windows 866 when the inner shaft 811 is within the outer shaft 822.

The inner shaft 811 can include a rotatable distal drill tip 803 similar to as described above with respect to devices 100 and 300 (e.g., can include any of the distal drill tip designs described with respect to devices 10 and 300). Likewise, the device 800 can alternatively or additionally include any of the materials and dimensions described above with respect to devices 100 and 300.

Figure 11A:
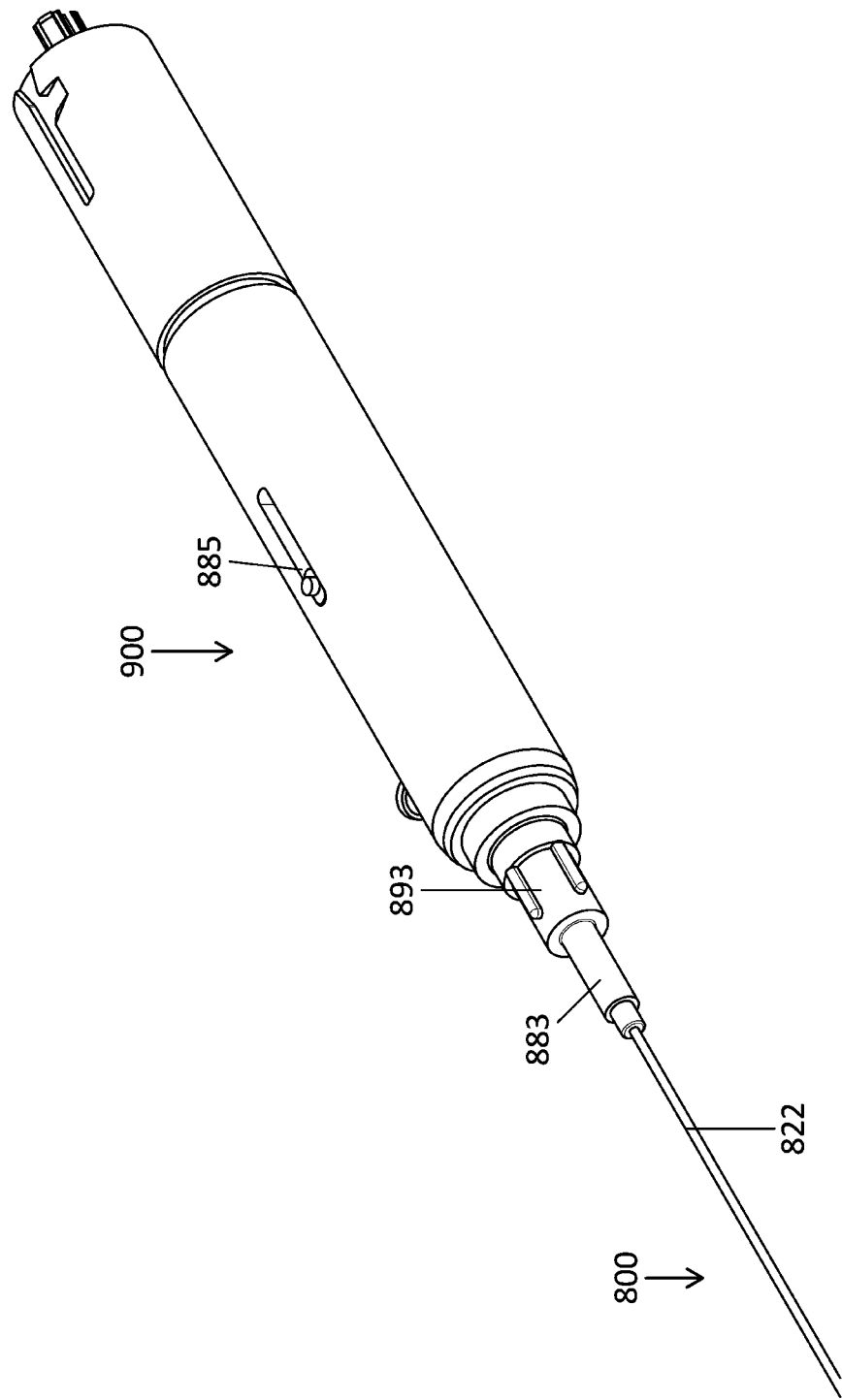
FIGS. 11A and 11B show an exemplary handle for use with the occlusion crossing device of FIGS. 8A-8B.
Figure 11B:
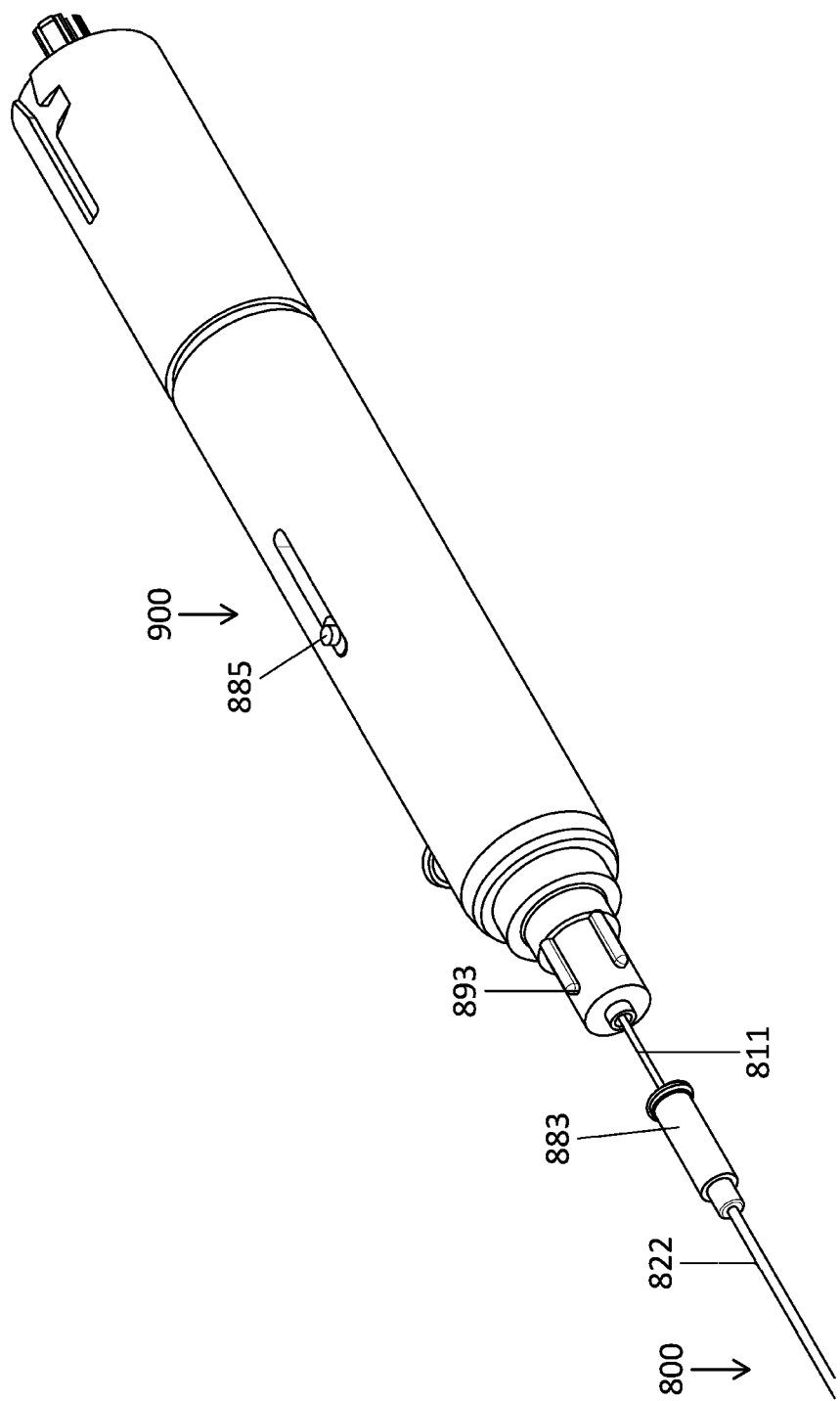

Referring to FIGS. 11A-11B, a handle 900 can be used to operate the device 800. The handle 900 can include a connector 883 configured to connect and lock the inner shaft 811 and outer shaft 822 together longitudinally. In some embodiments, the connector 883 is a luer lock, valve connector, joint fitting or gasket joint. The connector 883 can be configured to provide some relative longitudinal movement between the outer shaft 822 and the inner shaft 811 such that the inner shaft 811 can still move a small distance, such as between about 0.125 inches to 0.2 inches, to activate the selective bending feature 845. For example, the inner shaft 811 can include an accordion or elastomeric segment to provide the additional relative movement. The actual displacement distance depends on the diameter of the outer shaft of the catheter, the degree of bending that is desired and the elongation/compression of the outer and inner shaft, respectively. The larger the diameter of the outer shaft, the greater the desired degree of bending, and the more compression/elongation of the shafts, the greater the required amount of displacement. Further, the connector 883 can be configured to allow the inner shaft 811 to rotate freely within the outer shaft so as to provide rotation of the sharp distal drill tip 803 connected to the inner shaft 811. The connector 883 can be configured such that the outer shaft can be rotated relative to the position of the handle. With the shaft in the articulated position, rotating the outer shaft will direct the catheter around or towards obstacles during use. If the connector 883 is disconnected, as shown in FIG. 11B, the inner shaft 811 can be pulled out of the outer shaft 822 by the handle, leaving the outer shaft 822 in place, such as for guidewire placement.

The handle 900 can further include a lever 885 or ring configured to control the axial movement of the inner shaft 811 (and thus the articulation of the device 800). In some embodiments, the lever 885 can include a locking mechanism that allows the device 800 to stay bent at a set angle. The handle 900 can also include a rotation element 893 attached to the outer shaft 822 and configured to rotate the outer shaft 822, such as 360 degrees, to position the bend of the device 800 in the desired orientation.

Figure 12:
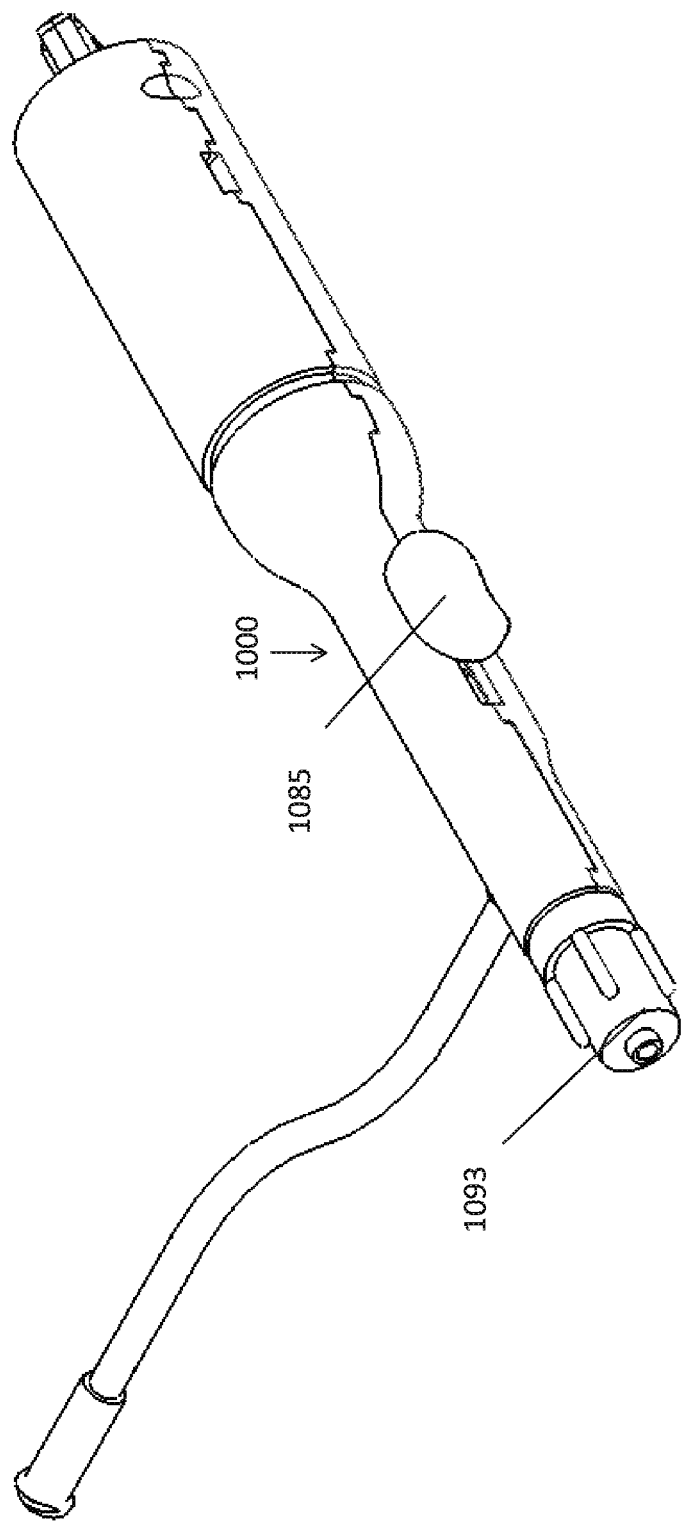
FIGS. 12 and 13 show another exemplary handle for use with the occlusion crossing device of FIGS. 8A-8B.
Figure 13:
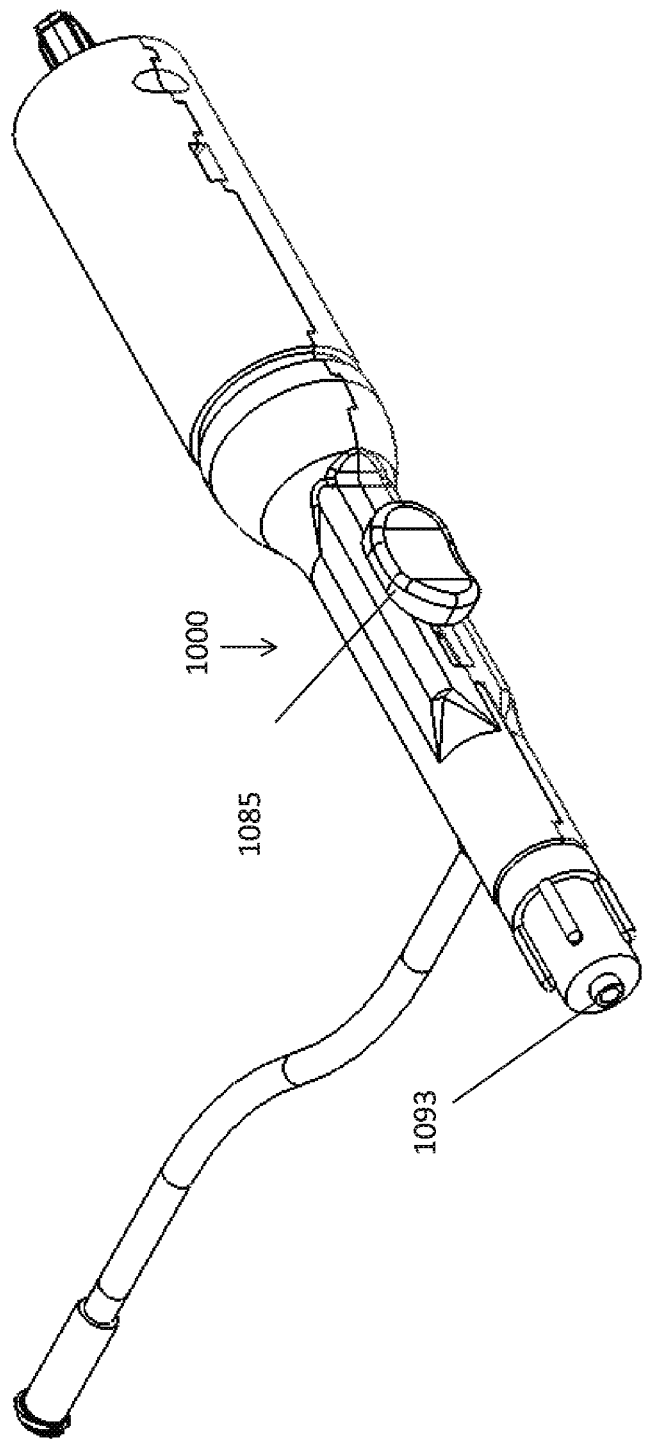

Another exemplary handle 1000 is shown in FIGS. 12-13. The handle 1000 can include many of the features of handle 900. A slide button 1085 can be used to control the axial movement of the inner shaft. The rotation element 1093 can be configured to rotate the outer shaft 822.

Furthermore, in some embodiments, the connection between the outer and inner shafts within the handle can be configured such that the two shafts snap together, axially fixing the proximal ends together, but allowing them to rotate independently. In other embodiments, a third element could be used to key, link, or peg the two shafts together.

Features of the handles 900, 1000, though described for use with catheter 800, can likewise be used with any of the catheters described herein.

The distal end of another embodiment of a catheter 1400 is shown in FIGS. 14A-14B. The catheter 1400 is similar to catheters 100, 300, 800 except that it includes a smooth distal drill tip 103 and a molded distal portion 1410. Thus, the distal tip 103 can have a smooth angled surface 1413 that is non-fluted and comes together in a slightly convex distal point 1415 (i.e., the drill tip can be frusto-conical). The distal drill tip 103 of FIGS. 14A, 14B can advantageously provide less aggressive drilling through the occlusion. The distal drill tip 103 of FIGS. 14A and 14B can be used in place of any of the distal drill tips described with respect to catheters 100, 300, 800. Likewise, the catheter 1400 can include a molded distal portion 1422. The molded distal portion 1412 can be similar to the distal end of the catheter 300 and can include a bushing 1424, a transparent section 1422, and selective bending support 1452 (also referred to as a scaffolding or chassis) of the outer shaft. The selective bending support 1452 may be positioned over at least a portion of a flexible portion of the outer shaft (e.g., braided or coiled portion). Further, an imaging fiber 1499 can run down the central axis of the device, as described above with respect to other embodiments. Any of the features of catheter 100, 300, 800 can be used in addition to, or as an alternative to, the features described with respect to catheter 1400. Likewise, the catheter 1400 can be used with a handle having some or all of the features of handles 200, 900, or 1000.

In some embodiments, all or a portion of the outer shaft of the catheters described herein can be clear to allow imaging therethrough. Further, in some embodiments, the catheters described herein can include a balloon to occlude for better imaging. The balloon can be a clear balloon to allow imaging therethrough.

In some embodiments, the selective bending feature of the outer shaft is in the form of a selective bending support that fits over and at least partially surrounds a flexible portion (e.g., flexible tube) of the outer shaft. That is, at least a portion of the selective bending support can radially overlap with the flexible portion of the outer shaft. This configuration is another way to provide a balance between providing flexibility (e.g., bendability) while allowing for biased bending of the distal end of the catheter.

Figure 22A:
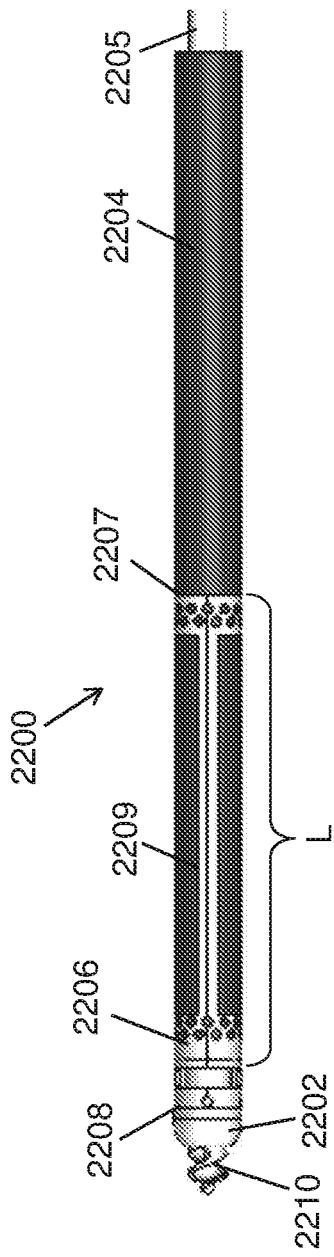
FIGS. 22A-22C show another exemplary occlusion crossing device having a selective bending support.
Figure 22B:
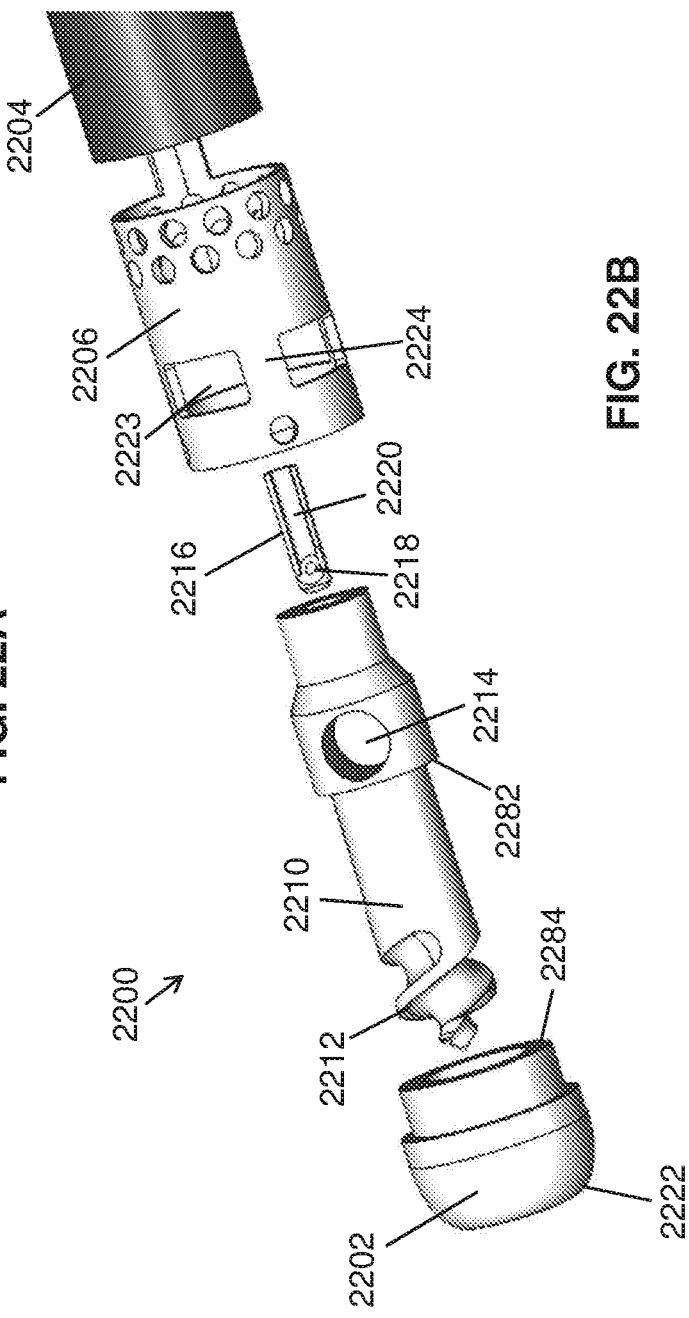
Figure 22C:
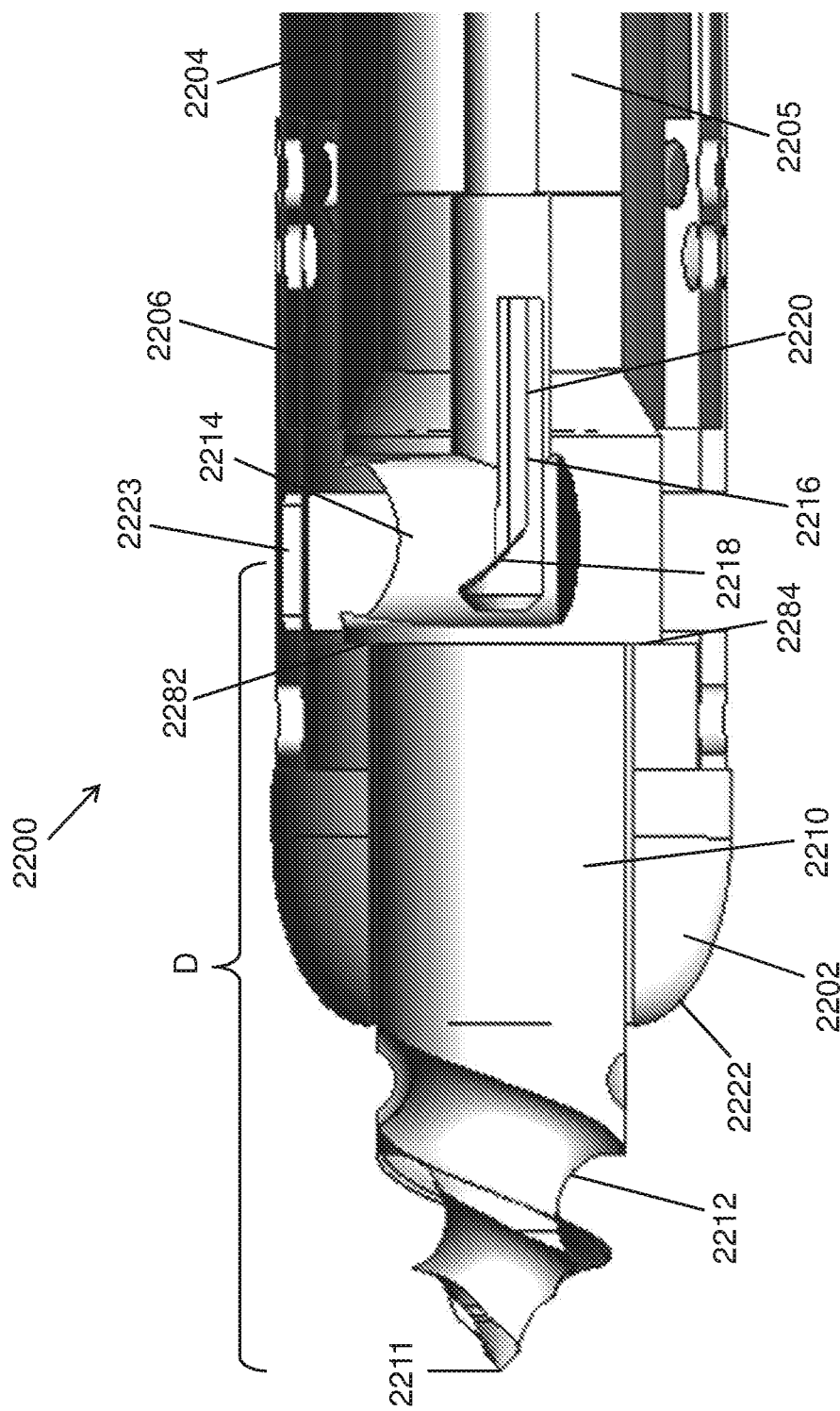

FIGS. 22A-22C show an exemplary catheter 2200 with a selective bending support 2206. Catheter 2200, like other catheters described herein, can include an outer shaft having a flexible portion 2204 (e.g., flexible tube), an inner shaft 2205 configured to be removable from the outer shaft, and a tip body 2210 coupled with the inner shaft 2205. The selective bending support 2206 can extend longitudinally along a portion of the length of the flexible portion 2204 of the outer shaft. In some embodiments, the selective bending support 2206 (and other selective bending supports described herein) can have a length L ranging from about 0.125 inches to about 3 inches. The selective bending support 2206 can be configured to provide selective rigidity to the flexible portion 2204 of the outer shaft at the distal end of the catheter. The selective bending support 2206 can include a proximal portion 2207 and a distal portion 2208 coupled with each other via a backbone 2209. The proximal portion 2207 and distal portion 2208 of the selective bending support 2206 can each have a shape (e.g., cylindrical) that defines an opening suitable for a portion of the flexible portion 2204 of the outer shaft to fit therethrough. That is the proximal portion 2207 and distal portion 2208 can surround or encompass at least a portion of a circumference of the flexible portion 2204. The proximal portion 2207 and a distal portion 2208 may be referred to as ribs. The proximal portion 2207 and a distal portion 2208 may be spaced apart from each other such that the flexible portion 2204 of the outer shaft between the proximal portion 2207 and the distal portion 2208 are uncovered by the selective bending support 2206, thereby allowing more flexibility for the side of the outer shaft opposite the backbone 2209 to expand. In some cases, the backbone 2209 has a surface shape corresponding to an outer surface of the flexible portion 2204 of the outer shaft. For example, the backbone 2209 may have a curved inner surface corresponding to a cylindrical shaped flexible portion 2204.

Further, the backbone 2209 can be configured to bias lateral bending of the catheter 2200. That is, as described with respect to other embodiments herein, the removable inner shaft 2205 can be used to control bending of the catheter 2200. For example, the tip body 2210 can include an annular lip 2282 that extends further radially outwards than anything on the tip 2210 that is distal to the annular lip 2282. As the inner shaft 2205 is inserted into the outer shaft 2204, the annular lip 2282 can butt up against the proximal edge of 2284 of the collar 2202. Further pushing of the inner shaft 2205 distally can cause the catheter 2200 to preferentially bend in the direction of the backbone 2209, since the flexible portion of the outer shaft 2204 can be more flexible and/or stretchable than the backbone 2209. That is, the backbone 2209 can provide more resistance to bending compared to the flexible portion of the outer shaft between proximal portion 2207 and the distal portion 2208.

As with other embodiments described herein, the tip body 2210 can include one or more flutes 2212 (e.g., spiral flutes) that may facilitate the driving of tip body 2210 at least partially through the occlusion as the inner shaft 2205 and tip body 2210 are rotated.

In some embodiments, an imaging element support 2216 is used to support and/or position the imaging element within the catheter 2200. In some cases, the imaging element support 2216 (which can otherwise be called a "molded lens") has a first surface 2220 that is (e.g., substantially) orthogonal to the axis of rotation of the tip body 2210, and a second surface 2218 that is non-orthogonal to the axis of rotation of the tip body 2210. The first surface 2220 may be elongated to support, for example, an optical fiber. The second surface 2218 may be configured to support a distal end of the optical fiber near the window 2214 of the tip body 2210 and to deflect the OCT signal into the tissue. Examples of such a molded lens are described in Application No. PCT/US2016/042152, titled "MICRO-MOLDED ANAMORPHIC REFLECTOR LENS FOR IMAGE GUIDED THERAPETUIC/DIAGNOSTIC CATHETERS," filed Jul. 13, 2016, the entirety of which is incorporated by reference herein.

In the exemplary catheter 2200 of FIGS. 22A-22C, the collar 2202 can have a distal outer surface 2222 that is rounded (i.e., convex) and tapered to give collar 2202 a bullet-like shape. In some applications, this rounded and tapered shape can allow collar 2202 and catheter 2200 to move more easily through the occlusion (e.g., compared to a non-rounded and/or un-tapered collar). The extent to which collar 2202 tapers can vary depending, in part, on application needs. In one embodiment, the collar 2202 can taper at an included angle between 15 degrees and 120 degrees Additionally, the tip can include a radius or a compound form such as an ellipse to create a tapered element without sharp corners.

In some embodiments, the tip body 2210 can include a window 2214 that is configured to allow an imaging element (e.g., one or more optical fibers) imaging access outside of the catheter 2200 and into the vessel. The window 2214 can correspond to an opening with the wall of the tip body 2210, which may be open or filled with a signal transmissive (e.g., optically transparent) material. The tip body 2210 can be configured to fit within the inner cavity (lumen) of the collar 2202 such that the window 2214 is axially aligned with one or more windows 2223 (e.g., three windows) in the selective bending support 2206. The one or more windows 2223 can further be separated by one or more markers 2224 (e.g., three markers). The inner shaft 2205 can be configured to rotate the tip body 2210 relative to selective bending support 2206 and collar 2202 such that the markers 2224 periodically pass in front of and are detected by the imaging element. The imaging element can be operationally coupled with a computer (e.g., controller) that is configured to use the periodic detection of the markers 2224 to determine the relative orientation of the catheter 2200 when in use.

The distance between the tip 2211 of the tip body 2212 and a center of the window 2214 along the length of the catheter 2200 can be measured as a distance D. The distance D can be, for example, 2.5 mm.

Figure 23C:
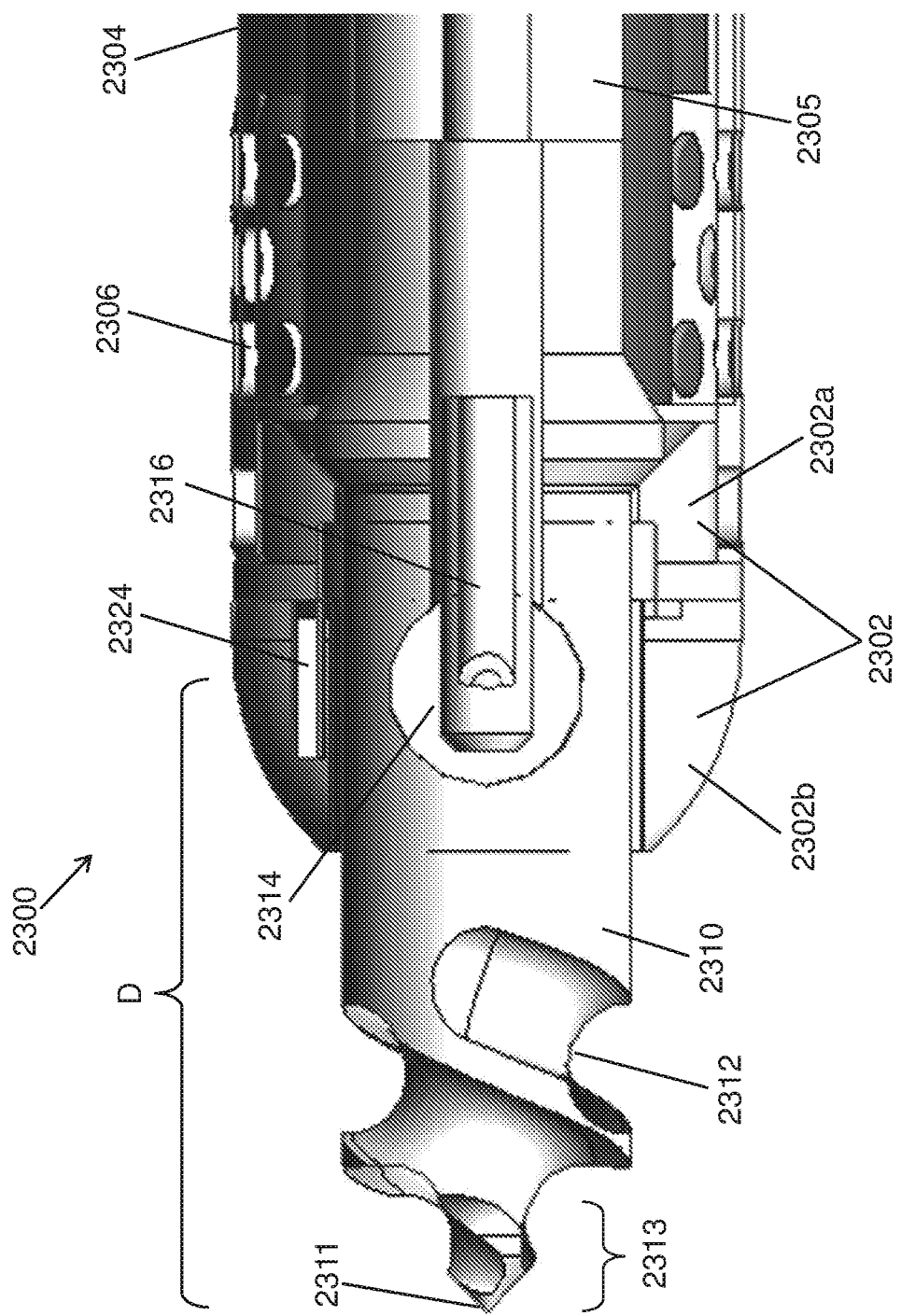

In some embodiments, the catheter includes features that allows the imaging device to be closer to the tip of the tip body (i.e., such that the distance D shown in FIG. 23C is less). To illustrate, FIGS. 23A-23C show an exemplary catheter 2300 that is similar to catheter 2200 (including an outer shaft 2304, a removable inner shaft 2305, a rotatable distal body 2310, and a selective bending support 2306) except that at least a portion of the collar 2302 is made of a material that allows at least partial transmission of a signal (e.g., OCT signal) therethrough.

In some embodiments, the collar 2302 is at least partial transparent to visible wavelengths of light (optically transparent). In some embodiments, the collar 2302 is configured to allow at least partial transmission of a signal having a wavelength of about 1310 nanometers. In some embodiments, the collar 2302 (or a portion thereof) is made of a signal-transmissive polymer material. A signal-transmissive collar 2302 can allow the imaging element to be at least partially covered by (overlap with) the collar 2302 while still being able to detect a signal from outside of the catheter 2300. For example, referring to FIG. 23C, at least a portion of the collar 2302 can axially overlap with the distal end of the imaging element support 2316 (e.g., having the imaging element) and with the imaging window 2314. Such a configuration can bring the imaging element closer to the rotating drill tip 2311 compared to configurations where the imaging element is more proximally positioned. For example, referring to FIG. 23C, a distance D between the drill tip 2311 and a center of the window 2314 of the tip body 2310 along the length of the catheter 2300 may be reduced. In some cases, the distance D is reduced by up to or by at least about 1 millimeter compared to configurations where the imaging element does not axially overlap with the collar. In some cases, the distance D is reduced by up to or by at least one-third compared to configurations where the imaging element does not radially overlap with the collar. For example, the distance D can be less than 2 mm. In this example, the drill tip include a proximal fluted region that extends distally, having a first diameter that is larger than the diameter of a second region 2313 that extends distally from the proximal region and has a smaller diameter; this second region may be pointed, and may act to prevent the drill end from deflecting from even hard (e.g., calcified) occlusions.

In some embodiments, the collar 2302 includes a proximal collar portion 2302a and a distal collar portion 2302b. The proximal collar portion 2302a can be configured to prevent optical transmission (e.g., be opaque) while the distal collar portion 2302b can be configured to allow optical transmission therethrough (e.g., be transparent). Further, the proximal portion 2302a can include tabs 2324 that are radially arranged around the central axis of the proximal collar portion 2302a and that are configured to extend within the second collar portion 2302b. In some embodiments, the distal collar portion 2302b and tabs 2324 can be axially aligned with the imaging element such that the tabs 2324 can act as markers as the imaging element rotates. As with the markers 2224 on the selective bending support 2206 described above with reference to FIGS. 22A-22B, the markers 2324 of collar 2302 can be configured to periodically pass in front of the imaging element as the imaging element rotates to provide information as to the relative orientation of the catheter 2300.

In any of the occlusion crossing devices described herein, a distal end of the outer shaft can include an angled tip that tapers asymmetrically. The asymmetry can be with respect to the central axis of the device, for example, the central axis of the outer shaft. This asymmetric shape can provide smoother entry and/or navigation of the device in the vessel. This asymmetric shape may also allow the tip to act as a marker for the optical sensor (e.g., OCT imaging sensor). The angled tip may be part of the outer shaft, or a part of the outer shaft. In some embodiments, the angled tip is on the collar of the device.

Figure 26A:
Figure 26B:
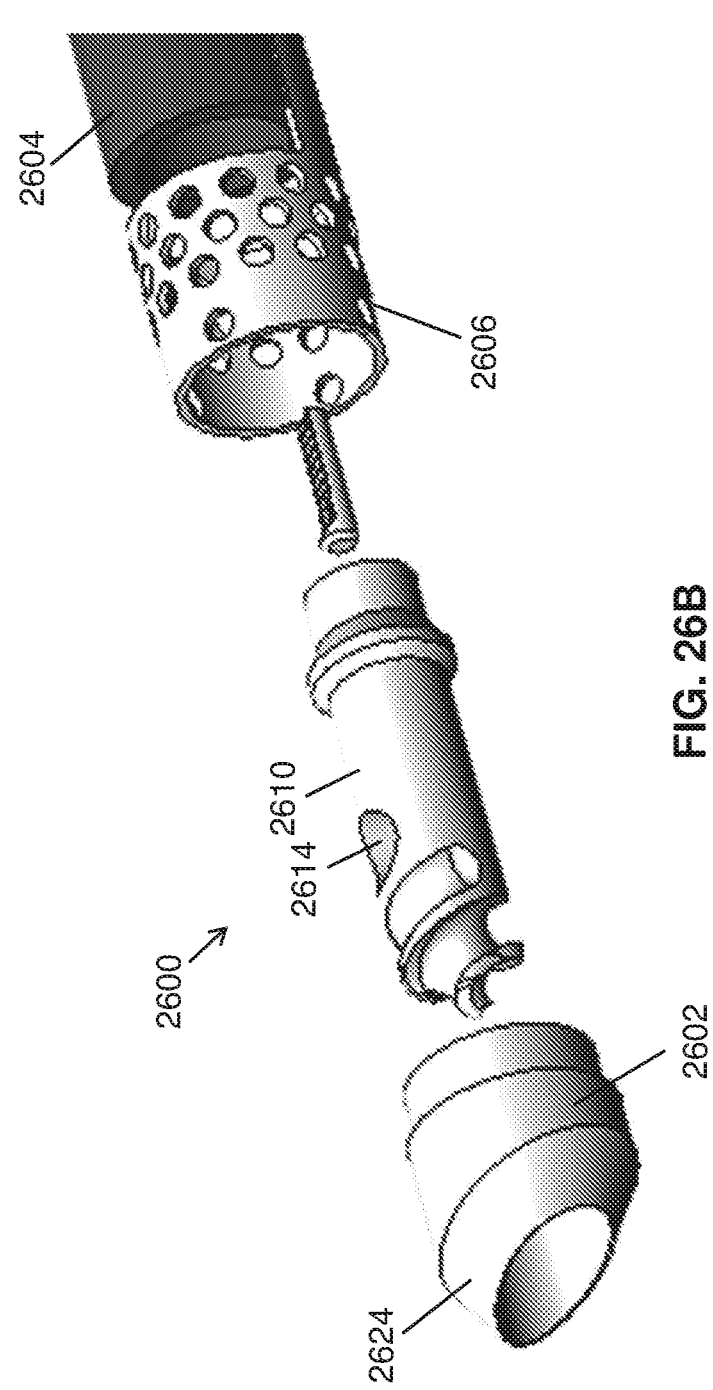

FIGS. 26A-26C show an exemplary catheter 2600 where the collar has an asymmetric shape. Catheter 2600 is similar to catheter 2200 (including having an outer shaft 2604, a removable inner shaft 2605, a rotatable distal tip body 2610, and a selective bending support 2606) except a distal end 2624 of the collar 2602 can be tapered asymmetrically to create an angular face for the distal end 2624 of the collar 2602. In some applications, the asymmetrically tapered distal end 2624 may act as a wedge or scoop that is configured to facilitate pushing through the occlusion. In some cases, the asymmetrically tapered distal end 2624 is configured to act as a marker to facilitate determining the relative orientation of the catheter 2600 when in use. For example, as illustrated in FIG. 26C, a first edge 2680 of the distal end 2624 of the collar 2602 can be configured to axially overlap with and/or extend distally beyond the imaging element (in imaging element support 2316), while a second edge 2682 of the distal end 2624 of the collar 2602 can be configured not to axially overlap with (i.e., is positioned proximally of) the imaging element. As the imaging element rotates with respect to the collar 2602, the first edge 2680 of the distal end 2624 of the collar 2602 can periodically pass in front of the imaging element, thereby acting as a marker to provide information as to the relative orientation of the catheter 2600. One of the advantages of the collar configuration of catheter 2600 can be that the imaging element may be positioned closer to the tip 2611 of the tip body 2610 compared to other embodiments. In some cases, the distance D (between tip 2611 and the center of the imaging element and/or window 2614) can be less than 1.5 mm (e.g., about 1 mm). In some embodiments, the outer surface of the collar 2602 does not have outer flutes. Further, in some embodiments, the collar 2602 is not optically transparent. As described above in FIGS. 23 and 24, the distal tip of the drill tip region may include a smaller-diameter region 2613 that helps prevent the tip from deflecting off of even hard occlusion material.

FIGS. 28A and 28B show an alternative selective bending support 2806 according to some embodiments. The selective bending support 2806 can be similar to the selective bending support 2206 (FIGS. 22A-22C) in that the selective bending support 2806 is configured to provide biased bending of the distal end of the catheter. The selective bending support 2806 includes a backbone 2809 that is connected to multiple ribs: a proximal portion 2807, a distal portion 2808 and one or more intervening ribs 2850. In some embodiments, the distal portion 2808 includes an engagement feature 2820 for engagement with, for example, a collar of the outer shaft. The intervening ribs 2850 can provide torsional strength. For example, the intervening ribs 2850 can provide lateral stability to the selective bending support 2806 (and the distal end of the catheter), thereby providing a resistance against a torsional force as the catheter winds through the vessel. Since the ribs are spaced apart, the selective bending support 2806 can still be flexible enough to bend laterally in the direction of the backbone 2809. The number, thickness and spacing between the ribs can be varied to achieve a desired compromise between flexibility and torsional strength. In some cases, spacings between ribs is determined by the diameter of the shaft flexible portion (e.g., braided portion) of the outer shaft.

FIGS. 29A and 29B show another selective bending support 2906 having similar features of selective bending support 2806, except that the selective bending support 2906 has a different intervening rib configuration. For example, intervening ribs 2950 are thinner than the intervening ribs 2850. Further, some of the intervening ribs 2950 are connected by connectors 2960. In some embodiments, the connectors 2960 can be oriented parallel to the backbone 2909.

Figure 27:
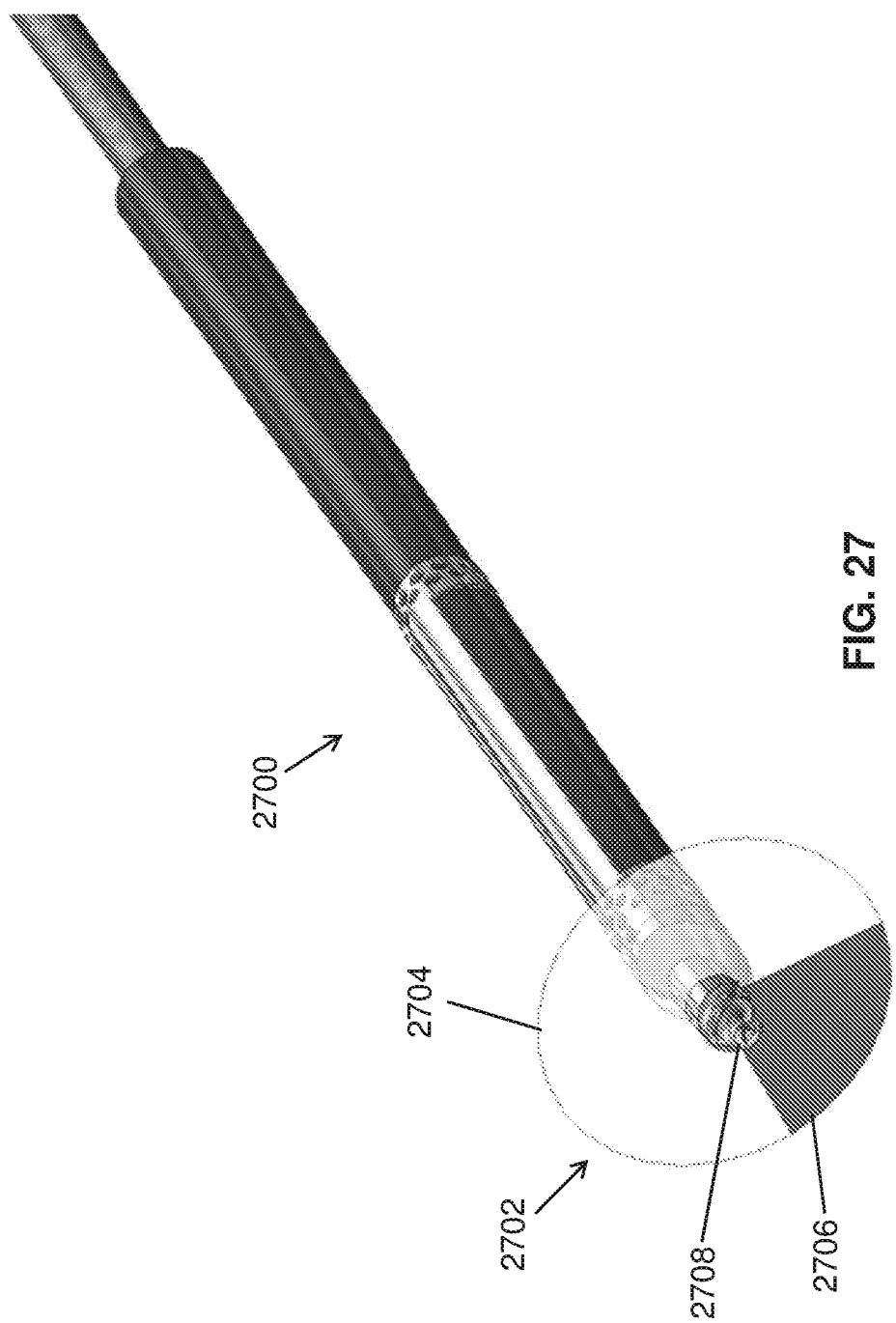
FIG. 27 illustrates imaging using an occlusion crossing device.

Any of the catheter variations described herein may include a guidewire lumen as part of or attached to the outer shaft for accommodating a guidewire therein. For example, the Any of the catheter variations described herein may include balloon as part of or attached to the outer shaft FIG. 27 shows how an occlusion crossing device 2700 similar to device 2600 may collect image data. Light can radiate from the distal region of device 2700 in a circular path 2702 as the imaging element (e.g., OCT fiber) rotates along a central axis of rotation. A first portion 2704 of the light can exit the device 2700, while a second portion 2706 of the light can be blocked by one or more markers of the device 2700. Since the marker(s) can be stationary relative to the device 2700 (including tip body 2708), the marker(s) can be used as a reference as to the location of the device 2700 (including tip body 2708).

In any of the occlusion crossing devices described herein, the imaging element can be configured to image a forward-looking image (in the distal direction). This configuration can be used instead of, or in addition to, a side-looking image.

Figure 24C:
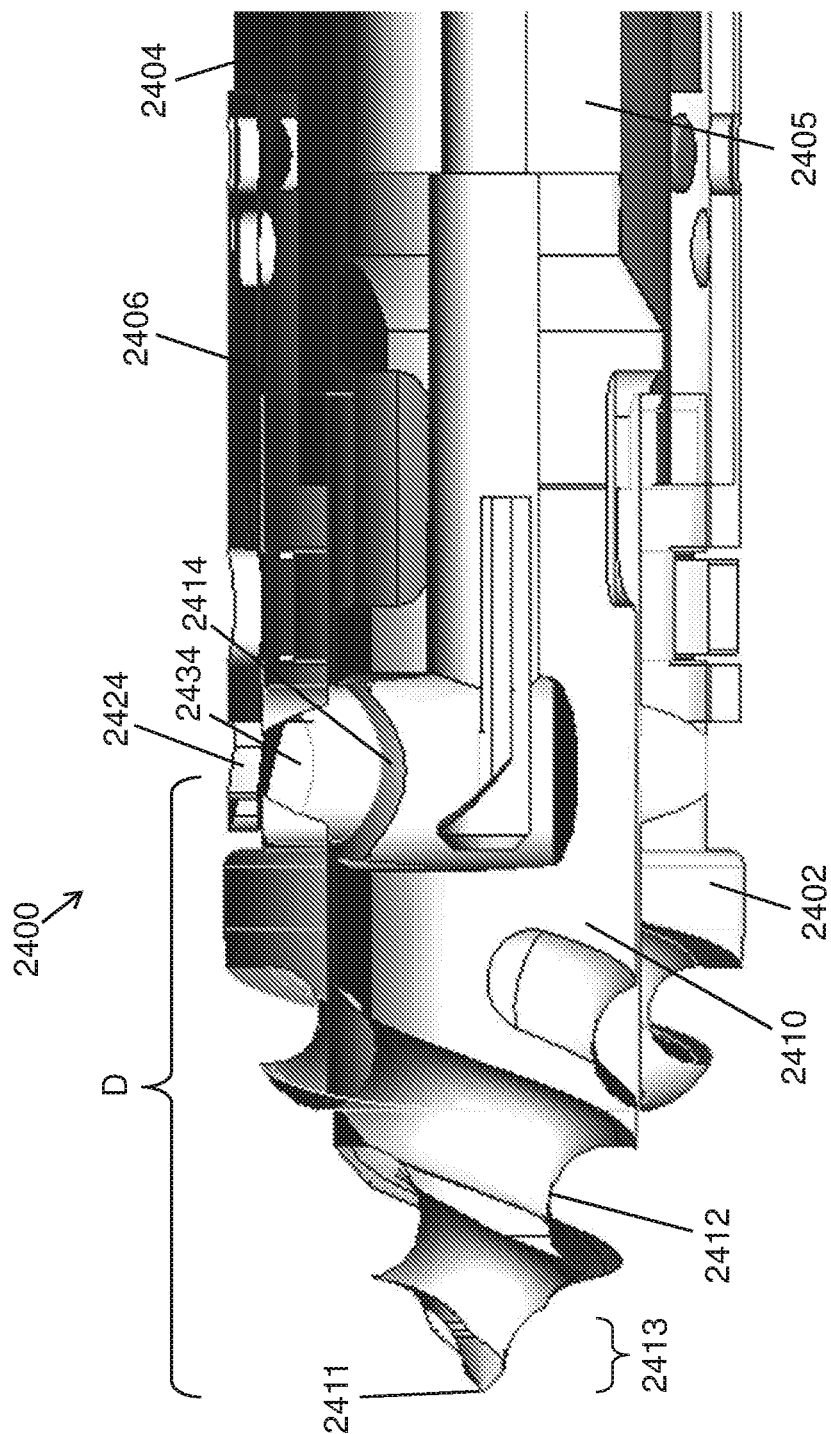

In some embodiments, the collar can be configured to rotate with the tip body. For example, FIGS. 24A-24C show a catheter 2400 that is similar to catheter 2200 (including an outer shaft 2404, a removable inner shaft 2405, a rotatable distal body 2410, and a selective bending support 2406) except the collar 2402 includes flutes 2442 that are configured to rotate with the tip body 2410. The flutes 2442 can have substantially the same pitch as the flutes 2412 of the tip body 2410 so as to provide substantially continuous cutting as the tip body 2410 and collar 2402 are rotated.

The collar 2402 can engage with the tip body 2410, for example, using a locking mechanism. The locking mechanism can be any of any type, such as a mechanical lock, friction lock or other coupling mechanism. For instance, the tip body 2410 can include a first keying member 2430 that is configured to align and engage with a corresponding second keying member 2432 of the collar 2402. In some embodiments, the first and second keying members 2430, 2432 correspond to tab and slot features, stepped features, and/or groove and tongue features. The first and second keying members 2430, 2432 can be positioned anywhere on the tip body 2410 and the collar 2402. In some cases, the first and second keying members 2430, 2432 are on the outer surfaces (e.g., outer walls) and/or inner surfaces (e.g., inner walls) of the tip body 2410 and/or the collar 2402. For example, the first keying member 2430 can correspond to a groove or indentation on an outer surface of the tip body 2410, and the second keying member 2432 can correspond to a protrusion of the collar 2402 having a shape configured to align and mate with the first keying member 2430 such that an inner surface of the second keying member 2432 engages with the outer surface of the tip body 2410. The rotating motion of the tip body 2410 can cause the collar 2402 to lock with the tip body 2410, thereby causing the collar 2402 to also rotate. As the tip body 2410 rotates and advances in a forward direction, a resulting pressure between the tip body 2410 and the collar 2402 can further reinforce the engagement of the first and second keying members 2430, 2432.

Further, the collar 2402 can include one or more windows 2434, which is/are configured to axially align with the one or more windows 2414 of the tip body 2410 when engaged with the tip body 2410 to provide signaling access to the imaging element outside the catheter 2400. In some cases, the user can be automatically informed when the tip body 2410 and the collar 2402 are not properly aligned and engaged. For example, if the collar 2402 becomes misallied with tip body 2410 (e.g., if tip 2411 is accidentally pushed proximally relative to the outer shaft 2404), the window(s) 2434 of the collar 2402 can become misaligned with window(s) 2414 of the tip body 2410, which signal can be detected by the imaging element and sent to the one or more controllers as feedback. The distal tip includes a region 2413 that has a smaller diameter than the rest of the fluted distal tip.

In some embodiments, the selective bending support 2408 can further include distally extending markers 2424 configured to axially align with the imaging windows 2414, 2434 so as to provide information regarding the relative orientation of the catheter 2400.

Further, in some embodiments, the collar 2402 can be optically transmissive (similar to the collar 2302 of FIGS. 23A-23C).

In some embodiments, the tip body and the collar can be configured to attenuate the rotation of the tip body in response to resistance applied to the tip body. For instance, FIGS. 25A and 25B show a collar 2502 that may replace the collar 2402 of catheter 2400. The collar 2502 can be similar to the collar 2402 except that a second keying member 2532 of collar 2502 can have a different geometry that the second keying member 2432 of collar 2402. The second keying member 2532 can have angled walls 2590 that are configured to allow the collar 2502 to give when experiencing rotational resistance above a particular amount. For instance, an edge (or lip) 2495 of the tip body 2410 can slide along one of the angled walls 2590 of the collar 2502 such that the first keying member 2430 can shift out of the first keying member 2430 of tip body 2410, causing the second keying member 2532 to disengage with the first keying member 2430 (e.g., in some cases moving the collar 2502 slightly laterally with respect to the tip body 2410). In this way, when the rotating tip body 2410 and collar 2502 meet the resistance limit, the locking mechanism can be broken, allowing the tip body 2410 to rotate without the collar 2502. In some applications, this can advantageously prevent bunching of tissue that can otherwise occur, for example, in the adventitia. In some embodiments, the user can determine that the collar 2502 is not rotating and can use that to inform action (e.g., to stop rotation of the tip body 2410 for readjustment of the catheter 2400 positioning).

As described above, any of the catheters described herein can include an imaging element. The imaging element can include an optical fiber, such as an optical coherence tomography (OCT) imaging fiber. The optical fiber can extend within the driveshaft or inner shaft so as to extend substantially along the central axis of the catheter for the entire length of the fiber. The fiber can be attached at the distal end of the driveshaft or inner shaft and/or the distal drill tip, but can be otherwise free to float within the driveshaft. The imaging fiber can transfer an OCT signal for imaging of the vessel in which the device is placed. In some embodiments, the imaging fiber can have a polyimide coating therearound within the length of the driveshaft to support and protect the fiber as it spins within the driveshaft. Further, the handles described herein can be configured to accommodate a certain amount of slack in the fiber to facilitate extension and retraction of drive shaft against hollow shaft.

The imaging element can further include a mirror oriented at an angle (such as a 30-60 degree angle, e.g., 45 degrees) with respect to the central axis of the fiber such that light coming out of the fiber will bounce off the mirror and into the adjacent tissue. Glue can be used to hold the distal end of the optical fiber in place. The glue can have a refractive index configured to be appropriately mismatched with the refractive index of the fiber, as described in U.S. patent application Ser. No. 12/790,703, titled "OPTICAL COHERENCE TOMOGRAPHY FOR BIOLOGICAL IMAGING," filed May 28, 2010, Publication No. US-2010-0305452-A1; and International Patent Application No. PCT/US2013/031951, titled "OPTICAL COHERENCE TOMOGRAPHY WITH GRADED INDEX FIBER FOR BIOLOGICAL IMAGING," filed Mar. 15, 2013, both of which are incorporated by reference in their entireties. Further, the glue can have a meniscus shape along its outer edge, as described in International Patent Application No. PCT/US2013/031951 titled "OPTICAL COHERENCE TOMOGRAPHY WITH GRADED INDEX FIBER FOR BIOLOGICAL IMAGING," filed Mar. 15, 2013, incorporated by reference herein. The meniscus shape can advantageously ensure that the light reflected back from the surface of the glue and back into the fiber is significantly less than the light referenced.

The driveshaft or inner shaft, and thus the imaging element or optical fiber, can be configured to rotate continuously at high speeds, such as greater than 500 rpm, greater than 600 rpm, greater than 700 rpm, greater than 800 rpm, greater than 900 rpm, or greater than 1,000 rpm, e.g., between 500-1,000 rpm, in one or both directions to provide OCT imaging around the inner circumference of the vessel. Such high speed rotation in a single direction or in different directions as chosen by the user (as opposed to requiring rotation alternately in both directions to manage the optical fiber) allows for the gathering of image data more quickly, thereby providing more accurate and up-to-date images during use of the device 100. For example, images can be generated at a rate of greater than 6 frames per section (fps), such as greater than or equal to 8 fps or greater than or equal to 10 fps, such as approximately 16.67 fps. In an exemplary embodiment, the rate of Laser sweep, such as approximately 20 KHz, can be configured to keep up with at 16.67 frames per second with about 1200 lines per frame.

Advantageously, because the optical fiber runs through the center of the catheters described herein, the catheters can be small in diameter. For example, the outer diameter of the catheters described herein can be less than 0.10", such as less than 0.08", such as less than 0.07", less than 0.06", or less than 0.05". Accordingly, the catheters described herein can advantageously be used in small-diameter peripheral arteries and coronary arteries.

In some embodiments, the catheters described herein can be configured to be attached to a drive system. The drive system can include a rotary optical junction configured to rotate the fiber. Exemplary drive systems that could be used in conjunction with the devices herein are described in U.S. patent application Ser. No. 13/654,357, titled "ATHERECTOMY CATHETERS AND NON-CONTACT ACTUATION MECHANISM FOR CATHETERS," filed Oct. 17, 2012 and International Patent Application No. PCT/US2013/032089, titled "ATHERECTOMY CATHETER DRIVE ASSEMBLIES," filed Mar. 15, 2013, each incorporated herein by reference in its entirety.

Figure 6A:
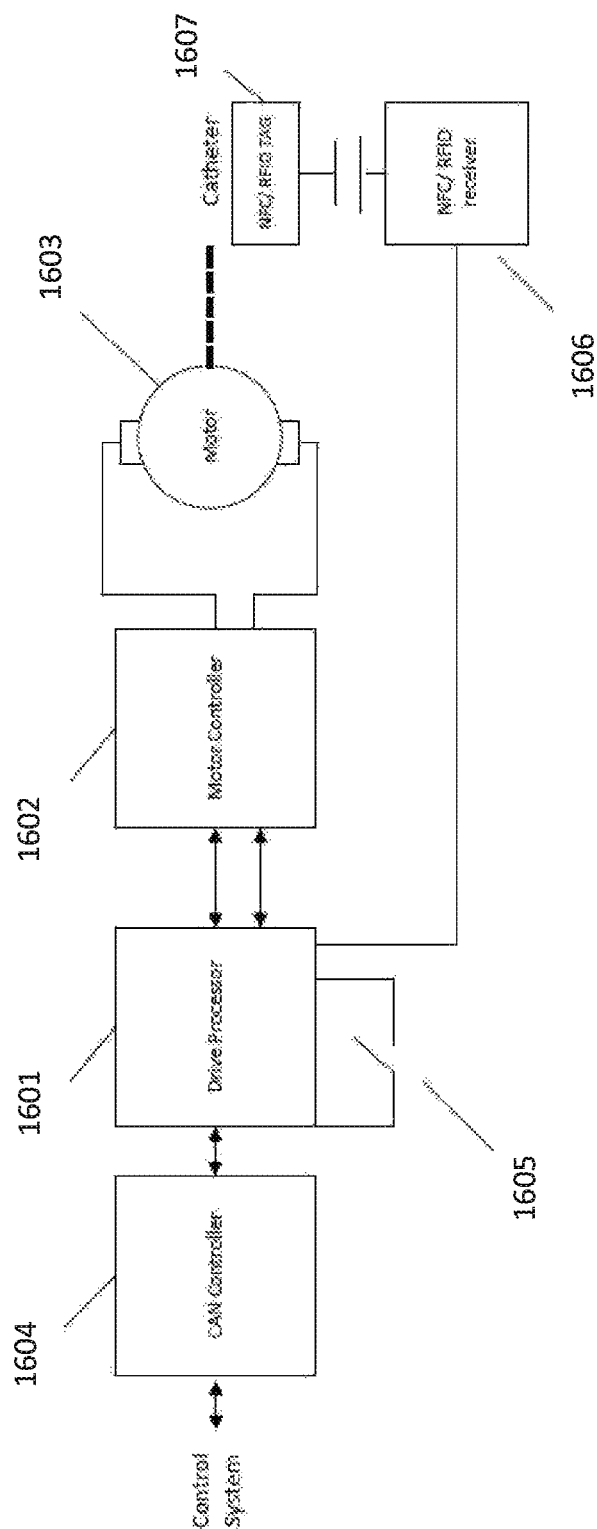
FIGS. 6A and 6B are exemplary block diagrams of drive systems for the catheters described herein.

In some embodiments, the drive system can communicate with the control system via a communication bus, which in some embodiments can be a CAN bus 2.0B. This communication can be employed to convey status to the control system or console, such as direction, speed, run status, and other information. It can also be employed to send control information to the drive system, such as run command, speed, direction, and setting of parameters for compensations of mechanical characteristics of the catheters. Referring to FIG. 6A, in one embodiment, a drive processor 1601 is used as the main controlling element for the drive system. The drive processor 1601 controls the motor 1603 through a motor controller 1602, which receives commands and returns status from/to the drive processor 1601. The drive processor 1601 can, in addition to simple speed and direction control, also implement algorithms to optimize catheter performance. The drive processor 1601 communicates with the control system (e.g., the console for the device) via the CAN controller 1604 to send and receive commands and status. In addition, in this embodiment a switch 1605 on the drive processor 1601 housing allows local control of the run state. The switch 1605 can be replaced with alternative hardware inputs, such as buttons, toggles, or knobs.

Figure 6B:
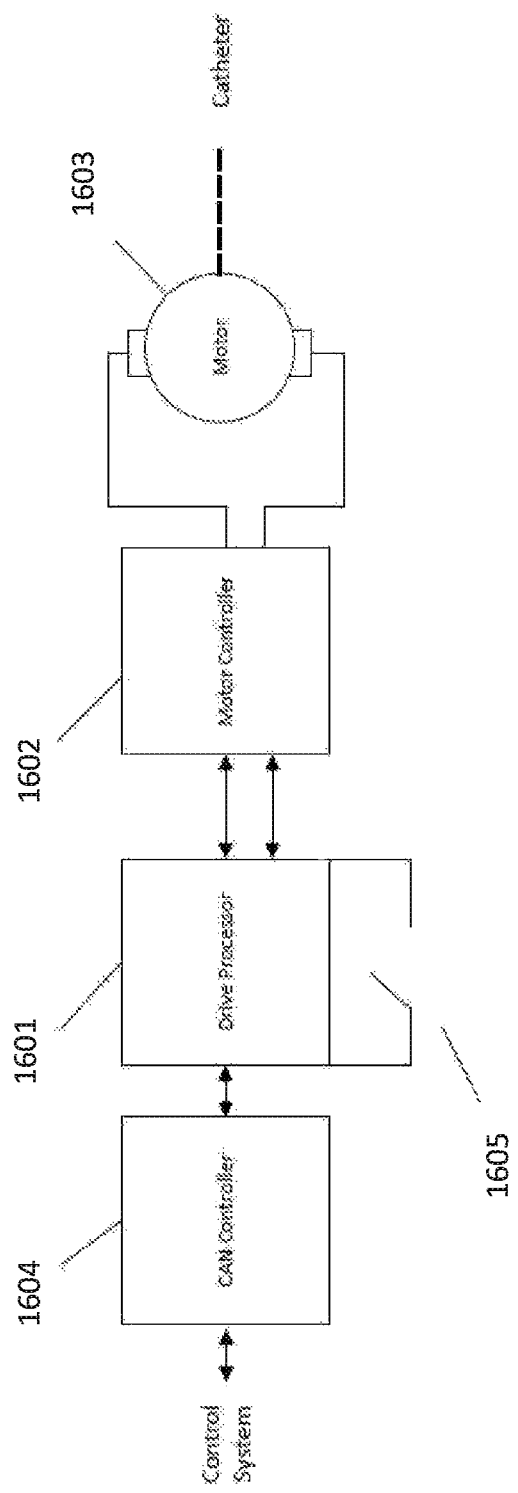

Further, in some embodiments the drive system can communicate with the catheter via NFC or RFID to obtain information about the catheter. As an example, this information can include catheter type, optimal rotational speed and direction, serial number, amongst many possible parameters. Referring to FIG. 6B, the drive system communicates with the catheter via a NFC/RFID reader 1606 and a NFC/RFID tag 1607 in the catheter to obtain information stored in the tag.

The drive system can be configured to allow the driveshaft and cutter to rotate continuously in the clockwise or the counterclockwise direction depending upon user preference. Therefore, in some embodiments, the drive system can include a user-addressable switch, such as a toggle, to set the desired direction.

Further, in some embodiments, the drive system can include a mechanism to determine the amount of rotation of the driveshaft in the clockwise or counterclockwise directions. Referring to FIGS. 6A and 6B, in one embodiment, for example, the drive system can provide information related to the direction of the motor. Speed and direction can be sensed by the control system (or console) by a data line in the umbilical, which can be a dedicated line or a multiplexed signal. The dedicated line can carry an analog or a digital signal. In one embodiment, a dedicated voltage line carries six discrete velocities (vector speed+direction) that are interpreted by the control system or console in order to infer speed and direction of the catheter.

Referring to FIGS. 7A-7B, in on embodiment, a flag in the drive system can include either an asymmetric design or an asymmetric positioning of the flags around the motor (see FIG. 7A). A controller can then sense motor direction by detecting the distinct series of flag spacing and/or width, as shown in FIG. 7B.

Further, in some embodiments, the drive system can be configured to rotate the driveshaft at several discrete rates and/or include a knob to allow for user-chosen continuously variable speeds.

Any of the catheters described herein can be shape-set or include shape-set features to enhance trackability and navigability.

As used herein, an imaging element can include the OCT optical fiber, such as the distal end of the optical fiber, as well as the mirror and adhesive used to hold the mirror and optical fiber in place.

As described above, the catheters described herein can include optical coherence tomography imaging, such as common path OCT. Such OCT systems are described in U.S. patent application Ser. No. 12/829,267, titled "CATHETER-BASED OFF-AXIS OPTICAL COHERENCE TOMOGRAPHY IMAGING SYSTEM," filed Jul. 1, 2010, Publication No. US-2010-0021926-A1; U.S. patent application Ser. No. 12/790,703, titled "OPTICAL COHERENCE TOMOGRAPHY FOR BIOLOGICAL IMAGING," filed May 28, 2010, Publication No. US-2010-0305452-A1; and International Patent Application PCT/US2013/031951 titled "OPTICAL COHERENCE TOMOGRAPHY WITH GRADED INDEX FIBER FOR BIOLOGICAL IMAGING," filed Mar. 15, 2013, all of which are incorporated by reference in their entireties. Alternatively, other types of imaging could be used with the catheters described herein. For example, the devices described herein could be configured to work with infrared spectroscopy or ultrasound.

The catheters described herein can be used for occlusion-crossing within blood vessels. Advantageously, the devices can advantageously provide increased trackability through bending/steering and high imaging speed during such crossing.

Although the features of the catheters described herein are illustrated with respect to specific examples, it is to be understood that some or all of the features of the catheters herein can be combined with some or all of the features of one or more other catheters described herein. For example, any of the drill tips described herein with respect to one embodiment can be substituted for any of the drill tips described with respect to another embodiment. Additionally, any feature described with respect to one catheter can be combined with or substituted for any feature described with respect to another catheter.

EXAMPLE

FIGS. 31A-31B illustrates one example of an occlusion crossing apparatus (e.g., occlusion crossing system) that incorporates at least some of the features described above. For example, in FIG. 31A, the occlusion crossing system 3100 includes an outer shaft 3101 that includes an inner lumen 3107 (shown in FIG. 31B). The outer shaft also includes a distal opening 3109 that is angled relative to a central axis of the outer shaft 3111 to form a distal-most tip 3113. The apparatus also includes an inner shaft 3103 extending within the lumen and configured to rotate with respect to the outer shaft. The inner shaft includes a distal end having a fluted tip 3133 that is configured to extend through the distal opening. The distal end of the inner shaft also includes a side-facing optical coherence tomography (OCT) imaging window 3135 on a lateral side of the inner shaft at a distal end region of the inner shaft.

The distal-most tip of the distal opening is configured to occlude the OCT imaging window at a defined rotational position as the inner shaft is rotated relative to the outer shaft while the first engagement region is engaged with the second engagement region, to provide a registration mark for OCT imaging.

In FIG. 31B, the apparatus of FIG. 31A is shown in a sectional view through the midline of the apparatus. The proximal end of the apparatus is not shown, but may include a proximal attachment configured to couple the inner member with a rotational driver and an imaging sub-system (e.g., for OCT imaging).

The outer shaft in this example also includes a backbone region 3141 at a distal end portion of the outer shaft that is configured to bias lateral bending of the distal end portion. This biasing may be in a plane that includes the midline of the central axis and the distal-most tip; in FIG. 31B, this plane is the plane of the section (e.g., bisecting the distal-most tip and passing through the midline of the central axis 3111). In FIGS. 31A and 31B the distal end of the apparatus is shown bent. In some variations the distal end region of the outer shaft may be configured to bend in a predetermined direction when the inner member is driven distally, beyond the stop position, relative to the outer member. Alternatively, the outer member and/or inner member may be biased to bend in the relaxed configuration and may be controllably straightened, e.g., by driving the inner member distally.

The distal opening of the distal end of the outer shaft is circumferentially beveled, as will be described in greater detail below, so that it appears as a cut-off tapered region (cut at an angle to the midline of the central axis to form the distal-most tip).

In this example, the inner shaft is configured to be removed proximally from the outer shaft (not shown), e.g. by withdrawing the inner shaft proximally to pull it out of the outer shaft. The inner shaft is prevented from extending further form the outer shaft by the engagement between a region of the outer shaft (a first engagement region) and the inner shaft (a second engagement region), which is illustrated in greater detail below.

Figure 32A:
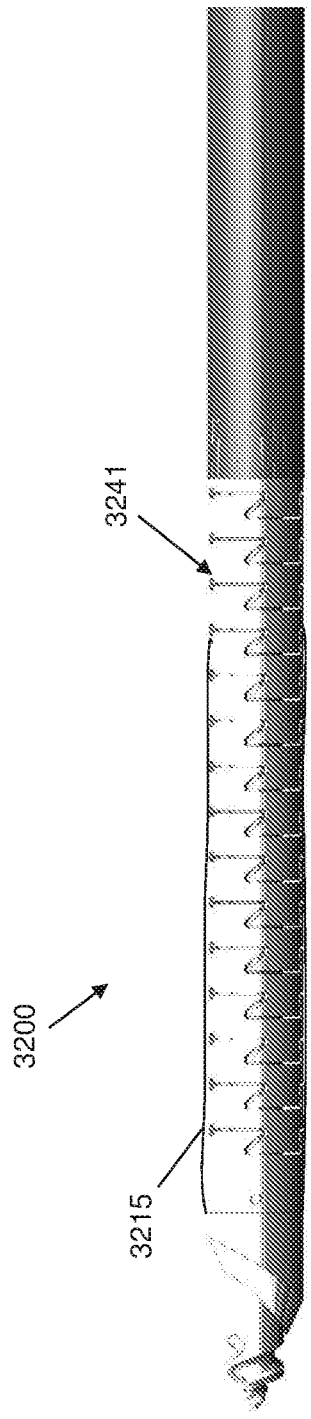
FIG. 32A is an example of an occlusion crossing apparatus without (FIG. 32A) and with (FIG. 32B) the use of a balloon, which may help center the apparatus and/or prevent blood flow around the device.
Figure 32B:
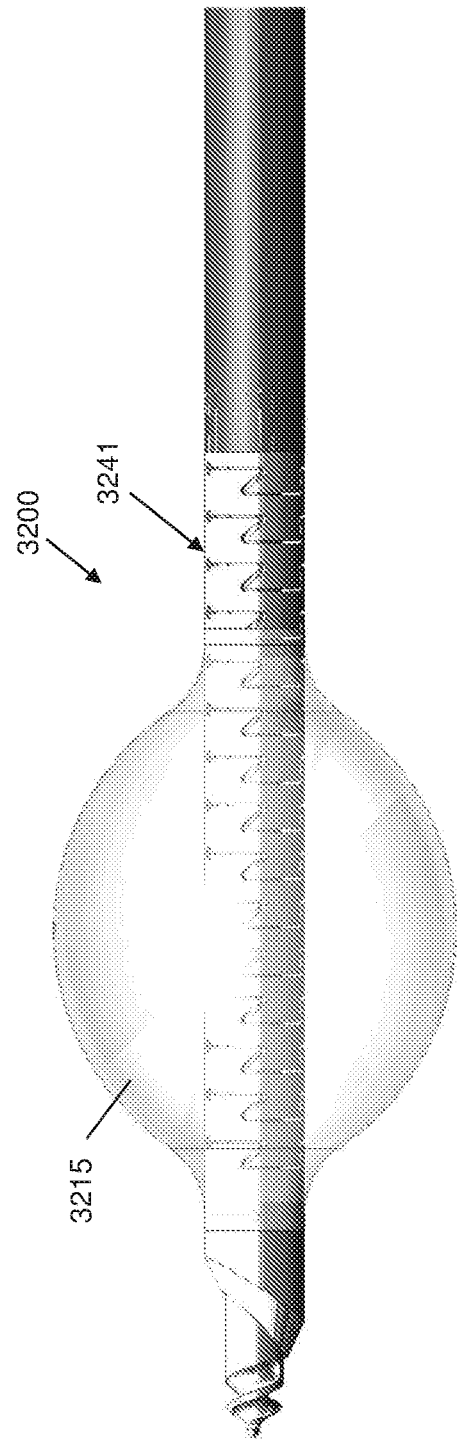

FIGS. 32A and 32B show another example of an occlusion crossing apparatus (e.g., occlusion crossing system) that is similar to the apparatus shown in FIG. 31A-31B, but may also include a balloon 3215. The balloon may be attached to the outside of the outer shaft (e.g., over all or a part of the backbone region 3241). In FIG. 32A the balloon is not inflated; FIG. 32B shows the balloon inflated. The balloon may be oversized so as to occlude the vessel (preventing or limiting blood flow), and may be inflated with saline from the proximal end (not shown).

Figure 33A:
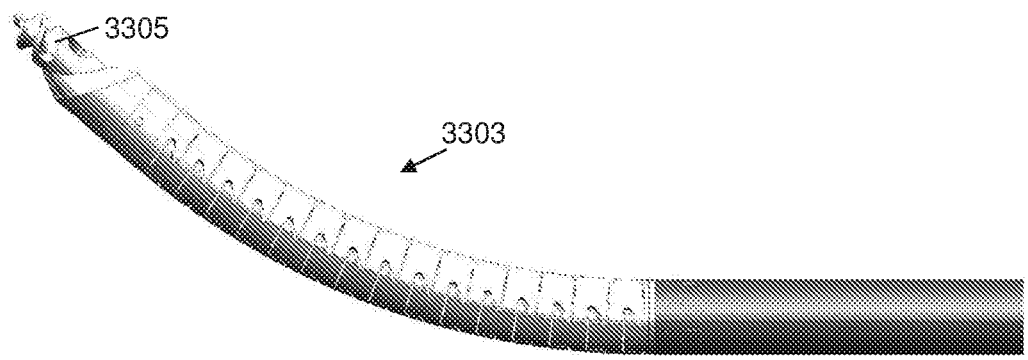
FIGS. 33A-33C illustrate one example of an occlusion crossing apparatus showing deflection of the distal end of the apparatus.
Figure 33B:
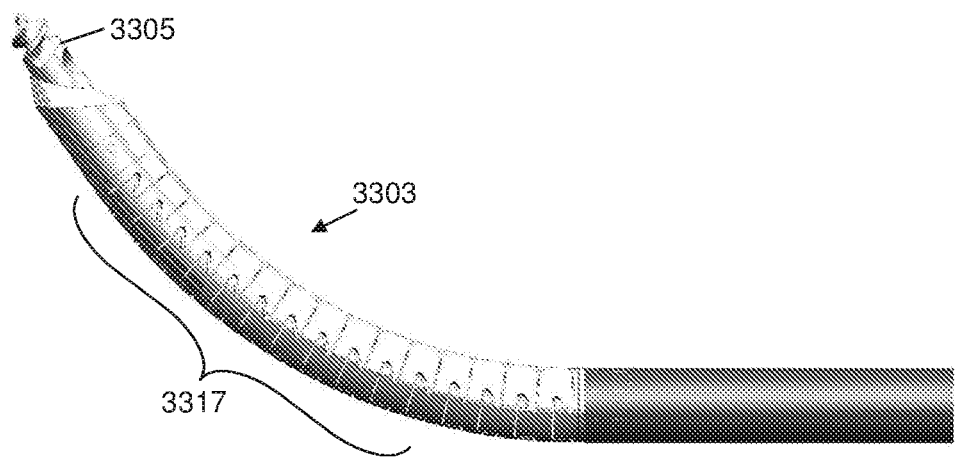
Figure 33C:
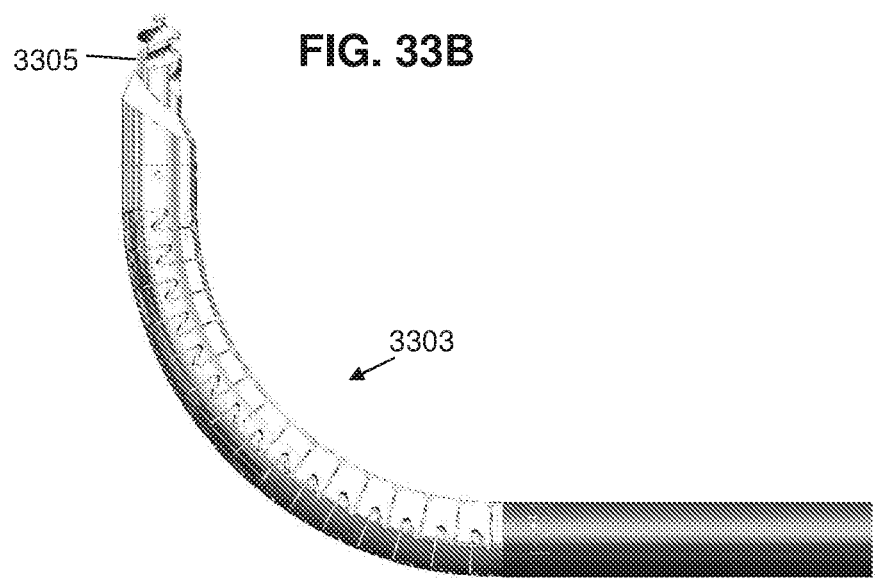

FIGS. 33A-33C illustrate bending of an occlusion crossing apparatus similar to that shown in FIGS. 31A-31B. Both the inner shaft 3305 and the outer shaft 3303 may bend together. In this example, the inner shaft may flexibly follow the bending of the outer shaft, which include a backbone region 3317 (shown in FIG. 33B) that may guide bending in a defined plane (in this example, the plane of the paper).

FIGS. 34A-34D show an enlarged view of the distal end of an occlusion crossing apparatus similar to that shown in FIGS. 31A-31B, above. In this example, the distal end of the outer shaft is formed of a rigid collar 3406 that includes an opening at the distal end out of which the fluted distal end of the inner shaft 3608 (e.g., the drill tip of the inner member) extends. The fluted distal end extends from the distal end opening until an internal stop is engaged. The distal opening the distal end of the outer shaft (e.g., formed by the rigid collar) is beveled inwardly at an angle, a, that angles towards the inner lumen, as shown in FIG. 34A (e.g., the outer member is circumferentially beveled). The bevel angle, a, is the same in FIG. 34A-34D, but may be different around the perimeter. In this example, the angle is between about 25-35 degrees (e.g., 30 degrees.

The threaded or fluted 3410 distal end of the inner shaft wraps around a region having a first diameter, D1, and a second distal end region 3412 having a second diameter, D2, extends from this first region, as shown in FIG. 32A. FIGS. 34B-34D show views of different sides of the same distal tip. In FIG. 34B, the back view shows the distal-most tip 3422 of the outer shaft distal opening.

FIG. 34D shows one example of a side-facing optical coherence tomography (OCT) imaging window 3432. As shown in this example, the imaging window is below the height of the distal-most end 3422 of the outer shaft. In operation, the inner shaft rotates while imaging trough the side-facing window; thus for every rotation, the imaging window will be temporarily occluded by the distal-most end of the outer shaft. As mentioned above, this provides an indication of the orientation of the device relative to the images (the lumen of the vessel). This may be used for both raw image viewing, but may also be used when processing the images, to reduce noise or drift.

In general, the inner shaft may be rotated relative to the outer shaft at any appropriate rate, and in either the clockwise or counterclockwise directions. Rotational direction may be advantageously used to position the distal end of the apparatus because the fluted distal end of the inner shaft may be rotated in a first direction (e.g., counterclockwise) to engage the sharp wedge-shapes of the flutes to cut tissue, or may be rotated in the less cutting/less traumatic second (e.g., clockwise) direction. Since imaging (e.g., OCT imaging) may occur when rotating, it may be desired in some situations to rotate the fluted distal tip for imaging even when cutting of the tissue is not desired.

FIG. 35 illustrates an example of a section through a distal end of a device such as the one shown in FIGS. 34A-34D. As shown in FIG. 35, the inner shaft 3505 may be advanced distally within the outer shaft 3503 so that the fluted distal end 3508 extends from the distal end opening of the outer shaft. The inner shaft may be advanced until an engagement region of the inner shaft 3519, shown as an annular region having a larger outer diameter than the rest of the inner shaft, engages against an engagement region 3521 on the inner lumen of the outer shaft, shown here as a region of narrowing diameter near the distal end of the outer shaft). In this example, the engagement region of the inner shaft may rotate against the engagement region of the outer shaft, so that the inner shaft may freely rotate relative to the outer shaft. This region may include a lubricant and/or may be coated or formed with a lubricious material. In some variations one or both surfaces may include small channels or cut-out regions forming fluid bearings. Although FIG. 35 shows the engagement region of the inner shaft as an annular ring, other configurations may be used, such as a plurality of discrete regions rather than a continuous ring. In FIG. 35, the inner shaft also includes a fiber optic line 3526 extending down the length of the inner shaft, which connects distally to the OCT imaging window 3536, and may form part of the imaging window.

Figure 36:
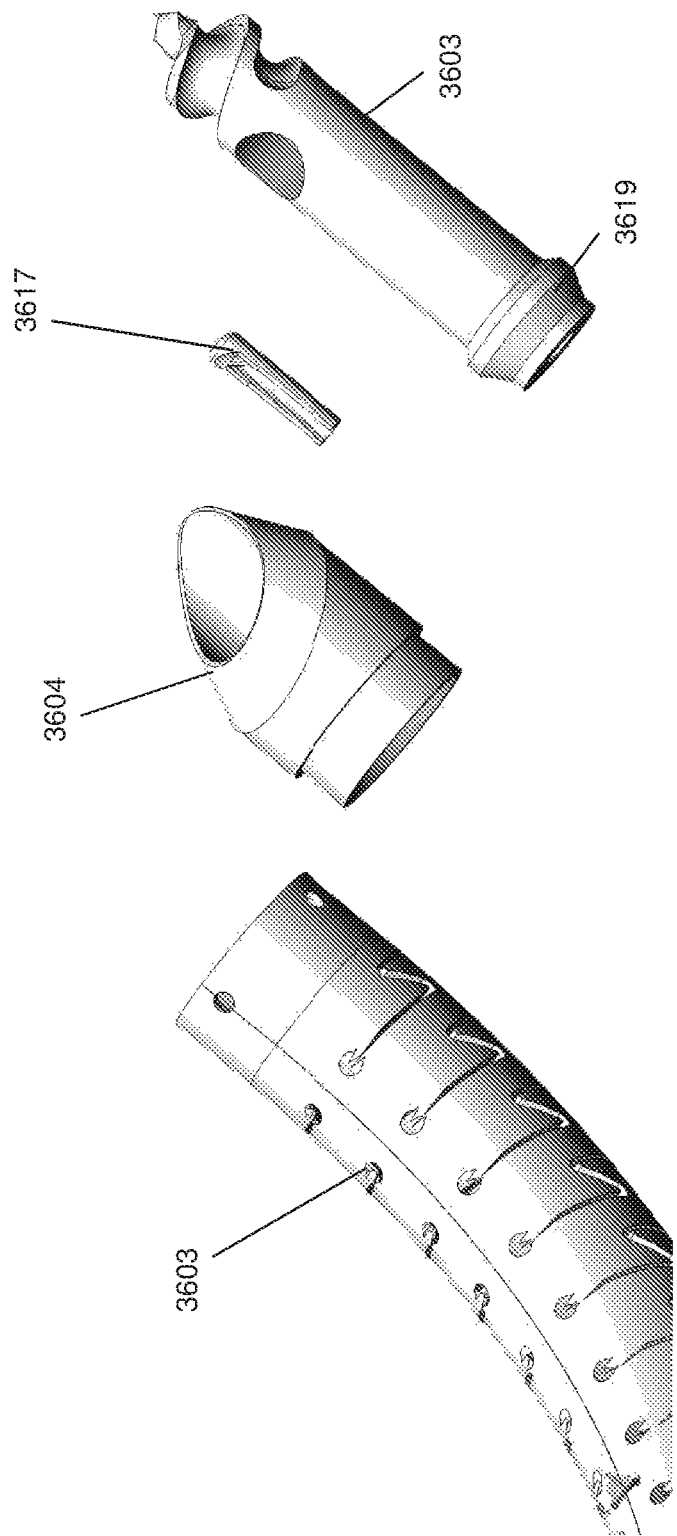
FIG. 36 is an exploded view of a distal end portion of one example of an occlusion crossing apparatus similar to that shown in FIG. 35, showing the backbone portion of the outer shaft, the distal end region of the outer shaft, an OCT imaging window, and the distal end of the inner shaft.
Figure 37C:
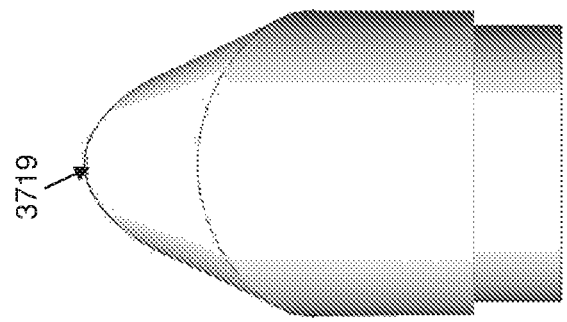
FIGS. 37A-37D show front, right side, back, and left side views, respectively of one example of a distal end region of an outer shaft, showing a distal opening that is angled relative to a central axis of the outer shaft to form a distal-most tip.
Figure 37E:
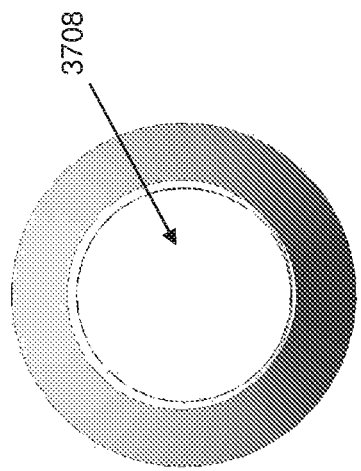
FIG. 37E shows a top view, looking down onto the distal end region of the outer shaft of the occlusion crossing apparatus of FIG. 37A-37D.
Figure 37B:
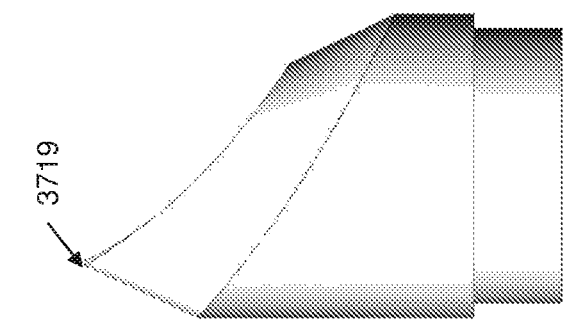
Figure 37D:
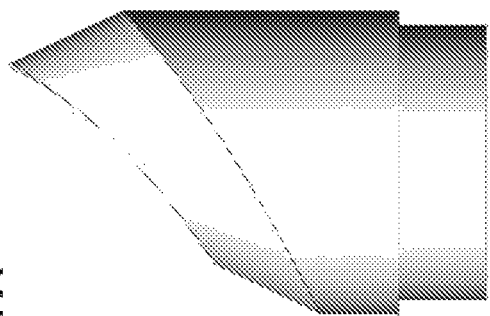
Figure 37A:
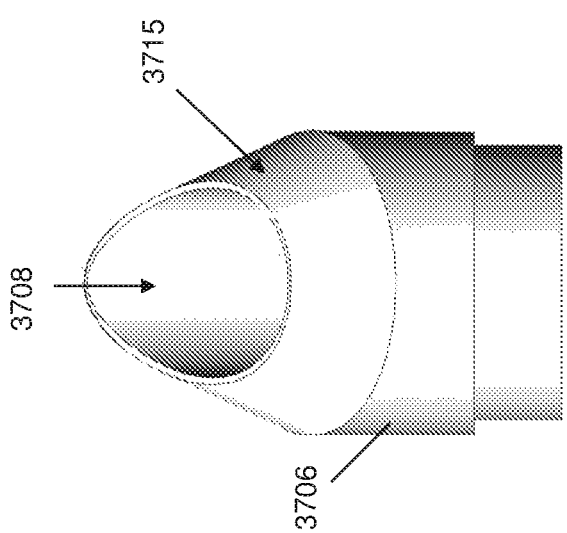
Figure 38E:
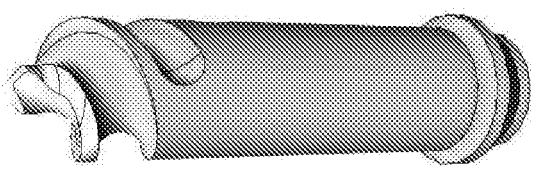
FIG. 38E is a back perspective view of the distal end region of the inner shaft of FIGS. 38A-38D.

FIG. 36 shows an exploded view of a distal end of the apparatus shown in FIGS. 34A-34D, including a backbone region of an outer shaft 3603, the distal end region 3604, including a distal-most tip, of the outer shaft, an OCT imaging window 3617, and a fluted distal end region 3603 of an inner shaft. The distal end region of the inner shaft also includes an annular engagement region 3619.

FIGS. 37A-37D illustrate rotational views of a distal end of an outer shaft that is formed as a rigid collar 3706 that includes an opening at the distal end 3708 and a circumferential bevel 3716, as described above. The distal end of the outer shaft also includes a distal-most tip 3719.

FIGS. 38A-38D show one example of a distal end region of an inner shaft, showing a fluted tip region 3844 that is configured to extend through the distal opening of an outer shaft. The fluted tip region has first fluted tip end 3847 having a first diameter, D1, and a second tip region 3845 extending from the first fluted tip region. The second tip region has a diameter D2 that is less than 60% the diameter of the first diameter (in this example, it is less than 40% of D1). The distal end of the inner shaft also includes a side-facing optical coherence tomography (OCT) imaging window 3814 on a lateral side of the inner shaft at a distal end region of the inner shaft. This imaging window may be distally located, e.g., adjacent to the fluted region or overlapping with the fluted region, as shown. In FIGS. 38A-38D, the distal end region of the inner shaft also includes an annular engagement region 3824 on an outer surface of the inner shaft that may limit a distal movement of the inner shaft within the outer shaft when it engages with an inner engagement region of the outer shaft, as described above in FIG. 35. FIG. 38E shows a back perspective view of the same distal end region shown in FIGS. 38A-38D.

Figure 39A:
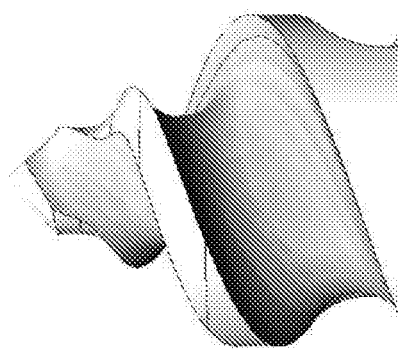
FIG. 39A-39D shows back, right side, front, and left side, respectively of an example of the fluted distal tip region of an inner shaft.
Figure 39B:
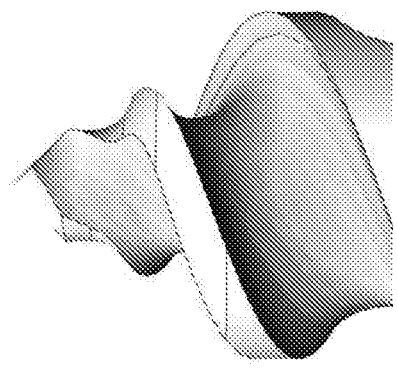
Figure 39C:
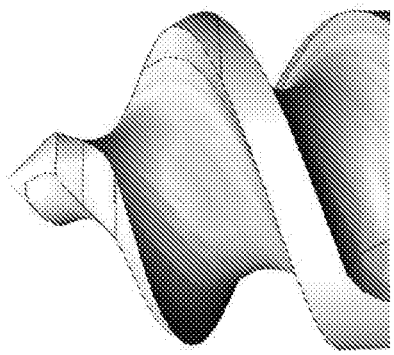
Figure 39D:
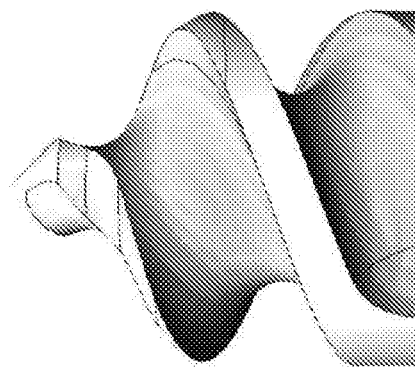
Figure 39E:
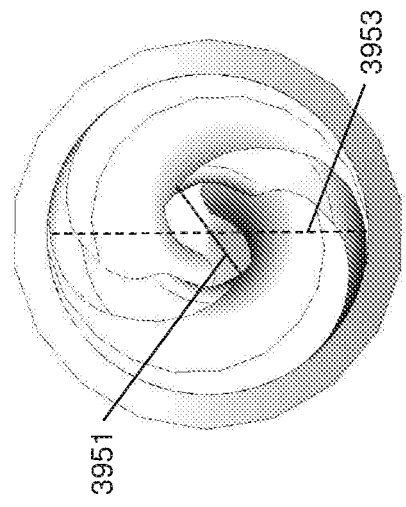
FIG. 39E is a top view, looking down onto the fluted distal tip region of the inner shaft of FIG. 39A-39D.

FIGS. 39A-39D show additional detail on the fluted distal end region of the inner shaft, similar to that shown in FIGS. 38A-38D, including the more proximal fluted region and a distal end projection that has a smaller diameter and, in this example, comes to a point. FIG. 39E shows a top view looking down on the fluted distal end of the inner shaft. The top view of FIG. 39E shows the relative diameters of the first fluted region, D1 3953, and the second fluted region, D2 3951.

Any of the catheter devices described herein can include interchangeable inner and outer shafts that can be removably and rotatably coupled to each other. In some embodiments, the inner and outer shafts are coupled by one or more connectors configured to allow the inner shaft to rotate with respect to the outer shaft. The connector(s) can be may be part of the handle (e.g., FIGS. 11A, 11B, 12 and 13) and may include any of a number of connector types (e.g., luer connector, valve connector, joint fitting, and/or gasket joint). In some embodiments, an inner shaft may be configured to couple to more than one type of outer shaft. Likewise, an outer shaft may be configured to couple to more than one type of inner shaft. This versatility can allow a user to easily change an inner or outer shaft between intravascular procedures. For instance, returning to FIGS. 32A and 32B, the outer shaft having the balloon 3215 can be decoupled from the inner shaft after a procedure and replaced with a different outer shaft without a balloon for a subsequent procedure.

Figure 40:
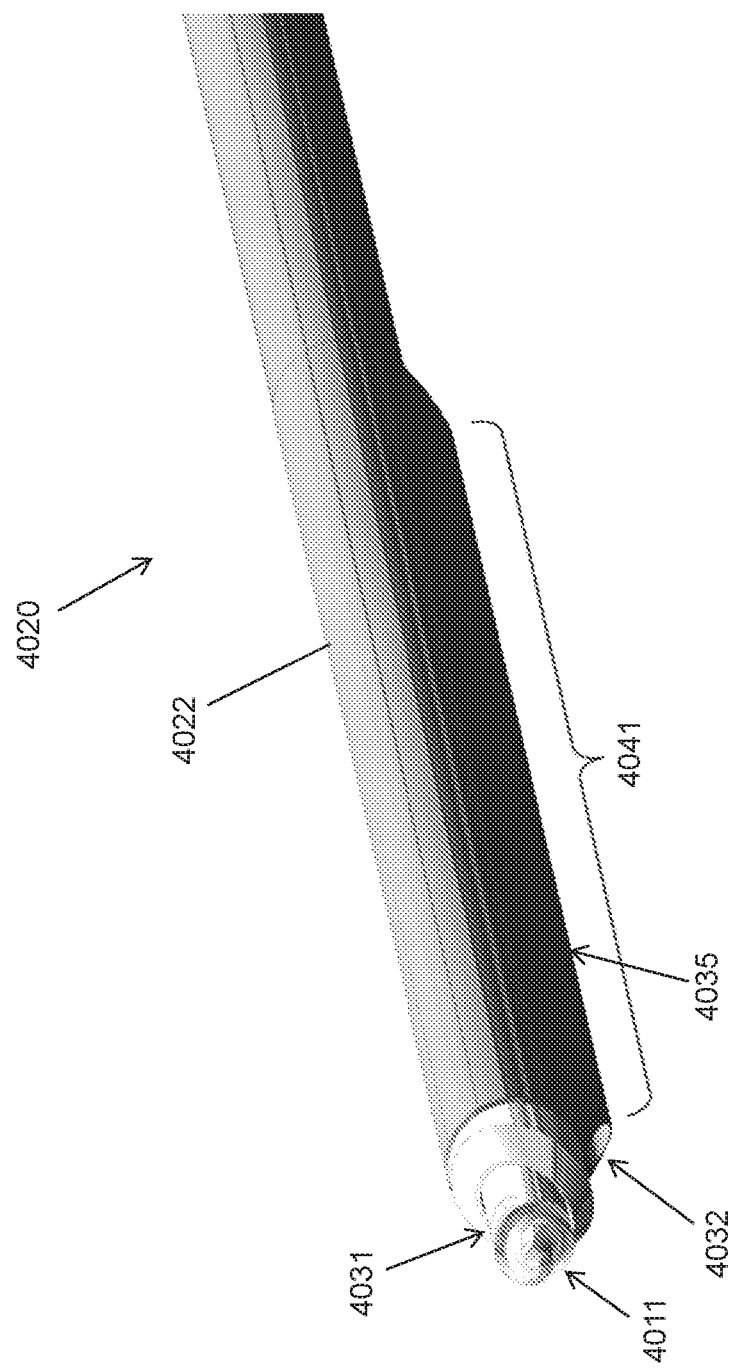
FIG. 40 shows an example of an occlusion crossing device with an outer shaft having a monorail guidewire lumen.

FIG. 40 shows another example of a catheter device 4020 having a different variation of an outer shaft 4022. The outer shaft 4022 can include a first lumen 4030 for accommodating an inner shaft 4031 and a second lumen 4032 (also referred to as a guidewire lumen or monorail guidewire lumen) for accommodating a guidewire. The outer shaft 4022 and the inner shaft 4031 may extend proximally and be rotatably coupled together by a connector at a handle region of the catheter device 4020. The monorail outer shaft 4022 configuration may be used in procedures in which a guidewire may support placement of the catheter device 4020 within an appropriate blood vessel, similar to outer shaft of FIG. 15. The diameter of the guidewire lumen 4032 may vary. In some embodiments, the diameter of the guidewire lumen 4032 is large enough to accommodate a standard guidewire (e.g., 0.014 inch diameter guidewires). The outer shaft 4022 may include, or be used with, a backbone 4035 to provide biased bending as described herein. In some cases, the guidewire lumen 4032 is radially aligned with the backbone 4035 to allow biased flexing of the catheter 4020. In some embodiments, the outer shaft 4022 does not include circumferential cuts (see e.g., FIG. 15).

The inner shaft 4031 can include any of the inner shaft features described herein, such as an imaging element/fiber, drill body/tip, collar and/or other inner shaft features described herein. In some cases, the outer shaft 4022 may be at least partially made of an optically transparent material to allow an imaging element in the inner shaft 4031 to take images through the outer shaft 4022. In other embodiments, the outer shaft 4022 is made of an optically opaque material. The guidewire lumen 4032 can extend a distance 4041 along the length of the outer shaft 4022. In some embodiments, the distance 4041 of the guidewire lumen 4032 runs along only a portion of length of the outer shaft 4022. In some cases, the distance 4041 ranges from about 10 centimeters (cm) and about 50 cm (e.g., about 10 cm, 20 cm, 25 cm, 30 cm, 45 cm, or 50 cm). In other embodiments, the distance 4041 of the guidewire lumen 4032 runs along substantially a full length of the outer shaft 4022. Thus, the distance of 4041 may extend proximally to, or close to, the handle. In general, longer guidewire lumens provide more support for the guidewire compared to shorter guidewire lumens.

The catheter device 4020 may be used in any of a number of ways. In one example, the inner shaft 4031 is placed within the first lumen 4030 of the outer shaft 4022, and the inner and outer shafts are coupled together at the handle; and a guidewire is placed within the second lumen 4032. The catheter device 4020 (with the inner shaft 4031 and the outer shaft 4022 rotatably coupled) can then be placed in the patient's blood vessel. The imaging device (e.g., including an optical fiber) within the inner shaft 4031 can be used to guide the assembly to a target location within the blood vessel, such as at or near an occlusion. For example, the optical fiber and the inner shaft 4031 can rotate with respect to the outer shaft 4022 to provide a panoramic view of the interior walls of the blood vessels during the positioning. In some cases, the outer shaft 4022 can be configured to allow imaging to occur through the walls of the outer shaft 4022. For example, the walls of the outer shaft 4022 may be optically transparent and/or include one or more windows. The drill tip 4011 may be used to cross the occlusion and the guidewire may be guided through the occlusion site. After the occlusion crossing procedure is complete and the catheter 4020 is removed from the blood vessel (e.g., by pulling the catheter 4020 proximally), the outer shaft 4022 may be decoupled from the inner shaft 4031 at the handle. The inner shaft 4031 may then be rotatably coupled with a different outer shaft for a different intravascular procedure.

FIGS. 41A and 41B show a further catheter device 4120 having a different variation of an outer shaft 4122 that may be removably coupled to any of the inner shafts (e.g., 4131) described herein. The outer shaft 4122 can include a first lumen 4130 for accommodating an inner shaft 4131 and a second lumen 4132 (also referred to as a guidewire lumen or monorail guidewire lumen) for accommodating a guidewire. In this configuration, the outer shaft 4122 may be adapted to guide the inner shaft 4131 through the blood vessel to take images of at least a portion of the blood vessel. The configuration may be configured not to use occlusion crossing features of the inner shaft 4131. The outer shaft 4122 may be have a closed distal end 4135 that covers the a tip body 4110 of the inner shaft 4131 such that the drill tip of the tip body 4110 does not travel outside of the outer shaft 4122 when inside the blood vessel. In some embodiments, the inner shaft 4131 does not include the tip body 4110. In some embodiments, the distal end 4135 of the outer shaft 4122 may have a tapered shape to facilitate the maneuvering of the distal end 4135 through the blood vessel. In some embodiments, the inner shaft 4131 may include an imaging component or element (e.g., imaging fiber) as part of an imaging system (e.g., OCT) therein and may be configured to rotate with the inner shaft 4131 with respect to the outer shaft 4122 to take images of the blood vessel. In some cases, the outer shaft 4122 may be at least partially made of an optically transparent material or may include one or more windows to allow an imaging element in the inner shaft 4131 to take images through the outer shaft 4122. In some cases, the distal portion of the outer shaft 4122 may include, or be used with, a backbone 4135 configured to provide biased bending along a plane, as described herein. In some cases, the guidewire lumen 4132 is radially aligned with the backbone 4135 (e.g., with respect to longitudinal axis of the first lumen or the inner shaft) to allow the biased flexing of the catheter 4120. In other embodiments, the distal portion of the outer shaft 4122 does not include a backbone. The guidewire lumen 4132 can extend a distance 4141 along the length of the outer shaft 4122. In some embodiments, the distance 4141 of the guidewire lumen 4132 runs along only a portion of length of the outer shaft 4122. In some cases, the distance 4141 ranges from about 10 centimeters (cm) and about 50 cm (e.g., about 10 cm, 20 cm, 25 cm, 30 cm, 45 cm, or 50 cm). In other embodiments, the distance 4141 of the guidewire lumen 4132 runs along a full length of the outer shaft 4122. Thus, the distance of 4141 may extend proximally to, or close to, the handle.

The catheter device 4120 may be used in any of a number of ways. In one example, the inner shaft 4131 (with or without the tip body 4110 attached thereto) is placed within the first lumen 4130 of the catheter device 4120 and coupled together at the handle; and a guidewire is placed within the second lumen 4132. The catheter device 4120 (with the inner shaft 4131 and the outer shaft 4122 rotatably coupled) can be placed in the patient's blood vessel. The inner shaft 4131 can be guided by the guidewire along a certain length of the blood vessel while the imaging device (e.g., including an optical fiber) within the inner shaft 4131 can be used to view the inside of the blood vessel. In some cases, the inner shaft 4131 is translated a distance within the outer shaft 4131 to collect images along a certain section of the blood vessel. The optical fiber and the inner shaft of the inner shaft 4131 may rotate with respect to the catheter device 4120 to provide a panoramic view of the interior walls of the blood vessels. The catheter device 4120 may be configured to allow imaging to occur through the walls of the catheter device 4120. For example, the walls of the catheter device 4120 may be optically transparent and/or include one or more windows. In this way, the catheter device 4120 can be used to visualize a section of the blood vessel before or after a different intravascular procedure. After the imaging is complete and the catheter 4120 is removed from the blood vessel (e.g., by pulling the catheter 4120 proximally), the outer shaft 4122 may be decoupled from the inner shaft 4131. The inner shaft 4131 may then be rotatably coupled with different outer shaft for a different intravascular procedure (e.g., occlusion crossing procedure).

Figure 42:
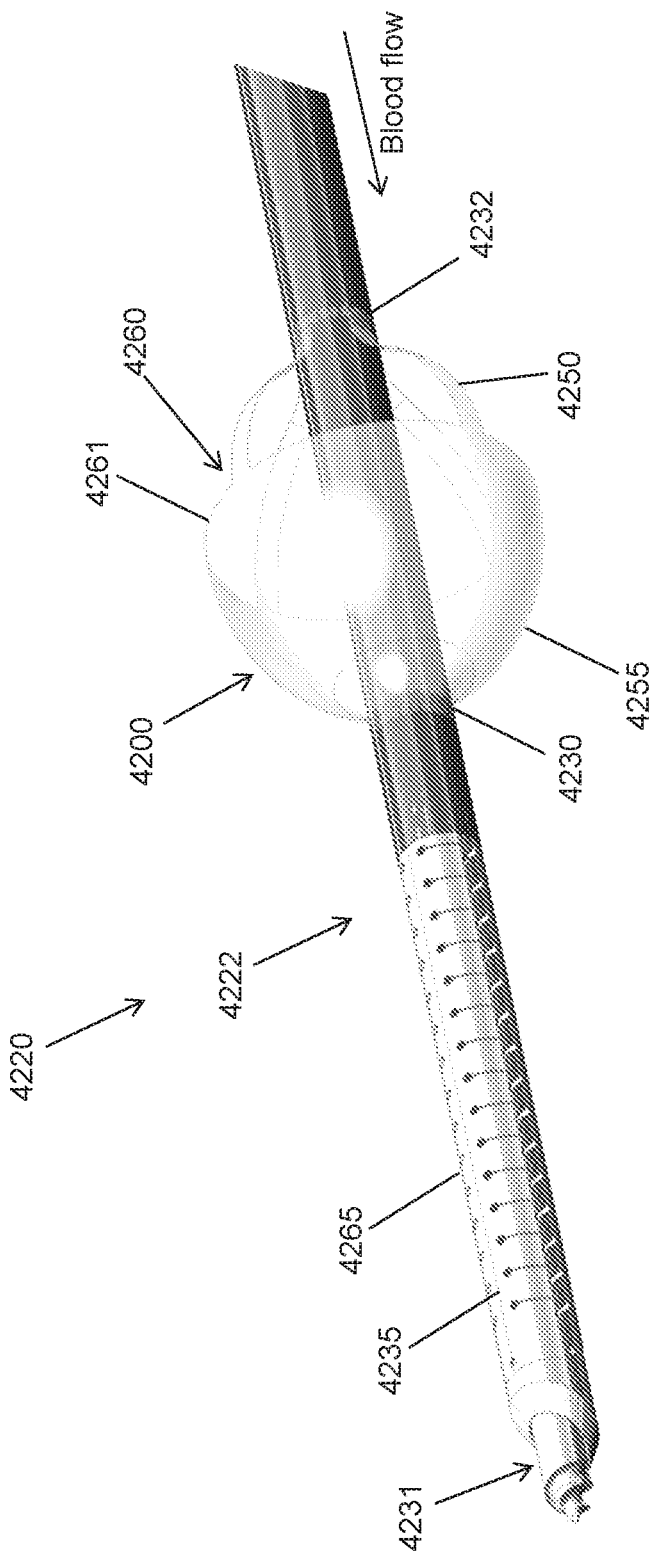
FIG. 42 shows an occlusion crossing device with an expandable sack configured to expand with blood flow within a blood vessel.

As described herein, the outer shaft can include an expandable device, such as a balloon (e.g., FIGS. 32A and 32B), to prevent or reduce the blood flow during at least a portion of a procedure. FIG. 42 shows another example of a catheter device 4220 having a different expandable device. In this case, the catheter 4220 includes an outer shaft 4222 that has an expandable sack 4200 (also referred to as a parachute), which may be used with any of the inner shafts (e.g., 4231) described herein. The sack 4200 can include a cap portion 4255, a proximal connection region 4232, an opening 4260 and one or more tethers 4250. The sack 4200 can be configured to maintain an expanded state, where a diameter of the sack 4200 is substantially larger than an outer diameter of the catheter 4220 (e.g., as shown in FIG. 42), or collapsed state, where the sack 4200 assumes a diameter close to the outer diameter of the catheter 4220. The catheter 4220 can be inserted and oriented within the blood vessel such that the flow of blood is primarily from a proximal location toward a distal location along the outer shaft 4222 and the cap portion 4255 is positioned distally along the catheter 4220 with respect to the opening 4260. The flow of blood through the opening 4260 can collect in the cap 4255 and cause the cap 4255 to expand. In an expanded state, the outer surface of the cap 4255 can contact the inner surfaces of the blood vessel and limit (e.g., reduce or prevent) blood flow within the vessel distally past the cap 4255. In some embodiments, the proximal connection region 4232 includes a ring that encircles the outer shaft 4222. The proximal connection region 4232 may be connected to the cap 4255 via one or more tethers 4250. In some cases, the tethers 4250 extend from an edge 4261 of the cap 4255 that at least partially defines the opening 4260. In the example of FIG. 42, the sack 4200 includes four tethers 4250; however, any number of tethers may be used (e.g., 1, 2, 3, 4, 5, 6, 10, 20 or more tethers).

The expandable sack 4200 may have similar functions as a balloon (e.g., FIGS. 32A and 32B). For example, the sack 4200 may be used to reduce or prevent blood flow around the imaging portion of the catheter 4220, which may allow better visualization within the blood vessel by the imaging device as the catheter 4220 is maneuvered within the blood vessel (e.g., before, during and/or after an occlusion crossing procedure). In some instances, the expanded sack 4200 may be used to apply a substantially uniform radial outward force to radially center the drill tip of the inner shaft 4231 within the blood vessel. This may prevent or reduce the occurrence injury to the blood vessel walls as the catheter 4220 is maneuvered within the blood vessel. For example, maintaining the drill tip substantially centered within the blood vessel may help prevent or reduce the occurrence of the drill tip from contacting and possibly damaging portions of the blood vessel walls as the catheter 4220 travels through the blood vessel to a target site and/or at the target site before, during and/or after an occlusion crossing procedure.

In some embodiments, the sack 4200 is configured to passively expand and collapse. For instance, the cap 4255 may be configured to expand only from the force of blood flow. To collapse the sack 4200, the catheter 4220 may be pulled proximally such that the blood vessel walls force the tethers 4250 to collapse radially inward toward the catheter 4220. The blood that is collected within the cap 4255 will be forced to exit the cap via the opening 4262 and between the tethers 4250 until the cap 4255 assumes a substantially collapse state against the outer shaft 4222 until the catheter 4220 is removed from the blood vessel.

The sack 4200 may be made of any of a number of materials. In some embodiments, at least a portion of the sack 4200 may be made of one or more flexible biocompatible materials, such as a thin sheet of flexible biocompatible polymer. In other embodiments, the sack 4200 includes a more rigid material, such as metal (e.g., Nitinol) and/or a rigid polymer material. For example, the sack 4200 may have a mesh or cage structure formed by a number wires of the rigid material. In such cases, at least the cap 4255 may be covered with a sheath (e.g., polymer and/or fabric) such that the cap 4255 can sufficiently hold the blood for expansion.

The sack 4200 may be attached to any part of the outer shaft 4222. In some embodiments, the sack 4200 is coupled to a biased bending portion 4265 at a distal region of the outer shaft 4222. In the example shown in FIG. 42, the sack 4200 is coupled to a portion of the outer shaft 4222 proximal to the biased bending portion 4265. The sack 4200 may alternatively be position partially on the biased bending portion 4265. For example, the distal end 4230 of the sack 4200 may be coupled to the biased bending portion 4265 while proximal connection region 4232 of the sack 4200 may be coupled to a region of the outer shaft 4222 proximal to the biased bending portion 4265.

The outer shaft 4222 can include one or more outer shaft features described herein. For example, the outer shaft 4222 can include a backbone 4235 to provide biased bending of the outer shaft and the catheter 4220. As another example, the outer shaft 4222 can include circumferential cuts that extend at least partially through a thickness of the outer shaft 4222. As another example, a tip region at a distal end of the outer shaft may be tapered and configured to pass in front of an imaging element as the imaging element rotates such that the tip region serves as a registration marker. As another example, the outer shaft can includes a first engagement region on an inner surface of the outer shaft that is configured to extend through a distal opening of the outer shaft, and the inner shaft can include a second engagement region on an outer surface of the inner shaft that is configured to engage with the first engagement region to limit a distal movement of the inner shaft within the outer shaft (e.g., FIG. 35).

Any of the catheter devices described herein can include a fluid flushing feature, where a fluid (e.g., saline solution) is expelled around the distal portion of the catheter. The fluid pressure of the fluid may be high enough to at least partially stop (e.g., hemostasis) or reduce blood flow at the distal end of the catheter. This can increase visibility around the distal end of the catheter so that the imaging device can obtain clear images inside the blood vessel during at least a portion of an intravascular procedure. The fluid may be carried to the distal end of the catheter by a channel that runs from a proximal portion of the catheter to the distal portion of the catheter. In some cases, the channel may be a tube or sheath within or attached to the lumen of the outer shaft and/or inner shaft. In some cases, the channel may be an elongate opening within a wall of the outer shaft and/or inner shaft that at least partially spans the length of the outer shaft and/or inner shaft. The fluid may exit one or more ports at the distal portion of the catheter, which may be in or on the outer shaft and/or inner shaft. The fluid pressure exiting the one or more ports may be controlled using one or more valves, pumps and/or regulators at a proximal portion of the catheter. In some cases, the fluid flushing is used in combination with other hemostasis or blood flow reducing mechanisms. For example, the fluid flushing catheter may include an expandable balloon (e.g., FIGS. 32A and 32B) or an expandable sack (e.g., FIG. 42). The balloon or sack can be expanded to at least partially occlude blood flow through the blood vessel while the fluid is expelled from the ports at the distal end of the catheter.

As described above, for example with reference to FIGS. 24A-24C and 25A-25B, the collar may be configured to rotate with the drill tip and inner shaft. FIGS. 43A-43I show an example of a catheter device 4300 having similar features of the catheter device 2400 (FIGS. 24A-24C) but with different collar features and optical window placement. Like the catheter device 2400, the collar 4302 is configured to rotate with the drill tip body 4310, which is coupled to and rotates with the inner (drive) shaft. Rotation of the collar 4302 during a cutting procedure can prevent the collar 4302 from getting caught up on tissue as the device 4300 is advanced through the blood vessel, thereby improving the cutting efficiency and forward movement of the catheter 4300.

In addition, as shown in FIGS. 43C and 43D, the collar 4302 can include surface features configured to cut tissue (e.g., the occlusion) to facilitate forward movement through the tissue. In this example, the distal end of the collar 4302 includes one or more grooves 4350a, 4350b, 4350c and 4350d that defined cutting edges (e.g., 4355a1, 4355a2, 4355c1 and 4355c2) for engaging with and cutting tissue when rotating to further increase forward movement. Compared to the spiral/helical flutes in other examples, the cutting edges (e.g., 4355a1, 4355a2, 4355c1 and 4355c2) can be non-helical (e.g., straight) and arranged so that the cutting edges are substantially parallel to the axis of rotation. In the example shown, the collar 4302 includes four surface grooves 4350a, 4350b, 4350c and 4350d, each defining two cutting edges. However, the collar can have any number of grooves and cutting edges. In some examples, one or more outer surfaces 4360 can include abrasive surface features such as one or more protrusions, one or more indentations and/or an adhered abrasive material (e.g., diamond particles) to further increase the cutting efficiency of the collar 4302.

Another difference of the device 4300 compared to the device 2400 of FIGS. 24A-24C is that the collar 4302 may not include an optical window. As shown in FIGS. 43E and 43F, an optical imaging window 4314 of the drill tip body 4310 can be configured to at least partially extend distally past the collar 4302 so that at last a portion of the window 4314 is at a distal position relative to the collar 4302, thereby allowing the imaging element to collect images from outside of the device 4300. This configuration may allow the window 4314 to be closer to the distal tip of the drill tip body 4310 compared to some other configurations, which can allow for images to be collected closer to the cutting area.

The device 4300 can include a similar locking mechanism as the device 2400 of FIGS. 24A-24C to allow the drill tip body 4310 to engage with and spin with the collar 4302. As shown in FIGS. 43E and 43F, a distal portion of the collar 4302 can include an edge 4317 that is configured to butt up against a stop 4315 protruding from an outer surface of the drill tip body 4310 to prevent the tip body 4310 from passing completely through the collar 4302. FIG. 43F shows the drill tip body 4310 translated distally within the collar 4302 such that the stop 4315 is engaged with (in contact with) the edge 4317 of the collar 4302, thereby preventing the drill tip body 4310 from extending distally all the way past the collar 4302. An outer surface of the drill tip body 4310 can include a first keying member at a proximal end region of the drill tip body 4310 that is configured to engage with a corresponding second keying member at a proximal end region of the collar 4302. In this example, the first keying member can correspond to one or more notches 4320 that extend laterally into the drill tip body 4310 and within the semi-annular-shaped stop 4315, thereby creating a flattened surface at the proximal region of the drill tip body 4310 at each of the notches 4320. The second keying member of the collar 4302 can include one or more bars 4322 that protrude laterally and proximally from a proximal edge of the collar 4302. The protruding bars 4322 of the collar 4302 can be configured to enter the notch 4320 of the tip body 4310 when the tip body 4310 is translated distally within the collar 4302. The walls 4324 on both side of a notch 4320 can retain the bar 4322 within the notch 4320 as the drill tip body 4310 rotates in either direction (clockwise or counterclockwise). This locking feature can become activated when the tip body 4310 is rotated to an extent that the walls 4324 become engaged with a corresponding bar 4322 that is positioned therein. In some cases, the collar 4302 is configured to rotate with the drill tip body 4310 when the stop 4315 of the drill tip body 4310 is in contact with, or nearly in contact with, the edge 4317 of the collar 4302. In some cases, the inner shaft and drill tip body 4310 are configured to rotate in both clockwise and counterclockwise directions. This may be advantageous, for example, in cases where the drill tip body 4310 provides differing cutting aggressiveness when rotated in each direction.

In the example shown, the collar 4302 includes two protruding bars 4322 that are on opposite sides of the collar 4302 and the drill tip body 4310 includes two notches 4320 that are on opposite sides of the drill tip body 4310. However, the collar and drill tip body may include any number of bars and notches (e.g., 1, 2, 3, 4, 5, 6, 8, 10, 20). To disengage the drill tip body 4310 from the collar 4302, for example when removing the inner shaft from the device 4300 for insertion of a guidewire or guide catheter, the inner shaft (with the drill tip body 4310 coupled thereto) can be translated proximally (e.g., toward the handle) to free the one or more bars 4322 from corresponding notches 4320.

Figure 43A:
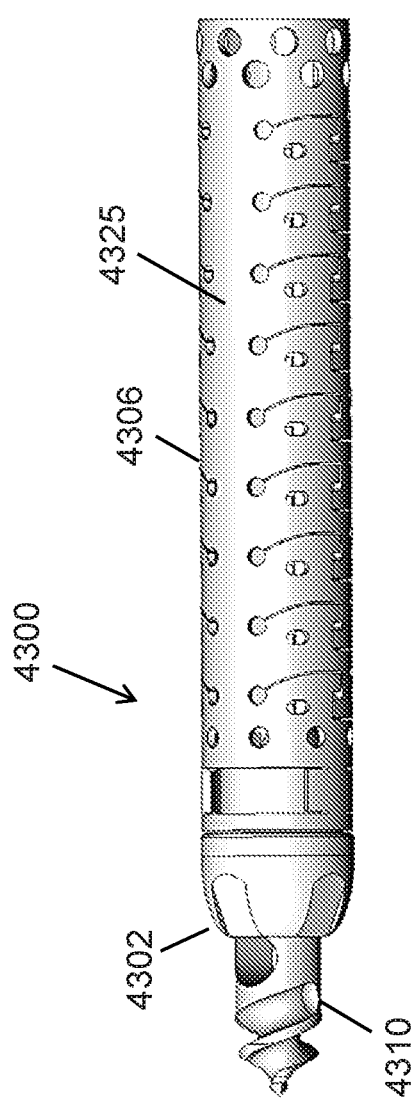
Figure 43B:
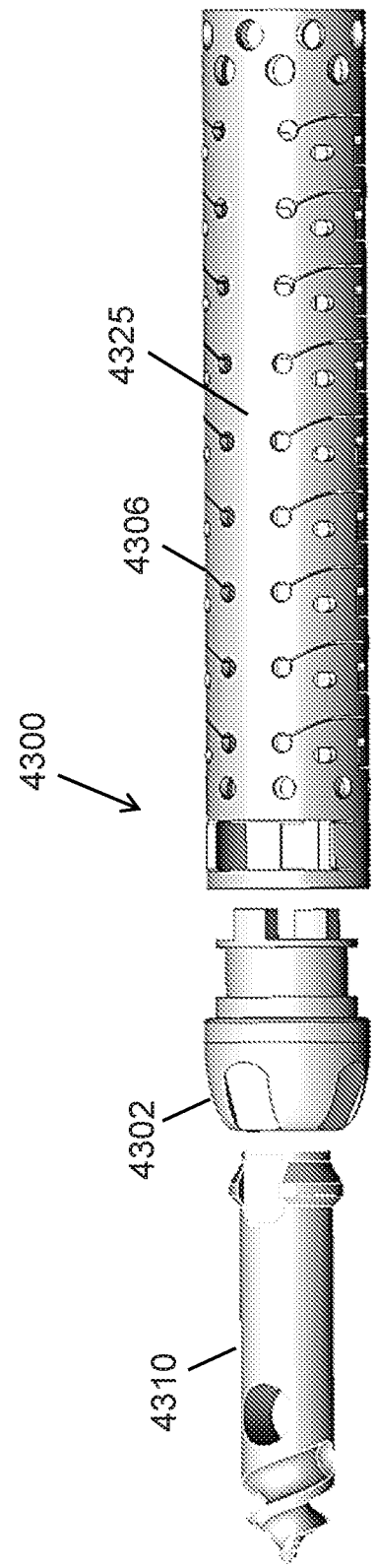
Figure 43H:
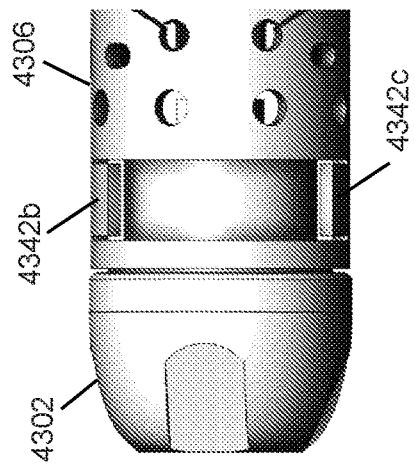
Figure 43G:
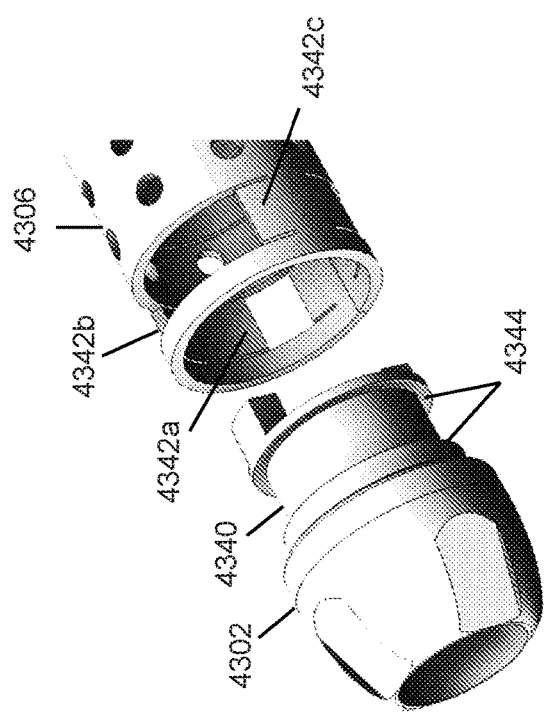
Figure 43I:
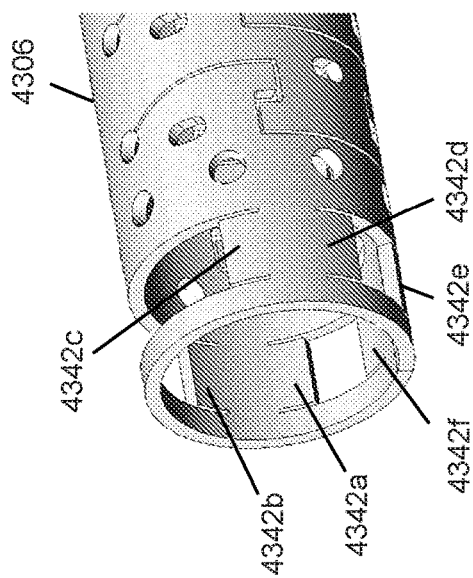

FIGS. 43G-43I illustrate how the collar 4302 can be configured to remain at a position longitudinally with respect to the outer shaft when rotating with respect to the outer shaft. The collar 4302 can include an annular groove 4340 that is configured to accommodate one or more tabs 4342*a*, 4342*b*, 4342*c*, 4342*d*, 4342*e* and 4342*f* of the outer shaft (e.g., scaffold 4306 portion of the outer shaft) to retain the collar 4302 at a position longitudinally with respect to the outer shaft when the collar 4302 rotates with respect to the outer shaft. In this example, the tabs 4342*a*-4342*f* are at a distal portion of the outer shaft and the groove 4340 is a proximal portion of the collar 4302. The tabs 4342*a*-4342*f* can be configured to be bent (e.g., during the assembly of the device 4300) so that they protrude radially within the annular groove 4340 (e.g., without contacting a bottom surface of the groove 4340). In the example shown, the outer shaft (scaffold 4306 portion of the outer shaft) includes six tabs 4342*a*-4342*f*. However, the outer shaft (e.g., scaffold portion of the outer shaft) can have any number of tabs (e.g., 1, 2, 3, 4, 5, 6, 7, 8, 9, 10, 15, 20 or more). When positioned within the groove, the tabs 4342*a*-4342*f* can contact edges 4344 that define the annular groove 4340 when the collar 4302 translates longitudinally, thereby retaining the collar 4302 longitudinally in position with respect to the outer shaft and keeping the collar 4302 from separating from the device 4300. The annular shape of the groove 4340 around the outer surface of the collar 4302 allows the collar 4302 to rotate freely with respect to the outer shaft. In some cases, the scaffold may not be configured to rotate (e.g., coupled to the handle so as not to substantially rotate).

Since the collar 4302 can be maintained longitudinally (axially) in place with respect to the outer shaft (e.g., selective bending support 4306 portion of the outer shaft), the catheter 4300 can be bent by applying a pushing force on the drill tip body 4310 against the collar 4302. For example, once the stop 4315 is pressed against the proximal edge 4317 of the collar 4302, the inner shaft can be pushed further in the distal direction to apply a pressing force against the proximal edge of the collar 4302, which can cause the bending region of the catheter 4300 to bend. As described above, the translation motion may be accommodated by a control mechanism at proximal end, which provides a relatively small amount of translational movement (e.g., between about 0.125 inches to about 0.75 inches) between the inner shaft and the outer shaft while still allowing the collar 4302 and the drill tip body 4310 to be rotationally coupled (e.g., via a connector, such as a luer lock). In some cases, the maximum translational movement provided by the control mechanism is about 0.75 inches. In some cases, the maximum translational movement provided by the control mechanism is about 0.50 inches. The control mechanism may be any mechanism that allows controlled translational movement of the inner shaft relative to the outer shaft. In some cases, the control mechanism may be part of the handle and include a slider (e.g., 303). Referring again to FIGS. 43A and 43B, applying the pressing force can cause a backbone 4325 of the scaffold 4306 (also referred to as selective bending support) to bend in the direction toward the backbone 4325 such that the side of the scaffold 4306 opposite of the backbone 4325 expands. As illustrated, the backbone 4325 can correspond to a narrow solid band that extends longitudinally along the outer shaft.

Figure 43J:
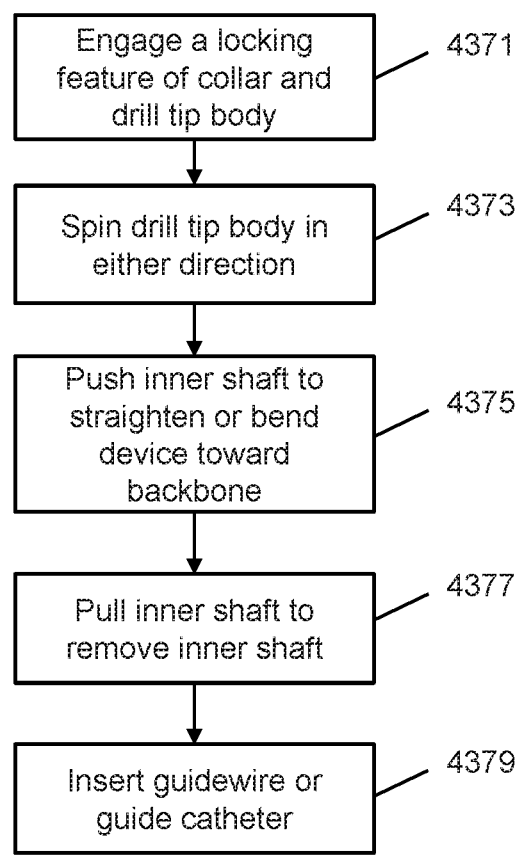
FIG. 43J is a flowchart illustrating an example method of using the catheter device shown in FIGS. 43A-43I.

FIG. 43J is a flowchart illustrating an example method of using the catheter device 4300. The locking feature of the collar 4302 and the drill tip body 4310 can be engaged (4371) by inserting the drill tip body 4310 into the collar 4302 in the distal direction. The drill tip body 4310 and collar 4302 can be spun in either direction (4373) (clockwise or counterclockwise), for example, to cross an occlusion within a blood vessel. The device 4300 can be straightened (e.g., if already in a bend configuration) or bent in a first direction (toward the backbone) while the drill tip body 4310 and collar 4302 are spinning by pushing the inner shaft (4375). The bending can facilitate navigation of the device 4300 within the blood vessel and through the occlusion. After the occlusion is crossed, the inner shaft can be removed from the outer shaft by pulling the inner shaft (4377) while leaving the outer shaft within the blood vessel. A guidewire or guide catheter can then optionally be inserted within the outer shaft (4379).

FIGS. 44A-44I show an example catheter device 4400 having similar features as catheter device 4300 but having a different optical window configuration and locking feature that allows for straightening and/or bi-directional bending of the device 4400. In this example, the locking feature of the collar 4402 and drill tip body 4410 can be configured to maintain the collar 4402 longitudinally in place when a pulling force is applied to the inner shaft. This can allow the catheter device to straighten out or bend in a direction opposite the backbone 4425 when a pulling force is applied to the inner shaft (in addition to bending toward the backbone when a pushing force is applied). The collar 4402 can include a pocket 4420 at a proximal end of the collar 4402 and that includes one or more keyways 4424*a* and 4424*b* for restraining distal and proximal movement of the drill tip body 4410. The keyways 4424*a* and 4424*b* can be configured to accept keys 4422*a* and 4422*b* of the drill tip body 4410, which protrude radially from an external surface of the drill tip body 4410. In this example, the collar 4402 includes two keyways 4424a and 4424b and the drill tip body 4410 includes two keys 4422a and 4422b. However, the devices described herein can have a collar including any number of keyways (e.g., 1, 2, 3, 4, 5, 6, 8, 10, or more) and a drill tip body including any number of keys (e.g., 1, 2, 3, 4, 5, 6, 8, 10, or more).

As shown in FIGS. 44C-44F, each keyway 4424a or 4424b can correspond to a T-shaped cutout having a gap (e.g., 4450) for allowing a key 4424a or 4424b of the drill tip body 4410 to enter and exit the keyway 4424a or 4424b when properly aligned. To engage the collar 4402 with the drill tip body 4410, the drill tip body 4410 is rotated until that the keys 4422a and 4422b are axially aligned with the gaps (e.g., 4450) and then translated distally (e.g., via pushing of the inner shaft) until the keys 4422a and 4422b enter corresponding cutouts. The keyway 4424b can have multiple edges for retaining a key 4424a or 4424b therein. A distal edge 4417 within the pocket 4420 of the collar 4402 can be configured to butt up against the key 4422b to prevent the tip body 4410 from passing completely through the collar 4402. Lateral edges 4425a and 4425b can restrict axial movement of the key 4422a or 4422b when within the keyway 4424b. Rotational movement of the drill tip body 4410 can cause the keys 4422a and 4422b to contact one of the lateral edges (e.g., lateral edges 4425a and 4425b), as shown in FIG. 44F. This way, when the drill tip body 4410 is spinning in either direction (clockwise or counterclockwise), the collar 4402 can remain engaged with the drill tip body 4410.

Undercut edges 4430a and 4430b can prevent the key 4422b from exiting the pocket 4420 when drill tip body 4410 is pulled proximally if the key 4422a or 4422b is not axially aligned with the gap 4450. For example, FIG. 44F shows the key 4422b within the keyway 4424b and not axially aligned with the gap 4450 so that the undercut edge 4430b prevent the key 4422b from exiting the gap 4450 when the drill tip body 4410 is pulled proximally. This way, when a translational force is applied to the drill tip body 4410 (e.g., via the inner shaft) in the proximal direction (pulling force) the collar 4402 can remain coupled to the drill tip body 4410. Additionally, an appropriate pulling force can be applied to the scaffold 4406 to straighten out the device, and in some cases, cause the device to bend in the direction opposite the backbone 4425. Details of how the scaffold 4406 can be configured for unidirectional and bidirectional bending, and to control the extent of bending of the device, are described further below with reference to FIGS. 47A-47C and 48A-48E.

To disengage the collar 4402 and the drill tip body 4410, the drill tip body 4410 can be rotated such that the keys 4422a and 4422b are again aligned with gaps (e.g., 4450) of the collar 4402, then the drill tip body 4410 can be translated proximally (e.g., via pulling of the inner shaft) until the keys 4422a and 4422b are released from the cutouts 4424a and 4424b. Disengagement may involve stopping spinning of the drill tip body 4410 and inner shaft, slightly rotating (e.g., less than one full rotation) the drill tip body 4410 to align the keys 4422a and 4422b with the respective gaps (e.g., 4450), then pulling the inner shaft (with the drill tip body 4410 attached thereto) until the keys 4422a and 4422b are out of the pocket 4420. Once disengaged from the collar 4402, the drill tip body 4410 and inner shaft can be removed from the catheter device to allow insertion of a guidewire or guide catheter.

The collar 4402 can include one or more optical imaging windows 4445a and 4445b that are configured to align with an optical imaging window 4446 of the drill tip body 4410 to provide optical access for an imaging element coupled to the inner shaft. The drill tip body 4410 may be configured to engage with the collar 4402 in multiple orientations. For instance, a first key 4422a can be configured to be captured within a first cutout 4424a or a second cutout 4424b depending on the axial orientation of the drill tip body 4410 with respect to the collar 4402. If the first key 4422a is captured within the first cutout 4424a, the imaging window 4446 of the drill tip body 4410 can be aligned with a first imaging window 4445a of the collar 4402.

Figure 44I:
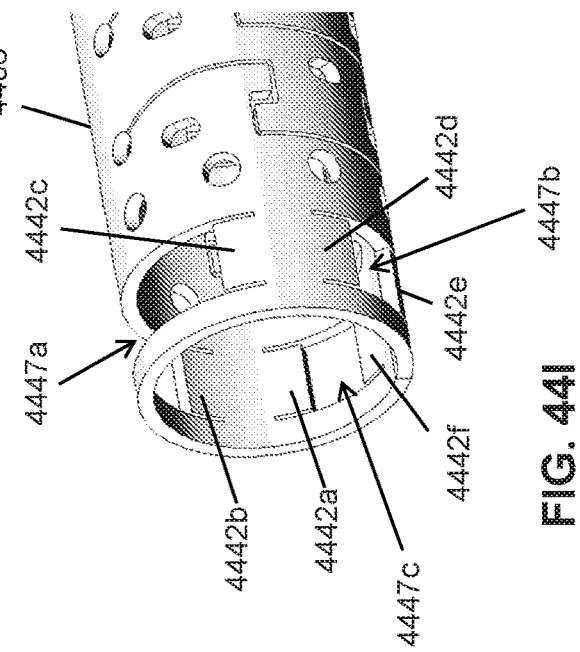
Figure 44G:
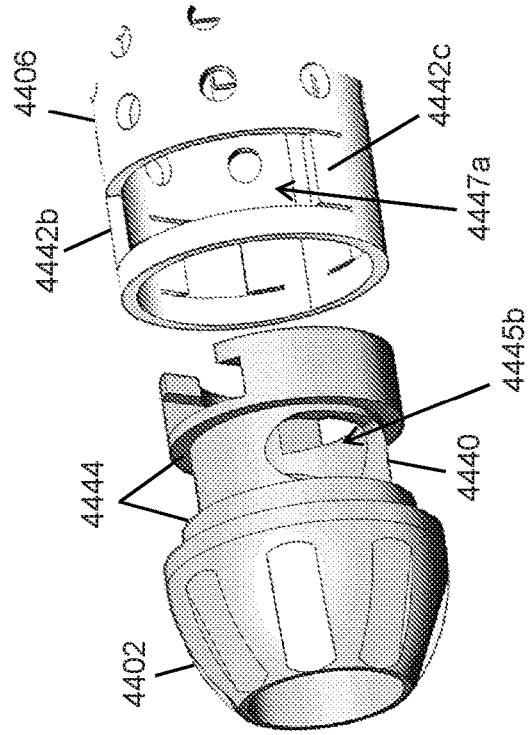
Figure 44H:
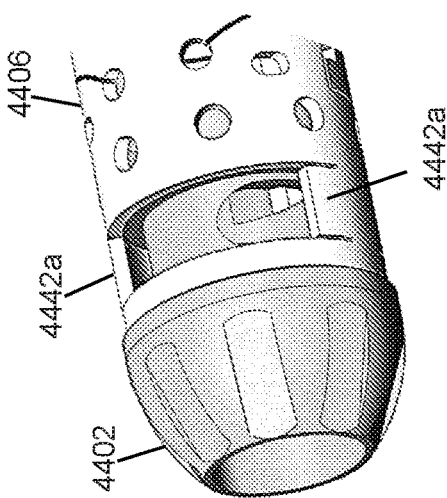

FIGS. 44G-44I illustrate how the collar 4402 can be rotationally coupled with the scaffold 4406 of the outer shaft. The collar 4402 can include an annular groove 4440 that is configured to accommodate one or more tabs 4442a, 4442b, 4442c, 4442d, 4442e and 4442f of the outer shaft (e.g., scaffold 4406 portion of the outer shaft) to retain the collar 4402 at a position longitudinally with respect to the outer shaft when the collar 4402 rotates with respect to the outer shaft. The tabs 4442a-4442f can be bent radially inward (e.g., during the assembly of the device 4400) so that they protrude radially within the annular groove 4440 (e.g., without contacting a bottom surface of the groove 4440). When positioned within the groove, the tabs 4442a and 4442b can contact the edges 4444 surrounding the annular groove 4440 when the collar 4402 translates longitudinally, thereby retaining the collar 4402 at a longitudinal position with respect to the outer shaft and keeping the collar 4402 from separating from the device 4400. In the example shown, the outer shaft (scaffold 4406 portion of the outer shaft) includes six tabs.

The one or more imaging windows 4445a and 4445b of the collar 4402 can be longitudinally aligned with one or more slots 4447a, 4447b and 4447c within the scaffold 4406 to provide optical access for the imaging element outside of the catheter device. When the drill tip body is engaged with and rotates with the collar 4402, the windows 4445 rotate with respect to the scaffold 4406 such that solid sections of the scaffold 4406 (including tabs 4442a-4442f) between the slots 4447a-4447c periodically pass in front of and are detected by the imaging element. These solid sections of the scaffold 4406 can be used as imaging markers to determine the relative orientation of the catheter 4400 when in use. The solid section markers can be arranged so that they are at predetermined radial distances from each other. In some cases, the solid section markers are arranged radially equidistantly apart from each other.

Figure 44J:
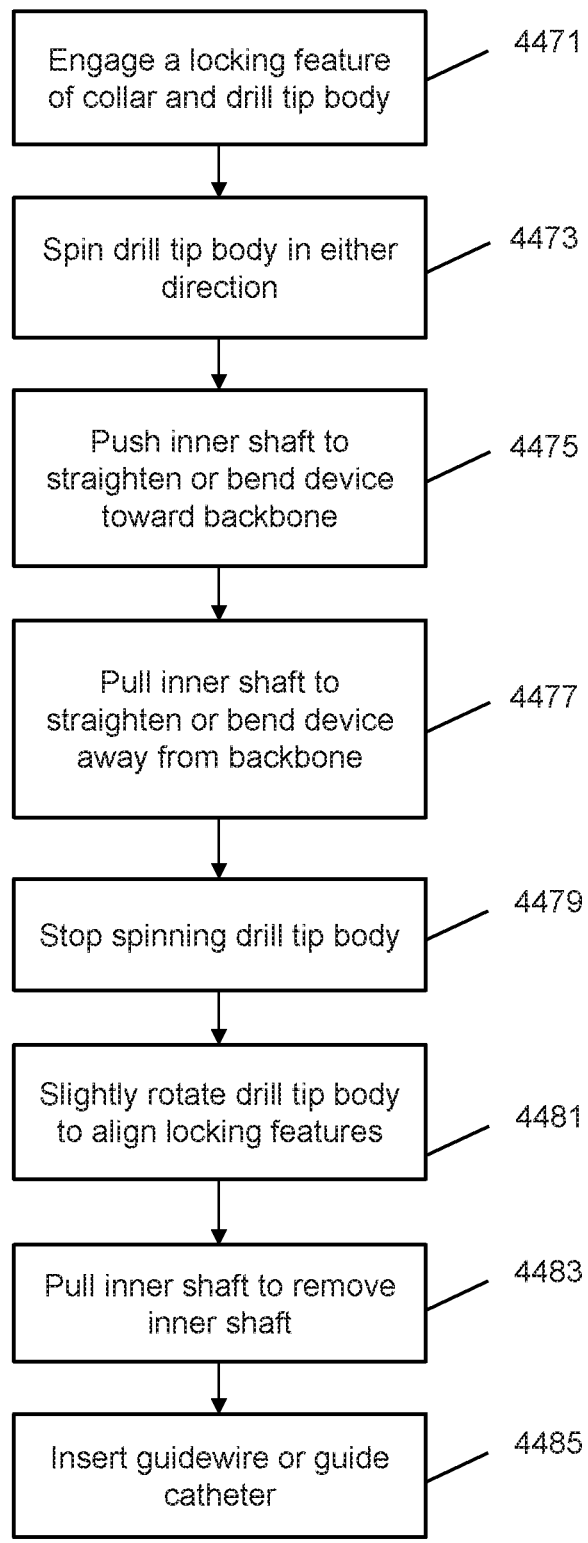
FIG. 44J is a flowchart illustrating an example method of using the catheter device shown in FIGS. 44A-44I.

FIG. 44J is a flowchart illustrating an example method of using the catheter device 4400. The locking feature of the collar 4402 and the drill tip body 4410 can be engaged (4471) by distally translating the drill tip body 4410 within the collar 4402 and rotating the drill tip body 4410 with respect to the collar 4402 in the clockwise or counterclockwise direction. The drill tip body 4410 and collar 4402 can be spun in clockwise or/or counterclockwise direction (4473), for example, to cross an occlusion within a blood vessel. The device 4400 can be straightened (e.g., if already in a bend configuration) or bent in a first direction (toward the backbone) while the drill tip body 4410 and collar 4402 are spinning by pushing the inner shaft (4475). The device 4400 can also be straightened or bent in a second direction (away from the backbone) while the drill tip body 4410 and collar 4402 are spinning by pulling the inner shaft (4477). The bending and straightening can facilitate navigation of the device 4400 within the blood vessel and through the occlusion. After the occlusion is crossed, the drill tip body 4410 can be stopped from spinning (4479), for example, via the inner shaft using the handle. The drill tip body 4410 can be slightly rotated (e.g., less than one full rotation) to align the keys 4422a and 4422b with respective gaps 4450 of the collar 4402 (4481). Once the keys 4422a and 4422b are aligned, the inner shaft can be removed from the outer shaft by pulling the inner shaft (4483) while leaving the outer shaft within the blood vessel. A guidewire or guide catheter can then optionally be inserted within the outer shaft (4485).

FIGS. 45A-45D show another example catheter device 4500 having similar features as catheter device 4400 but having a collar 4502 and drill tip body 4510 with a different locking feature variation. Like the device 4400, the scaffold 4506 can include a backbone 4525 to control bending of the device 4500. In this example, the collar 4502 has keyways 4524a and 4524b corresponding to L-shaped cutouts. The L-shaped keyway 4524b has an undercut edge 4530 on one side to retain the key 4522b of the drill tip body 4510 within the keyways 4524b when the drill tip body 4510 is pulled proximally, thereby allowing the catheter to straighten and in some cases bend in the direction opposite the backbone (bidirectionally bend). The other side of the L-shaped keyway 4524b includes a gap 4550 that allows the key 4424b to exit the keyway 4524b when the key 4424b is axially aligned with the gap 4550 and the drill tip body 4510 is pulled proximally. This can allow removal of the inner shaft by rotating the drill tip body 4510 in the direction to align the key 4424b with the gap 4550. Note that the collar 4502 can be engaged with and rotate with the drill tip body 4510 when the drill tip body 4510 is rotated in either direction (clockwise or counterclockwise). Thus, this locking feature variation can allow for: (1) the drill tip body 4510 to bend towards the backbone when the drill tip body 4510 is spinning in either direction (due to spinning and proximal force on the inner shaft); (2) the drill tip body 4510 to be pulled proximally to enable straightening (or bending in the direction opposite to the backbone) when the drill tip body 4510 is rotated in the clockwise direction 4595 because of engagement with the L-shaped keyway 4524b; and (3) the drill tip body 4510 to be removed when spinning is stopped and the tip is rotated slightly (e.g., less than one full rotation) in the counterclockwise direction 4596 to disengage from the L-shaped keyway. One advantage of this design relative to the device 4400 is that it may be easier to remove the inner shaft since you may not need to align the locking feature for removal of the inner shaft. Note that in other examples the L-shaped keyway(s) may be configured to lock the key(s) when rotated in the counterclockwise direction 4596 and unlock the key(s) when rotated in the clockwise direction 4595.

Figure 45E:
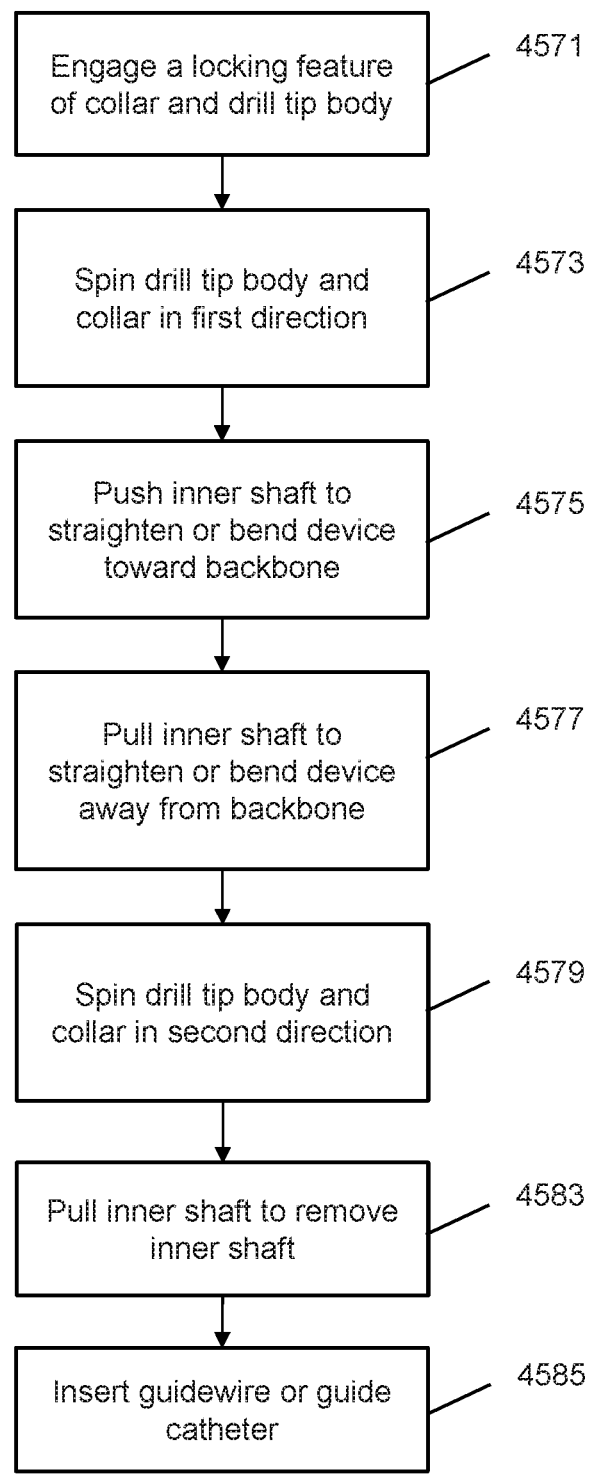
FIG. 45E is a flowchart illustrating an example method of using the catheter device shown in FIGS. 45A-45D.

FIG. 45E is a flowchart illustrating an example method of using the catheter device 4500. The locking feature of the collar 4502 and the drill tip body 4510 can be engaged (4571) by distally translating the drill tip body 4510 within the collar 4502 and rotating the drill tip body 4510 (e.g., slightly) with respect to the collar 4502 in first direction (e.g. clockwise). The drill tip body 4510 and collar 4502 can be spun in a first direction (4573) (e.g., clockwise 4595) via the inner shaft, for example, to cross an occlusion within a blood vessel. The device 4500 can be straightened (e.g., if already in a bend configuration) or bent in a first direction (toward the backbone) while the drill tip body 4510 and collar 4502 are spinning by pushing the inner shaft (4575). The drill tip body 4510 and collar 4502 can be spun in the first direction (e.g., clockwise 4595) or second direction (e.g., counterclockwise 4596), for example, to facilitate navigation through the vessel and/or occlusion. Spinning in the first direction (e.g., clockwise 4595) can cause the keys (e.g., 4522b) to be retained within respective L-shaped keyways (e.g., 4524b) by undercut edges (e.g., 4530) when a pulling force is applied to the drill tip body 4510. This can allow the catheter to straighten or bend in a second direction (away from the backbone) while the drill tip body 4510 and collar 4502 are spinning in the first direction (e.g., clockwise 4595) by pulling on the inner shaft (4577). To remove the inner shaft, the inner shaft and drill tip body 4510 can be spun in a second direction (4579) (e.g., counterclockwise 4596) to cause the keys (e.g., 4522b) to butt up against a lateral edge (e.g., 4525b) and align with gaps (e.g., 4550) of respective L-shaped keyways (e.g., 4524b). The inner shaft can then be pulled to remove the inner shaft (4583). Once the inner shaft (with the drill tip body 4510) is removed, a guidewire or guide catheter can optionally be inserted within the outer shaft (4585).

FIGS. 46A-46D show another example catheter device 4600 having similar features as catheter device 4400 but having a collar 4602 and drill tip body 4610 with a different locking feature variation. Like the device 4400, the scaffold 4606 can include a backbone 4625 to control bending of the device 4600. In this variation, the collar 4602 has keyways (e.g., 4624b) with tapered undercut edges (e.g., 4630a and 4630b) that modulate the amount of pulling force required to disengage the drill tip body 4610 from the collar 4602. For example, the tapered undercut edges 4630a and 4630b can be angled to urge the key 4622b toward the gap 4650 when the drill tip body 4610 is pulled proximally (e.g., via the inner shaft). One advantage of this locking feature relative to the locking feature of device 4400 is that less alignment may be required to unlock the drill tip body 4610 from the collar 4602 since the tapered undercut edges 4630a and 4630b can help to align the key 4622b for unlocking while still allowing for rotation in the clockwise and counterclockwise directions when pulling the drill tip body 4610 proximally. When the drill tip body 4610 is spinning, the rotational force can cause the key 4622b to butt up against the lateral edge 4525a or 4525b so that the collar 4502 can spin with the drill tip body 4510 while the two are locked. Also, the undercut edge 4630a or 4630b (depending on the rotation direction) can retain the key 4622b within the keyway 4624b while the drill tip body 4610 and the collar 4502 are spinning. Thus, a pulling force applied to the drill tip body 4610 (e.g., via the inner shaft) can cause the catheter to straighten or bend in the direction opposite the backbone 4625 when the drill tip body 4610 is spinning. When the drill tip body 4610 is not spinning and the rotational forces are not applied, a pulling force can cause the key 4622b to slide along the angled undercut edge 4630a or 4630b and eventually exit the gap 4650. In some cases, the angled undercut edge 4630a or 4630b can causes the drill tip body 4610 to slightly rotate and align the key 4622b with the gap 4650 when the pulling force is applied to the drill tip body 4610. The angle of the undercut edges 4630a and 4630b can be chosen based on a desired pulling force required to disengage the drill tip body 4610 from the collar 4602, with larger angles providing more urging of the key 4622b toward the gap 4650.

Figure 46A:
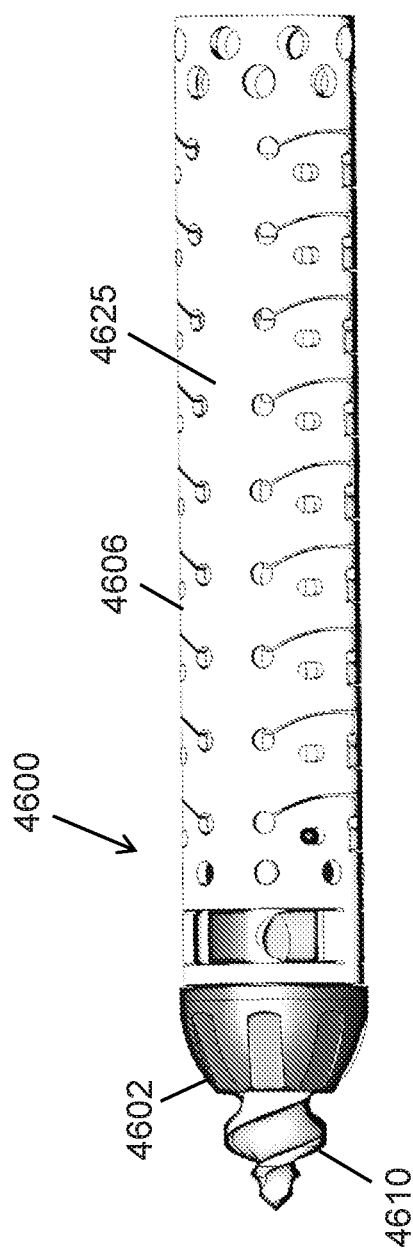
Figure 46B:
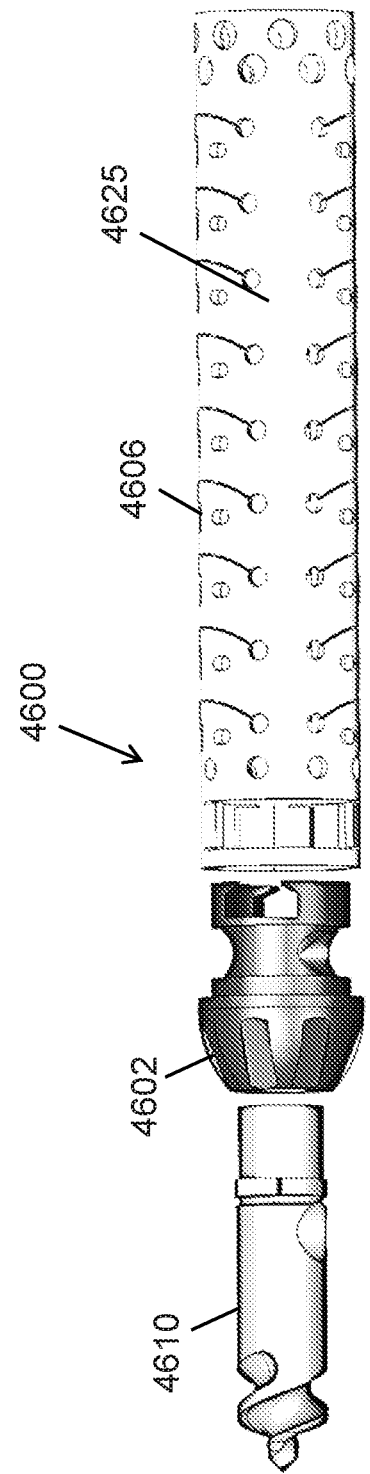
Figure 46E:
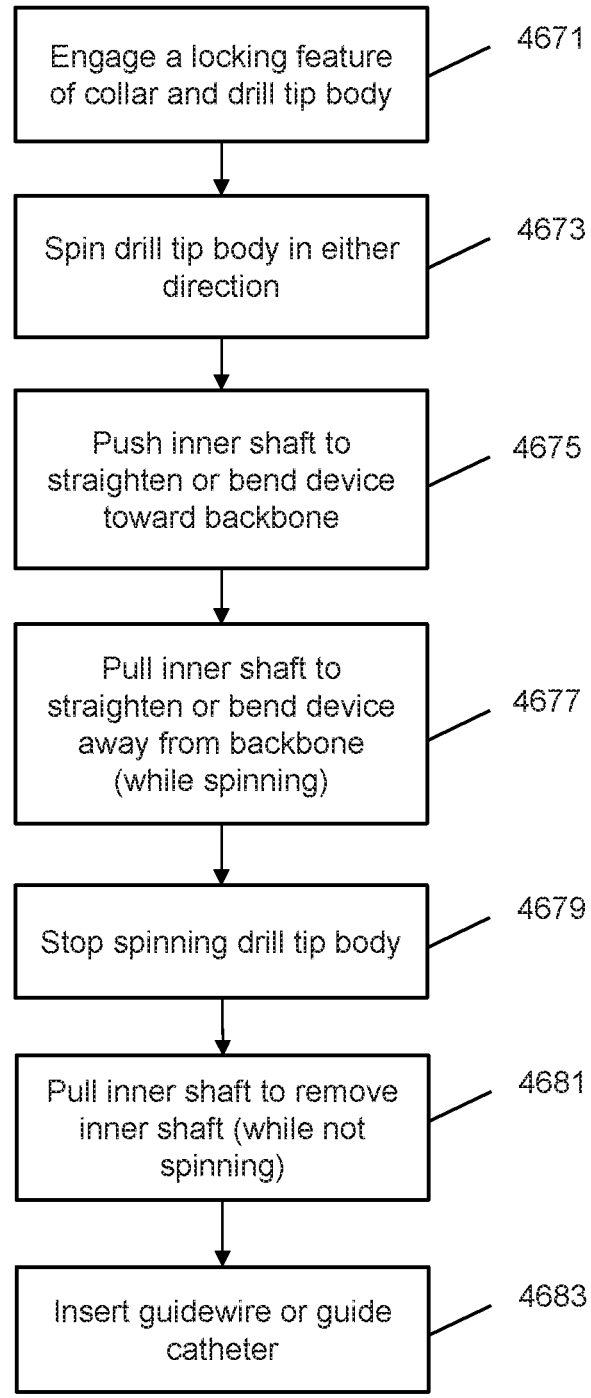
FIG. 46E is a flowchart illustrating an example method of using the catheter device shown in FIGS. 46A-46D.

FIG. 46E is a flowchart illustrating an example method of using the catheter device 4600. The locking feature of the collar 4602 and the drill tip body 4610 can be engaged (4671) by distally translating the drill tip body 4610 into the collar 4602 and rotating the drill tip body 4610 (e.g., slightly) with respect to the collar 4502 in clockwise or counterclockwise direction. The drill tip body 4510 and collar 4502 can be spun in a first direction (4573) (e.g., clockwise 4595) via the inner shaft, for example, to cross an occlusion within a blood vessel.

The locking feature of the collar 4602 and the drill tip body 4610 can be engaged (4671) by inserting the drill tip body 4610 into the collar 4602 and axially translating the drill tip body 4610 in the distal direction. The drill tip body 4610 and collar 4602 can be spun in either direction (4673) via the inner shaft, for example, to cross an occlusion within a blood vessel. The device 4600 can be straightened (e.g., if already in a bend configuration) or bent in a first direction (toward the backbone) while the drill tip body 45610 and collar 4602 are spinning by pushing the inner shaft (4675). The device 4600 can also be straightened or bent in a second direction (away from the backbone) while the drill tip body 4610 and collar 4602 are spinning by pulling the inner shaft (4677). To remove the inner shaft, the inner shaft, drill tip body 4510 and collar 4602 can be stopped from spinning (4679) and the inner shaft can be axially translated in the proximal direction (pulled) (4681). Once the inner shaft (with the drill tip body 4610) is removed, a guidewire or guide catheter can optionally be inserted within the outer shaft (4683).

As described above with reference to FIGS. 43A-43J, 44A-44J, 45A-45E and 46A-46E, the locking feature of the collar and drill tip body can restrain translational movement of the drill tip body/inner shaft with respect to the collar when the locking feature is engaged. In some embodiments, the drill tip body/may be allowed to translate with respect to the collar by less than about 1 millimeter (mm).

As described herein, the locking features of the drill tip body and collar can be configured to allow for pulling and/or pushing of the drill tip body/inner shaft to cause unidirectional bending, unidirectional bending plus straightening, or bidirectional bending of the catheter device. The bending directionality of the catheter device can also depend on the configuration of the scaffold. FIGS. 47A-47C and 48A-48E illustrate of two example scaffolds showing how a scaffold can control directional bending of the catheter device, either of which may be implemented in any of the catheter devices described herein.

Figure 47A:
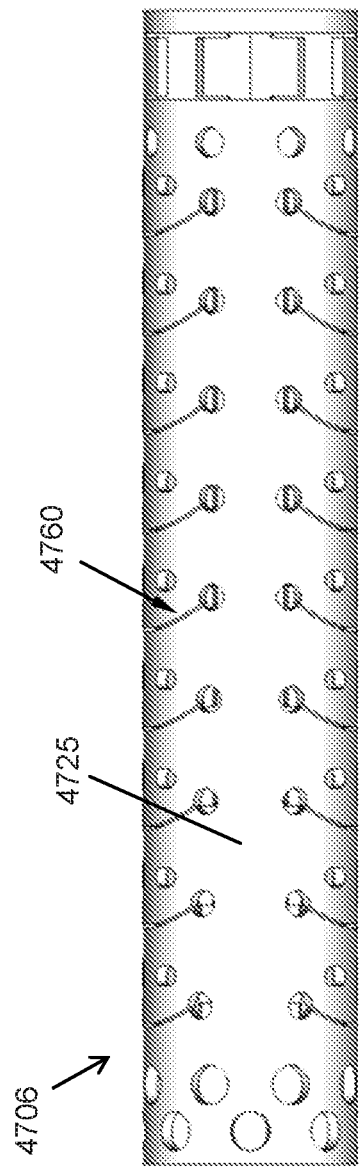
Figure 47B:
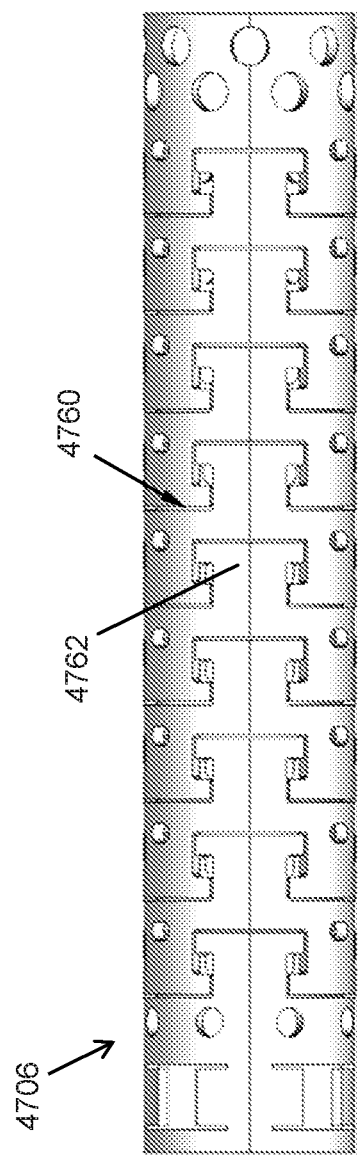

FIGS. 47A-47C illustrate features of an example scaffold 4706 configured for unidirectional bending. FIG. 47A shows a side of a scaffold 4706 that includes the backbone 4725, and FIG. 47B shows a side of the scaffold 4706 opposite the backbone 4725. The scaffold 4706 can include a series of axial slits 4760 (also referred to as axial or circumferential cuts) longitudinally arranged along at least a portion of the scaffold 4706. As shown, in FIG. 47B, each of the slits 4760 can form a T-shaped segment 4762 within the scaffold 4706 in the side of the scaffold 4706 opposite the backbone 4725. When the scaffold 4706 bends toward the backbone 4725, the side of the scaffold 4706 with the backbone 4725 contracts and the side of the scaffold 4706 opposite the backbone 4725 expands. When the scaffold 4706 bends away from the backbone 4725, the side of the scaffold 4706 with the backbone 4725 expands and the side of the scaffold 4706 opposite the backbone 4725 contracts. The spaces around the T-shaped segments 4762 can dictate how much the scaffold 4706 can bend toward and away from the backbone 4725. In the example of scaffold 4706, the spacing around the T-shaped segments 4762 allow for bending toward the backbone 4725 and little to no bending away from the backbone 4725.

FIG. 47C shows a close-up view of the side of the scaffold 4706 opposite the backbone 4725 with details of the spacing around the T-shaped segments 4762. The slits 4760 can be shaped to provide first spaces 4764a and 4764b on a first side (e.g., distal side) of each T-shaped segment 4762 and a second space 4766 on a second side (e.g., proximal side) of each T-shaped segment 4762. The longitudinal widths 4768 (as measured along the longitude of the scaffold 4706) of the first spaces 4764a and 4764b can dictate how much the scaffold 4706 can bend in a lateral direction toward the backbone 4725. The longitudinal width 4770 (as measured along the longitude of the scaffold 4706) of the second space 4766 can dictate how much the scaffold 4706 can bend in a lateral direction away from the backbone 4725. For example, the first spaces 4764a and 4764b allow room for the side of the scaffold 4706 opposite the backbone 4725 to expand the scaffold 4706 from a straightened (neutral) configuration to bent configuration toward the backbone 4725 when a longitudinal force is applied to scaffold 4706 in the distal direction (e.g., by pushing the drill tip body/ inner shaft). Further pushing of the drill tip body/inner shaft can cause the T-shaped segment 4762 to contact a first edge 4792 on the first side (e.g., distal side) of the T-shaped segment 4762, thereby preventing the scaffold 4725 from further bending toward the backbone 4725. Thus, the first edge 4792 can serve as a stop element to limit lateral bending of the scaffold 4706 in the direction toward the backbone. The larger the longitudinal widths 4768 of the first spaces 4764a and 4764b, the more the scaffold 4706 can bend in a direction toward the backbone 4725. A longitudinal force can be applied to the scaffold 4706 in the proximal direction (e.g., by pulling the drill tip body/inner shaft) to straighten the scaffold 4706 back to the straightened (neutral) position. Once the scaffold 4706 is in a straightened (neutral) position, further pulling of the drill tip body/inner shaft can cause the T-shaped segment 4762 to contact a second edge 4794 on the second side (e.g., proximal side) of the T-shaped segment 4762, thereby preventing the scaffold 4706 from bending in the direction opposite the backbone 4725. In this way, the second edge 4794 can serve as a stop element to limit lateral bending of the scaffold 4706 in the direction away from the backbone. Since the longitudinal width 4770 of the second space 4766 is very small, the side of the scaffold 4706 with the backbone 4725 can be prevented from contracting (prevent lateral bending of the scaffold 4706 away from the backbone 4725).

Figure 48A:
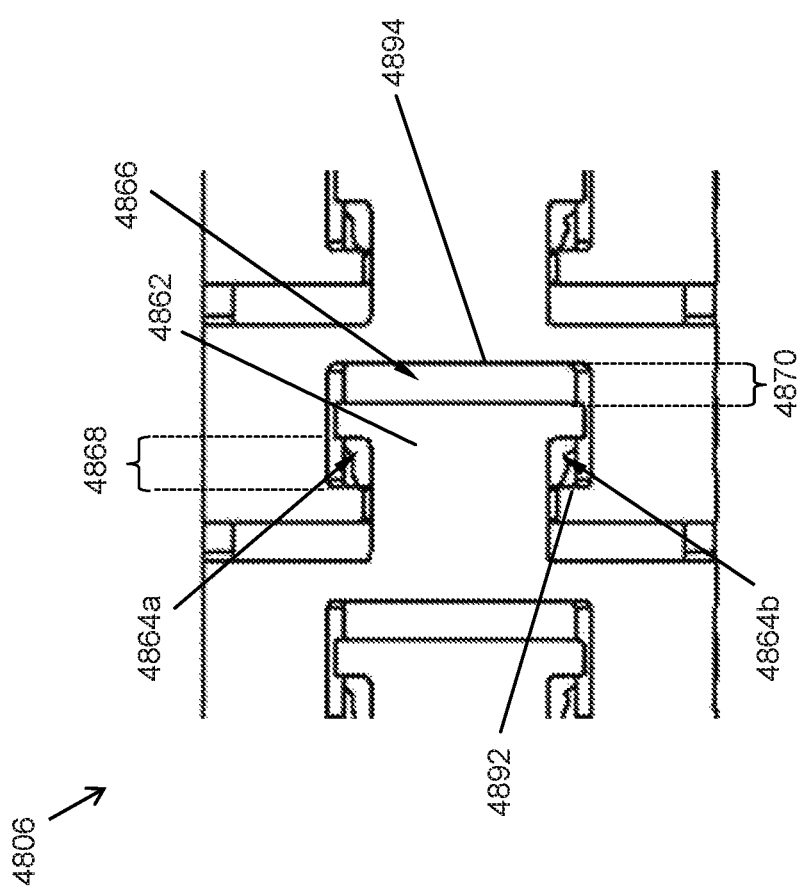

FIGS. 48A-48E illustrate an example scaffold 4806 having similar features as the scaffold 4706 in FIGS. 47A-47C except that the scaffold 4806 is configured for bidirectional bending. FIG. 48A shows a close-up view of the side of the scaffold 4806 opposite the backbone 4825, illustrating the first spaces 4864a and 4864b on a first side (e.g., distal side) and a second space 4866 on the second side (e.g., proximal side) of each T-shaped segment 4862. As with the scaffold 4706 in FIGS. 47A-47C, the longitudinal widths 4868 of the first spaces 4864a and 4864b can dictate how much the scaffold 4706 can bend in a lateral direction toward the backbone 4825, and the longitudinal width 4870 of the second space 4866 can dictate how much the scaffold 4806 can bend in a lateral direction away from the backbone 4825. In this case, the second space 4866 is large enough to allow the scaffold 4806 to bend away from the backbone 4825.

For example, from a straightened (neutral) position of the scaffold 4806, a longitudinal force applied to scaffold 4806 in the distal direction (e.g., by pushing the drill tip body/ inner shaft), the first spaces 4864a and 4864b allow room for the side of the scaffold 4806 opposite the backbone 4825 to expand (and the side of the scaffold 4806 having the backbone 4825 to contract), thereby allowing the scaffold 4806 to bend toward the backbone 4825 (as shown in FIGS.

48B and 48C). Further pushing of the drill tip body/inner shaft can cause the T-shaped segment 4862 to contact a first edge 4892 on a first side (e.g., distal side) of the T-shaped segment 4862, thereby preventing the scaffold 4825 from further bending. Thus, the first edge 4892 can serve as a stop element to limit lateral bending of the scaffold 4806 in the direction toward the backbone. A longitudinal force can be applied to the scaffold 4806 in the proximal direction (e.g., by pulling the drill tip body/inner shaft) to straighten the scaffold 4806 back to the straightened (neutral) position. When a further longitudinal force is applied to the scaffold 4806 in the proximal direction (e.g., by pulling the drill tip body/inner shaft), the space 4866 on the second side (e.g., proximal side) of the T-shaped segment 4862 can allow the side of the scaffold 4806 having the backbone 4825 to expand (and the side of the scaffold 4806 opposite the backbone 4825 to contract), thereby causing the scaffold 4806 to bend away from the backbone 4825 (as shown in FIGS. 48D and 48E). Further pulling of the drill tip body/ inner shaft can cause the T-shaped segment 4862 to contact a second edge 4894 on the second side (e.g., distal side) of the T-shaped segment 4862, thereby preventing the scaffold 4825 from further bending away from the backbone 4825. In this way, the second edge 4894 can serve as a stop element to limit lateral bending of the scaffold 4806 in the direction away from the backbone.

It should be understood that any element or feature described herein with respect to one embodiment can be combined with or substituted for any element or feature described herein with respect to another embodiment.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the examples described herein, but only by the plain meaning of the claim terms employed.

What is claimed is:

1. An occlusion crossing device comprising:
an inner shaft operatively coupled to a rotational driver for rotating the inner shaft, the inner shaft including a distal end with a drill tip body configured to pass through an occlusion within a blood vessel, the inner shaft further including an optical coherence tomography (OCT) imaging element at a distal end region of the inner shaft that is configured to collect images outside of the device;
an outer shaft removably coupled to the inner shaft so that the inner shaft can rotate and translate longitudinally within the outer shaft in a distal direction and a proximal direction; and
a collar rotatably coupled to a distal end of the outer shaft and having a central opening to accommodate the drill tip body therein, wherein the drill tip body and the collar include a lock configured to lock the collar to the drill tip body so that the collar and drill tip body are rotatable together, wherein when the collar is locked with the drill tip body:
distal movement of the inner shaft relative to the outer shaft causes the occlusion crossing device to bend, and
proximal movement of the inner shaft relative to the outer shaft causes the occlusion crossing device to straighten.

2. The occlusion crossing device of claim 1, wherein the lock is configured to unlock the collar from the drill tip body by stopping rotation of the drill tip body and translating the drill tip body proximally relative to the collar.

3. The occlusion crossing device of claim 2, wherein unlocking the collar from the drill tip body further comprises rotating the drill tip body relative to the collar by less than a full rotation before translating the drill tip body proximally relative to the collar.

4. The occlusion crossing device of claim 1, wherein the lock allows the drill tip body and the inner shaft to be removed from the outer shaft.

5. The occlusion crossing device of claim 1, wherein the drill tip body includes a stop that prevents the drill tip body from extending completely through the central opening of the collar when the drill tip body is translated in the distal direction.

6. The occlusion crossing device of claim 5, wherein the stop of the drill tip body is configured to press against a proximal edge of the collar to prevent the drill tip body from extending completely through the central opening of the collar.

7. The occlusion crossing device of claim 1, wherein the lock includes one or more keyways of the collar that is configured to retain one or more keys of the drill tip body to lock the collar and the drill tip body.

8. The occlusion crossing device of claim 1, wherein the collar is configured to remain at a position longitudinally with respect to the outer shaft when rotating with respect to the outer shaft.

9. The occlusion crossing device of claim 1, wherein an outer surface of the collar includes one or more abrasive surface features configured to cut tissue.

10. The occlusion crossing device of claim 9, wherein the one or more abrasive surface features includes one or more protrusions, one or more indentations or an adhered abrasive material.

11. The occlusion crossing device of claim 1, wherein the outer shaft includes a backbone that extends longitudinally along at least a portion of the outer shaft, wherein the backbone is configured to bias lateral bending of a distal portion of the occlusion crossing device along a plane.

12. The occlusion crossing device of claim 11, further comprising a handle having a connector configured to rotatably lock the inner shaft to the outer shaft, wherein the connector allows the inner shaft to rotate with respect to the outer shaft when the inner shaft is rotatably locked to the outer shaft.

13. The occlusion crossing device of claim 12, wherein the connector is configured to provide longitudinal movement between the inner shaft and the outer shaft such that the inner shaft can translate longitudinally a small distance to activate lateral bending of the backbone.

14. The occlusion crossing device of claim 13, wherein the connector includes one or more of a luer lock, a valve connector, a joint fitting, and a gasket joint.

15. The occlusion crossing device of claim 1, wherein the outer shaft includes a backbone that is configured to bend the occlusion crossing device upon application of a pushing force on the inner shaft, wherein the occlusion crossing device is configured to bend toward the backbone in response to the pushing force such that a side of the outer shaft opposite the backbone expands.

16. The occlusion crossing device of claim 15, wherein the occlusion crossing device is configured to straighten or bend away from the backbone upon application of a pulling force on the inner shaft.

17. The occlusion crossing device of claim 1, wherein an optical window of the collar is configured to align with the optical window of the drill tip body when the collar and the drill tip body are locked.

18. The occlusion crossing device of claim 17, wherein the optical window of the collar is longitudinally aligned with one or more optical windows of the outer shaft.

19. An occlusion crossing device comprising:
an outer shaft;
a rotatable inner shaft comprising a distal cutting tip and an optical coherence tomography (OCT) imaging element; and
a collar rotatably attached to the outer shaft and configured to removably couple the inner shaft within the outer shaft, wherein the collar comprises a lock, the lock configured such that:
when the lock is engaged, the collar is rotatable with the inner shaft relative to outer shaft, translation of the inner shaft relative to the outer shaft in a first axial direction causes the occlusion crossing device to bend, and translation of the inner shaft relative to the outer shaft in a second axial direction causes the occlusion crossing device to straighten; and
when the lock is disengaged, the rotatable inner shaft is removable from within the outer shaft.

20. A method of operating an occlusion crossing device, the occlusion crossing device including an inner shaft having a distal end with a drill tip body attached thereto, and an outer shaft having a distal end with a collar rotatably coupled thereto, the method comprising:
engaging a lock of the collar and the drill tip body by distally translating the inner shaft and the drill tip body within the outer shaft and rotating the inner shaft and the drill tip body with respect to the collar;
spinning the inner shaft while the collar and the drill tip body are locked together so that the collar spins with the drill tip body and the inner shaft;
laterally bending the occlusion crossing device in a first direction by applying a pushing force on the inner shaft while the collar and the drill tip body are locked together; and
straightening the occlusion crossing device by applying a pulling force on the inner shaft while the collar and the drill tip body are locked together.

21. The method of claim 20, further comprising removing the inner shaft from the outer shaft by:
stopping spinning of the inner shaft, the drill tip body, and the collar;
disengaging the lock of the collar and the drill tip body by rotating the inner shaft and the drill tip body less than one full rotation; and
proximally translating the inner shaft with respect to the outer shaft until the inner shaft is removed from a lumen of the outer shaft.

22. The method of claim 20, further comprising removing the inner shaft from the outer shaft by:
stopping spinning of the inner shaft, the drill tip body, and the collar; and
proximally translating the inner shaft with respect to the outer shaft to disengage the lock of the collar and the drill tip body and remove the inner shaft from the outer shaft.

23. The method of claim 20, wherein the lock includes a key protruding from an outer surface of the drill tip body and a keyway at a proximal end of the collar, wherein engaging the lock includes capturing the key within the keyway.

24. The method of claim 23, wherein capturing the key within the keyway includes rotating the drill tip body to align the key with a gap of the keyway and distally translating the drill tip body with respect to the outer shaft so that the key enters the keyway.

25. The occlusion crossing device of claim 19, wherein the inner shaft is operatively coupled to a rotational driver configured to rotate the inner shaft relative to the outer shaft.

* * * * *